US007396905B1

(12) United States Patent
McKeon et al.

(10) Patent No.: US 7,396,905 B1
(45) Date of Patent: Jul. 8, 2008

(54) CALCIPRESSINS: ENDOGENOUS INHIBITORS OF CALCINEURIN, USES AND REAGENTS RELATED THERETO

(76) Inventors: Frank McKeon, 311 Commonwealth Ave., Boston, MA (US) 02115; Kimbara Kayako, 1455 Beacon St., Brookline, MA (US) 02446; Sandra W. Ryeom, 227 Washington St., Apartment 4, Brookline, MA (US) 02445

( * ) Notice: Subject to any disclaimer, the term of this patent is extended or adjusted under 35 U.S.C. 154(b) by 0 days.

(21) Appl. No.: 09/575,580

(22) Filed: May 22, 2000
(Under 37 CFR 1.47)

Related U.S. Application Data

(60) Provisional application No. 60/161,195, filed on Oct. 22, 1999, provisional application No. 60/135,431, filed on May 21, 1999.

(51) Int. Cl.
*C07K 14/00* (2006.01)
*C12Q 1/00* (2006.01)

(52) U.S. Cl. .............. 530/350; 530/387.1; 514/12; 536/23.1; 536/23.5; 435/4; 435/325

(58) Field of Classification Search ............ 536/23.5, 536/23.1; 514/12; 530/350, 387.1; 435/7.1, 435/4, 325
See application file for complete search history.

(56) References Cited

U.S. PATENT DOCUMENTS

| | | | |
|---|---|---|---|
| 4,522,752 A | 6/1985 | Sisto et al. | 260/112.5 R |
| 4,833,080 A | 5/1989 | Brent et al. | 435/172.3 |
| 4,868,116 A | 9/1989 | Morgan et al. | 435/240.2 |
| 4,897,355 A | 1/1990 | Eppstein et al. | 435/240.2 |
| 5,061,811 A | 10/1991 | Pinori et al. | 549/274 |
| 5,096,815 A | 3/1992 | Ladner et al. | 435/69.1 |
| 5,176,996 A | 1/1993 | Hogan et al. | 435/6 |
| 5,190,762 A | 3/1993 | Yarosh | 424/450 |
| 5,198,346 A | 3/1993 | Ladner et al. | 435/69.1 |
| 5,223,409 A | 6/1993 | Ladner et al. | 435/69.7 |
| 5,252,348 A | 10/1993 | Schreier et al. | 424/450 |
| 5,256,775 A | 10/1993 | Froehler | 536/25.6 |
| 5,264,564 A | 11/1993 | Matteucci | 536/23.1 |
| 5,283,317 A | 2/1994 | Saifer et al. | 528/405 |
| 5,288,514 A | 2/1994 | Ellman | 427/2 |
| 5,359,115 A | 10/1994 | Campbell et al. | 558/110 |
| 5,362,899 A | 11/1994 | Campbell | 558/108 |
| 5,459,039 A | 10/1995 | Modrich et al. | 435/6 |
| 5,498,531 A | 3/1996 | Jarrell | 435/91.31 |
| 5,869,318 A | 2/1999 | Palleja et al. | 435/232.3 |

FOREIGN PATENT DOCUMENTS

| | | |
|---|---|---|
| EP | A43075 | 6/1982 |
| EP | 0259149 | 9/1988 |
| WO | WO8902468 | 3/1989 |
| WO | WO8907136 | 8/1989 |
| WO | WO9002909 | 3/1990 |
| WO | WO9106309 | 5/1991 |
| WO | WO9207573 | 5/1992 |
| WO | WO9209690 | 6/1992 |
| WO | WO9210092 | 6/1992 |
| WO | WO9215694 | 9/1992 |
| WO | WO9320242 | 10/1993 |
| WO | WO9325234 | 12/1993 |
| WO | WO9406920 | 3/1994 |
| WO | WO9408051 | 4/1994 |
| WO | WO9410300 | 5/1994 |
| WO | WO9416101 | 7/1994 |

OTHER PUBLICATIONS

Abremski et al., "Bacteriophage P1 Site-Specific Recombination, Purification and Properties of the Cre Recombinase Protein", J. Biol. Chem. 259: 1509-1514 (1984).
Arkin and Yourvan. "An Algorithm for Protein Engineering: Simulations of Recursive Ensemble Mutagenesis", PNAS USA 89:7811-7815 (1992).
Armentano et al., "Expression of Human Factor IX In Rabbit Hepatocytes By Retrovirus-Mediated Gene Transfer: Potential for Gene Therapy of Hemophilia B". PNAS USA 87:6141-6145 (1990).
Ausubel, F.M. et al., "Preparation of a Specific Retrovirus Producer Cell Line". Current Protocols in Molecular Biology Sections 9.10-9.14 (eds.) Greene Publishing Associates (1989).
Balinderan et al., "Preliminary Crystallization Studies of Calmodulin-Dependent Protein Phosphatase (Calcincurin). From Bovine Brain". Molecular and Cellular Biochemistry 149/150:127-130 (1995).
Ballas et al., "Liposomes Bearing a Quaternary Ammonium Detergent as an Efficient Vehicle for Functional Transfer of TMV-RNA Into Plant Protoplasts". Biochim Biophys Acta 939:8-18 (1988).
Banga et al., "Hydrogel-Based Iontotherapeutic Delivery Devices for Transidermal Delivery of Peptide/Protein Drugs". Pharm Res. 10:697-702 (1993).
Barany, "Gentic Disease Detection and DNA Amplification Using Cloned Thermostable Ligase", PNAS USA 88 189-193 (1991).
Barford D., "Molecular Mechanisms of the Protein Serine/Threonine Phosphatases", TIBS 21:407-412 (1996).
Bartel et al., "Elimination of False Positives That Arise in Using the Two-Hybrid System", BioTechniques 14:920-924 (1993).
Bartlett et al., "CAVEAT: A Program to Facilitate the Structure-derived Design of Biologically Active Molecules", Spec. Publ., Roy Soc. Chem. 78:182-196 (1989).
Bauerfeind et al., Ampothiphysin I Is Associated with Coated Endocytic Intermediatesand Undergoes Stimulation-dependent Dephosphorylation in Nep Terminals Biol. Chem. 272:30984-30992 (1997).
Beals et al., "Nuclear Localization of NF-ATc by a Calcineurin-Dependent. Cyclosporin-Sensitive Intramolecular Interaction", Genes and Dev. 11:824-834 (1997).
Behr et al, "Efficient Gene Transfer Into Mammalian Primary Endocrine Cells with Lipopolyamine-Coated DNA", PNAS 86:6982-6986 (1989).

(Continued)

*Primary Examiner*—Chih-Min Kam
(74) *Attorney, Agent, or Firm*—Foley Hoag LLP

(57) ABSTRACT

This invention discloses endogenous calcineurin inhibitors, Calcipressin, Csp1, Csp2, and Csp3, as shown in SEQ ID Nos: 4-5, or 24. This invention also discloses nucleic acid sequences that can activate or regulate transcription of the CSP family of polypeptides.

13 Claims, 34 Drawing Sheets

OTHER PUBLICATIONS

Berkner et al., "Development of Adenovirus Vectors for the Expression of Heterologous Genes", BioTechniques 6:616-629 (1988).

Benoist et al., "In Vivo Sequence Requirements of the SV40 Early Promoter Region", Nature 290:304-310 (1981).

Blondelle et al, "Soluble Combinatorial Libraries of Organic. Peptidomimetic and Peptide Diversities", Trends Anal. Chem 14:83-92 (1995).

Bradley et al., "Embryo-Derived Stem Cells: A Tool for Elucidating the Developmental Genetics of the Mouse", Current Topics in Devel. Biol. 20:357-371 (1986).

Bradley et al., "Formation of Germ-Line Chimaeras from Embryo-Derived Teratocarcinoma Cells Lines", Nature 309:255-258 (1984).

Brinster et al., "Regulation of Metallothionein-Thymidine Kinase Fusion Plasmids Injected into Mouse Eggs", Nature 296:39-42 (1982).

Brinster et al., "Factors Affecting the Efficiency of Introducing Foreign DNA into Mice by Microinjecting Eggs", PNAS 82:4438-4442 (1985).

Brooks et al., CHARMM: A Program for Macromolecular Energy, Minimization, and Dynamics Calculations, J Comput Chem 4:187-217 (1983).

Buiting et al., "Detection of Aberrant DNA Methylation in Unique Prader-Willi Syndrome Patients and its Diagnostic Implications", Human Mol. Genet. 3:893-895 (1994).

Burbaum et al. "Understanding Structural Relationships in Proteins of Unsolved Three-Dimensional Structure", Proteins 7 99-111 (1990).

Chen et al. "'Analogous' Organic Synthesis of Small-Compound Libraries: Validation of Combinatorial Chemistry in Small-Molecule Synthesis" JACS 116:2661-2663 (1994).

Clackson et al., "Making Antibody Fragments Using Phage Display Libraries", Nature 352:624-628 (1991).

Cohen et al., "Emerging Technologies for Sequencing Antisense Oligonucleotides: Capillary Electrophoresis and Mass Spectrometry", Adv Chromatogr 36:127-162 (1996).

Cole et al., Monoclonal Antibodies and Cancer Therapy. Alan R. Liss. Inc. pp. 77-96 (1985).

Cotton et al., "Reactivity of Cytosine and Thymine in Single-Base-Pair Mismatches with Hydroxylamine and Osmium Tetroxide and Its Application to the Study of Mutations", PNAS USA 85:4397-4401 (1988).

Cotton, "Current Methods of Mutation Detection", Mutat Res 285:125-144 (1993).

Crawford et al., "Hamster adapt78 mRNA Is a Down Syndrome Critical Region Homologue That Is Inductible by Oxidative Stress", Arch. Biochem. Biophys. 342:6-12 (1997).

Cwirla et al., "Peptides On Phage: A Vast Library of Peptides for Identifying Ligands", PNAS 87:6378-6382 (1990).

Dai et al., "Gene Therapy Via Primary Myoblasts: Long-Term Expression of Factor IX Protein Following Transplantation In Vivo", PNAS USA 89:10892-10895 (1992).

Dann et al., "Human Renin: A New Class of Inhibitors", Biochem Biophys Res Commun 134:71-77 (1986).

Danos et al., "Safe and Efficient Generation of Recombinant Retroviruses With Amphotropic ad Ecotropic Host Ranges", PNAS USA 85:6460-6464 (1988).

Delgrave et al., "Recursive Ensemble Mutagenesis", Protein Engineering 6(3):327-331 (1993).

Derossi et al., "The Third Helix of the Antennapedia Homcodomain Translocates Through Biological Membranes", J Biol Chem 269:10444-10450 (1994).

Derossi et al., "Cell Internalization of the Third helix of the Antennapedia Homeodomain Is Receptor-Independent", J Biol Chem 271:18188-18193 (1996).

DesJarlais et al., "Docking Flexible Ligands to Macromolecular Receptors by Molecular Shape", J. Med. Chem. 29(1):2149-2153 (1986).

DesJarlais. "Using Shape Complementarity as an Initial Screen in Designing Ligands for a Receptor Binding Site of Known Three-Dimensional Structure", J. Med Cam 31(4) 722-729 (1988).

Dev et al., "Electrochemotherapy—A Novel Method of Cancer Treatment ", Cancer Treat Rev. 20:105-115 (1994).

Doctschman et al., "The In Vitro Development of Blastocyst-Derived Embryonic Stem Cell Lines: Formation of Visceral Yolk Sac, Blood Islands and Myocardium", J. Embryol. Exp. Morph. 87:24-45 (1985).

Duzgunes, N., "Membrane Fusion", Subcellular Biochemistry 11:195-286 (1985).

Eglitis et al., "Gene Expression in Mice After High Efficiency Retroviral-Mediated Gene Transfer", Science 230:1395-1395 (1985).

Egloff et al., "Crystal Structure of the Catalytic Subunit of Human Protein Phosphatase 1 and its Complex with Tungstates", J. Mol. Biol. 254(5):942-959 (1995).

Eisenfield et al., "Constrained Optimization and Protein Structure Determination", Am J Physiol 261:C376-386 (1991).

Elliott et al., "intercellular Trafficking and Protein Delivery by a Herpesvirus Structural Protein", Cell 88:223-233 (1997).

Etienne-Julan et al., "The Efficiency of Cell Targeting By Recombinant Retroviruses Dependes On the Nature of the Receptor and the Composition of the Artifical Cell-Virus Linker", J. Gen Virol 73:3251-3255 (1992).

Eubanks et al., "Peptide Substrates and Inhibitors of N-myristoyl Transferase", Peptides. Chemistry and Biology, Garland Marshall (ed.)., ESCOM, Leiden, pp. 566-69 (1988).

Evans et al., "Establishment in Culture of Pluripotential Cells From Mouse Embryos", Nature 292:154-156 (1981).

Evans et al., "An Engineered Poliovirus Chimaera Elicits Broadly Retroactive HIV-1 neutralizing Antibodies", Nature 339:385-388 (1989).

Ewenson et al., Ketomethylene Pseudopeptide Analogues of Substance P: Synthesis and Biological Activity, J Med Chem 29:295-299 (1986).

Faux et al., "Regulation of the AKA79-Protein Kinase C Interaction by $Ca^{2+}$/Calmodulin", JBC 272:17038-17044 (1997).

Felgner et al., "Lipofection: A Highly Efficient, Lipid-Mediated DNA-Transfection Procedure", PNAS 84:7413-7417 (1987).

Ferry et al. "Retroviral-Mediated Gene Transfer Into Hepatocytes In Vivo", PNAS USA 88:8377-8381 (1991).

Flotte et al, "Gene Expression From Adeno-Associated Virus Vectors in airway Epithelial Cells", Am J. Respir Cell Mol Biol 7:349-356 (1992).

Flotte et al., "Expression of the Cystic Fibrosis Transmembrane Conductance Regulator from a Noval Adeno-Associated Virus Promoter", J. Biol. Chem. 268:3781-3790 (1993).

Froimowitz, "The Development of Computer Simulations of the Geometries and Thermadynamics of Biological Molecules", BioTechniques 8:640-644 (1990).

Fuentes et al., "A New Human Gene From the Down Syndrome Critical Region Encodes a Proline-Rich Protein Highly Expressed in Fetal Brain and Heart", Hum. Mol. Genet. 4:1935-1944 (1995).

Gariej et al., "Synthesis of conformationally constrained CCK-4 analogs containing a substituted gamma lactam ring", Peptides: Chemistry and Bio Marshall ed., ESCOM Publisher: Leiden, Netherlands, 123-125 (1988).

Gasparini et al., "Restriction Site Generating-Polymerase Chain Reaction (RG-PCR) for the Probeless Detection of Hidden Genetic Variation Application to the Study of Some Common Cystic Fibrosis Mutations", Mol. Cell Probes 6:1-7 (1992).

Gautier et al., "DNA IV: anomeric and anomeric tetrathymidylates covalently linked to intercalating oxazolopyridocarbazone. Synthesis physicochemical properties and poly (rA) binding", Nucl. Acids res. 15:6625-6641 (1987).

Gibbs et al., "Detection of single DNA base difference by competitive oligonucleotide priming", Nucleic Acids Res. 17:2437-2448 (1989).

Goldberg et al., "Three-dimensional structure of the catalytic subunit of protein serine/threonine phosphatase-1", Nature 376:745-753 (1995).

Goodford et al., "A Computational Procedure for Determining Energetically Favorable Binding Sites on Biologically Important Macromolecules", J. Med. Cam. 28:849-857 (1985).

Gordon et al., "Design of Peptide Derived Amino Alcohols as Transition-State Analog Inhibitors of angiotensin Converting Enzyme", Biochem Biophys Res Commun 126:419-426 (1985).
Gossler et al., "Transgenesis by means of blastocyst-derived embryonic stem cell lines", PNAS 83:9065-9069 (1986).
Goud et al., "Antibody-Mediated Binding of a Murine Ecotropic Moloney Retroviral Vector to Human Cells Allows Internalization But Not the Establishment of the Proviral State", Virology 163:251-254 (1988).
Graham et al., "Manipulation of Adenovirus Vectors", Methods in Molecular Biology, E.J. Murray, Ed. vol. 7, pp. 109-127 (Humana, Clifton, NJ. 1991).
Green and Lowenstein, "Autonomous Functional Domains of Chemically Synthesized Human Immunodeficiency Virus Tat Trans-Activator Protein", Cell 55:1179-1188 (1988).
Griffin et al., "DNA Sequencing Recent Innovations and Future Trends", Appl Biochem Biotechnol 38:47-159 (1993).
Griffith et al, "X-Ray Structure of Calcinicurin Inhibited by the Immunophilin-Immunosuppressant FKBP12-PK506 Complex", Cell 82 507-522 (1995).
Griffiths et al, "Human anti-self antibodies with high specificity from phage display libraries", EMBO J 12:725-734 (1993).
Gunning, P. et al., "A human β-actin expression vector system directs high-level accumulation of antisense transcripts", PNAS 84: 4831-4835 (1987).
Haj-Ahmand and Graham, "Development of a Helper-Independent Human Adenovirus Vector and Its Use in the Transfer of the Herpes Simplex Virus Thymidine Kinase Gene", J. Virol. 57:267-274 (1986).
Hart St. et al., Cell Binding and Internalization by Filamentous Phage Displaying a Cyclic Arg-Gly-Asp-containing Peptide, J. Biol. Chem. 269-1246.
Hayashi. "PCR-SSCP: A Method for Detection of Mutations". Genet Anal Tech Appl 9(3):73-79 (1992).
Helene C., et al., "Control of Gene Expression by Triple Helix-Forming Oligonucleotides the Antigene Strategy." Ann, N.Y. Acad. Sci. 660:27-36 (1992).
Helene C., "The anti-gene strategy: control of gene expression by triplex-forming-oligonucleotides". Anticancer Drug Des. 6(6):469-84 (1991).
Hermonat et al., Use of adeno-associated virus as a mammalian DNA cloning vector: Transduction of neomycin resistance into mammalian tissue culture cells, Proc. Natl. Acad. Sci. USA 81:6466-6470 (1984).
Higashijima, T. et al., "Regulation of Gi and Go by Mastoparan. Related Amphiphilic Peptides. and Hydrophobic Ammes". J. Biol. Chem. 265:14176-14186 (1990).
Hirschberg, C. et al., "Topography of Glycosylation in the Rough Endoplasmic Reticulum and Golgi Apparatus", Ann. Rev. Biochem. 56:63-87 (1987).
Hoffman, P. et al., "Stimulation of Human and Murine Adherent Cells by Bacterial Lipoprotein and Synthetic Lipopeptide Analogues", Immunobiol. 177:158-170 (1988).
Hsu et al., "Detection of DNA point mutations with DNA mismatch repair enzymes", Carcinogens 15:1657-1662 (1994).
Huang et al., "Vacciniak Virus Recombinants Expressing an 11-Kilodalton β-Galactosidase Fusion Protein Incorporate Active β-Galactosidase in Virus Particles", J. Virol. 62:3855-3861 (1988).
Huber et al., "Retroviral-mediated gene therapy for the treatment of hepatocellular carcinoma: An innovative approach for cancer therapy", Proc. Natl. Acad. Sci. USA 88:8039-8043 (1991).
Huffman et al., "Reverse turn mimics", Peptides: Chemistry and Biology, G.R. Marshall ed., ESCOM Publisher; Leiden, Netherlands, 105-108 (1988).
Hwu et al., "Functional and Molecular Characterization of Tumor-Infiltrating Lymphocytes Transduced with Tumor Necrosis Factor-α cDNA for the Gene Therapy of Cancer in Humans", J. Immunol. 150:4104-4115 (1993).
Ike et al., "Solid phase synthesis of polynucleotides, VIII. Synthesis of mixed olgodeoxyribonucleotides by the phosphotriester solid phase method", Nucleic Acid Res. 11:477-488 (1983).
Inoue et al., "Synthesis and hybridization studies on two complementary nona(2'-O-methyl)ribonucleotides", Ncul. Acids Res. 15:6131-6148 (1987).

Ioffe et al., "WW6: An embryonic stem cell line with an inert genetic market that can be traced in chimeras", PNAS 92:7357-7361 (1995).
Itakura et all, "Synthesis and Use of Synthetic Oligonucleotides", Annu. Rev. Biochem. 53:323-356 (1984).
Itakura et al., "Chemical Synthesis and Application of Oligonucleotides of Mixed Sequence". Recombinant DNA. Proc 3rd Cleveland Sympos. Macromolecules. ed. AG Walton, Amsterdam: Elsevier Scientific Publishing Co.: 273-289 (1981).
Itakura, "Expression in Escherichia coli of a Chemically Synthesized Gene for the Hormone Somatostatin", Science 198:1056 (1984).
JUPAC-IUB Commission on Biochemical Nomenclature. Symbols for Amino-Acid Derivatives and Peptides[1] Recommendations (1971) (see Biochemistry 11:1726-1732 (1972).).
Iwabuchi et al., "Use of the two-hybrid system to identify the domain of p53 involved in oligomerization", Oncogene 8:1693-1696 (1993).
Jaenich, R., "Germ line intergration and Mendelian transmission of the exogenous Moloney leukemia virus", PNAS 73:1260-1264 (1976).
Jaenisch, R., "Transgenic Animals", Science 240:1468-1474 (1988).
Jahner et al., De novo methylation and expression of retroviral genomes during mouse embryogenesis, Nature 298:623-628 (1982).
Jahner et al., Insertion of the bacterial gpt gene into the germ line of mice by retroviral infection, PNAS 82:6927-6931 (1985).
John Wiley & Sons. N.Y., Current Protocols in Molecular Biology 6.3.1.-6.3.6 (1989).
Jones et al., "Isolation of Adenovirus Type 5 Host Range Deletion Mutants Defective for Transformation or Rat Embryo Cells", Cell 16:683-689 (1979).
Karasuyama et al., "Autocrine Growth and Tumorigenicity of Interleuin 2-Dependent Helper T Cells Transfected with 11.-2 Gene", J. Exp. Med. 169 13-25 (1989).
Kawamura et al, "Interaction of FKBP12-FK506 with Calcincurin A at the B Subunit-binding Domain", JBC 270 15463 1-7 (1995).
Kay et al., "Human Gene Therapy: Persistant Expression of Human al-Antitrypsin in Mice after Direct Gene deliver In Vivo". 3:641-647.
Kim et al, "Peptides Constrained to Type VI β-Turns 1 Evidence for an Exceptionally Stable Intramolecular Hydrogen Bond", J Org Chem 62:2847-2852 (1997).
Kissinger et al., "Crystal structures of human calcineurin and the human FKBP12-FK506-calcineurin complex", Nature 378, 641-644 (1995).
Klec et al., "Calcineurin ", Adv enzymol 61:149-200 (1988).
Klessing et al., "Introduction. Stable integration, and Controlled Expression of a Chimeric Adenovirus Gene Whose Product is Toxic to the Recipient Human Cell" Mol. Cell Biol. 4:1354-1362 (1984).
Kohler and Milstein, "Continuous cultures of fused cells secreting antibody of predefined specefcity", Nature 256:(494-197).
Kozbar et al, "The Production of monoclonal antibodies from human lymphocytes", Immunology Today 4:72-79 (1983).
Kuntz et al., "A Geometric Approach to Macromolecule-Ligand Interactions", J. Mol. Biol 161:269-288 (1982).
Kuppuswamy et al., "Multiple functional domains of Tat, the trans-activator of HIV-1, defined by mutational analysis", Nucl. Acids Res. 17:3551-3561 (1989).
Lakso et al., "Targeted oncogene activation by site-specific recombination in transgenic mice", PNAS 89:6232-6236 (1992).
Landegran et al., "A Ligase-Mediated Gene Detection Technique", Science 241:1077-1080 (1998).
Lemaitre et al., "Specific antiviral of a poly(L-lysine)-conjugated oligodeoxyribonucleotide sequence complementary to vesicular stomatitis virus N protein mRNA initiation site", Proc. Natl. Acad. Sci. 84:648-652 (1987).
Leonard, N. J., "Trimethylene Bridges as Synthetic Spacers for the Detection of Intermolecular Interactions", Accounts of Chem. Res. 12: 423-429 (1979).
Letsinger et al., "Cholesteryl-conjugated oligonucleotides: Synthesis, properties, and activity as inhibitors of replication of human immunodeficiency virus in cell culture." Proc. Nat. Acad. Sci. USA 86:6553-6556 (1989).
Liu et al., "Inhibitions of T Cell Signaling by Immunophilin-Ligand Complexes Correlates with Loss of Calcineurin Phosphatase Activity", Biochemistry 31:3896-3901 (1992).

Liu et al, "Calcineurin Is a Common Target of Cyclophilin-Cyclosporin A and FKBP-FK506 Complexes", Cell 66, 807-815 (1991).

Loots et al., "Acyl lysinamido phosphonates Potent, long-acting inhibitors of angiotensin-converting enzyme", Peptides: Chemistry and Biology, (Escom Science Publishers, Leiden, p. 118 (1988).

Lybrand, "Molecular Simulation and Drug Desing", J. Pharm Belg 46 49-54 (1991).

Maher, L.J., "DNA Triple-Helix Formation: An Approach to Artificial Gene Repressors?", Bioassays 14(12):807-15 (1992).

Marks et al., "Molecular Polution of Proteins on Filamentous Phage", J. Bil. Chem. 267:16007-16010 (1992).

Martin et al., "Isotope effects on the mechanism of calcineurin catalysis: kinetic solvent isotope exchange studies", Biochim. Et Bioph. Acta. 1206:136-142 (1994).

Maxim and Gilbert, "A new method for sequencing DNA", Proc. Natl. Acad Sci USA 74:560-564 (1977).

McLaughlin et al., "Adeno-Associated Virus General Transduction Vectors: Analysis of Proviral Structures", J. Virol. 62:1963-1973 (1989).

Milan et al., "The Latch Region of Calcineurin B Is Involved in Both Immunosuppressant-Immunophilin Complex Docking and Phosphatase Activation", Cell 79. 437-447 (1994).

Miller, A.D., "Progress Toward Human Gene Therapy", Blood 76:271-278 (1990).

Mitra-Kirtley et al., "Determination of the Nitrogen Chemical Structures in Petroleum Asphaltenes Using XANES Spectroscopy", JACS 115:252-158 (1993).

Mitragotri et al., "Ultrasound-Mediated Transdermal Protein Delivery", Science 269:850-853 (1995).

Miyazaki et al., "Molecular Cloning of a Novel Thyroid Hormone-responsive Gene, ZAKI-4, in Human Skin Fibroblasts", J. Biol. Chem. 271, 14567-14571 (1996).

Mizuno et al., No Shinekei Geka 20:547-551 (1992), abstract only.

Muzyezka et al., "Use of Adeno-Associated Virus as a General Transduction Vector for Mammalian Cells", Curr. Topics in Micro and Immunol. 158:97-129 (1992).

Myers et al., "Detection of Single Base Substitutions in Total Genomic DNA", Nature 313:495-498 (1985).

Myers et al., "Detection of Single Base Substitutions by Ribonuclease Cleavage at Mismatches in RNA DNA Duplexes", Science 230:1242-1246 (1985).

Naeve, C.W. et al., "Accuracy of Automated DNA Sequencing: A Multi-Laboratory Comparison of Sequencing Results", BioTechniques 19:448-453 (1995).

Nagai et al "Synthesis of a Bicyclic Dipeptide with the Shape of β-turn Central Part", Tetrahedron Lett 26 647-650 (1985).

Narang, SA, "DNA Synthesis", Tetrahedron 39:3-22 (1983).

Narelli et al., "A Chemically Defined Synthetic Vaccine Model for HIV-1", Journal of Immunology, 148:914-920 (1992).

Natarajan et al., "Ketomethyldipeptides I. A New Class of Angiotensin Converting Enzyme Inhibitors", Biochem Biophys Res Commun 124: 141-147 (1984).

Navia, "Protein-drug complexes important for immunoregulation and organ transplantation", Curr. Op. Struct. Bio. 6:838-847 (1996).

Neda et al., "Chemical Modification of an Ecotropic Murine Leukemia Virus Results in Redirection of Its Target Cell Specificity", J Biol Chem 266:14143-14146 (1991).

Nelson et al., "Synthesis and Immunosuppressive Activity of Some Side-Chain Variants of Mycophenolic Acid", J. Med. Cam. 33:833-838 (1990).

O'Gorman et al., "Recombinase-Mediated Gene Activation and Site-Specific Integration in Mammalian Cells", Science 251:1351-1355 (1991).

Orban et al., "Tissue- and site-specific DNA recombination in transgenic mice", PNAS 89:6861-6865 (1992).

Orita et al., "Detection of polymorphisms of human DNA by gel electrophoresis as single-strand conformation polymorphisms", Proc Natl. Acad. Sci USA 86:2766-2770 (1989).

Pederson, "Conformational Properties of Molecules by ab Initio Quantum Mechanical Energy Minimization", Environ Health Perspect 61:185-190 (1985).

Perez et al., "Antennapedia homeobox as a signal for the cellular internalization and nuclear addressing of a small exogenous peptide", J Cell Sci 102:717-722 (1992).

Politino et al., "Calcineurin-Phospholipid Interactions", JBC 265:7619-7622 (1990).

Posnett et al., "A Novel Method for Producing Anti-peptide Antibodies", JBC 263:1719-1725 (1988).

Prossner, J., "Detecting single-base mutations", TIBTech 11: 238-246 (1993).

Quinlan et al., "Emergence of Activity-Dependent, Bidirectional Control of Microtubule-Associated Protein MAP2 Phosphorylation during Postnatal Development", J Neuroscience 16:7627-7637 (1996).

Roark et al., "Synthesis and antagonist activities of backbone-modified angiotensin II analogs", Peptides: Chemistry and Biology, G.R. Marshall ed., ESCOM Publisher: Leiden, Netherlands, 134-136 (1988).

Roberts et al., "Directed evolution of a protein: Selection of potent neutrophil elastase inhibitors displayed on M13 fusion phage", PNAS 89:2429-2433 (1992).

Robertson et al., "line transmission of genes introduced into cultured pluripotential celss by retroviral vector", nature 322:445-448 (1986).

Rosenbaum et al., "Temperature-gradient gel electrophoresis; Thermodynamic analysis of nucleic acids and proteins in purified form and in cellular extracts", Biophys Chem 26: 235-246 (1987).

Rosenfeld et al., "In Vivo Transfer of the Human Cystic Fibrosis Transmembrane Conductance Regulator Gene to the Airway Epithelium", Cell 68:143-155 (1992).

Rosenfeld et al., "Adenovirus-Mediated Transfer of a Recombinant α1-Antitrypsin Gene to the Lung Epithelium in Vivo", Science 252:431-434 (1991).

Roux et al, PNAS 86:9079-9083 (1989).

Ruben et al., "Structural and Functional Characterization of Human Immunodeficiency Virus tat Protein", J. Virol. 63:1-8 (1989).

Ruoslahti, "Fibronectin and its Receptors", E. Ann. Rev. Biochem. 57:375-413 (1988).

Saiki et al., Analysis of enzymatically amplified β-globin and HLA-DQα DNA with allele-specific oligonucleotide probes, Nature 324:163-166 (1986).

Saiki et al., "Genetic analysis of amplified DNA with immobilized sequence-specific oligonucleotide probes", PNAS U 86: 6230-6234 (1989).

Saleeba et al., "Chemical Cleavage of Mismatch to Detect Mutations", Methods Enzymod. 217:286-295 (1993).

Samulski et al., "Helper-Free Stocks of Recombinant Adeno-Associated Viruses: Normal Integration Does Not Require Viral Gene Expression", J. Virol 63:3822-3828 (1989).

Sanger et al., "DNA sequencing with chain-terminating inhibitors", Proc. Nat. Acad. Sci 74:5463-5467 (1977).

Sarin et al., "Inhibition of acquired immunodeficiency syndrome virus by oligodeoxynucleoside methylphosphonates", Proc Natl. Acad Sci USA 85 74487451 (1988).

Sato et al., "Synthesis and Antibiotic Activity of a Gramicidin S Analogue containing Bicycle β-Turn Dipeptides", J. Chem. Soc. Perkin Trans 1: 1231-1234 (1986).

Scott et al., "Searching for Peptide ligands with an Epitope Library", Science 249: 386-390 (1990).

Sells et al., "Delivery of Protein into Cells Using Polycationic Liposomes", Biotechniques 19:72-78 (1995).

Shen et al., "Conjugation of poly-L-lysine to albumin and horseradish peroxidase" A novel method of enhancing the cellular uptake of proteins, PNAS 75.

Shue, Y.K. et al., "Amide Bond Surrogates: A General Synthetic Route to Trans Carbon-Carbon Double Bond Isoteres", Tetrahedron Letters 28:3225-3228 (1987).

Small et al., "Analysis of a Transgenic Mouse Containing Simian Virus 40 and v-mye Sequences", Mol. Cell Biol. 5:642-648 (1985).

Smithies et al., Nature 317: "Insertion of DNA sequences into the human chromosomal β-globin locus by homologous recombination", 230-234 (1985).

Sprague "Expression of a Recombinant DNA Gene Coding for the Vesicular Stomatitis Virus Nucleocapsid Protein", et al., J. Virol. 45:773-781 (1983).

Stein et al., "Oligodeoxynucleotides as Inhibitors of Gene Expression: A Review", Cancer Res 48:2659-2668 (1988).

Stein et al., "Physicochemical properties of phosphorothioate oligodeoxynucleotides", Nucl. Acids res. 16:3209 (1988).

Stewart et al., "Expression of retroviral vectors in transgenic mice obtained by embryo infection", EMBO J. 6:383-388 (1987).

Stoddard et al., "Calcineurin-immunosuppressor complexes", Curr Opin Struct Biol 6:770-775 (1996).

Subbarao et al., "pH-Dependent Bilayer Destabilization by an Amphipatic Peptide", Biochemistry 26:2964-2972 (1987).

Templeton et al., "N-Terminal Amino Acid Sequences of the Polyoma Middle-Size T Antigen Are Important for Protein Kinase Activity and Cell Transformation", Mol. Cell Biol. 4:817-821 (1984).

Thomas & Capecchi, "Site-Directed Mutagenisis by Gene Targeting in Mouse Embryo-Derived Stem Cells", Cell 51:503-512 (1987).

Thompson et al, "Germ Line Transmission and Expression of a Corrected HPRT Gene Produced by Gene Targeting in Embryonic Stem Cells", Cell 5:313-321 (1989).

Tratschin et al., "Genetic Analysis of Adeno-Associated Virus: Properties of Deletion Mutants Contructed In Vivo and Evidence for an Adeno-Associated Virus Replication Function", J. Virol. 51:611-619 (1984).

Tratschin et al, "Adeno-Associated Virus Vector for High-Frequency Integration, Expression, and Rescue of Genes in Mammalian Cells", Mol. Cell. Biol. 5:3251-3260 (1985).

van Beusechem et al, "Long-term expression of human adenosine deaminase in thesus monkeys transplanted with retrovirus-infected bone-marrow cells", Proc. Natl Acad Sci USA 89 7640-7644 (1992).

Van der Krol et al., "Modulation of Eukaryotic Gene Expressioon by Complementary RNA or DNA Sequences", Biotechniques 6:958-976 (1988).

Van der Putten et al., "Efficient insertion of genes into the mouse germ line via retroviral vectors", PNAS 82:6148-6152 (1985).

Wagner et al., "Nucleotide sequence of the thymidine kinase gene of herpes simplex virus type 1", Proc. Natl. Acad. Sci. USA 78:1441-1445 (1981).

Watanabe et al., "Identification in the Calcineurin A Subunit of the Domain That Binds the Regulatory B Subunit", JBC 270:456-460 (1995).

Webb and Hurskainen, "Transcription-Specific Assay for Quantifying mRNA: A Potential Replacement for Reporter Gene Assays", Journal of Biomolecular Screening 1:119-121 (1996).

Wei et al., "Mutagenesis of the L7 Loop Connecting 7/8 Strands of 12 and 13 of Calcineurin: Evidence of a Structural Role in Activity Changes", Biochemistry 36, 7418-7424 (1997).

Weiner et al., "A New Force Field For Molecular Mechanical Simulation of Nucleic Acids and Proteins", J. Am. Chem. Soc.. 106:765-784 (1984).

Weiner, P.K et al., "AMBER: Assisted Model Building with Energy Refinement. A General for Modeling Molecules and Their Interactions", J. Comput. Chem. 2 (3): 287-303 (1981).

Williams et al., "2-Substituted Piperazines as Constrained Amino Acids. Application to the Synthesis of Potent, Non Carboxylic Acid Inhibitors of Farnesyltransferase", J. Med. Chem. 39:1345-1348 (1996).

Wilson et al., "Retrovirus-mediated transduction of adult hepatocytes", Proc. Natl. Acad. Sci. USA 85:3014-3018 (1988).

Wolfe et al., "Herpesvirus vector gene transfer and expression of β-glucuronidase in the central nervous system of MPSVII mice", nature Genetics 1:379-384 (1992).

Wondisford et al., "Cloning of the Human Thyrotropin β-Subunit Gene and Transient Expression of Biologically Active Human Thyrotropin after Gene Transfection", Mol. Endocrinol. 2:32-39 (1988).

Xi et al., J "Elevated Conformational Regidy in Dipeptides Incorporating Piperazie Acid Derivatives", Am. Chem. Soc. 120 80-86 (1988).

Yamada et al., "Overproduction of the protein product of a nonselected foreign gene carried by an adenovirus vector", PNAS 82:3567-3571 (1985).

Yourvan et al., "Recursive Ensemble Mutagenesis: A Combinatorial Optimization Technique for Protein Engineering" Parallel Problem Solving from Nature, 2, Manner and Manderick, eds., Elsevir Publishing Co., Amsterdam: 401-410 (1992).

Zervos et al., "Mxil, a Protein That Specifically Interacts with Max to Bind Mye-Max Recognition Sites", Cell 72:223-232 (1993).

Zhuo et al. Mutational Analysis of a Ser/Thr Phosphatase, JBC 269:26234-238 (1994).

Zon, "Oligonucleotide Analogues as Potential Chemotherapeutic Agents", Pharm. Res. 5:539-549 (1988).

Purroy, eta l. (2000). Detection of Two Novel Large Deletions is SLC3A1 by Semi-Quantitative Fluorescent Multiplex PCR. *Human Mutation* 115:373-379.

Fuentes, et al., (1999), Application of Alu-Splice PCT on chromosome 21: DSCR1 and Intersection: *Jouranl of Neural Transmission Suppl.* 578, 337-352.

Guimera, et al., (1997), Cosmid Contig and Transcriptional Map of Three Regions of Human Chromosome 21q22: Identification of 37 Novel Transcripts by Direct Selection: *Genomics* 45, 59-67.

Strippoli et al. (2000). A new Gene Family Including DSCR1 (Down Syndrome Candidate Region 1) and ZAKI-4: Characterization from Yeast to Human and Identification of DSCRI-like 2, a Novel Human Member (DSCR11.2), *Genomic*, 64,252-263.

Fuentes, et al. (1997), Genomic Organization, Alternative Splicing, and Expression Patterns of the DSCR1 (Down Syndrome Candidate Regional) Gene, *Genomics*, 44, 358-361.

Rothermel et al (2000), A Protein Encoded within the Down Syndrome Critical Region Is Enriched in Striated Muscles and Inhibits Calcineurin Signaling, *J. Biol Chem.* vol. 275, Issue 12, 8719-8725.

Figure 2
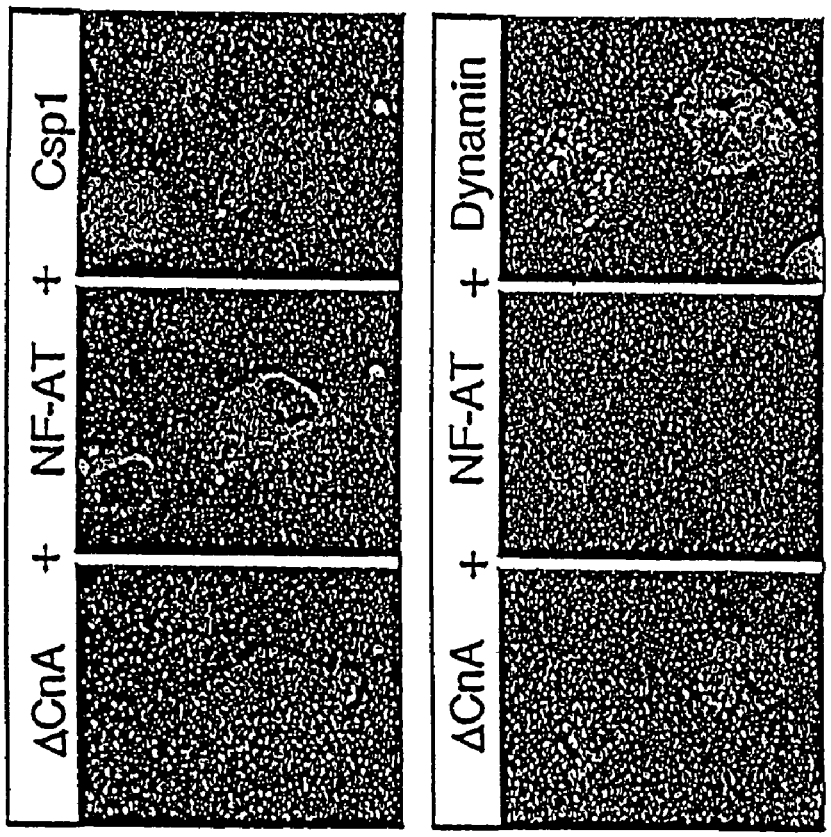
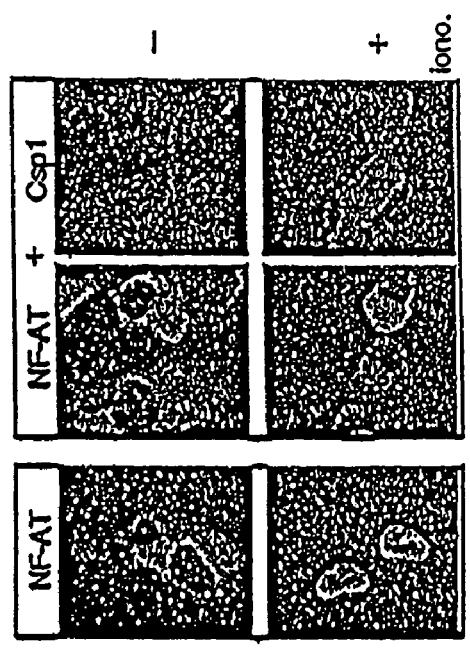
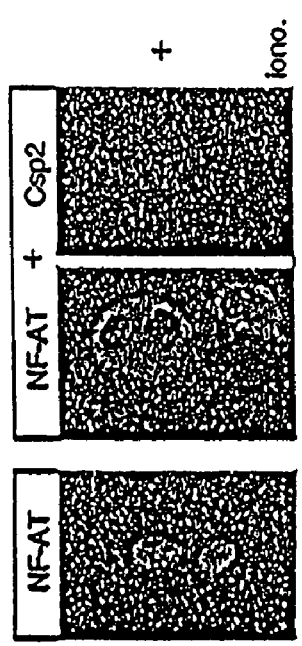

Figure 3
A.
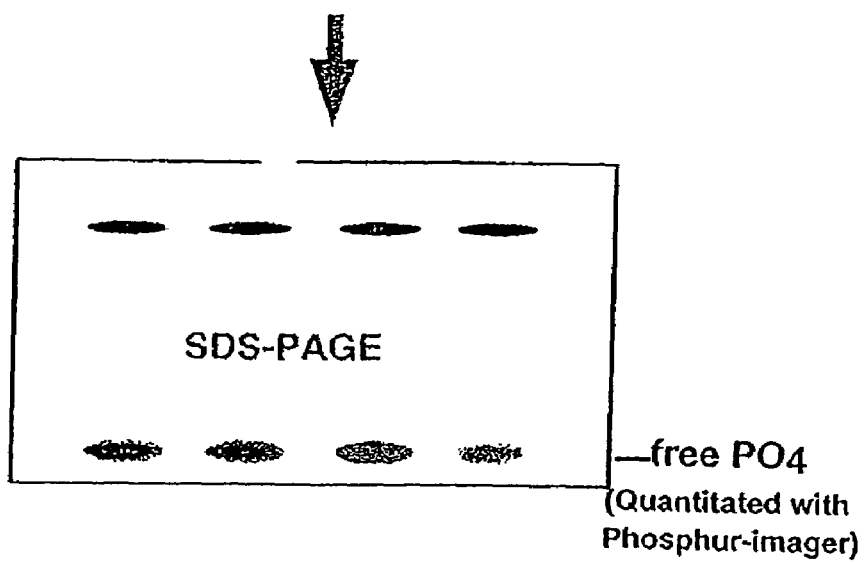
B.
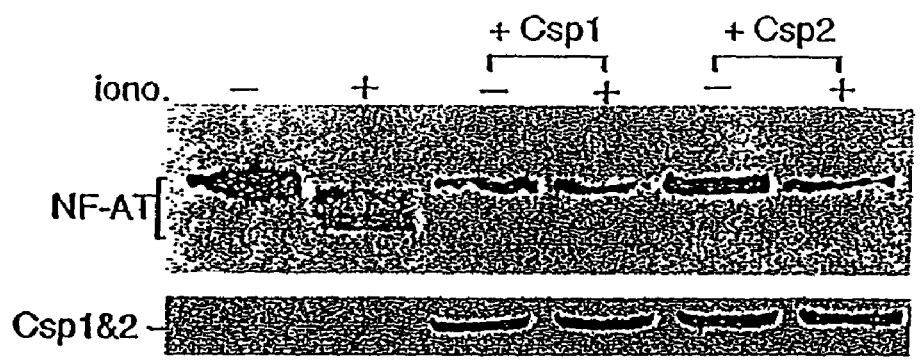

Figure 4
A.
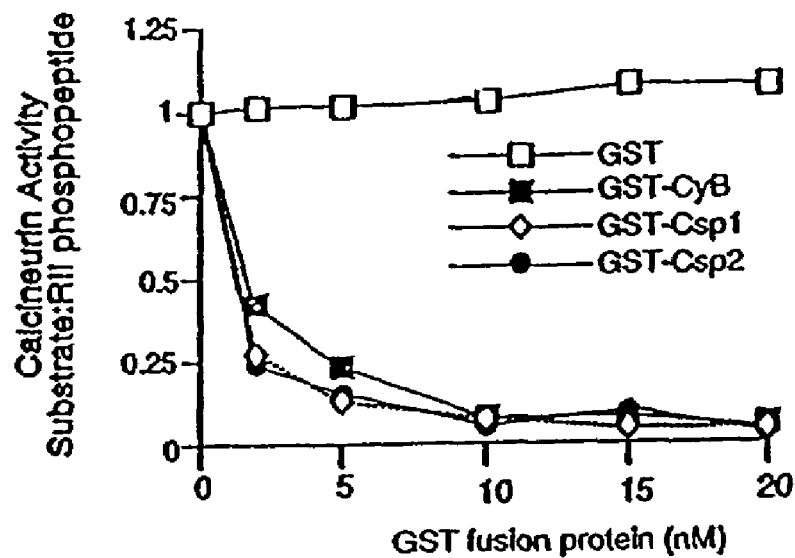
B.
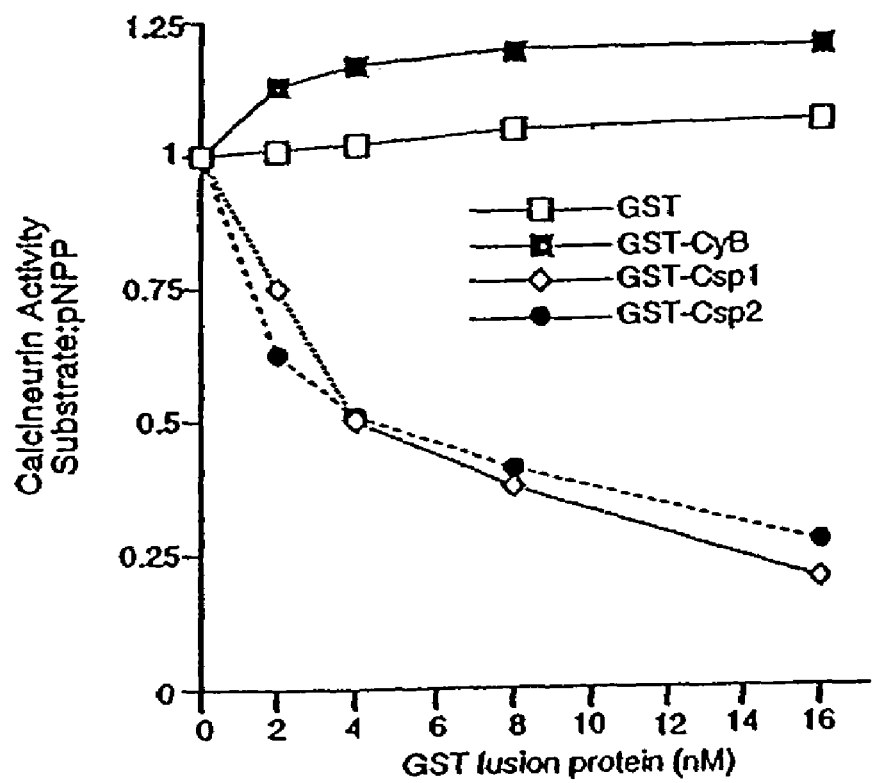

human Csp1 promoter (2.5kb)  (SEQ ID NO: 1)   Figure 9

```
   1 cttgggttta gctccctgag gacacaaact gtcctaagac tatgataata
     gtaatcatag aaccgtgcac atggcaagtt ctgaataaat ctcagctgtt  100  MyoD
 101 ggatatactt tttgttataa ttactaacac ttcctaacta gagagtaagc
     ctactctaag aaaaaatata actgtaattt cacaacctcc aaagaaccca  200
 201 gtgcataaac agctaccatt tattaagcac tgactgaatt cttagtaata
     tgtcttcatt ttttcagat gaggaaacta agattcagct tatttgtaca   300  MyoD, NF-AT
 301 agtagttaaa aagcaaagct gaaattcaga cccaagttct cactgtatca
     tactgtccaa aaaagaattc tatttttcag gaagagacat gtctgctcac  400
 401 ttgaggtcct cttattttttc cgctattccc caaaggaaag gggtgatctc       NF-AT,NF-AT
     ttaattcttt cgttatgtcc tattgtacat agcatataat ggtaattcag  500
 501 aaaaattact tctaattaca taaattttca caatggtata gtgactaata
     cgctgaaata gaaaagtaag gcattgttat catggtctag ttcagtcttt  600  NF-AT
 601 attgcgacta tatctgataa tatacggtaa gcatctaacc acttgccagg
     ggccacagag ccacagggag actatgtctc gcttaaattc ccaaaagtgg  700
 701 gccctgtgc ttcaaaacgt ccccgcatgg gaaccacaaa aacgttgcct
     ccccagttat caccccaagg gcccaagagc cgaggactct gcccggcgtc   800
 801 cttcagctgg caccagctgt cagaaagcg gaactgggga cgaggacttt        MyoD
     gcccctaacc aacatggccg ccctgaggct tcgggcttcg ggcggcagaa  900
 901 ggaaggtcac gtgaagagaa ttccgttcct ttattggccc cgtctcctgg       MyoD
     aaggggcgggg tacaataacc caaccggcgc cggccttaaa ggggccaccg 1000
1001 ttggatctgc cggtggccgg cctaggggc tggggggcg gtcgccgcgc
     cgggcttctg ccctcccgc gcggaacggt gacgggcggg gctggcgctg  1100
1101 ggaggccgtg tgctgggag actgctgaca gcccgccgcc tgccgccgcg
     cgattccgag ggggttaacg gcggagccgc cggccgggcg cggaccggag  1200
1201 cgcgtgaggc tccggcgcgc aagcccggag cagcccgctg gggcgcacag
     ggtcgcgcgg gcgcgggat ggaggacggc gtggccggtc cccagctcgg   1300
1301 ggccgcggcg gaggcggcgg aggcggccga ggcgcgagcg cggcccgggg
     tgacgctgcg gcccttcgcg cccctctcgg gggcggccga ggcggacgag  1400
1401 ggcggcggcg actggagctt cattgactgc gagatggagg aggtggacct
     gcaggacctg cccagcgcca catcgcctg tcacctggac ccgcgcgtgt   1500  MyoD
1501 tcgtggacgg cctgtgccgg gtgaggaccg cgccgggcgg gccgtcgggg
     cggagggcgg acacttgttg cccgaggagg cggcgcgggt cgcagcgccc  1600  MyoD
1601 agtcccggcc gcgcgcgggg cggggaggca gcgacgtccc ccgggctgct
     cggccgcgga cccgtcaggg ctgggcgtg gggacggcgc cccgagggtc   1700
1701 ccggtccct agcaccccg gggcgcgcgg agctcactgc agagtccac
     aggctcgctc cggccccgt gtgcgcccag gctggtgcga ctagggggt    1800
1801 gaattcgctc cccaaggtgg ggcagcgccg ccgcccctg cgctctcgcc
     atcgcccgc atttactcgc tggaggaggg ggtcacctca ttcctaggga   1900
1901 ggaggaaaca gacattgagc ggcgacgtga ctcagtgttc ataaatagga       NF-AT, TATA
     cgacgtccct gcattcccaa tctgcactat tggaagaaaa gccaatgttt  2000
2001 gggtgaggat ccgtggttgc tcattagcca gcggctggcc agtttggtg
     gaattgtgtt gggggggaagg ggaccatctt tcagaccttt aggatattta 2100
2101 gtcaagaacc ttgccccctt gtgtgaaggt gtggcttgcc gccatcgggg
     acaccagta catggggagt cgactccttc ccccgcctcc ccccacccccc 2200
2201 gcaaaatcca cacaatttag acactttgga gggtgagggg caggtatgag
     taatcaataa tggtggtggg gaggaagaat ttatttcaaa tctgcagtta  2300
2301 ttgtgcagaa taaaatgtgg acaacgtggg cgtcacagaa tgaaaccggt
     ctttgagaga tgccccatta ggagagcagc tgtcaaaaaa agcagtgctt  2400
2401 tcagcgcttg gctgtgggtc cacaaatgct gtcaatgaac tatagttgaa
     ggctgctgcc aatacaacac cactgtgaaa caga                   2484
```

Figure 10 murine Csp1 (SEQ ID NO: 2)

```
1                              31
ATG GAG GAG GTG GAT CTG CAG GAC CTG CCG AGC GCC ACC ATC GCC TGC CAC CTG GAC CCG
61                             91
CGC GTG TTC GTG GAC GGC CTG TGC CGG GCC AAA TTT GAA TCC CTC TTC AGA ACA TAT GAC
121                            151
AAG GAC ACC ACC TTC CAG TAT TTT AAG AGC TTC AAA CGT GTC CGG ATA AAC TTC AGC AAC
181                            211
CCC TTA TCT GCA GCC GAT GCC AGG CTG CGG CTG CAC AAG ACC GAG TTC CTG GGG AAG GAA
241                            271
ATG AAG TTG TAT TTT GCT CAG ACT TTA CAC ATA GGA AGT TCA CAC CTG GCT CCG CCC AAT
301                            331
CCC GAC AAA CAG TTC CTC ATC TCC CCT CCG GCC TCT CCT CCC GTT GGC TGG AAA CAA GTA
361                            391
GAA GAT GCC ACC CCC GTC ATA AAT TAC GAT CTT TTA TAT GCC ATC TCC AAG CTG GGG CCA
421                            451
GGA GAG AAG TAT GAA CTG CAT GCA GCG ACA GAC ACC ACT CCC AGT GTG GTG GTC CAC GTG
481                            511
TGT GAG AGT GAC CAA GAG AAT GAG GAG GAA GAG GAA GAG ATG GAG AGA ATG AAG AGA CCC
541                            571
AAG CCC AAA ATC ATC CAG ACA CGG AGA CCG GAG TAC ACA CCC ATC CAC CTC AGC TGA
``` coding sequence: 597 nucleotides

Figure 11 murine Csp2 (SEQ ID NO: 3)

```
1                                     31
GAA TTC GTC GAC CCA CGC GTC CGC CCA CGC GTC CGC TTG GGG CAG CAG GCA TCT ATC CCT
61                                    91
GAA GAT GGG GGA CTT TTC TTC CTC TGC TGC ATA GAC AGA GAC TGG GCT GTC ACT CAG TGT
121                                   151
TTT GCT GAA GAG GCC TTC CAA GCA CTC ACT GAC TTC AGT GAT CTC CCC AAC TCA TTG TTT
181                                   211
GCC TGC AAT GTT CAC CAG TCT GTG TTT GAA GAA GAG GAG AGC AAG GAA AAA TTC GAG GGA
241                                   271
CTG TTC CGG ACC TAT GAT GAA TGT GTG ACG TTC CAG CTG TTT AAG AGT TTC CGA CGG GTT
301                                   331
CGA ATA AAT TTC AGC CAT CCC AAA TCT GCA GCC CGT GCC CGG ATA GAG CTT CAT GAG ACT
361                                   391
CAG TTC AGA GGG AAG AAG CTA AAA CTC TAC TTC GCC CAG GTC CAG ACC CCA GAG ACA GAT
421                                   451
GGA GAC AAA CTG CAT TTG GCA CCT CCA CAG CCT GCC AAA CAG TTC CTC ATC TCA CCC CCT
481                                   511
TCA TCT CCA TCT GTT GGC TGG AAG CCT ATC AGC GAT GCC ACA CCA GTC CTC AAC TAT GAC
541                                   571
CTT CTT TAT GCT GTG GCC AAA CTA GGA CCA GGA GAG AAA TAT GAG CTG CAC GCT GGA ACT
601                                   631
GAG TCT ACC CCG AGC GTC GTG GTG CAT GTG TGT GAC AGC GAC ATG GAG AGG GAG GAG GAC
661                                   691
CCA AAG ACT TCC CCA AAG CCA AAA ATC AAT CAG ACC CGG CGG CCT GGC CTG CCA CCC TTC
721
GGT CAC TGA
``` coding sequence: 729 nucleotides

Figure 12 murine Csp1 (SEQ ID NO: 4)

```
1/1                                             31/11
ATG GAG GAG GTG GAT CTG CAG GAC CTG CCG AGC GCC ACC ATC GCC TGC CAC CTG GAC CCG
 M   E   E   V   D   L   Q   D   L   P   S   A   T   I   A   C   H   L   D   P
61/21                                           91/31
CGC GTG TTC GTG GAC GGC CTG TGC CGG GCC AAA TTT GAA TCC CTC TTC AGA ACA TAT GAC
 R   V   F   V   D   G   L   C   R   A   K   F   E   S   L   F   R   T   Y   D
121/41                                          151/51
AAG GAC ACC ACC TTC CAG TAT TTT AAG AGC TTC AAA CGT GTC CGG ATA AAC TTC AGC AAC
 K   D   T   T   F   Q   Y   F   K   S   F   K   R   V   R   I   N   F   S   N
181/61                                          211/71
CCC TTA TCT GCA GCC GAT GCC AGG CTG CGG CTG CAC AAG ACC GAG TTC CTG GGG AAG GAA
 P   L   S   A   A   D   A   R   L   R   L   H   K   T   E   F   L   G   K   E
241/81                                          271/91
ATG AAG TTG TAT TTT GCT CAG ACT TTA CAC ATA GGA AGT TCA CAC CTG GCT CCG CCC AAT
 M   K   L   Y   F   A   Q   T   L   H   I   G   S   S   H   L   A   P   P   N
301/101                                         331/111
CCC GAC AAA CAG TTC CTC ATC TCC CCT CCG GCC TCT CCT CCC GTT GGC TGG AAA CAA GTA
 P   D   K   Q   F   L   I   S   P   P   A   S   P   P   V   G   W   K   Q   V
361/121                                         391/131
GAA GAT GCC ACC CCC GTC ATA AAT TAC GAT CTT TTA TAT GCC ATC TCC AAG CTG GGG CCA
 E   D   A   T   P   V   I   N   Y   D   L   L   Y   A   I   S   K   L   G   P
421/141                                         451/151
GGA GAG AAG TAT GAA CTG CAT GCA GCG ACA GAC ACC ACT CCC AGT GTG GTG GTC CAC GTG
 G   E   K   Y   E   L   H   A   A   T   D   T   T   P   S   V   V   V   H   V
481/161                                         511/171
TGT GAG AGT GAC CAA GAG AAT GAG GAG GAA GAG GAA GAG ATG GAG AGA ATG AAG AGA CCC
 C   E   S   D   Q   E   N   E   E   E   E   E   E   M   E   R   M   K   R   P
541/181                                         571/191
AAG CCC AAA ATC ATC CAG ACA CGG AGA CCG GAG TAC ACA CCC ATC CAC CTC AGC TGA
 K   P   K   I   I   Q   T   R   R   P   E   Y   T   P   I   H   L   S   *
```

198 amino acids and 597 nucleotides

Figure 13 murine Csp2 (SEQ ID NO: 5)

```
1/1                                        31/11
GAA TTC GTC GAC CCA CGC GTC CGC CCA CGC GTC CGC TTG GGG CAG CAG GCA TCT ATC CCT
 E   F   V   D   P   R   V   R   P   R   V   R   L   G   Q   Q   A   S   I   P
61/21                                      91/31
GAA GAT GGG GGA CTT TTC TTC CTC TGC TGC ATA GAC AGA GAC TGG GCT GTC ACT CAG TGT
 E   D   G   G   L   F   F   L   C   C   I   D   R   D   W   A   V   T   Q   C
121/41                                     151/51
TTT GCT GAA GAG GCC TTC CAA GCA CTC ACT GAC TTC AGT GAT CTC CCC AAC TCA TTG TTT
 F   A   E   E   A   F   Q   A   L   T   D   F   S   D   L   P   N   S   L   F
181/61                                     211/71
GCC TGC AAT GTT CAC CAG TCT GTG TTT GAA GAA GAG GAG AGC AAG GAA AAA TTC GAG GGA
 A   C   N   V   H   Q   S   V   F   E   E   E   E   S   K   E   K   F   E   G
241/81                                     271/91
CTG TTC CGG ACC TAT GAT GAA TGT GTG ACG TTC CAG CTG TTT AAG AGT TTC CGA CGG GTT
 L   F   R   T   Y   D   E   C   V   T   F   Q   L   F   K   S   F   R   R   V
301/101                                    331/111
CGA ATA AAT TTC AGC CAT CCC AAA TCT GCA GCC CGT GCC CGG ATA GAG CTT CAT GAG ACT
 R   I   N   F   S   H   P   K   S   A   A   R   A   R   I   E   L   H   E   T
361/121                                    391/131
CAG TTC AGA GGG AAG AAG CTA AAA CTC TAC TTC GCC CAG GTC CAG ACC CCA GAG ACA GAT
 Q   F   R   G   K   K   L   K   L   Y   F   A   Q   V   Q   T   P   E   T   D
421/141                                    451/151
GGA GAC AAA CTG CAT TTG GCA CCT CCA CAG CCT GCC AAA CAG TTC CTC ATC TCA CCC CCT
 G   D   K   L   H   L   A   P   P   Q   P   A   K   Q   F   L   I   S   P   P
481/161                                    511/171
TCA TCT CCA TCT GTT GGC TGG AAG CCT ATC AGC GAT GCC ACA CCA GTC CTC AAC TAT GAC
 S   S   P   S   V   G   W   K   P   I   S   D   A   T   P   V   L   N   Y   D
541/181                                    571/191
CTT CTT TAT GCT GTG GCC AAA CTA GGA CCA GGA GAG AAA TAT GAG CTG CAC GCT GGA ACT
 L   L   Y   A   V   A   K   L   G   P   G   E   K   Y   E   L   H   A   G   T
601/201                                    631/211
GAG TCT ACC CCG AGC GTC GTG GTG CAT GTG TGT GAC AGC GAC ATG GAG AGG GAG GAG GAC
 E   S   T   P   S   V   V   V   H   V   C   D   S   D   M   E   R   E   E   D
661/221                                    691/231
CCA AAG ACT TCC CCA AAG CCA AAA ATC AAT CAG ACC CGG CGG CCT GGC CTG CCA CCC TTC
 P   K   T   S   P   K   P   K   I   N   Q   T   R   R   P   G   L   P   P   F
721/241
GGT CAC TGA
 G   H   *
```

242 amino acids and 729 nucleotides

Figure 14
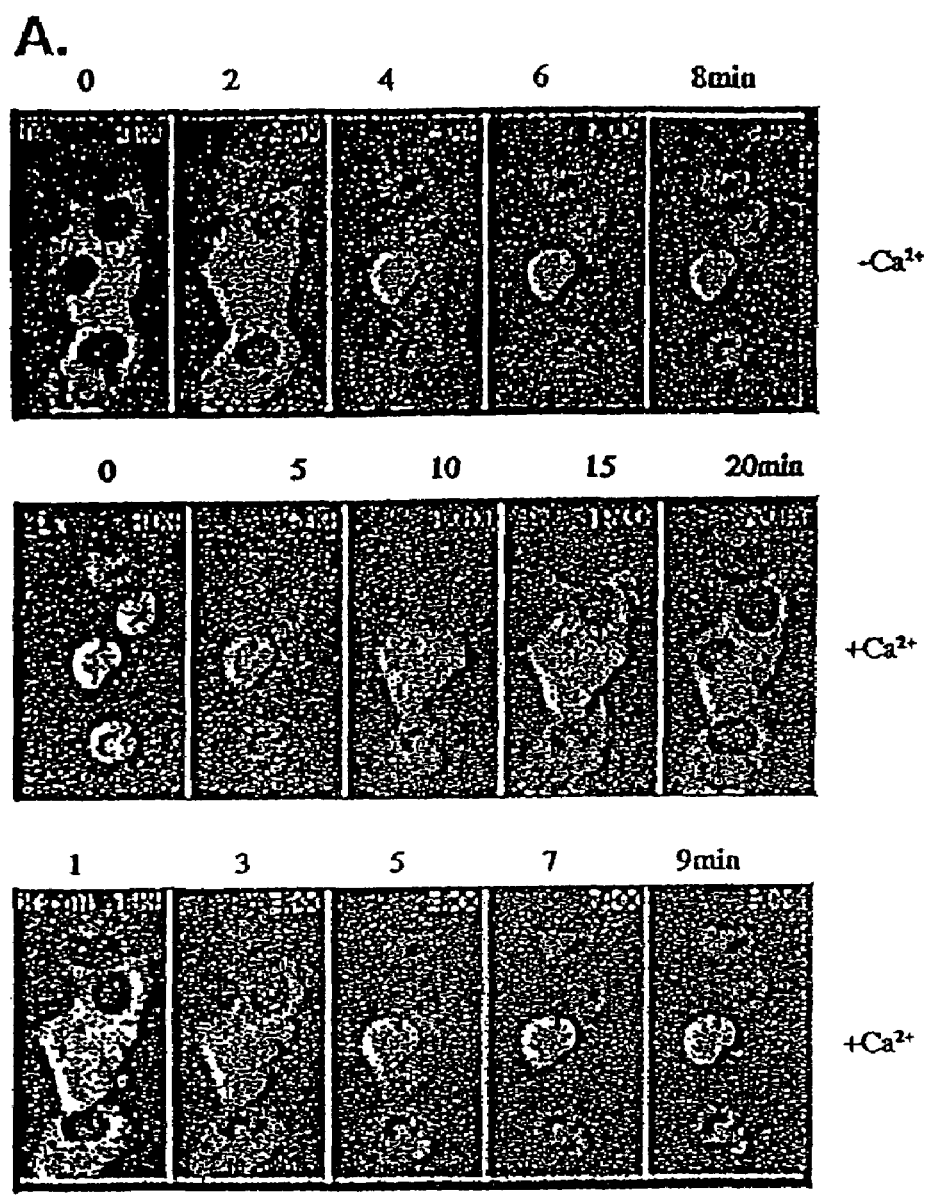
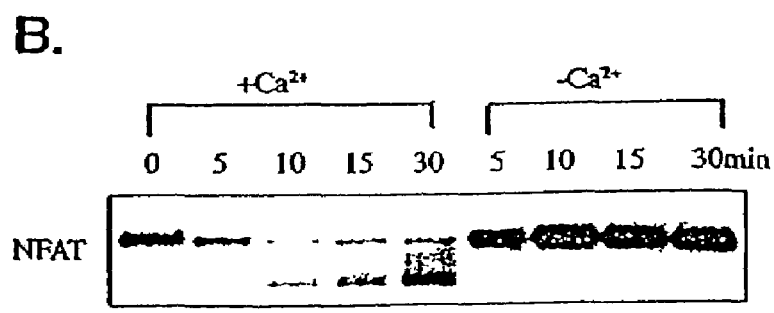

Figure 15
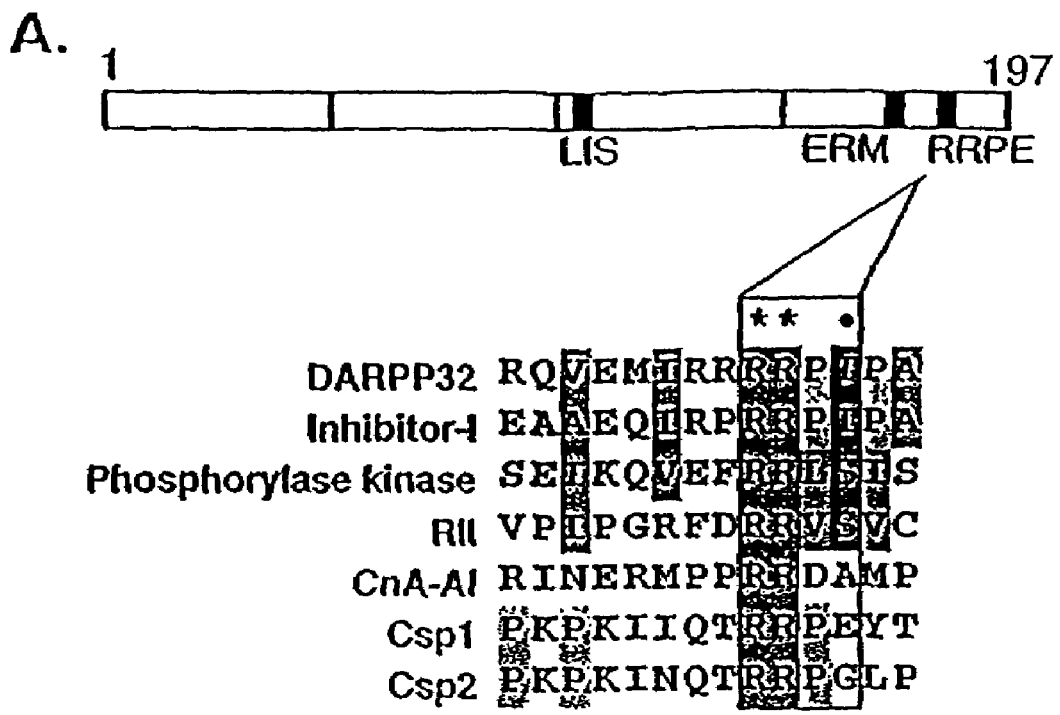
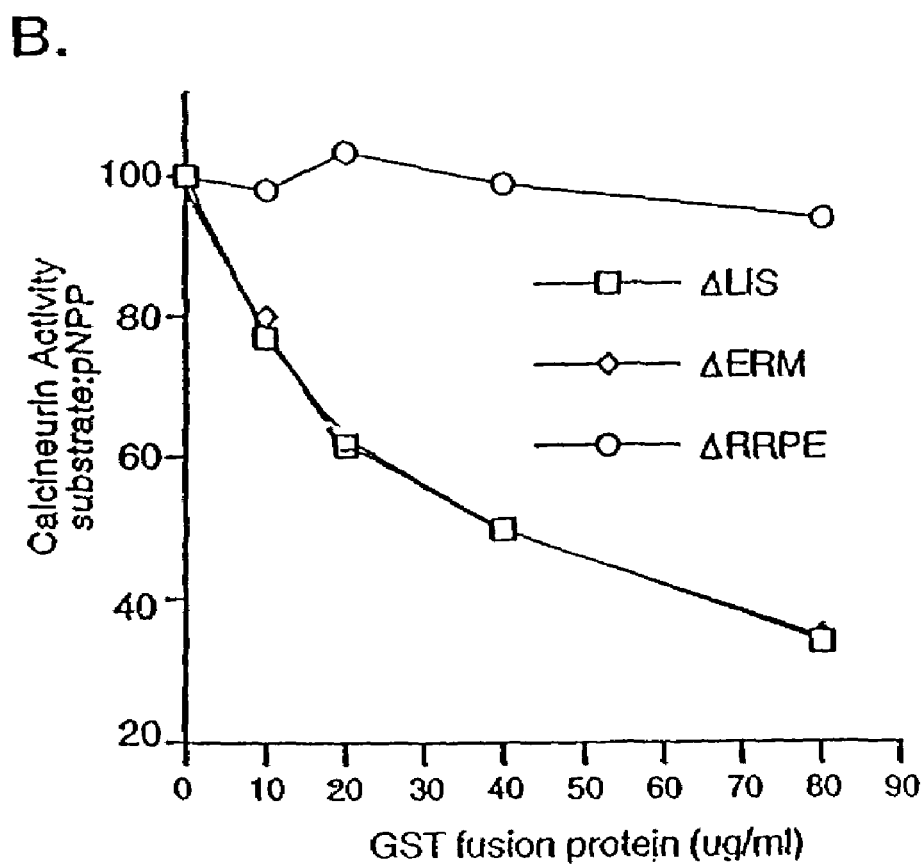

Figure 16
A.
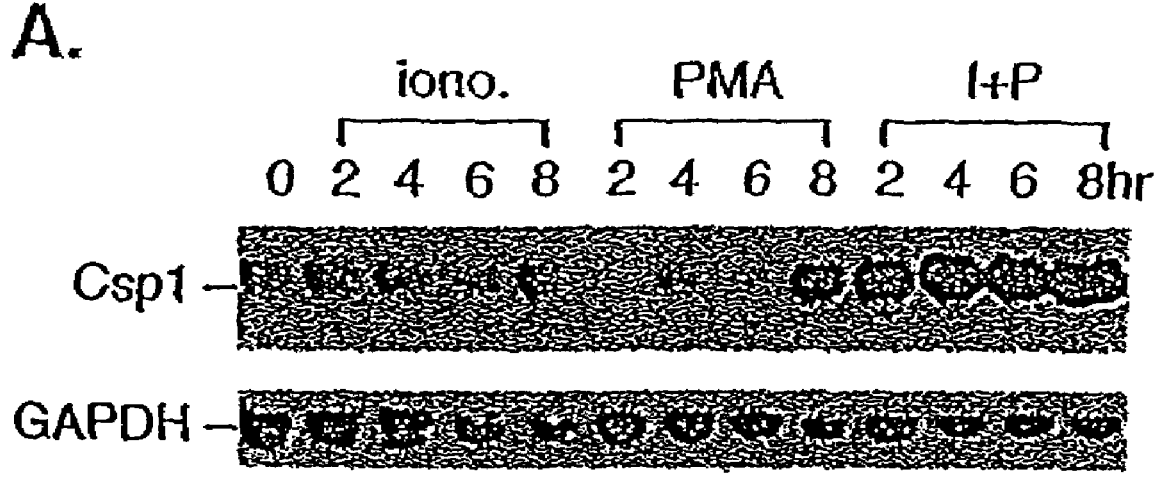
B.
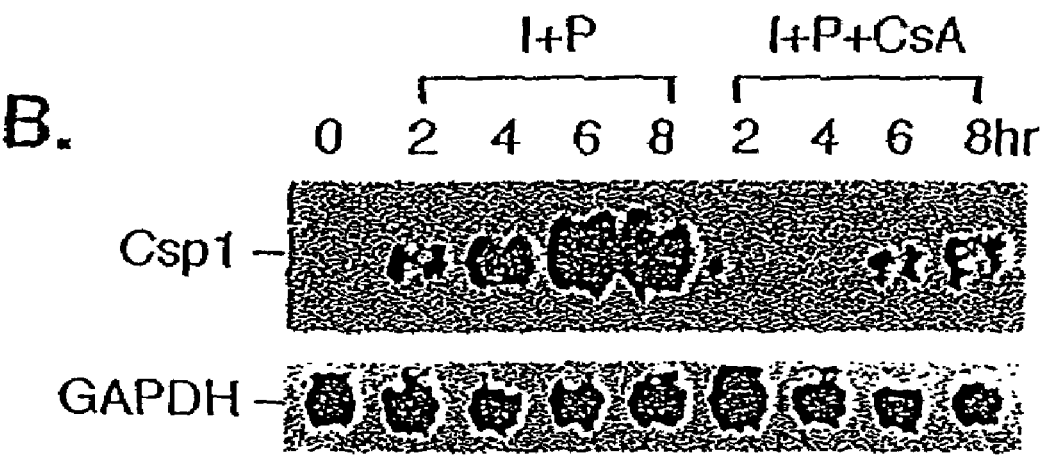

Figure 18

Murine Csp3 (SEQ ID No: 22)
cDNA Nucleic acid sequence (coding)

atgctccgagacagcctgaaatcttggaatgacagccagtcagacctctgtagcagcgaccaggaggaggaagaggagatggtcttcggt
gaaaatgaggacggactggaagagatgatggacctaagtgacctgcccacctcactctttgcttgcagtgtccatgaagcagtgtttgaggt
ccaagagcaaaaggagaggtttgaggccctgttcaccctctacgatgaccaggtcacattccagttgttcaagagttttcgcagagtgaggat
caacttcagcaagcccgcaagagcgcggatagagctccacgagagtgagttccacggacggaagctgaagctttacttcgcacaggtgca
ggtgtccggggaggcccgggacaagtcctacttactgccaccacaacccaccaagcagttcctcatctccctcccgcttcatccccgtgg
ggtggaagcagagtgaagatgcgatgccagtgatcaactatgacctgctctgcgctgtctccaagctgggcccaggggagaaatacgaac
tgcacgcgggaaccgagtccaccccagtgtggtggtgcacgtctgtgagagcgaaactgaagaggaagaagacacaaaaaatccaaaa
cagaaaatcacgcagacgcggcgcccggaggctcccacggcggcactgagtgagcggctggactgtgcactctga

Figure 19 cDNA nucleic acid sequence
(entire coding + 5' and 3' UTR) (SEQ ID No: 23)

gccgctgcggcccgcgttgagggcgtggtggctccgggtggtgagggtctgtccgccccaggccgcgctcgtggg
catccccctcgggcctctcccctcgagcgcacagaagtatctggcaggcatcctagaactttacagagaagatgctc
cgagacagcctgaaatcttggaatgacagccagtcagacctctgtagcagcgaccaggaggaggaagaggagatg
gtcttcggtgaaaatgaggacggactggaagagatgatggacctaagtgacctgcccacctcactctttgcttgcagtg
tccatgaagcagtgtttgaggtccaagagcaaaaggagaggtttgaggccctgttcaccctctacgatgaccaggtca
cattccagttgttcaagagttttcgcagagtgaggatcaacttcagcaagcccgcaagagcgcggatagagctccacg
agagtgagttccacggacggaagctgaagctttacttcgcacaggtgcaggtgtccggggaggcccgggacaagtc
ctacttactgccaccacaacccaccaagcagttcctcatctcccctcccgcttcatccccgtggggtggaagcagagt
gaagatgcgatgccagtgatcaactatgacctgctctgcgctgtctccaagctgggcccaggggagaaatacgaact
gcacgcgggaaccgagtccaccccagtgtggtggtgcacgtctgtgagagcgaaactgaagaggaagaagacac
aaaaaatccaaaacagaaaatcacgcagacgcggcgcccggaggctcccacggcggcactgagtgagcggctgg
actgtgcactctgagcggctgcggtgcctgccgcgcctgcctgtcccaccactacagctgcgcctgtctaggagcaca
gcccagggatgctcttgcatccgtcag

Figure 20

Murine Csp3 (SEQ ID NO: 24)
Amino acid sequence

MLRDSLKSWNDSQSDLCSSDQEEEEEMVFGENEDGLEEMMDLSDLPTSLFACSVHEAV
FEVQEQKERFEALFTLYDDQVTFQLFKSFRRVRINFSKPARARIELHESEFHGRKLKLYF
AQVQVSGEARDKSYLLPPQPTKQFLISPPASSPVGWKQSEDAMPVINYDLLCAVSKLGP
GEKYELHAGTESTPSVVVHVCESETEEEEDTKNPKQKITQTRRPEAPTAALSERLDCALZ

Figure 21

Identification of a Third Calcipressin Family Member, Csp3

```
csp2    1   ------------------------------------HDCDVSTLVAGVTDVEVPT
csp3    1   HLRDSLKSVEDSQSDLCSSDQEEEEEHVFGENEDGLEPHMDLSDLPTSLFACSVHEAVPE
csp1    1   ------------------------------HEEVDLQDLPSATIACHLDPRVFV csp2    20  NQEVKEEFEGLFRTIDECVTFQLFKSFRRVRINFSHPKSAARARIELHETQPRGKKLKLI
csp3    61  VQEQKERFEALFTLIDDQVTFQLFKSFRRVRINFSEP---ARARIELHESEFHGRKLKLI
csp1    25  DGLCRAKFESLFRTIDKDTTFQTFKSFERVRINFSEPLSAADARLRLEKTEFLGKEHKLI csp2    80  FAQIQTPETDGDELHLAPPQPAKQFLISPPSSPSTGVEPISDATPVLHIDLLIAVAKLGP
csp3    118 FAQIQTSGEARDKSTLLPPQPTKQFLISPPASSPTGVKQSEDAMPVIHIDLLCAVSKLGP
csp1    85  FAQTLHIGS----SHLAPPLPDKQFLISPPASPPTGVKQVEDATPVIHIDLLIAISKLGP csp2    140 GEKIELHAGTESTPSVVTHVCDSDHEEEEDPETS------PEPKILQTRRPGLPPFVSH--
csp3    178 GEKIELHAGTESTPSVVTHVCESETBEEEDTKI------PKQKITQTRRPEAPTAALSER
csp1    141 GEKIELHAATDTTPSVVTHVCESDQEVEEEEEHERHKRPKPKITQTRRPETTPIHLS-- csp2    -----
csp3    232 LDCAL
csp1    -----
```

A third calcipressin family member, termed csp3, was cloned from murine
T cells and found to have high sequence homology with csp1 and csp2.

Calcipressin 3 Inhibits Calcineurin Mediated Translocation of NFAT

Figure 22

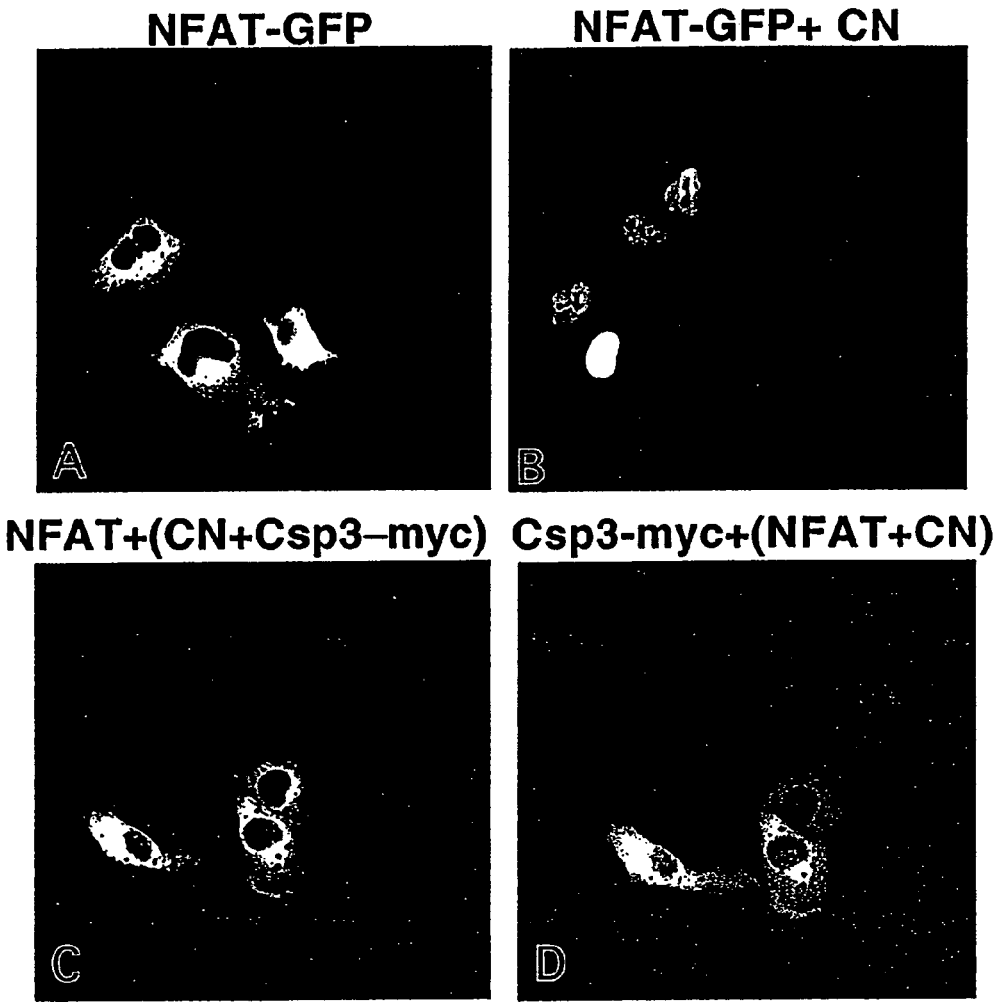

Panel A demonstrates the cytoplasmic expression pattern of the transcription factor NFAT tagged with green fluorescent protein (GFP) in the absence of stimulus. Upon co-expression of calcineurin (CN), NFAT shuttles into the nucleus as seen in panel B.

Panel C demonstrates the cytoplasmic expression of NFAT in the presence of calcineurin and calcipressin 3 (Csp3), suggesting inhibition of CN activity by Csp3. Csp3 co-expression is demonstrated in panel D by immunostaining with an anti-myc antibody to detect the myc-tagged Csp3 protein.

Generation of anti-Csp2 and anti-Csp1 Monoclonal Antibodies

Monoclonal antibodies (mAb) were generated against Csp1 and Csp2. 3F4A mAb was biotinylated and demonstrated to recognize cells transfected with both myc-tagged csp2 (top panel) and csp1 (bottom panel), as verified by immunostaining with a myc pAb.

Figure 24A

```
         10        20        30        40        50        60        70
GCCAAATTTGAATCCCTCTTCAGAACATATGACAAGGACACCACCTTCCAGTATTTTAAGAGCTTCAAAC  70
GTGTCCGGATAAACTTCAGCAACCCCTTATCTGCAGCCGATGCCAGGCTGCGGCTGCACAAGACCGAGTT 140
CCTGGGGAAGGAAATGAAGTTGTATTTTGCTCAGGTAAGTGTGTTCATTGTGAAGCGGGTTCCTCCCGGC 210
AAAGCACCTTATACATTGGAAACCTAGAGGTCACCTCAAAACAGACAGGATTCCAACCTTGAGTTCTTAA 280
GGTCTCCCTGCTGTGTAAAGGGATCTGGTGAAGGGGACAGTAAGCCTGGACCTTCCTGGGTTAAACCGTG 350
        360       370       380       390       400       410       420
AAGGAAGGAGAGCAAGCTTCCCTTGGTCACCAGAAAGCTTAGGGATTTGGAGGGGAGAAGAGGGCATCGC 420
TGCCCCCCTCCCTGCACACTAGTCAGCTTCACTGGGACTAGGCCAGCGACCTGTCAAGAGCTGTCTCAAG 490
CCAGTGCAGGTTCTCCACGCCTCACCTTGTAAGCCTGTATTCAGATCAGCACAGGGCTGTCAGTCGGGGC 560
AGGGGTGAGGGTCATCACATGGTTGAGACTCTTAGCTGAGGGGCAGAAAAGGGGGCTGTGGATGAGTTGT 630
CCATTGTTCTGCCAACCTCGGGGACACCTTCAAGGCAGCTCCCAACTTCCATGTGACTGTAACGGGGACT 700
        710       720       730       740       750       760       770
GGTAGATCGCAGCTTCTCGTTGTTATCCCCAAGGTAATGTCAGTCCTTGCCAGGCTCTGAAGCCGCTTCC 770
TTTCTTCTCAGTTGTCTACACTCACTTCCTGCCAGCTTAGGGCCAGCGGAGTCCTGTGGAGTGTGGCTCA 840
TGGCCCTCACCTCTCGGTAATGGTAGATTTTGACCATGAAATACCCTCTGTGGCTCATGTATTTGAATAC 910
TTGGGTCCTCTGTGGTGCAGTTTTACAGTTAGGGAACTTTAGGAGGTGGGGCCTCCCTAAAGGAATGAGA 980
TCCCCGAGGCAGACTCTGAGGGGTTAGAGCCCAGCCCCTTGTCAGATTGAAGCTCTTTGCTTCCTGGTTG 1050
       1060      1070      1080      1090      1100      1110      1120
GCACCATGTAACAGGTTACCACAGGCTTCTGCAGCCTCTAGCTACCATGACATCCGTCTTTTCTGCCTTC 1120
CCTATGATGGCTGCGCACTCTCGAACTGTGAGCCAGGATAAGGCCTTCCCGCTTTGGTTTTCATCCAGGG 1190
CTGTCATAGACACTTGAAAAGTTTACCCAACACAGGCACCAAATCCGGAATTCAGTCCTTCCTTCACCTC 1260
TATACAGACCACATTTCTGCTTCTTGGAATCGTACCTGGTCCAGAGCCTGACCATCGGTCTGCCCTTCCA 1330
TGCTTGCCTTCCAGAAGCTTCCATGAACTGTCGTGACCTCGCTCGCTTGCTGCATAATGATGAACTCATT 1400
       1410      1420      1430      1440      1450      1460      1470
TCTCTCCTCAGACTTTACACATAGGAAGTTCACACCTGGCTCCGCCCAATCCCGACAAACAGTTCCTCAT 1470
CTCCCCTCCGGCCTCTCCTCCCGTTGGCTGGAAACAAGTAGAAGATGCCACCCCCGTCATAAATTACGAT 1540
CTTTTATATGCCATCTCCAAGCTGGGGCCAGGTAAGCAGCACCCTCAGGTGGGAAAGTGTCGGGAGGTGT 1610
GGAGAGACTCTCTGGGGTCCCCAGGCCTCACGCGCCCCCATGCTGTCGTATGGTGTGACCCCTGCGTTAT 1680
TCCACATTGCTGCAGCTCGTGCTGGAGTGTGTGCCCCTTGGAGGATTCCAGGAGATGGTAGCAACCTGTG 1750
       1760      1770      1780      1790      1800      1810      1820
GGTTTGTGCACCACTGTCCCCCCCCAAGTGTCCCCCGAATCTATCCCTTCACCCAGCAGGCACACCTGTG 1820
TGGCTCACTCCAGGCCCCAGATCATGTTGTTCCAGGTGGGATGGGAAAGGGCAAACAGACCAACCTCTAG 1890
GGAGTCTCGTCAACTGTCATTCCTACTTCCGTACTGGGTGGGAGGGATGTGCGCATCTCTCACCCCACAC 1960
AGCAAGCCGAATCAGCACTGCCCATCAGCCCCTCGTCATCTGAAGTTCCTTTAGGGCAAGGGTTTTATTT 2030
TCATGGCTCATCAGCAGAAAGATTACATTTCTGAGAACACAGCCTAAATGGAAATTCCTCCCGCGGTACA 2100
```

Figure 24B

```
        2110      2120      2130      2140      2150      2160      2170
AACTGAGACTCACGTTACTAGTGCTAATTGTAGCATGAAGGTCAAAAGTGGAAACGGCCAGTGTGAGCAA 2170
GGAGACGGCTCAGCATGGCGGCTCTCAGCACAGTTGAGGGGTCTGTTGTCTGTGGATGTGTTATACATGG 2240
ACACAGACCTCCATCTGCCGCAAGGGAACAGGCTGTTCCAGAGGCAGGAATTGAGGCGAGCCTTCTGTCT 2310
TTAAGAACCCAAACCAGAAATGAAGGGGCTGAAACATTCCTACCAGGGCCATGACAGAGTTCTCCACACC 2380
CAGAGCCAGCACACTTCAGTCAGCCTTCGGGGCTGCAAAGGCGGCTTGTGGAGAGCAGTCTGACCTTCAT 2450
        2460      2470      2480      2490      2500      2510      2520
CCACGAAGTTAGTGCTGTGTGTGTCTGTGCGTGCCCGCAGCTCTCTACCTTTGGGCCAAGGGTAGATAGG 2520
TATAGAAACGCCCCCTCCACTTACAGTTTTCCCAGCAGCCCTCAACACTTGGGGAGAGCCGAGCTCCTTC 2590
GTTTTTTTAGCCTCATTGGTGGGGTAGAGAGGCCATGCTGCCTCGTTGTTCATGAGTTCTGTGCCTCCCA 2660
CATCTATGGAGCAGACTAAAAAGCAGGCAGCCTCACCAAGCCGCTACAGCAGCTGGAAACTTAGCCGGTT 2730
TAACAACAGGGCTCAAACCCGGGCCTTGCATCTGCTGGCAAGCACCCCTTGTCTAGTCTACATCCCCAGC 2800
        2810      2820      2830      2840      2850      2860      2870
ACCCTCCATTTGTAAATCTAGGTGGCATTTGTCAAGGTATGTATGTCATGAGCCCGCCGCTGGGCGTTTT 2870
GGATTTGTTCTCTCATGGAAATGGCCCCACCAATGCCTTTGCTGCCCCATTTACAGAGGAGGCGAAAGGC 2940
ACAAAGAAGTGAGACAGCCCGGGGACAAGTCCTCATCCACTCACTCCCCACCATACACGGCCACTCCGCC 3010
ATGCCACCTCCCCTCAGTGTCTAGTGCAGACCCCCTCAAGGGAAATCCCAGACCCTTCCTTTCCAGCCAG 3080
GTTTCTTGGTGACAGAAGGCCCATCCTAATCTTGCTATGCCACAGTGGTGTGAAGGTGCTTGAGCCTGGG 3150
        3160      3170      3180      3190      3200      3210      3220
CAAGCTCAGGCTAGCCCAGAAGAGCAAGGAGGGAGCGATAGATAGATAGATAGATAGATAGATAGATAGA 3220
TAGATAGATAGATAGATGGATGATGGTGTGGCTGAAGGTGTCACTTGGGCATGAAGCACTTGGCCT 3290
CCAGTGTCACATAAATCAGGCATGGTGGTGCAGAACCTCTGGTCCCAGCATCCAGAAGGTGAGGCAAGAG 3360
CAGCAGACATCTAAGGTCAAATGCAGCCATCAGTGAGTTCCAGGCAGCTCATACATAAACAATATAAAAC 3430
CAAGGAAAGGATGTTAAGGTTGAGCAGATTCACCTGGGGCTCTCTGCTGCCATGCTCTGGAGCCCCACCT 3500
        3510      3520      3530      3540      3550      3560      3570
ACAGGACATTTGTCTCCAGCAGTGGCATTTGCTCATGTTTTCTCTGTACTGATGCCTCCCATAACCTGCC 3570
CTTGGAGAATGCTGCTGGGAGCCCCTGGGTGGACATGAGAAAGGTTAGCGAACAGCGCTTGACTGAGAGC 3640
AATTCTGCGGTGCAAATGTTCTGTCTTGTGAATAAGTTATCCATGAGGAGGCACAAGGGCAGACTGTGTC 3710
TGGCCAAGCAAACCCTGGTGTCCCTCCAGGTCCCTGCCCTCCATGCTCAGGGACAAGCCGCGGTTACCAC 3780
TCACCATGCTCTTGTCTCCTTCCCCCAGGAGAGAAGTATGAACTGCATGCAGCGACAGACACCACTCCCA 3850
        3860      3870      3880      3890      3900      3910      3920
GTGTGGTGGTCCACGTGTGTGAGAGTGACCAAGAGAATGAGGAGGAAGAGGAAGAGATGGAGAGAATGAA 3920
GAGACCCAAGCCCAAAAATCATCCAGACACGGAGACCGGAGTACACACCCATCCACCTCAGCTGA 3984
```

Figure 25A

```
         10        20        30        40        50        60        70
GAAAAATTCGAGGGACTGTTCCGGACCTATGATGAATGTGTGACGTTCCAGCTGTTTAAGAGTTTCCGAC  70
GGGTTCGAATAAATTTCAGCCATCCCAAATCTGCAGCCCGTGCCCGGATAGAGCTTCATGAGACTCAGTT 140
CAGAGGGAAGAAGCTAAAACTCTACTTCGCCCAGGTGAGTCTTTAACCTGCTGGTTTGGCACAACATTTA 210
GAGGACGTGTTGCTATTGGAGTAGAATCAGATTCAATTTCCAGCATGCACATGGTGGTTCACAAACATCT 280
GGTGCCCTCCTCTGACCCTTTAGGGTACCACACACACACAGACACACACACACACACACACACACACACA 350
         360       370       380       390       400       410       420
CATACACACACAGTACATACACATAAGTGTGGGCAATACATTCATGCACATAAATTAAATTTAGAAGTAT 420
AAAAAGTCATTGTTAATTGGAAAATAAATAAATTAAATTAAAATGTAAATGAGGACCTCGGGAGATGGTT 490
ATGCAGTTAAGAAAGCTGGCTGCTCTTCTAGAGGACATGAGTTCGAGTCCTAGCACTCATATGGTGTCTC 560
ATAATTGTTTGTAACCCCTGTTACAGGGGAACCAATGCCTTCTTCTAGCCTCCTACACACCCACAAATAG 630
GTTTGCTGTTACAGTTACTTCACTAAGAAATTAATTTAGTGGTTGTCTAAGACCTGCCCAAGATAAACCA 700
         710       720       730       740       750       760       770
GTCAACATTCTAGCATGGAGAGAAAAGGGGGACCCTGAGCCCAGACCTCCAACTGAGGGACTTTCAACAG 770
TTGATGGATGCTTGGGGGGGGGATGTTTCCTTGGTGGTTTGGTCTCTGGTAGGTTGAGTATGGTCCAGG 840
GGATGGTCCCACACCCATGCTCATCTGGACAGCACTAACTGGACTCAGCGGATATGAAAACATAAAGAAC 910
ACGAGGAAGGGAAAGGAATGGAAGCAAATCTGATCAAAATATATTTATACATGTATGAAATCCTCCGAGC 980
TATTTATACATGTATGAAATCCTCTGAGCTAATGTTCTTAAAATAAGGAAAGAAACAGACACTGACAGTG 1050
         1060      1070      1080      1090      1100      1110      1120
AGTTCCAGATTGAGCAGTATCTGTGTCCTAGGACAGAGGCTCTAAGACCTGCCAAGCTAAGTTCTAACTA 1120
GGACAAGTCTCAGAACCTCACTGGGACTCAGAGTCCTCATCTATAAGATGGCAATGAAGACATTATCAAC 1190
CCATGTAGCTGCTGTGATGGTGACATGGAAAGCTGTGTGCAGCTGTGCCTAGATTTCTGGTAAAGGGACA 1260
ATAATTTCCAGCTAGGAACTGCAACAGAACTGATCTCACCACAGCCGACTCCTAACCTTCCCGACAGGGT 1330
TGTGATTAAAATTTAAATGATATGTTTAATGGTATACTAAATACATTCATGATAAAAGTTATAAATCCA 1400
         1410      1420      1430      1440      1450      1460      1470
TGAAAATTAATTGTATGTTTTGCAAAGCCAAATACTCATTATCCTGAACAGGGATGGGTAGTTCTTAGGG 1470
ATGTTCATGAAGCCCACAGCACTAGTTGTCGGTATTCACTCTCCATCAAGGCCTTATCCATCACTAGGCA 1540
ACAGTCACCTCTCAAGGATGGCTTCAGCTGCTGACTCCTGCTAAAATCCTACATCTCTTATAAATTCATG 1610
TAGCTAGAACAATCTTAGATCATCATTTATTAAAACCTGCATCAGAACTAGTTGTGTCAGCTGTAGACTC 1680
CTGCTAAAATCCTACATCTCTTACAAATTCATGTAGCTAGAACACACTTAGATCATCATTTATTAAAACC 1750
```

Figure 25B

```
              1760      1770      1780      1790      1800      1810      1820
         ....|....|....|....|....|....|....|....|....|....|....|....|....|....|
TGCATCAGGACCAGTTGGCCTGAGGCAGGAGACCTTGCATTCAAGGCCAGCCTGAGCTATCCAGTAAGGT 1820
CCTGTCTCAAAAAGACTGTGTGTGTGTGTGTGTGTGTGTGTGTGTGTGTGTGTGTGTGTGTGTGTGTGTG 1890
TTTAATATGTGTGTGTGTGTGTGTGTTTAATATGTGTGTGTATATATATATGATATATGGGTACATAGATAT 1960
ATGATACATACATACATGATAGACACATACATAGATACATACATAGCTATATAGATACGAGAGAGAGACA 2030
GAGAGAGAGATTTCCATTAAAAGATAACATGGAGTTACCATGTGACTCGTAAATTCTCTTCTAGGTTCTA 2100
              2110      2120      2130      2140      2150      2160      2170
         ....|....|....|....|....|....|....|....|....|....|....|....|....|....|
AAAATCATGAACTCAAACAAATAGTTAAGCAAGAATTCACAGCAGCACTGTTCACAATAGGCCAACAGTG 2170
AGAACTACCTAAAGATCTTCAACAGATAAAGGGATAAAGAGACAATAGTATGTTCACACAAAGGAATATT 2240
ATTCAGCTGAGAGAGAGAGAGAGAGAGATGTTGATAATCCATCACCAAATAATGGGCCTTTAAAAATGCAA 2310
TGGAAGCTAGACACAAAAGCTCATCTGTTCTGTGGTTCCATTCTCATAAAAGAGTTAGATAAGTTCAGAG 2380
AAGTAGACACAGCTTGACAACCATCAGGGGTAGTAGGAAACTACATTAGTAGTCGTTATTTAAGGGATGC 2450
              2460      2470      2480      2490      2500      2510      2520
         ....|....|....|....|....|....|....|....|....|....|....|....|....|....|
ATAGTTGGGGTTGGAGAGATGACTTAGCAGTTAAGAGCACTGAATGCTCTTTCGAAGGCCCTGAGTTCAA 2520
ATCCCAGCAACCATATGGTGGCTCACAACCATCCATAATGAGATCTGATGCCCTTTTCTGGAGTGTCTGG 2590
AGACAGCTACCATGTACTCACATATAATAAATAAATAAATCTTTTTAAAAAAGGGGTGTGTGTGTGCATA 2660
GTTATCCTTAGAGCCATGGGAAGGGTTAGGGTAGTTGTTCTCAACCTTCCTAATGCTGTGACCCTTTAAT 2730
ACTCATGAAGTGGTGATCCCCAGCCACAAAATCCTTTTCGTTGCTGCTTTATAACTGTAATTTTGCTAGT 2800
              2810      2820      2830      2840      2850      2860      2870
         ....|....|....|....|....|....|....|....|....|....|....|....|....|....|
ACTATGAATTATGATACCACTGTGTGTGTTTTCTGATGGTCTTAGGCAGCACTCTGGCTTGCTCACCATC 2870
TAGCCTAACCTTATTGGTGAGATCAAGGTTTTTGGGTTGTTTTTTTTAAAGGGCACTGTTACCTAAGGA 2940
AGGACATTAGAAGTTGTCCACTAGCTTCCACATGTACACACTCATAAGGGCACACAATGTAGTACAGGGC 3010
TTGGTGACCCTGGTGCTCATTAAAAGATGGAAACTGCTGTTTTTTTAGGATTATGTAAACAATGAGTTCA 3080
GCACACTGTGTACTGTAAGGAGTGATTGCTACTGCAGTCTGGCCCTCAGTGAAGCCCTGCCCAGCTGCAA 3150
              3160      3170      3180      3190      3200      3210      3220
         ....|....|....|....|....|....|....|....|....|....|....|....|....|....|
GCATGGACAATCACATGTCTCATTATCTTGTTTGAAAGGTCCAGACCCCAGAGACAGATGGAGACAAACT 3220
GCATTTGGCACCTCCACAGCCTGCCAAACAGTTCCTCATCTCACCCCCTTCATCTCCATCTGTTGGCTGG 3290
AAGCCTATCAGCGATGCCACACCAGTCCTCAACTATGACCTTCTTTATGCTGTGGCCAAACTAGGACCAG 3360
```

Figure 26A

```
       10        20        30        40        50        60        70
CGGAAGCTGAAGCTTTACTTCGCACAGGTAATGGCCGTTCTGCGCCTGCGCACACAGCCTGCTCCAGTTC  70
CCGCTCCAGCACGGGGTCAGAGGTCTGTGAGGTCAGCAGTCACGTGAGCCAGGGCTGCCGTGCTTTTTCT 140
GACTTTACACATACGTCATTTCATGTATTTTAGGAGCACATTAAGCCTCTGTTCATGTTTCTCTGAGACG 210
AACACCTAAGGGGTTCATTTTTCTGGCGATTTTGCTCAGCTAGGGCTCTGTGAGGGAAGTCCTGATACTT 280
CGAAGTTGGCAGATTAAACACTGTGCATCTAAAATGGCACCGAGGACATGACATCCGTGGGAAAACAGAA 350
      360       370       380       390       400       410       420
CAAAACCTTCAAGGGTCATCAAGATGGCCCAGGGGGTGAAGGTGCTTGCCACCAAGCCTGGCAGCCCGAG 420
TTTGATCCCAGGAACTCATCCACGGGTGGAAGGAAAGAACCAACCTGTGTCCTCTGAGGACCACATATGC 490
AGTTTTCTCTCTTCTGAGACAGTAGTGTGTTAGTCAGCCCTTCCCAGCGAATTAGTTACTGGGATGAGAC 560
ACTGTGACCAAAAGCACCCAGGAGACAAAAGGTGTATGTACTTTACTTATAATGAATCACCATTCATTGA 630
GGGAAGCCAAGGCAAGAACTCAACCTGGGCAGAAACCTGGAGGCAGAGGCCATGGAGGGGCGCTGTTTAC 700
      710       720       730       740       750       760       770
TGGCTCCTCATGGCCTACTCAGCCTGCTTTCTTTTTTTTGTTTTGTTTTTGTTTTTTGAGACAGGGTTT  770
CTCTGTATAGCCCTGGCTGTCCTGAAACTCACTCTGTAGACCAGGCTGGCCTCGAACTCAGAAATCCGCC 840
TGCCTCTGCCTCCCGAGTGCTGGGATTAAAGGCGTGTGCCACTGTGCCTGGCTTCAGCCTGCTTTCTTAT 910
AGAACCTAGAACCACAACCCAGGCTGGTATCATCCACAGTGGGCAGGGCCTTCCCCACATTGGTCACTAA 980
GAAAACTTCCTGCCTGCAGTCAGGTCTTCTGGAGACATTTTCTCAGTTGGGTTCCTGTCTCTTGATGACT 1050
      1060      1070      1080      1090      1100      1110      1120
AAAGCTTGCATCAGGTTGACATATAGTAGCCAGCACACCCACTCACACCACTAGCAAATACCTGGGAGAG 1120
TCAGCTGTAAAGGAGAAAAGTCTCGGCTTGTGGTTTGCAGGTTTCAGTCTGCATGTGATTGGCACTTTTC 1190
CTGTGAGCCTGCTGTGCAGTAGCACATAGGGGCAGAGCAAAGCTCTTCACTTCGTTCATGGGAAGCAGGA 1260
AGAGTAAGGGGTTGGGGTTCCACTGTCCCTTAGGGTATGTCCCCATGACTAAAGGCCTCCCTGCCTCCTG 1330
AAGGCTCCCAGTTTGACCTCTCAGGGGAGCAAGCCTCTATTTACTATGTAGAGCCCAAGGGTCACTTAGA 1400
      1410      1420      1430      1440      1450      1460      1470
GCCCAGACCACAGAGTAGCACGTTTATCAAGGGTCCAGGGCCTGTGGCCACTTCCAGTCCACCACCTGGA 1470
AGGTCACAGACAGTTTGAGAGACAGTTTTAATCACCCCTCCAAGAAAGTAACAATTACCATAAAGTTGGA 1540
AATGAAAGCCCTGTGGTGATGGTGCAGGCCTTTAATCTAAGAACTGGAGGCAGAGACCGTGAGATCTGTG 1610
AGTCAGGCCTACAGAGTGAGTTCCAGGACAGCCAGGGATACACGGAGAAACCCTGTCTCAGAAAAAGAAA 1680
AGAAAGGACAGCTGCTCACAAGCACGCCTTTCCCTGCAGGTGCAGGTGTCCGGGGAGGCCCGggacaagt 1750
      1760      1770      1780      1790      1800      1810      1820
cctacttaCTGCCACCACAGCCCACCAAGCAGTTCCTCATCTCCCCTCCCGCCTCACCCCCCGTGGGGTG 1820
GAAGCAGAGTGAAGATGCAATGCCAGTGATCAACTATGACCTGCTCTGCGCTGTCTCCAAGCTGGGCCCA 1890
GGTACTGCATTCCACCTTCGCTCTCCGCGTCCTCGGACATTGCTGTTCTGTGTGTTGGAGACTGTGTGCA 1960
GTATGGGGTGCAGAGCCCAGCAACACCAGCACCGTCCAGTGGGCGGTGTGGCCACACCAGTCTGAGTTCA 2030
CACTCGAGCTGTACACTTTCCAGTGCTGTGGTCCTCAGCCAGTTGCCTAGCCTGGGTTATCTGAGTGTGT 2100
```

Figure 26B

```
        2110      2120      2130      2140      2150      2160      2170
  ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
TCTAAGGATTAAACGCTGTCTGCAGCGTGATAACTTTAGCCATTCAGCCAGAAGTTAATATAGGCGGTTA 2170
GTGAACATCCTCACTGCTTTCTCTCTGCAAGCCAGTCAGCACAGTGTCTGTCGTTTGGCAGCTGCTTTGG 2240
GTGACAGTGACAATGACCTATCGCCCTTCCAAAGTTCTATCTCTCTCTCTTTTCACTTCTTACTTCCTTC 2310
TTTTCTTGCTCGGTCTCACTCATCTTTAATACTGCAAGAAGCCGATTCTTCTAGGGCACTTCAGAGGCTT 2380
TTGAGAAGGCACTCTATGCTCCTGGGCGGNTGAGCTCTTCGATGGCAGAGGCCCTACCGTAGACACCGCT 2450
        2460      2470      2480      2490      2500      2510      2520
  ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
GCCTAGAGCTTAGCCAGTGCCTCCCATGGCGCCCCAACACCACTGTGAATTTAACTATCCCACCTTAGTT 2520
ATCTATAGAACAGCAGTTAGCATTTATATTAACATTTTAATTAGTATTTATGTAATATAATCAATGGGTT 2590
CTCGTCTTCTTCCTGAGCACAAAGCCAGAGTAAGCATAGAACAGAAGAGACAAGAAGAGAAGAGATAGGA 2660
AGAGACAGGAGCTGTTTGCAAAGCAAGCCCTCCCCGAGTGAAGGAAGCTGTGTATATTCATACAGTGGCA 2730
TGTGCACTCCTGAGCACGCGCAGTTGAAAATCATGGAGATGAACATGGTGGACAGGGTGTGCTTGGGTTC 2800
        2810      2820      2830      2840      2850      2860      2870
  ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
GCTTGCACCATGAAGTTTCACTTGAAAATAAGAGAAGGATGGTTTTAAGGTGTGTGCTAACAGGAGTCTG 2870
CCTTGAAGGTGCCTGAAGTGCTTGGATTTAACTCCTAGGGCTCAGGACAGAAGGGACGGTGTCTTTATTT 2940
ATTTTTTTTTAAGACTTATGTATATGAGTACATTGTAGCTGTACAGATGGCTGTGAGCCTTCATGTGGTT 3010
GGGAATTGAATTTTTAGGACCTTTGCTTGCTCCCATCAACCCCTCTCGCTCTGGTCGGCCCTGCTCGCTA 3080
GTCCCTGCTTGCTCCAGCCCAAAGATTTATTTATTATTATATATAAGTACACTGTAGCTGACTTCAGACG 3150
        3160      3170      3180      3190      3200      3210      3220
  ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
TACCAGAAGAGGACATCAGATCTCATTGCGGGTAGTTGTGAGCCACTATGTGGTTGCTGGGATTTGAACT 3220
CTTCGGAAGAGCATCAAGTGTTCTTACTCACTGAGCCATCGCATTAGCCCGACAGTGTCTTTACAAATAG 3290
AATTTCTGCAGGGCATGGTGGTACTCAACTTTAACAGCACTTGGGAGGCAGAGGCTGGCAGCTCCCTGGG 3360
AGTTCCAGGTCAGCCTGTCTACACAGTGAGCCTAGGCCAGCCTGGGCTACATAGTGCGACTCCAGGGAGT 3430
TTTTGTTTTTGTTTTTGTTTTTTTTAAATGCCAGCACTTGGGAGATGGAAGCAGAAGAATTAGAGTTCAA 3500
        3510      3520      3530      3540      3550      3560      3570
  ┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
GGTCAGCCTCAGCTACAGCAGCAAGTTTCTAACTGGCCCAGATTTCATGAGACGCAGTCTTAAAAAAAAA 3570
AAAAAAAAATCAGCCACTGAATGACGTAGTAGAAGAGGAAGTTGGGAGATAGAAGAACTTGATTTCCTTC 3640
ACTGGGAGTAAGGCTCCTTCCTGTGCTTGCAGGGGAGAAATACGAACTGCACGCGGGAACCGAGTCCACC 3710
CCCAGTA 3717
```

Figure 27

**Schematic Representation of the Gene-targeting Vectors
Used to Disrupt the Csp1, -2, and -3 Genes**

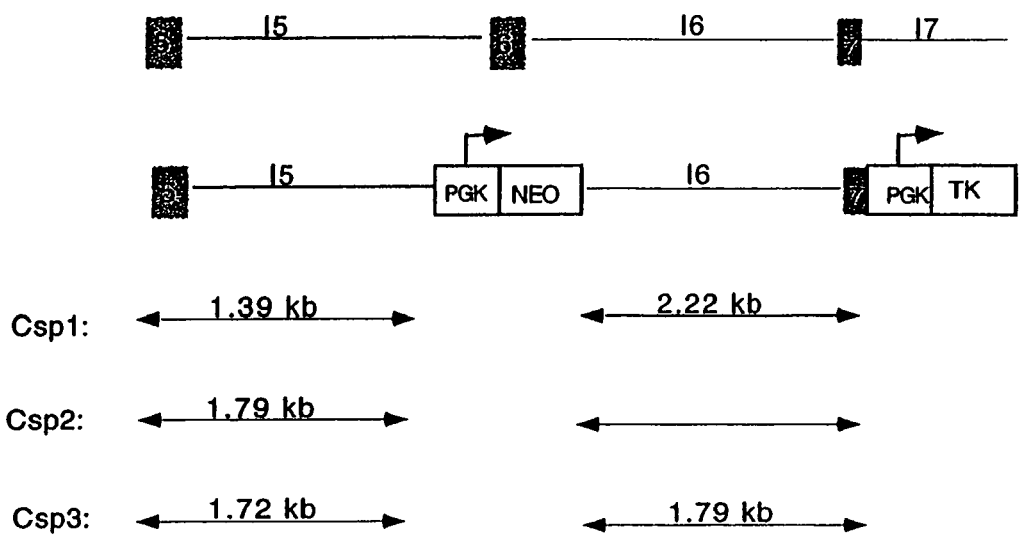

This schematic diagram shows the organization of the Csp genes (top) and
the targeting vectors (middle)constructed to disrupt the Csp genes. Our
targeting vector will replace exon 6 with the neomycin drug resistance genes.
This exon contains the start of the inhibitory, or c-terminal domain of all three
genes which should effectively destroy the calcineurin inhibition activity. The
genomic structure of all three genes is relatively similar with different size introns
(I5, I6). Exons are denoted by the shaded boxes with numbers.

Constructs Used to Generate Tissue-Specific Expression of Csp1 in Transgenic Mice

Figure 28

Cardiac Specifc Expression:

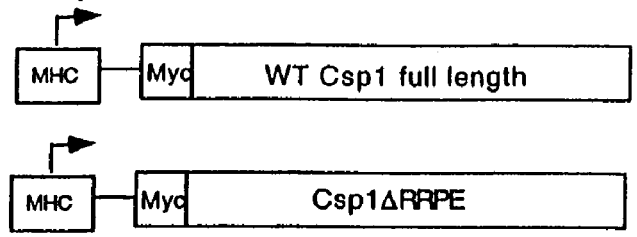

T-Cell Specific Expression:

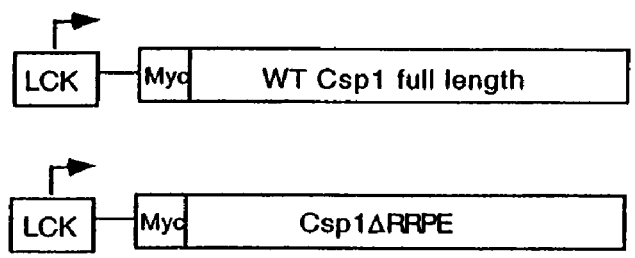

This schematic diagram demonstrates the constructs injected into blastocysts to generate transgenic mice. Wild-type full length myc-tagged Csp1 under the control of a myosin heavy chain (MHC) promoter (top half) will ensure cardiac specific expression. Similarly Csp1 with the sequence element, amino acids,188-191,"RRPE" deleted is also expressed under the MHC promoter.

Myc-tagged wild type Csp1 and Csp1ΔRRPE are also expressed under the LCK promoter which will ensure T-cell specific expression (bottom half).

SEQUENCE LISTING

<160> NUMBER OF SEQ ID NOS: 49

<210> SEQ ID NO 1
<211> LENGTH: 2484
<212> TYPE: DNA
<213> ORGANISM: Homo sapiens

<400> SEQUENCE: 1

```
cttgggttta gctccctgag gacacaaact gtcctaagac tatgataata gtaatcatag        60
aaccgtgcac atggcaagtt ctgaataaat ctcagctgtt ggatatactt tttgttataa       120
ttactaacac ttcctaacta gagagtaagc ctactctaag aaaaaatata actgtaattt       180
cacaacctcc aaagaaccca gtgcataaac agctaccatt tattaagcac tgactgaatt       240
cttagtaata tgtcttcatt tttttcagat gaggaaacta agattcagct tatttgtaca       300
agtagttaaa aagcaaagct gaaattcaga cccaagttct cactgtatca tactgtccaa       360
aaaagaattc tattttcag gaagagacat gtctgctcac ttgaggtcct cttattttc        420 cgctattccc caaaggaaag gggtgatctc ttaattcttt cgttatgtcc tattgtacat       480
agcatataat ggtaattcag aaaaattact tctaattaca taaattttca caatggtata       540
gtgactaata cgctgaaata gaaagtaagc gcattgttat catggtctag ttcagtcttt       600
attgcgacta tatctgataa tatacggtaa gcatctaacc acttgccagg ggccacagag       660
ccacagggag actatgtctc gcttaaattc ccaaaagtgg gccctgtgc ttcaaaacgt        720 ccccgcatgg gaaccacaaa aacgttgcct ccccagttat caccccaagg gcccaagagc       780
cgaggactct gcccggcgtc cttcagctgg caccagctgt cagaaaagcg gaactgggga       840
cgaggacttt gcccctaacc aacatggccg ccctgaggct tcgggcttcg ggcggcagaa       900
ggaaggtcac gtgaagagaa ttccgttcct ttattggccc cgtctcctgg aagggcgggg       960
tacaataacc caaccggcgc cggccttaaa ggggccaccg ttggatctgc cggtggccgg      1020 ccctagggc tggggggcg gtcgccgcgc cgggcttctg cccctcccgc gcggaacggt        1080
gacgggcggg gctggcgctg ggaggccgtg tcgctgggag actgctgaca gcccgccgcc      1140
tgccgccgcg cgattccgag ggggttaacg gcggagccgc cggccgggcg cggaccggag      1200
cgcgtgaggc tccggcgcgc aagcccggag cagcccgctg gggcgcacag ggtcgcgcgg      1260
gcgcggggat ggaggacggc gtggccggtc cccagctcgg ggccgcggcg gaggcggcgg      1320
aggcggccga ggcgcgagcg cggcccgggg tgacgctgcg gcccttcgcg ccctctcgg       1380 gggcggccga ggcggacgag ggcggccggcg actggagctt cattgactgc gagatggagg     1440
aggtggacct gcaggacctg cccagcgcca ccatcgcctg tcacctggac ccgcgcgtgt      1500
```

```
tcgtggacgg cctgtgccgg gtgaggaccg cgccgggcgg gccgtcgggg cggagggcgg      1560
acacttgttg cccgaggagg cggcgcgggt cgcagcgccc agtcccggcc gcgcgcgggg      1620
cggggaggca gcgacgtccc ccgggctgct cggccgcgga cccgtcaggg ctggggcgtg      1680
gggacggcgc cccgagggtc ccggtcccct agcaccccg gggcgcgcgg agctcactgc       1740
agagtcccac aggctcgccc cggccccgt gtgcgcccag gctggtgcga ctagggggt        1800 gaattcgctc cccaaggtgg ggcagcgccg ccgcccctg cgctctcgcc atcgccccgc       1860
atttactcgc tggaggaggg ggtcacctca ttcctaggga ggaggaaaca gacattgagc      1920
ggcgacgtga ctcagtgttc ataaatagga cgacgtccct gcattcccaa tctgcactat     1980
tggaagaaaa gccaatgttt gggtgaggat ccgtggttgc tcattagcca gcggctggcc     2040
agttttggtg gaattgtgtt gggggggaagg ggaccatctt tcagacctt aggatattta     2100 gtcaagaacc ttgcccccctt gtgtgaaggt gtggcttgcc gccatcgggg acacccagta    2160
catggggagt cgactccttc ccccgcctcc ccccacccc gcaaaatcca cacaatttag      2220
acactttgga gggtgagggg caggtatgag taatcaataa tggtggtggg gaggaagaat     2280
ttatttcaaa tctgcagtta ttgtgcagaa taaaatgtgg acaacgtggg cgtcacagaa     2340
tgaaaccggt ctttgagaga tgccccatta ggagagcagc tgtcaaaaaa agcagtgctt    2400
tcagcgcttg gctgtgggtc cacaaatgct gtcaatgaac tatagttgaa ggctgctgcc     2460
aatacaacac cactgtgaaa caga                                             2484

<210> SEQ ID NO 2
<211> LENGTH: 597
<212> TYPE: DNA
<213> ORGANISM: Mus musculus

<400> SEQUENCE: 2
atggaggagg tggatctgca ggacctgccg agcgccacca tcgcctgcca cctggacccg       60
cgcgtgttcg tggacggcct gtgccgggcc aaatttgaat ccctcttcag aacatatgac      120
aaggacacca ccttccagta ttttaagagc ttcaaacgtg tccggataaa cttcagcaac      180
cccttatctg cagccgatgc caggctgcgg ctgcacaaga ccgagttcct ggggaaggaa      240
atgaagttgt attttgctca gactttacac ataggaagtt cacacctggc tccgcccaat     300
cccgacaaac agttcctcat ctccccctcg gcctctcctc ccgttggctg gaaacaagta    360
gaagatgcca cccccgtcat aaaattacgat cttttatatg ccatctccaa gctggggcca    420
ggagagaagt atgaactgca tgcagcgaca gaccccactc ccagtgtggt ggtccacgtg     480
tgtgagagtg accaagagaa tgaggaggaa gaggaagaga tggagagaat gaagagaccc     540
aagcccaaaa tcatccagac acggagaccg gagtacacac cgatccacct tagctga       597

<210> SEQ ID NO 3
<211> LENGTH: 729
<212> TYPE: DNA
<213> ORGANISM: Mus musculus

<400> SEQUENCE: 3
gaattcgtcg acccacgcgt ccgccacgc gtccgcttgg ggcagcaggc atctatccct        60
gaagatgggg gacttttctt cctctgctgc atagacagag actgggctgt cactcagtgt     120
tttgctgaag aggccttcca agcactcact gacttcagtg atctccccaa ctcattgttt     180
gcctgcaatg ttcaccagtc tgtgtttgaa gaagaggaga gcaaggaaaa attcgaggga    240
ctgttccgga cctatgatga atgtgtgacg ttccagctgt ttaagagttt ccgacgggtt     300
```

```
cgaataaatt tcagccatcc caaatctgca gcccgtgccc ggatagagct tcatgagact      360
cagttcagag ggaagaagct acccctctac ttcgcccagg tccagacccc agagacagat      420
ggagacaaac tgcatttggc acctccacag cctgccaaac agttcctcat ctcaccccct      480
tcatctccat ctgttggctg aagcctatc agcgatgcca caccagtcct caactatgac       540
cttctttatg ctgtggccaa actaggacca ggagagaaat atgagctgca cgctggaact      600
gagtctaccc cgagcgtcgt ggtgcatgtg tgtgacagcg acatggagag ggaggaggac      660
ccaaagactt ccccaaagcc aaaaatcaat cagacccggc ggcctggcct gccacccttc      720
ggtcactga                                                              729
```

<210> SEQ ID NO 4
<211> LENGTH: 198
<212> TYPE: PRT
<213> ORGANISM: Mus musculus

<400> SEQUENCE: 4

```
Met Glu Glu Val Asp Leu Gln Asp Leu Pro Ser Ala Thr Ile Ala Cys
  1               5                  10                  15

His Leu Asp Pro Arg Val Phe Val Asp Gly Leu Cys Arg Ala Lys Phe
             20                  25                  30

Glu Ser Leu Phe Arg Thr Tyr Asp Lys Asp Thr Thr Phe Gln Tyr Phe
         35                  40                  45

Lys Ser Phe Lys Arg Val Arg Ile Asn Phe Ser Asn Pro Leu Ser Ala
     50                  55                  60

Ala Asp Ala Arg Leu Arg Leu His Lys Thr Glu Phe Leu Gly Lys Glu
 65                  70                  75                  80

Met Lys Leu Tyr Phe Ala Gln Thr Leu His Ile Gly Ser Ser His Leu
                 85                  90                  95

Ala Pro Pro Asn Pro Asp Lys Gln Phe Leu Ile Ser Pro Pro Ala Ser
            100                 105                 110

Pro Pro Val Gly Trp Lys Gln Val Glu Asp Ala Thr Pro Val Ile Asn
        115                 120                 125

Tyr Asp Leu Leu Tyr Ala Ile Ser Lys Leu Gly Pro Gly Glu Lys Tyr
    130                 135                 140

Glu Leu His Ala Ala Thr Asp Pro Thr Pro Ser Val Val His Val
145                 150                 155                 160

Cys Glu Ser Asp Gln Glu Asn Glu Glu Glu Glu Met Glu Arg
                165                 170                 175

Met Lys Arg Pro Lys Pro Lys Ile Ile Gln Thr Arg Arg Pro Glu Tyr
            180                 185                 190

Thr Pro Ile His Leu Ser
        195
```

<210> SEQ ID NO 5
<211> LENGTH: 242
<212> TYPE: PRT
<213> ORGANISM: Mus musculus

<400> SEQUENCE: 5

```
Glu Phe Val Asp Pro Arg Val Arg Pro Arg Val Arg Leu Gly Gln Gln
  1               5                  10                  15

Ala Ser Ile Pro Glu Asp Gly Gly Leu Phe Phe Leu Cys Cys Ile Asp
             20                  25                  30

Arg Asp Trp Ala Val Thr Gln Cys Phe Ala Glu Glu Ala Phe Gln Ala
```

-continued

```
                35                  40                  45
Leu Thr Asp Phe Ser Asp Leu Pro Asn Ser Leu Phe Ala Cys Asn Val
 50                  55                  60

His Gln Ser Val Phe Glu Glu Glu Ser Lys Glu Lys Phe Glu Gly
 65                  70                  75                  80

Leu Phe Arg Thr Tyr Asp Glu Cys Val Thr Phe Gln Leu Phe Lys Ser
                 85                  90                  95

Phe Arg Arg Val Arg Ile Asn Phe Ser His Pro Lys Ser Ala Ala Arg
                100                 105                 110

Ala Arg Ile Glu Leu His Glu Thr Gln Phe Arg Gly Lys Lys Leu Pro
            115                 120                 125

Leu Tyr Phe Ala Gln Val Gln Thr Pro Glu Thr Asp Gly Asp Lys Leu
        130                 135                 140

His Leu Ala Pro Pro Gln Pro Ala Lys Gln Phe Leu Ile Ser Pro Pro
145                 150                 155                 160

Ser Ser Pro Ser Val Gly Trp Lys Pro Ile Ser Asp Ala Thr Pro Val
                165                 170                 175

Leu Asn Tyr Asp Leu Leu Tyr Ala Val Ala Lys Leu Gly Pro Gly Glu
                180                 185                 190

Lys Tyr Glu Leu His Ala Gly Thr Glu Ser Thr Pro Ser Val Val Val
            195                 200                 205

His Val Cys Asp Ser Asp Met Glu Arg Glu Glu Asp Pro Lys Thr Ser
        210                 215                 220

Pro Lys Pro Lys Ile Asn Gln Thr Arg Arg Pro Gly Leu Pro Pro Phe
225                 230                 235                 240

Gly His

<210> SEQ ID NO 6
<211> LENGTH: 192
<212> TYPE: PRT
<213> ORGANISM: Homo sapiens

<400> SEQUENCE: 6

Met Asp Cys Asp Val Ser Thr Leu Val Ala Cys Val Val Asp Val Glu
  1               5                  10                  15

Val Phe Thr Asn Gln Glu Val Lys Glu Lys Phe Glu Gly Leu Phe Arg
                 20                  25                  30

Thr Tyr Asp Asp Cys Val Thr Phe Gln Leu Phe Lys Ser Phe Arg Arg
             35                  40                  45

Val Arg Ile Asn Phe Ser Asn Pro Lys Ser Ala Ala Arg Ala Arg Ile
         50                  55                  60

Glu Leu His Glu Thr Gln Phe Arg Gly Lys Lys Leu Lys Leu Tyr Phe
 65                  70                  75                  80

Ala Gln Val Gln Thr Pro Glu Thr Asp Gly Asp Lys Leu His Leu Ala
                 85                  90                  95

Pro Pro Gln Pro Ala Lys Gln Phe Leu Ile Ser Pro Pro Ser Ser Pro
            100                 105                 110

Pro Val Gly Trp Gln Pro Ile Asn Asp Ala Thr Pro Val Leu Asn Tyr
        115                 120                 125

Asp Leu Leu Tyr Ala Val Ala Lys Leu Gly Pro Gly Glu Lys Tyr Glu
    130                 135                 140

Leu His Ala Gly Thr Glu Ser Thr Pro Ser Val Val Val His Val Cys
145                 150                 155                 160

Asp Ser Asp Ile Glu Glu Glu Glu Asp Pro Lys Thr Ser Pro Lys Pro
```

```
                           165                 170                 175
Lys Ile Ile Gln Thr Arg Arg Pro Gly Leu Pro Pro Ser Val Ser Asn
                180                 185                 190

<210> SEQ ID NO 7
<211> LENGTH: 170
<212> TYPE: PRT
<213> ORGANISM: Homo sapiens

<400> SEQUENCE: 7

Met Val Tyr Ala Lys Phe Glu Ser Leu Phe Arg Thr Tyr Asp Lys Asp
  1               5                  10                  15

Ile Thr Phe Gln Tyr Phe Lys Ser Phe Lys Arg Val Arg Ile Asn Phe
                 20                  25                  30

Ser Asn Pro Phe Ser Ala Ala Asp Ala Arg Leu Gln Leu His Lys Thr
             35                  40                  45

Glu Phe Leu Gly Lys Glu Met Lys Leu Tyr Phe Ala Gln Thr Leu His
 50                  55                  60

Ile Gly Ser Ser His Leu Ala Pro Pro Asn Pro Asp Lys Gln Phe Leu
 65                  70                  75                  80

Ile Ser Pro Pro Ala Ser Pro Pro Val Gly Trp Lys Gln Val Glu Asp
                 85                  90                  95

Ala Thr Pro Val Ile Asn Tyr Asp Leu Leu Tyr Ala Ile Ser Lys Leu
                100                 105                 110

Gly Pro Gly Glu Lys Tyr Glu Leu His Ala Ala Thr Asp Thr Thr Pro
            115                 120                 125

Ser Val Val His Val Cys Glu Ser Asp Gln Glu Lys Glu Glu Glu
            130                 135                 140

Glu Glu Met Glu Arg Met Arg Arg Pro Lys Pro Lys Ile Ile Gln Thr
145                 150                 155                 160

Arg Arg Pro Glu Tyr Thr Pro Ile His Leu
                165                 170

<210> SEQ ID NO 8
<211> LENGTH: 197
<212> TYPE: PRT
<213> ORGANISM: Cricetulus griseus

<400> SEQUENCE: 8

Met His Phe Arg Asp Phe Asn Tyr Asn Phe Ser Ser Leu Ile Ala Cys
  1               5                  10                  15

Val Ala Asn Gly Asp Val Phe Ser Glu Ser Thr Arg Ala Lys Phe
                 20                  25                  30

Glu Ser Leu Phe Arg Thr Tyr Asp Lys Asp Ile Thr Phe Gln Tyr Phe
             35                  40                  45

Lys Ser Phe Lys Arg Val Arg Ile Asn Phe Ser Asn Pro Leu Ser Ala
 50                  55                  60

Ala Asp Ala Arg Leu Gln Leu His Lys Thr Glu Phe Leu Gly Lys Glu
 65                  70                  75                  80

Met Lys Leu Tyr Phe Ala Gln Thr Leu His Ile Gly Ser Ser His Leu
                 85                  90                  95

Ala Pro Pro Asn Pro Asp Lys Gln Phe Leu Ile Ser Pro Pro Ala Ser
                100                 105                 110

Pro Pro Val Gly Trp Lys Gln Val Glu Asp Ala Thr Pro Val Ile Asn
            115                 120                 125

Tyr Asp Leu Leu Tyr Ala Ile Ser Lys Leu Gly Pro Gly Glu Lys Tyr
```

-continued

```
            130                 135                 140
Glu Leu His Ala Ala Thr Asp Thr Thr Pro Ser Val Val His Val
145                 150                 155                 160

Cys Glu Ser Asp Gln Glu Asn Glu Glu Glu Met Glu Arg Met
                165                 170                 175

Lys Arg Pro Lys Pro Lys Ile Ile Gln Thr Arg Arg Pro Glu Tyr Thr
                180                 185                 190

Pro Ile His Leu Ser
            195

<210> SEQ ID NO 9
<211> LENGTH: 207
<212> TYPE: PRT
<213> ORGANISM: Caenorhabditis elegans

<400> SEQUENCE: 9

Met Val Ala Asp Asn Ser Glu Lys Ser Thr Lys Ser Val Ala Asn Gly
  1               5                  10                  15

Ser Leu Ile Ser Thr Val Ser Ser Lys Asp Asp Leu Pro Asn Ala Ile
                 20                  25                  30

Ile Val Thr Gln Val Pro Glu Asp Val Phe Asp Asn Lys Gln Asp Lys
             35                  40                  45

Ala Asn Phe Ser Ser Leu Phe Thr Gln Ile Glu Lys Asp Ile His Phe
 50                  55                  60

Asp Phe Leu Arg Ser Phe Arg Arg Val Arg Val Ile Phe Ser Ser Pro
 65                  70                  75                  80

Glu Asn Ala Thr Ala Ala Lys Leu Ile Val Gln Gly Phe Ser Phe Lys
                 85                  90                  95

Gly His Glu Leu Lys Ala Phe Phe Ala Gln Arg Ile Tyr Met Ser Ala
                100                 105                 110

Asn Ser Gln Met Leu Ser Pro Pro Leu Glu Lys Gln Phe Leu Ile
             115                 120                 125

Ser Pro Pro Cys Ser Pro Pro Val Gly Trp Glu Gln Thr Lys Asp Met
130                 135                 140

Pro Pro Val Val Cys Asn Phe Asp Leu Met Ala Arg Leu Ala Ser Phe
145                 150                 155                 160

Ala Ile Asp Glu Lys Tyr Glu Val His Asn Gly Asp Glu Leu Thr Pro
                165                 170                 175

Ala Ile Ile Val His Pro Cys Glu Thr Pro Ile Asp Val Pro Ser Ala
             180                 185                 190

Ile Glu Met Pro Arg Thr Pro Arg Pro Ser Ser Pro Cys Glu Gln
         195                 200                 205

<210> SEQ ID NO 10
<211> LENGTH: 211
<212> TYPE: PRT
<213> ORGANISM: Saccharomyces cerevisiae

<400> SEQUENCE: 10

Met Gly Asn Ile Ile Thr Asp Thr Ile Ile Thr Ser Asp Lys Cys
  1               5                  10                  15

Asp Ile Val Asp Asn Asp Asn Val Glu Arg Ile Gln Val Trp Leu Ser
                 20                  25                  30

Lys Asn Ile Leu Arg Lys Phe Gln Ile Asn Glu Asn Glu Pro Leu Gln
             35                  40                  45

Leu Ile Ile Leu Lys Arg Phe Lys Arg Ile Leu Leu Ile Cys Pro Ser
```

-continued

```
                      50                  55                  60
His Asp Ile Ser Gln His Val Met Asp Ala Ser Arg Ala Leu Glu Met
 65                  70                  75                  80

Glu Asn Phe Asn Phe Ser Tyr Ser Leu Gln Asp Gly Gln Arg Asn Leu
                 85                  90                  95

Thr Lys Gln Tyr Leu Lys Val Pro Glu Ser Glu Lys Met Phe Leu Ile
            100                 105                 110

Ser Pro Ala Ser Pro Pro Glu Phe Asp Phe Ser Lys Cys Glu
        115                 120                 125

Asp Ala Pro Gln Arg His Ile Gln Ser His Ile Gln Gln Asp Gln Gln
130                 135                 140

Gln Arg Leu Glu Ala Ser Gln Leu Leu Pro Asn Asn Pro Asp Lys Asn
145                 150                 155                 160

Asn Asn Gly Thr Phe Thr Leu Leu Lys Ser Lys Val Gly Ala Ile Thr
                165                 170                 175

Ile Asp Arg Cys Pro Thr Asn Asp Gly Asn Gly Gln Met Gln Leu Ala
            180                 185                 190

Asp His Val Lys Thr Ala Phe Pro Pro Lys Ser Ile Phe Asp Thr Asp
        195                 200                 205

Asp Asp Asp
    210
```

<210> SEQ ID NO 11
<211> LENGTH: 163
<212> TYPE: PRT
<213> ORGANISM: Schizosaccharomyces pombe

<400> SEQUENCE: 11

```
Met Leu Val Phe Thr Thr Ser Pro Asp His Val Asp Glu Leu Asn Glu
  1               5                  10                  15

Phe Val Gln Gln Leu Asn Pro Val Ala Phe Thr Arg Val Leu Arg Gly
             20                  25                  30

Leu Gly Lys Val Leu Ala Ser Tyr Asn Asp Lys Ala Val Glu Glu Asp
         35                  40                  45

Thr Leu Lys Lys Ser Ser Thr Gly Ser Leu Pro Ser Gly Gln Gln Val
 50                  55                  60

His Cys Gln Tyr Val Leu Asp Asp Pro Asn His Val Glu Gly Ile Ser
 65                  70                  75                  80

Val Asp Gln Ser Leu Gln Val Pro Lys Phe Glu Lys Asn Trp Leu Ile
                 85                  90                  95

Ser Pro Pro Gly Ser Pro Val Gly Trp Glu Pro Ile Val Glu Glu
            100                 105                 110

Ser Pro Asn Ser Gln His Leu Ala His Asp Ile Gln Leu Lys Leu Asp
        115                 120                 125

Glu Leu Gly Asn Ala Leu Leu Asn Asp His Ser Ala Gly Pro Gln Ile
130                 135                 140

Val Ile Ser Glu His Asn Asn Thr Lys Glu Thr Ser Pro Ser Arg Gln
145                 150                 155                 160

Phe Glu His
```

<210> SEQ ID NO 12
<211> LENGTH: 8
<212> TYPE: PRT
<213> ORGANISM: Homo sapiens

<400> SEQUENCE: 12

```
Lys Gln Phe Leu Ile Ser Pro Pro
  1               5
```

<210> SEQ ID NO 13
<211> LENGTH: 11
<212> TYPE: PRT
<213> ORGANISM: Homo sapiens

<400> SEQUENCE: 13

```
Pro Lys Pro Lys Ile Asn Gln Thr Arg Arg Pro
  1               5                  10
```

<210> SEQ ID NO 14
<211> LENGTH: 16
<212> TYPE: PRT
<213> ORGANISM: Homo sapiens

<400> SEQUENCE: 14

```
Glu Arg Met Lys Arg Pro Lys Pro Lys Ile Asn Gln Thr Arg Arg Pro
  1               5                  10                  15
```

<210> SEQ ID NO 15
<211> LENGTH: 14
<212> TYPE: PRT
<213> ORGANISM: Homo sapiens

<400> SEQUENCE: 15

```
Arg Gln Val Glu Met Ile Arg Arg Arg Pro Thr Pro Ala
  1               5                  10
```

<210> SEQ ID NO 16
<211> LENGTH: 14
<212> TYPE: PRT
<213> ORGANISM: Homo sapiens

<400> SEQUENCE: 16

```
Glu Ala Ala Glu Gln Ile Arg Pro Arg Arg Pro Thr Pro Ala
  1               5                  10
```

<210> SEQ ID NO 17
<211> LENGTH: 14
<212> TYPE: PRT
<213> ORGANISM: Homo sapiens

<400> SEQUENCE: 17

```
Ser Glu Ile Lys Gln Val Glu Phe Arg Arg Leu Ser Ile Ser
  1               5                  10
```

<210> SEQ ID NO 18
<211> LENGTH: 14
<212> TYPE: PRT
<213> ORGANISM: Homo sapiens

<400> SEQUENCE: 18

```
Val Pro Ile Pro Gly Arg Phe Asp Arg Arg Val Ser Val Cys
  1               5                  10
```

<210> SEQ ID NO 19
<211> LENGTH: 14
<212> TYPE: PRT
<213> ORGANISM: Homo sapiens

<400> SEQUENCE: 19

```
Arg Ile Asn Glu Arg Met Pro Pro Arg Arg Asp Ala Met Pro
```

<210> SEQ ID NO 20
<211> LENGTH: 14
<212> TYPE: PRT
<213> ORGANISM: Homo sapiens

<400> SEQUENCE: 20

Pro Lys Pro Lys Ile Ile Gln Thr Arg Arg Pro Glu Tyr Thr
 1               5                  10

<210> SEQ ID NO 21
<211> LENGTH: 14
<212> TYPE: PRT
<213> ORGANISM: Homo sapiens

<400> SEQUENCE: 21

Pro Lys Pro Lys Ile Asn Gln Thr Arg Arg Pro Gly Leu Pro
 1               5                  10

<210> SEQ ID NO 22
<211> LENGTH: 724
<212> TYPE: DNA
<213> ORGANISM: Mus musculus

<400> SEQUENCE: 22

```
atgctccgag acagcctgaa atcttggaat gacagccagt cagacctctg tagcagcgac      60
caggaggagg aagaggagat ggtcttcggt gaaaatgagg acggactgga agagatgatg     120
gacctaagtg acctgcccac ctcactcttt gcttgcagtg tccatgaagc agtgtttgag     180
gtccaagagc aaaaggagag gtttgaggcc ctgttcaccc tctacgatga ccaggtcaca     240
ttccagttgt tcaagagctt tcgcagagtg aggatcaact cagcaagcc cgaggctgcg      300
gcaagagcgc ggatagagct ccacgagagt gagttccacg gacggaagct gaagctttac     360
ttcgcacagg tgcaggtgtc cggggaggcc cgggacaagt cctacttact gccaccacaa     420
cccaccaagc agttcctcat ctcccctccc gcctcacccc ccgtggggtg gaagcagagt     480
gaagatgcga tgccagtgat caactatgac ctgctctgcg ctgtctccaa gctgggccca     540
ggggagaaat acgaactgca cgcgggaacc gagtccaccc ccagtgtggt ggtgcacgtc     600
tgtgagagcg aaactgaaga ggaagaagac acaaaaaatc caaaacagaa aatcacgcag     660
acgcggcgcc cggaggctcc cacggcggca ctgagtgagc ggctggactg tgcactctga     720
gcgg                                                                  724
```

<210> SEQ ID NO 23
<211> LENGTH: 958
<212> TYPE: DNA
<213> ORGANISM: Mus musculus

<400> SEQUENCE: 23

```
gccgctgcgg cccgcgttga gggcgtggtg gctccgggtg gtgagggtct gtccgcccca      60
ggccgcgctc gtgggcatcc ccctcgggc ctctcccctc gagcgcacag aagtatctgg     120
caggcatcct agaactttac agagaagatg ctccgagaca gcctgaaatc ttggaatgac     180
agccagtcag acctctgtag cagcgaccag gaggaggaag aggagatggt cttcggtgaa     240
aatgaggacg gactggaaga gatgatggac ctaagtgacc tgcccacctc actctttgct     300
tgcagtgtcc atgaagcagt gtttgaggtc caagagcaaa aggagaggtt tgaggccctg     360
ttcaccctct acgatgacca ggtcacattc cagttgttca agagctttcg cagagtgagg     420
```

```
atcaacttca gcaagcccga ggctgcggca agagcgcgga tagagctcca cgagagtgag      480
ttccacggac ggaagctgaa gctttacttc gcacaggtgc aggtgtccgg ggaggcccgg      540
gacaagtcct acttactgcc accacaaccc accaagcagt tcctcatctc ccctcccgcc      600
tcaccccccg tggggtggaa gcagagtgaa gatgcgatgc cagtgatcaa ctatgacctg      660
ctctgcgctg tctccaagct gggcccaggg gagaaatacg aactcacgc gggaaccgag       720 tccaccccca gtgtggtggt gcacgtctgt gagagcgaaa ctgaagagga agaagacaca      780
aaaaatccaa aacagaaaat cacgcagacg cggcgcccgg aggctcccac ggcggcactg      840
agtgagcggc tggactgtgc actctgagcg gctgcggtgc ctgccgcgcc tgcctgtccc      900
accactacag ctgcgcctgt ctaggagcac agcccaggga tgctcttgca tccgtcag       958
```

<210> SEQ ID NO 24
<211> LENGTH: 236
<212> TYPE: PRT
<213> ORGANISM: Mus musculus

<400> SEQUENCE: 24

```
Met Leu Arg Asp Ser Leu Lys Ser Trp Asn Asp Ser Gln Ser Asp Leu
 1               5                  10                  15

Cys Ser Ser Asp Gln Glu Glu Glu Glu Met Val Phe Gly Glu Asn
             20                  25                  30

Glu Asp Gly Leu Glu Glu Met Met Asp Leu Ser Asp Leu Pro Thr Ser
         35                  40                  45

Leu Phe Ala Cys Ser Val His Glu Ala Val Phe Glu Val Gln Glu Gln
     50                  55                  60

Lys Glu Arg Phe Glu Ala Leu Phe Thr Leu Tyr Asp Asp Gln Val Thr
 65                  70                  75                  80

Phe Gln Leu Phe Lys Ser Phe Arg Arg Val Arg Ile Asn Phe Ser Lys
                 85                  90                  95

Pro Ala Arg Ala Arg Ile Glu Leu His Glu Ser Glu Phe His Gly Arg
            100                 105                 110

Lys Leu Lys Leu Tyr Phe Ala Gln Val Gln Val Ser Gly Glu Ala Arg
        115                 120                 125

Asp Lys Ser Tyr Leu Leu Pro Pro Gln Pro Thr Lys Gln Phe Leu Ile
    130                 135                 140

Ser Pro Pro Ala Ser Pro Val Gly Trp Lys Gln Ser Glu Asp Ala
145                 150                 155                 160

Met Pro Val Ile Asn Tyr Asp Leu Leu Cys Ala Val Ser Lys Leu Gly
                165                 170                 175

Pro Gly Glu Lys Tyr Glu Leu His Ala Gly Thr Glu Ser Thr Pro Ser
            180                 185                 190

Val Val Val His Val Cys Glu Ser Glu Thr Glu Glu Glu Asp Thr
        195                 200                 205

Lys Asn Pro Lys Gln Lys Ile Thr Gln Thr Arg Pro Glu Ala Pro
    210                 215                 220

Thr Ala Ala Leu Ser Glu Arg Leu Asp Cys Ala Leu
225                 230                 235
```

<210> SEQ ID NO 25
<211> LENGTH: 3983
<212> TYPE: DNA
<213> ORGANISM: Mus musculus

<400> SEQUENCE: 25

```
gccaaatttg aatccctctt cagaacatat gacaaggaca ccaccttcca gtattttaag      60
agcttcaaac gtgtccggat aaacttcagc aaccccttat ctgcagccga tgccaggctg     120
cggctgcaca agaccgagtt cctggggaag gaaatgaagt tgtattttgc tcaggtaagt     180
gtgttcattg tgaagcgggt tcctcccggc aaagcacctt atacattgga aacctagagg     240
tcacctcaaa acagacagga ttccaacctt gagttcttaa ggtctccctg ctgtgtaaag     300
ggatctggtg aaggggacag taagcctgga ccttcctggg ttaaaccgtg aaggaaggag     360
agcaagcttc ccttggtcac cagaaagctt agggatttgg aggggagaag agggcatcgc     420 tgccccctc cctgcacact agtcagcttc actgggacta ggccagcgac ctgtcaagag      480
ctgtctcaag ccagtgcagg ttctccacgc ctcaccttgt aagcctgtat tcagatcagc     540
acagggctgt cagtcggggc aggggtgagg gtcatcacat ggttgagact cttagctgag     600
gggcagaaaa gggggctgtg gatgagttgt ccattgttct gccaacctcg ggacacctt      660 caaggcgact cccaacttcc atgtgactgt aacggggact ggtagatcgc agcttctcgt     720
tgttatcccc aaggtaatgt cagtccttgc caggctctga agccgcttcc tttcttctca     780
gttgtctaca ctcacttcct gccagcttag ggccagcgga gtcctgtgga gtgtggctca     840
tggccctcac ctctcggtaa tgtagatttt tgaccatgaa atacccctg tggctcatgt      900 atttgaatac ttgggtcctc tgtggtgcag ttttacagtt agggaacttt aggaggtggg     960
gcctccctaa aggaatgaga tccccgaggc agactctgag gggttagagc ccagcccctt    1020
gtcagattga agctctttgc ttcctggttg gcaccatgta acaggttacc acaggcttct    1080
gcagcctcta gctaccatga catccgtctt ttctgccttc cctatgatgg ctgcgcactc    1140
tcgaactgtg agccaggata aggccttccc gctttggttt tcatccaggg ctgtcataga    1200
cacttgaaaa gtttacccaa cacaggcacc aaatccggaa ttcagtcctt ccttcacctc    1260
tatacagacc acatttctgc ttcttggaat cgtacctggt ccagagcctg accatcggtc    1320
tgcccttcca tgcttgcctt ccagaagctt ccatgaactg tcgtgacctc gctcgcttgc    1380
tgcataatga tgaactcatt tctctcctca gactttacac ataggaagtt cacacctggc    1440
tccgcccaat cccgacaaac agttcctcat ctcccctccg gcctctcctc ccgttggctg    1500
gaaacaagta gaagatgcca ccccgtcat aaattacgat cttttatatg ccatctccaa     1560
gctggggcca ggtaagcagc accctcaggt gggaaagtgt cgggaggtgt ggagagactc    1620 tctgggtcc ccaggcctca cgcgccccca tgctgtcgta tggtgtgacc cctgcgttat     1680
tccacattgc tgcagctcgt gctggagtgt gtgccccttg gaggattcca ggagatggta    1740
gcaacctgtg ggtttgtgca ccactgtccc cccccaagtg tcccccgaat ctatcccttc    1800
acccagcagg cacacctgtg tggctcactc caggccccag atcatgttgt tccaggtggg    1860
atgggaaagg gcaaacagtc caacctgtag ggagtctcgt caactgtcat tcctacttcc    1920
gtactgggtg ggagggatgt gcgcatctct caccccacac agcaagccga atcagcactg    1980
cccatcagcc cctcgtcatc tgaagttcct ttagggcaag ggtttatttt tcatggctca    2040
tcagcagaaa gattacattt ctgagaacac agcctaaatg gaaattcctc ccgtggtaca    2100
aactgagact cacgttacta gtgctaattg tagcatgaag gtcaaaagtg gaaacgccca    2160
gtgtgagcaa ggagacggct cagcatggcg gctctcagca cagttgaggg gtctgttgtc    2220
tgtggatgtg ttatacatgg acacagacct ccatctgccg caagggaaca ggctgttcca    2280
gaggcaggaa ttgaggcgag ccttctgtct ttaagaaccc aaaccagaaa tcaaggggct    2340
```

| | | | | | |
|---|---|---|---|---|---|
| gaaacattcc | taccagggcc | atgacagagt | tctccagacc | cagagccagc | acacttcagt | 2400 |
| cagccttcgg | ggctgcaaag | gcggcttgtg | gagagcagtc | tgaccttcat | ccacgaagtt | 2460 |
| agtgctgtgt | gtgtctgtgc | gtgcccgcag | ctctctacct | ttgggccaag | ggtagatagg | 2520 |
| tatagaaacg | cccctccac | ttacagtttt | cccagcagcc | ctcaagactt | ggggagagcc | 2580 |
| gagctccttc | gttttttag | cctcattggt | ggggtagaga | ggccatgctg | cctcgttgtt | 2640 |
| catgagttct | gtgcctccca | catctatgga | gcagactaaa | aagcaggcag | cctcaccaag | 2700 |
| ccgctacagc | agctggaaac | ttagccggtt | taacaacagg | gctcaaaccc | gggccttgca | 2760 |
| tctgctggca | agcacccctt | gtctagtcta | catcccagc | accctccatt | tgtaaatcta | 2820 |
| ggtggcattt | gtcaaggtat | gtatgtcatg | agcccgccgc | tgggcgtttt | ggatttgttc | 2880 |
| tctcatggaa | atggccccac | caatgccttt | gctgccccat | ttacagagga | ggcgaaaggc | 2940 |
| acaaagaagt | gagacagccc | ggggacaagt | cctcatccac | tcactcccca | ccatacacgg | 3000 |
| ccactccgcc | atgccacctc | ccctcagtgt | ctagtgcaga | cccctcaag | ggaaatccca | 3060 |
| gacccttcct | ttccagccag | gtttcttggt | gacagaaggc | ccatcctaat | cttgctatgc | 3120 |
| cacagtggtg | tgaaggtgct | tgagcctggg | caagctcagg | ctagcccaga | gagcaagga | 3180 |
| gggagcgata | gatagataga | tagatagata | gatagataga | tagatagata | gatagataga | 3240 |
| tggatgatgg | tgtggctgaa | ggtgtcactt | gggcatgaag | cacttggcct | ccagtgtcac | 3300 |
| ataaatcagg | catggtggtg | cagaacctct | ggtcccagca | tccagaaggt | gaggcaagag | 3360 |
| cagcagacat | ctaaggtcaa | atgcagccat | cagtgagttc | caggcagctc | atacataaac | 3420 |
| aatataaaac | caaggaaagg | atgttaaggt | tgagcagatt | caccctgggc | tctctgctgc | 3480 |
| catgctctgg | agcccacct | acaggacatt | tgtctccagc | agtggcattt | gctcatgttt | 3540 |
| tctctgtact | gatgcctccc | ataacctgcc | cttggagaat | gctgctggga | gccctgggt | 3600 |
| ggacatgaga | aaggttagcg | aacagcgctt | gactgagagc | aattctgcgg | tgcaaatgtt | 3660 |
| ctgtcttgtg | aataagttat | ccatgaggag | gcacaagggc | agactgtgtc | tggccaagca | 3720 |
| aaccctggtg | tccctccagg | tccctgccct | ccatgctcag | ggacaagccg | cggttaccac | 3780 |
| tcaccatgct | cttgtctcct | tcccccagga | gagaagtatg | aactgcatgc | agcgacagac | 3840 |
| accactccca | gtgtggtggt | ccacgtgtgt | gagagtgacc | aagagaatga | ggaggaagag | 3900 |
| gaagagatgg | agagaatgaa | gagacccaag | cccaaaatca | tccagacacg | gagaccgagt | 3960 |
| acacacccat | ccacctcagc | tga | | | | 3983 |

<210> SEQ ID NO 26
<211> LENGTH: 3360
<212> TYPE: DNA
<213> ORGANISM: Mus musculus

<400> SEQUENCE: 26

| | | | | | |
|---|---|---|---|---|---|
| gaaaaattcg | agggactgtt | ccggacctat | gatgaatgtg | tgacgttcca | gctgtttaag | 60 |
| agtttccgac | gggttcgaat | aaatttcagc | catcccaaat | ctgcagcccg | tgccccggat | 120 |
| agagcttcat | gagctcagtt | cagagggaag | aagctaaaac | tctacttcgc | ccaggtgagt | 180 |
| ctttaacctg | ctggtttggc | acaacattta | gaggacgtgt | tgctattgga | gtagaatcag | 240 |
| attcaatttc | cagcatgcac | atggtggttc | acaaacatct | ggtgccctcc | tctgacccct | 300 |
| tagggtacca | cacacacaca | cacacacaca | cacacacaca | cacacacaca | catacacaca | 360 |
| cagtacatac | acataagtgt | gggcaataca | ttcatgcaca | taaattaaat | ttagaagtat | 420 |
| aaaaagtcat | tgttaattgg | aaaataaata | aattaaatta | aaatgtaaat | gaggacctcg | 480 |

```
ggagatggtt atgcagttaa gaaagctggc tgctcttcta gaggacatga gttcgagtcc    540
tagcactcat atggtgtctc ataattgttt gtaacccctg ttacagggga accaatgcct    600
tcttctagcc tcctacacac ccacaaatag gtttgctgtt acagttactt cactaagaaa    660
ttaatttagt ggttgtctaa gacctgccca agataaacca gtcaacattc tagcatggag    720 agaaagggg gaccctgagc ccagacctcc aactgaggga ctttcaacag ttgatggatg    780 cttgggggg gggatgtttc cttggtggtt tggtctctgg taggttgagt atggtccagg    840
ggatggtccc acacccatgc tcatctggac agcactaact ggactcagcg gatatgaaaa    900 cataagaac acgaggaagg gaaggaatg gaagcaaatc tgatcaaaat atatttatac    960
atgtatgaaa tcctccgagc tatttataca tgtatgaaat cctctgagct aatgttctta    1020
aaataaggaa agaaacagac actgacagtg agttccagat tgagcagtat ctgtgtccta    1080
ggacagaggc tctaagacct gccaagctaa gttctaacta ggacaagtct cagaacctca    1140
ctgggactca gagtcctcat ctataagatg gcaatgaaga cattatcaac ccatgtagct    1200
gctgtgatgg tgacatggaa agctgtgtgc agctgtgcct agatttctgg taaagggaca    1260
ataatttcca gctaggaact gcaacagaac tgatctcacc acagccgact cctaaccttc    1320
ccgacagggt tgtgattaaa atttaaatga tatgtttaat ggtatactaa atacattcat    1380
gataaaaagt tataaatcca tgaaaattaa ttgtatgttt tgcaaagcca aatactcatt    1440
atcctgaaca gggatgggta gttcttaggg atgttcatga agcccacagc actagttgtc    1500
ggtattcact ctccatcaag gccttatcca tcactaggca acagtcacct ctcaaggatg    1560
gcttcagctg ctgactcctg ctaaaatcct acatctctta taaattcatg tagctagaac    1620
aatcttagat catcatttat taaaacctgc atcagaacta gttgtgtcag ctgtagactc    1680
ctgctaaaat cctacatctc ttacaaattc atgtagctag aacacactta gatcatcatt    1740
tattaaaacc tgcatcagga ccagttggcc tgaggcagga ccttgcat tcaaggccag    1800 cctgagctat ccagtaaggt cctgtctcaa aaagactgtg tgtgtgtgtg tgtgtgtgtg    1860
tgtgtgtgtg tgtgtgtgtg tgtgtgtgtg tttaatatgt gtgtgtgtgt gtgtttaata    1920
tgtgtgtgta tatatatatg atatatgggt acatagatat atgatacata catacatgat    1980
agacacatac atagatacat acatagctat atagatacga gagagagaca gagagagaga    2040

tttccattaa aagataacat ggagttacca tgtgactcgt aaattctctt ctaggttcta    2100
aaaatcatga actcaaacaa atagttaagc aagaattcac agcagcactg ttcacaatag    2160
gccaacagtg agaactacct aaagatcttc aacagataaa gggataaaga gacaatagta    2220
tgttcacaca aaggaatatt attcagctga gagagagaga gagagagatg ttgataatcc    2280
atcaccaaat aatgggcctt taaaatgcaa tggaagctag acacaaaagc tcatctgttc    2340
tgtggttcca ttctcataaa agagttagat aagttcagag aagtagacac agcttgacaa    2400
ccatcagggg tagtaggaaa ctacattagt agtcgttatt taagggatgc atagttgggg    2460

ttggagagat gacttagcag ttaagagcac tgaatgctct ttcgaaggcc ctgagttcaa    2520
atcccagcaa ccatatggtg gctcacaacc atccataatg agatctgatg cccttttctg    2580
gagtgtctgg agacagctac catgtactca catataataa ataaataaat ctтттттaaaa    2640 aagggtgtg tgtgtgcata gttatcctta gagccatggg aagggttagg gtagttgttc    2700

tcaaccttcc taatgctgtg accctttaat actcatgaag tggtgatccc cagccacaaa    2760
atccttttcg ttgctgcttt ataactgtaa ttttgctagt actatgaatt atgataccac    2820
```

| | |
|---|---:|
| tgtgtgtgtt ttctgatggt cttaggcagc actctggctt gctcaccatc tagcctaacc | 2880 |
| ttattggtga gatcaaggtt tttgggttgt tttttttaa agggcactgt tacctaagga | 2940 |
| aggacattag aagttgtcca ctagcttcca catgtacaca ctcataaggg cacacaatgt | 3000 |
| agtacagggc ttggtgaccc tggtgctcat aaaagatgg aaactgctgt tttttagga | 3060 |
| ttatgtaaac aatgagttca gcacactgtg tactgtaagg agtgattgct actgcagtct | 3120 |
| ggccctcagt gaagccctgc ccagctgcaa gcatggacaa tcacatgtct cattatcttg | 3180 |
| tttgaaaggt ccagacccca gagacagatg gagacaaact gcatttggca cctccacagc | 3240 |
| ctgccaaaca gttcctcatc tcacccctt catctccatc tgttggctgg aagcctatca | 3300 |
| gcgatgccac accagtcctc aactatgacc ttctttatgc tgtggccaaa ctaggaccag | 3360 |

<210> SEQ ID NO 27
<211> LENGTH: 3717
<212> TYPE: DNA
<213> ORGANISM: Mus musculus
<220> FEATURE:
<221> NAME/KEY: modified_base
<222> LOCATION: (2410)
<223> OTHER INFORMATION: n=a, c, g, or t

<400> SEQUENCE: 27

| | |
|---|---:|
| cggaagctga agctttactt cgcacaggta atggccgttc tgcgcctgcg cacacagcct | 60 |
| gctccagttc ccgctccagc acggggtcag aggtctgtga ggtcagcagt cacgtgagcc | 120 |
| agggctgccg tgcttttct gactttacac atacgtcatt tcatgtattt taggagcaca | 180 |
| ttaagcctct gttcatgttt ctctgagacg aacacctaag gggttcattt ttctggcgat | 240 |
| tttgctcagc tagggctctg tgagggaagt cctgatactt cgaagttggc agattaaaca | 300 |
| ctgtgcatct aaaatggcac cgaggacatg acatccgtgg gaaaacagaa caaaaccttc | 360 |
| aagggtcatc aagatggccc aggggtgaa ggtgcttgcc accaagcctg gcagcccgag | 420 |
| tttgatccca ggaactcatc cacgggtgga aggaaagaac caacctgtgt cctctgagga | 480 |
| ccacatatgc agttttctct cttctgagac agtagtgtgt tagtcagccc ttcccagcga | 540 |
| attagttact gggatgagac actgtgacca aaagcaccca ggagacaaaa ggtgtatgta | 600 |
| ctttacttat aatgaatcac cattcattga gggaagccaa gcaagaact caacctgggc | 660 |
| agaaacctgg aggcagaggc catggagggg cgctgtttac tggctcctca tggcctactc | 720 |
| agcctgcttt cttttttg ttttgttttt tgttttttga gacagggttt ctctgtatag | 780 |
| ccctggctgt cctgaaactc actctgtaga ccaggctggc ctcgaactca gaaatccgcc | 840 |
| tgcctctgcc tcccgagtgc tgggattaaa ggcgtgtgcc actgtgcctg gcttcagcct | 900 |
| gctttcttat agaacctaga accacaaccc aggctgtat catccacagt gggcagggcc | 960 |
| ttccccacat tggtcactaa gaaaacttcc tgcctgcagt caggtcttct ggagacattt | 1020 |
| tctcagttgg gttcctgtct cttgatgact aaagcttgca tcaggttgac atatagtagc | 1080 |
| cagcacaccc actcacacca ctagcaaata cctgggagag tcagctgtaa aggagaaaag | 1140 |
| tctcggcttg tggtttgcag gtttcagtct gcatgtgatt ggcacttttc ctgtgagcct | 1200 |
| gctgtgcagt agcacatagg ggcagagcaa agctcttcac ttcgttcatg ggaagcagga | 1260 |
| agagtaaggg gttggggttc cactgtccct tagggtatgt ccccatgact aaaggcctcc | 1320 |
| ctgcctcctg aaggctccca gtttgacctc tcaggggagc aagcctctat ttactatgta | 1380 |
| gagcccaagg gtcacttaga gcccagacca cagagtagca cgtttatcaa gggtccaggg | 1440 |
| cctgtggcca cttccagtcc accacctgga aggtcacaga cagtttgaga gacagttta | 1500 |

```
atcacccctc caagaaagta acaattacca taaagttgga aatgaaagcc ctgtggtgat    1560
ggtgcaggcc tttaatctaa gaactggagg cagagaccgt gagatctgtg agtcaggcct    1620
acagagtgag ttccaggaca gccagggata cacggagaaa ccctgtctca gaaaaagaaa    1680
agaaaggaca gctgctcaca agcacgcctt tccctgcagg tgcaggtgtc cggggaggcc    1740
cgggacaagt cctacttact gccaccacag cccaccaagc agttcctcat ctcccctccc    1800
gcctcacccc ccgtggggtg gaagcagagt gaagatgcaa tgccagtgat caactatgac    1860
ctgctctgcg ctgtctccaa gctgggccca ggtactgcat tccaccttcg ctctccgcgt    1920
cctcggacat tgctgttctg tgtgttggag actgtgtgca gtatggggtg cagagcccag    1980
caacaccagc accgtccagt gggcggtgtg gccacaccag tctgagttca cactcgagct    2040
gtacactttc cagtgctgtg gtcctcagcc agttgcctag cctgggttat ctgagtgtgt    2100
tctaaggatt aaacgctgtc tgcagcgtga taactttagc cattcagcca gaagttaata    2160
taggcggtta gtgaacatcc tcactgcttt ctctctgcaa gccagtcagc acagtgtctg    2220
tcgtttggca gctgctttgg gtgacagtga caatgaccta tcgcccttcc aaagttctat    2280
ctctctctct tttcacttct tacttccttc ttttcttgct cggtctcact catctttaat    2340
actgcaagaa gccgattctt ctagggcact tcagaggctt ttgagaaggc actctatgct    2400
cctgggcggn tgagctcttc gatggcagag gccctaccgt agacaccgct gcctagagct    2460
tagccagtgc ctcccatggc gccccaacac cactgtgaat ttaactatcc caccttagtt    2520
atctatagaa cagcagttag catttatatt aacattttaa ttagtattta tgtaatataa    2580
tcaatgggtt ctcgtcttct tcctgagcac aaagccagag taagcataga acagaagaga    2640
caagaagaga agagatagga agagacagga gctgtttgca aagcaagccc tccccgagtg    2700
aaggaagctg tgtatattca tacagtggca tgtgcactcc tgagcacgcg cagttgaaaa    2760
tcatggagat gaacatggtg gacagggtgt gcttgggttc gcttgcacca tgaagtttca    2820
cttgaaaata agagaaggat ggttttaagg tgtgtgctaa caggagtctg ccttgaaggt    2880
gcctgaagtg cttggattta actcctaggg ctcaggacag aagggacggt gtctttattt    2940
attttttttt aagacttatg tatatgagta cattgtagct gtacagatgg ctgtgagcct    3000
tcatgtggtt gggaattgaa ttttaggac ctttgcttgc tcccatcaac ccctctcgct    3060
ctggtcggcc ctgctcgcta gtccctgctt gctccagccc aaagatttat ttattattat    3120
atataagtac actgtagctg acttcagacg taccagaaga ggacatcaga tctcattgcg    3180
ggtagttgtg agccactatg tggttgctgg gatttgaact cttcggaaga gcatcaagtg    3240
ttcttactca ctgagccatc gcattagccc gacagtgtct ttacaaatag aatttctgca    3300
gggcatggtg gtactcaact ttaacagcac ttgggaggca gaggctggca gctccctggg    3360
agttccaggt cagcctgtct acacagtgag cctaggccag cctgggctac atagtgcgac    3420
tccagggagt ttttgttttt gttttgttt tttttaaatg ccagcacttg ggagatggaa    3480
gcagaagaat tagagttcaa ggtcagcctc agctacagca gcaagtttct aactggccca    3540
gatttcatga gacgcagtct taaaaaaaaa aaaaaaaaat cagccactga atgacgtagt    3600
agaagaggaa gttgggagat agaagaactt gatttccttc actgggagta aggctccttc    3660
ctgtgcttgc aggggagaaa tacgaactgc acgcgggaac cgagtccacc cccagta      3717

<210> SEQ ID NO 28
<211> LENGTH: 12
<212> TYPE: PRT
```

```
<213> ORGANISM: Artificial Sequence
<220> FEATURE:
<223> OTHER INFORMATION: Description of Artificial Sequence: general
      calcineurin antagonist peptide
<220> FEATURE:
<221> NAME/KEY: SITE
<222> LOCATION: (6)
<223> OTHER INFORMATION: Xaa=any amino acid residue

<400> SEQUENCE: 28

Pro Lys Pro Lys Ile Xaa Gln Thr Arg Arg Pro Glu
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: calcineurin
      antagonist

<400> SEQUENCE: 29

Pro Lys Pro Lys Ile Ile Gln Thr Arg Arg Pro Glu
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: calcineurin
      antagonist

<400> SEQUENCE: 30

Pro Lys Pro Lys Ile Asn Gln Thr Arg Arg Pro Gly
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: EGF-derived
      peptide

<400> SEQUENCE: 31

Cys Met His Ile Glu Ser Leu Asp Ser Tyr Thr Cys
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: EGF-derived
      peptide

<400> SEQUENCE: 32

Cys Met Tyr Ile Glu Ala Leu Asp Lys Tyr Ala Cys
 1               5                  10

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence:
      pH-dependent membrane-binding internalizing peptide
<220> FEATURE:
```

```
<221> NAME/KEY: SITE
<222> LOCATION: (1)
<223> OTHER INFORMATION: Xaa=preferably a unique residue, such as Cys or
      Lys, that facilitates chemical conjugation of the
      internalizing peptide to a targeting protein
      conjugate
<220> FEATURE:
<221> NAME/KEY: SITE
<222> LOCATION: (2)..(3)
<223> OTHER INFORMATION: Xaa=residues selected to modulate the affinity
      of the internalizing peptide for different membranes

<400> SEQUENCE: 33

Xaa Xaa Xaa Glu Ala Ala Leu Ala Glu Ala Leu Ala Glu Ala Leu Ala
 1               5                  10                  15

Glu Ala Leu Ala Glu Ala Leu Ala Glu Ala Leu Glu Ala Leu Ala Ala
            20                  25                  30

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: peptide
      substrate

<400> SEQUENCE: 34

Gly Asn Ala Ala Ala Ala Arg Arg
 1               5

<210> SEQ ID NO 35
<211> LENGTH: 75
<212> TYPE: DNA
<213> ORGANISM: Artificial Sequence
<220> FEATURE:
<221> NAME/KEY: CDS
<222> LOCATION: (4)..(75)
<220> FEATURE:
<223> OTHER INFORMATION: Description of Artificial Sequence: synthetic
      construct

<400> SEQUENCE: 35 cat atg ggt ggc tgc cgt ggc gat atg ttc ggt tgc ggt gct cct cca      48
    Met Gly Gly Cys Arg Gly Asp Met Phe Gly Cys Gly Ala Pro Pro
     1               5                  10                  15 aaa aag aag aga aag gta gct gga ttc                                  75
Lys Lys Lys Arg Lys Val Ala Gly Phe
             20

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: synthetic
      construct

<400> SEQUENCE: 36

Met Gly Gly Cys Arg Gly Asp Met Phe Gly Cys Gly Ala Pro Pro Lys
 1               5                  10                  15

Lys Lys Arg Lys Val Ala Gly Phe
            20

<210> SEQ ID NO 37
<211> LENGTH: 225
<212> TYPE: DNA
<213> ORGANISM: Artificial Sequence
<220> FEATURE:
```

```
<223> OTHER INFORMATION: Description of Artificial Sequence: synthetic
      construct
<220> FEATURE:
<221> NAME/KEY: CDS
<222> LOCATION: (4)..(225)

<400> SEQUENCE: 37 cat atg gag cca gta gat cct aga cta gag ccc tgg aag cat cca gga       48
    Met Glu Pro Val Asp Pro Arg Leu Glu Pro Trp Lys His Pro Gly
    1               5                   10                  15 agt cag cct aaa act gct tgt acc aat tgc tat tgt aaa aag tgt tgc       96
Ser Gln Pro Lys Thr Ala Cys Thr Asn Cys Tyr Cys Lys Lys Cys Cys
                20                  25                  30 ttt cat tgc caa gtt tgt ttc ata aca aaa gcc ctt ggc atc tcc tat      144
Phe His Cys Gln Val Cys Phe Ile Thr Lys Ala Leu Gly Ile Ser Tyr
            35                  40                  45 ggc agg aag aag cgg aga cag cga cga aga cct cct caa ggc agt cag      192
Gly Arg Lys Lys Arg Arg Gln Arg Arg Pro Pro Gln Gly Ser Gln
        50                  55                  60 act cat caa gtt tct cta agt aag caa gga ttc                          225
Thr His Gln Val Ser Leu Ser Lys Gln Gly Phe
    65                  70

<210> SEQ ID NO 38
<211> LENGTH: 74
<212> TYPE: PRT
<213> ORGANISM: Artificial Sequence
<220> FEATURE:
<223> OTHER INFORMATION: Description of Artificial Sequence: synthetic
      construct

<400> SEQUENCE: 38

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Gly Phe
65                  70

<210> SEQ ID NO 39
<211> LENGTH: 912
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: CDS
<222> LOCATION: (4)..(912)

<400> SEQUENCE: 39 cat atg acc tct cgc cgc tcc gtg aag tcg ggt ccg cgg gag gtt ccg       48
    Met Thr Ser Arg Arg Ser Val Lys Ser Gly Pro Arg Glu Val Pro
    1               5                   10                  15 cgc gat gag tac gag gat ctg tac tac acc ccg tct tca ggt atg gcg       96
Arg Asp Glu Tyr Glu Asp Leu Tyr Tyr Thr Pro Ser Ser Gly Met Ala
                20                  25                  30 agt ccc gat agt ccg cct gac acc tcc cgc cgt ggc gcc cta cag aca      144
Ser Pro Asp Ser Pro Pro Asp Thr Ser Arg Arg Gly Ala Leu Gln Thr
            35                  40                  45
```

```
cgc tcg cgc cag agg ggc gag gtc cgt ttc gtc cag tac gac gag tcg        192
Arg Ser Arg Gln Arg Gly Glu Val Arg Phe Val Gln Tyr Asp Glu Ser
         50                  55                  60 gat tat gcc ctc tac ggg ggc tcg tca tcc gaa gac gac gaa cac ccg        240
Asp Tyr Ala Leu Tyr Gly Gly Ser Ser Ser Glu Asp Asp Glu His Pro
 65                  70                  75 gag gtc ccc cgg acg cgg cgt ccc gtt tcc ggg gcg gtt ttg tcc ggc        288
Glu Val Pro Arg Thr Arg Arg Pro Val Ser Gly Ala Val Leu Ser Gly
 80                  85                  90                  95 ccg ggg cct gcg cgg gcg cct ccg cca ccc gct ggg tcc gga ggg gcc        336
Pro Gly Pro Ala Arg Ala Pro Pro Pro Pro Ala Gly Ser Gly Gly Ala
                100                 105                 110 gga cgc aca ccc acc acc gcc ccc cgg gcc ccc cga acc cag cgg gtg        384
Gly Arg Thr Pro Thr Thr Ala Pro Arg Ala Pro Arg Thr Gln Arg Val
            115                 120                 125 gcg act aag gcc ccc gcg gcc ccg gcg gcg gag acc acc cgc ggc agg        432
Ala Thr Lys Ala Pro Ala Ala Pro Ala Ala Glu Thr Thr Arg Gly Arg
        130                 135                 140 aaa tcg gcc cag cca gaa tcc gcc gca ctc cca gac gcc ccc gcg tcg        480
Lys Ser Ala Gln Pro Glu Ser Ala Ala Leu Pro Asp Ala Pro Ala Ser
145                 150                 155 acg gcg cca acc cga tcc aag aca ccc gcg cag ggg ctg gcc aga aag        528
Thr Ala Pro Thr Arg Ser Lys Thr Pro Ala Gln Gly Leu Ala Arg Lys
160                 165                 170                 175 ctg cac ttt agc acc gcc ccc cca aac ccc gac gcg cca tgg acc ccc        576
Leu His Phe Ser Thr Ala Pro Pro Asn Pro Asp Ala Pro Trp Thr Pro
                180                 185                 190 cgg gtg gcc ggc ttt aac aag cgc gtc ttc tgc gcc gcg gtc ggg cgc        624
Arg Val Ala Gly Phe Asn Lys Arg Val Phe Cys Ala Ala Val Gly Arg
            195                 200                 205 ctg gcg gcc atg cat gcc cgg atg gcg gcg gtc cag ctc tgg gac atg        672
Leu Ala Ala Met His Ala Arg Met Ala Ala Val Gln Leu Trp Asp Met
        210                 215                 220 tcg cgt ccg cgc aca gac gaa gac ctc aac gaa ctc ctt ggc atc acc        720
Ser Arg Pro Arg Thr Asp Glu Asp Leu Asn Glu Leu Leu Gly Ile Thr
225                 230                 235 acc atc cgc gtg acg gtc tgc gag ggc aaa aac ctg ctt cag cgc gcc        768
Thr Ile Arg Val Thr Val Cys Glu Gly Lys Asn Leu Leu Gln Arg Ala
240                 245                 250                 255 aac gag ttg gtg aat cca gac gtg gtg cag gac gtc gac gcg gcc acg        816
Asn Glu Leu Val Asn Pro Asp Val Val Gln Asp Val Asp Ala Ala Thr
                260                 265                 270 gcg act cga ggg cgt tct gcg gcg tcg cgc ccc acc gag cga cct cga        864
Ala Thr Arg Gly Arg Ser Ala Ala Ser Arg Pro Thr Glu Arg Pro Arg
            275                 280                 285 gcc cca gcc cgc tcc gct tct cgc ccc aga cgg ccc gtc gag gaa ttc        912
Ala Pro Ala Arg Ser Ala Ser Arg Pro Arg Arg Pro Val Glu Glu Phe
        290                 295                 300

<210> SEQ ID NO 40
<211> LENGTH: 303
<212> TYPE: PRT
<213> ORGANISM: Artificial Sequence
<220> FEATURE:
<223> OTHER INFORMATION: Description of Artificial Sequence: synthetic
      construct

<400> SEQUENCE: 40

Met Thr Ser Arg Arg Ser Val Lys Ser Gly Pro Arg Glu Val Pro Arg
 1               5                  10                  15
```

```
Asp Glu Tyr Glu Asp Leu Tyr Tyr Thr Pro Ser Ser Gly Met Ala Ser
             20                  25                  30

Pro Asp Ser Pro Pro Asp Thr Ser Arg Arg Gly Ala Leu Gln Thr Arg
         35                  40                  45

Ser Arg Gln Arg Gly Glu Val Arg Phe Val Gln Tyr Asp Glu Ser Asp
     50                  55                  60

Tyr Ala Leu Tyr Gly Gly Ser Ser Ser Glu Asp Asp Glu His Pro Glu
 65                  70                  75                  80

Val Pro Arg Thr Arg Arg Pro Val Ser Gly Ala Val Leu Ser Gly Pro
                 85                  90                  95

Gly Pro Ala Arg Ala Pro Pro Pro Ala Gly Ser Gly Gly Ala Gly
                100                 105                 110

Arg Thr Pro Thr Thr Ala Pro Arg Ala Pro Arg Thr Gln Arg Val Ala
                115                 120                 125

Thr Lys Ala Pro Ala Ala Pro Ala Ala Glu Thr Thr Arg Gly Arg Lys
130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
                180                 185                 190

Val Ala Gly Phe Asn Lys Arg Val Phe Cys Ala Ala Val Gly Arg Leu
            195                 200                 205

Ala Ala Met His Ala Arg Met Ala Ala Val Gln Leu Trp Asp Met Ser
        210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
        275                 280                 285

Pro Ala Arg Ser Ala Ser Arg Pro Arg Arg Pro Val Glu Glu Phe
    290                 295                 300

<210> SEQ ID NO 41
<211> LENGTH: 120
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: CDS
<222> LOCATION: (4)..(120)

<400> SEQUENCE: 41 cat atg gac gtc gac gcg gcc acg gcg act cga ggg cgt tct gcg gcg      48
    Met Asp Val Asp Ala Ala Thr Ala Thr Arg Gly Arg Ser Ala Ala
     1               5                  10                  15 tcg cgc ccc acc gag cga cct cga gcc cca gcc cgc tcc gct tct cgc      96
Ser Arg Pro Thr Glu Arg Pro Arg Ala Pro Ala Arg Ser Ala Ser Arg
             20                  25                  30 ccc aga cgg ccc gtc gag gaa ttc                                    120
Pro Arg Arg Pro Val Glu Glu Phe
            35
```

```
<210> SEQ ID NO 42
<211> LENGTH: 39
<212> TYPE: PRT
<213> ORGANISM: Artificial Sequence
<220> FEATURE:
<223> OTHER INFORMATION: Description of Artificial Sequence: synthetic
      construct

<400> SEQUENCE: 42

Met Asp Val Asp Ala Ala Thr Ala Thr Arg Gly Arg Ser Ala Ala Ser
 1               5                  10                  15

Arg Pro Thr Glu Arg Pro Arg Ala Pro Ala Arg Ser Ala Ser Arg Pro
            20                  25                  30

Arg Arg Pro Val Glu Glu Phe
        35

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 43
aggaggtgga tctgc                                                             15

<210> SEQ ID NO 44
<211> LENGTH: 6
<212> TYPE: PRT
<213> ORGANISM: Mus musculus

<400> SEQUENCE: 44

Glu Arg Met Arg Arg Pro
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: consensus
      sequence

<400> SEQUENCE: 45

Glu Arg Met Pro Pro Arg Arg Asp
 1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence:
      cross-species conserved motif
<220> FEATURE:
<221> NAME/KEY: MOD_RES
<222> LOCATION: (6)
<223> OTHER INFORMATION: Variable amino acid

<400> SEQUENCE: 46

Leu Ile Ser Pro Pro Xaa Ser Pro
 1               5

<210> SEQ ID NO 47
<211> LENGTH: 4
```

```
-continued

<212> TYPE: PRT
<213> ORGANISM: Artificial Sequence
<220> FEATURE:
<223> OTHER INFORMATION: Description of Artificial Sequence: calcineurin
      antagonist peptide fragment
<220> FEATURE:
<221> NAME/KEY: MOD_RES
<222> LOCATION: (4)
<223> OTHER INFORMATION: Any amino acid residue other than Ser or Thr

<400> SEQUENCE: 47

Arg Arg Pro Xaa
 1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: calcineurin
      antagonist peptide fragment
<220> FEATURE:
<221> NAME/KEY: MOD_RES
<222> LOCATION: (4)
<223> OTHER INFORMATION: Ala, Gly or Glu

<400> SEQUENCE: 48

Arg Arg Pro Xaa
 1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: calcineurin
      antagonist peptide fragment

<400> SEQUENCE: 49

Arg Arg Pro Glu
 1
```

CALCIPRESSINS: ENDOGENOUS INHIBITORS OF CALCINEURIN, USES AND REAGENTS RELATED THERETO

CROSS-REFERENCE TO RELATED APPLICATIONS

This application claims the benefit of U.S. Provisional Application No. 60/135,431, filed May 21, 1999 and U.S. Provisional Application No. 60/161,195, filed Oct. 22, 1999, the contents of which are specifically incorporated by reference herein.

BACKGROUND OF THE INVENTION

In the last 50 years, two fields of study have converged on the protein calcineurin (CaN) because of it's pivotal role in signal transduction, particularly T-cell activation and memory development. CaN is ubiquitously produced with pleiotropic roles. It has been found that the physiological consequence of inhibition of CaN is sustained neurotransmitter release and eventual blockage of many cellular functions, including signal transduction pathways. See, Barford D. (1996) *TIBS* 21:407. With the improvement in organ transplant and the proliferation of the HIV virus, much attention has been focused on the immune system. While this system is an interesting physiological field by any counts, pharmaceutical companies also see the advantages in being able to control many immune response mechanisms. For example, inflammation is an immune response, one that can interfere with healing.

The other field is neurochemistry, where the study of memory has been found to be linked to differing potentiation rates of neurons during development. CaN appears to play an important role in calcium signaling and neural transmitter amplification as well as neuron development in infants. See, e.g., Quinlan et al. (1996) *J Neuroscience* 16:7627.

Since protein phosphorylation controls so many cellular events, regulation requires many levels. It must be controlled quite tightly in order to keep competing processes in balance. CaN offers a wonderful opportunity to observe many different regulatory mechanisms at work. These include site localization, Ca2+-activation, auto-inhibition (by auto-inhibitory domain—AID), CnB-activation, CaM-activation. In addition, there are a number of recent studies elucidating the great complexity of the regulation to which CaN is subject.

In understanding the regulation mechanism for Cn, the FKBP12-FK506-binding site is very important. It appears to be the same binding site for binding of cyclophilin-cyclosporin A(CyP-CsA) (found by genetic methods) and the site for binding of AKAP79. See, for example, Liu et al. (1992) *Biochemistry* 31:3896-3901; and Faux et al. *JBC* 272: 17038. All three exhibit classical noncompetitive inhibition, suggesting a common mechanism. The suggested CaN-binding domain on AKAP79 is has high sequence similarity to residues 32-47 of FKBP12. It has also been found that a 22-residue peptide encompassing this FKBP12 sequence inhibits CaN by other than steric hindrance. Kawamura et al. (1995) *JBC* 270:15463.

Mutational studies of the b12/b 13 loop of yeast CaN results in CyP resistance, suggesting that these loops are important in binding the immunosuppressant complexes, and, perhaps, AKAP79. Wei and Lee recently showed that mutagenesis of the L7 loop (310-314+) connecting b-strands 12 and 13 has significant effects on activity. Wei et al. (1997) *Biochemistry* 36:7418. Both modification of the L7 loop and truncation of the C-terminus lead to the hyperactivitation of CaN. They also determined that the effects of mutation of the L7 loop are separable from the effects of deletion of the AID. Since mutations to L7 increase the catalytic efficiency of the enzyme towards pNPP, it must have something to do with changes in the active site. It is thought that CnA exists in a conformationally restrained state that is not completely relaxed by CnB and CaM. It has double inhibition to ensure that it only acts when needed. The mechanism of inhibition by AID is more than mere steric hindrance to binding.

One regulatory mechanism is that kinases and phosphatases are maintained at discrete cellular locations through their interaction with anchoring proteins. Enzymes may be positioned in close proximity to specific substrates, which then can be efficiently modified in response to the appropriate signals. Ser-Thr kinases and phosphatases are often maintained by scaffold proteins. In it's function in neuronal signaling, AKAP79 has been investigated in connection with CaN. Structural studies of CaN, AKAP79, and FKBP12 suggest that this regulation by inhibition is not merely by steric hindrance. Politino & King suggested in 1990 that it might function in membrane anchoring, from studies with phospholipid interactions (Politino et al. (1990) *JBC* 265:7619). Griffith has noted that other EF-hand superfamily proteins use Ca2+ as a switch, extruding the myristic acid upon Ca2+ binding to allow adherence to the cell membrane (Griffith et al. (1995) *Cell* 82:507).

There is an autoinhibitory domain (AID) at the carboxyl terminal of the CnA subunit. It lies over the substrate-binding channel of the catalytic domain. When CaN is auto-inhibiting, the CaM-binding domain, which is an amphipthic a-helix at the carboxyl terminus of the CnA, lies under the CnB-binding helix, linked at one end to the AID. This places the AID close to the active site where it could inhibit the binding of substrates and inhibitors. A Glu sidechain H-bonds with two of the metal-bound water molecules, sterically hindering substrate binding. See, for example, Stoddard et al. (1996) *Curr Opin Struct Biol.* 6:770. In human CaN this segment is Ser 469-Arg 486, with Glu 481-Arg-Met-Pro 484 making the most contact with the substrate-binding cleft. This segment consists of 2 short a-helical regions plus a 5-residue extension. It is missing from the bovine CaN-FKBP12-FK506 complex shown here.

Upon the addition of Ca2+, both CaM and CnB are activated. (Even without CaM, CnB confers some activation on CnA.) This activation apparently disrupts the interaction between CaM and the CnB-binding helix on CnA, moving the AID away from its inhibitory position(Barford D. (1996) *TIBS* 21:407)

The CnB-binding site on CnA is a long 22-residue a-helix. In 1995, Watanabe, et al. identified the CnB-binding helix as residues 328-390 (Watanabe et al. (1995) *JBC* 270:456). How CnB binds to CnA is very different from how CaM binds, even though they are very similar. The two domains of CnB can be superimposed by translation of 22 Å along the helix. The Kissinger structure of the human CaN structure (which is not yet available for download) has an additional CnA amino-terminal sequence that assists in CnB-binding. This sequence forms a part of the binding cleft for the carboxyl-terminal lobe of CnB. While there seems to be some conformational change in CnA upon the binding of CnB, it is not clear how the information is transmitted to the active site on the CnA subunit.

Klee et al. showed in 1988 that Ca2+/CaM activates CaN by increasing Vmax, whereas Ca2+ binding to CnB decreases Km and increases Vmax. See, for example, Klee et al. (1988) *Adv. Enzymol.* 61:149. Watanabe et al. in 1995 showed that the CnB-binding hydrophobic fragment is between the CaM-binding area and the active domain. This enabled Griffith to identify the subunit not present in the crystal structure to be the CaM-binding domain. Watanabe used a GST fusion protein expressed in Sf9 insect cells. A very highly conserved sequence on the CnA subunit was tested with site-directed mutagenesis, concluding that residues 349/350 and 356/357 Glu in the CnA are essential to binding CnB.

CaM and CnB apparently activate CnA by different but complimentary mechanisms. In the Kissinger structure, the predicted CaM-binding domain is quite disordered. It is thought to lie between residues 390-414. In contrast with CnB, CaM binds with the two domains on opposite sides of the helix related by a 2-fold rotation axis. Without that part of the crystal structure it would be interesting to model the interaction discussed in the literature. The primary sequence is available at Swiss-prot and adding the CaM-binding helix with the CaM docking might also help understand the mechanism of AKAP79-binding and cell localization better. For now, it is clear that how the myristoyl group is extruded by the coordinating structures is difficult to see since where the MYR group is linked to the CnB molecule is not definite.

CaN is not a huge protein, but it does offer great opportunities to observe the many ways such a small protein can exert broad influence. CaN is a heterodimer, with a 59-kDa CnA (catalytic) subunit and a 19-kDa CnB (regulatory) subunit. See, Cohen et al. (1989) *JBC* 264:21435.

At least 2 genes encoding isoforms of CnA have been identified from complimentary DNA cloning of the major catalytic subunit of CaN in mammalian brain. The a and b genes are localized on human chromosomes 4 and 10 respectively. A major difference between two isoforms was a long polyPRO helix (11 Pro) in b which may play a role in regulation (Zhuo et al. 1994) *JBC* 269:26234). The catalytic subunits of the other Ser-Thr phosphatases share the same gene family as CnA, sharing ~40% sequence identity. There is an additional isoform in mammalian CnA with 54% identity (CaNw) that is similar around the CaM-binding domain but may have a distinct substrate specificity.

Only 1 gene for CnB, located on human chromosome 2 has been found (Navia (1996) *Curr. Op. Struct. Bio.* 6:838). Kawamura et al. (1995) *JBC* 270:15463 shows the primary sequence structure of the binding site of the subunits of the heterodimer on CnA. It also shows the parts of the molecule not found on the Griffith structure (dCnA).

Various domains have been identified on the CaN subunits. A distorted b-sandwich motif forms the core of the globular part of the enzyme. It includes most of the active-site residues, the metal-coordinating residues, and an auto-inhibitory domain. This globular domain is approximately 35 Å×35 Å×45 Å. A motif on the edge of this b-sheet sandwich coordinates the metal ions necessary for activity. See 5Stoddard et al., (1996) supra.

The mechanism of calcineurin and the other Ser/Thr protein phosphatases depends on the divalent metal coordinating site. The core structure of the globular domain is a central distorted b-sandwich of 11 b-strands surrounded on one side by seven a-helices and on the other by 3 a-helices and a three-stranded b-sheet. A shallow catalytic channel is created by the interface of the two b-sheets. Three parallel b-strands of sheet 1 constitute a mononucleotide-binding domain with the secondary structure organization b-a-b-a-b. The three invariant sequence motifs form loops connecting the carboxyl terminus of the b-strand with a-helices (6 Goldberg et al. (1995) *Nature* 376:745). These loops, together with those emanating from the carboxyl terminus of two b-strands of the opposite b-sheet, provide the catalytic residues. $Zn^{2+}$ and $Fe^{3+}$ are coordinated in this active site.

$Zn^{2+}$ is coordinated by 1 Asn and 2 His side-chains. 2 Asp, 1 His, and 1 water coordinate $Fe^{3+}$. Both metals have a coordinating oxygen from a bound phosphate in the CaN Griffith structure. The metal ions are located 3 Å apart in the active site, and have an Asp side chain that acts as a monodentate-bridging ligand between the metals. The bound phosphate in the structure could represent the labile phosphate in the dephosphorylation reaction. It is stabilized by interactions with guanidinium groups of two Arg residues and with the Ne2 of a single His residue. See, Griffith et al. (1995) *Cell* 82:507.

The CnB-binding site is a long 22-residue a-helix (sometimes called the b-binding helix: BBH). It is linked to the globular portion of the molecule by a short linker sequence. The CaM-binding site and the auto-inhibitory sites are missing in this structure, cleaved before crystallography. From structures of CaM and protein kinase II, an amphipathic a-helix is posited for the CaM-binding area of the molecule. It is after the CnB-binding helix.

CnB has 2 EF-hand $Ca^{2+}$-coordinating domains. Each domain coordinates 2 $Ca^{2+}$ atoms. The EF-hand motif consists of 2 a-helices joined by a b-loop. In this way, CnB is very similar to CaM, except without the long linking a-helix (8 Griffith, et al. (1995), supra). At the carboxyl end of the CnB molecule is a 14-carbon myristoyl residue, which recent studies link with regulation and cell-localization. See, Politino et al. (1990) *JBC* 265:7619.

The mechanism of calcineurin and the other protein phosphatases depends on the divalent metal coordinating site. The metal ions activate water molecules to catalyze hydrolysis of the phosphate in a single-step reaction. The mechanism is as follows: a metal-bound water attacks the phosphorus at in an SN2 nucleophilic mechanism. The metals act as Lewis acids to make water more nucleophilic and phosphorous more electrophilic. Histidine donates a proton to the oxygen leaving group from the Ser or Thr side chain (Barford (1996) *TIBS* 21: 407)

This is supported by studies showing that CaN cannot catalyze transphosphorylation reactions. See, Guerini (1997) *Biochem. Biophys. Res. Comm.* 235:271. Extensive studies show that no intermediates have been identified and the reaction must occur in a concerted manner (Barford D. (1996), supra). In studies of other similar PPases, purple acid phosphatase-mediated catalysis occurs with inversion of configuration, supporting SN2. In addition, Martin & Graves showed a pH dependence to CaN-mediated catalysis of pNPP; at pH 9 Vmax dropped precipitously, indicating that a monoanion is preferred as a substrate (Martin et al. (1994) *Biochim. Et Bioph. Acta.* 1206:136)

The activation of CaN by $Mn^{2+}$ may be due to its substitution for $Zn^{2+}$ or $Fe^{3+}$. CaN is extremely similar to PP-1, which coordinates $Mn^{2+}$ and $Fe^{3+}$; Mn and Fe have similar atomic numbers See, Egloff et al. (1995) 254:942. However, according to Balinderan et al, ((1995) *Molecular and Cellular Biochemistry* 149/150:127 metal ions added to the solvent are probably responsible for a complex set of metal assisted equilibria and conformational transitions in CnA. In any case, this activation is most likely an artifact from in vitro studies.

As noted in discussing regulation, Wei and Lee recently showed that mutagenesis of the L7 loop (310-314+) connecting b-strands 12 and 13 has significant effects on activity. This clearly affects the active site, but how is not known. See, for example, Wei et al. (1997) *Biochemistry* 36, 7418-7424.

Figure 1:
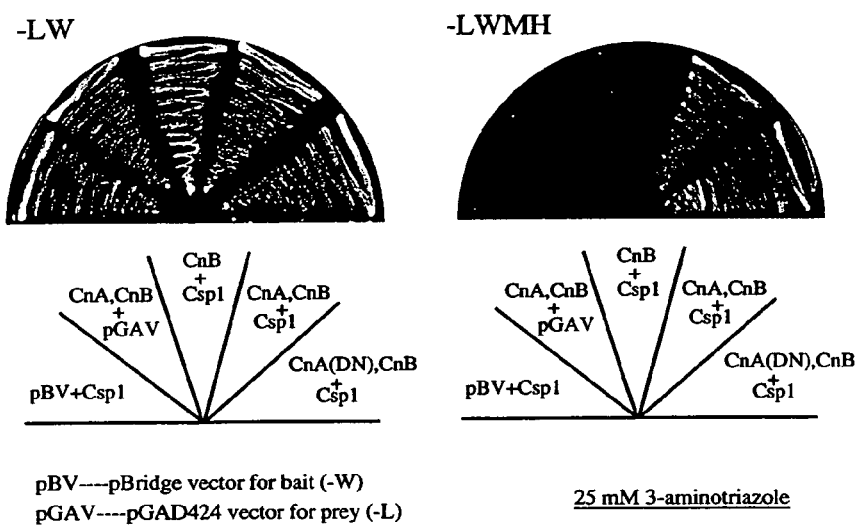
FIG. 1 Two-hybrid Screening for Calcineurin-Interacting Proteins in Hippocampus

1A. Alignment of Calcipressin Homologs: Primary amino acid sequences of Csp2 (Zaki-4) and Csp1 (DSCR1) homologs of human and mice are shown together with related sequences derived from hamster, worms, and yeast. Note that all sequences share a common, central motif LISPPxSP (SEQ ID NO: 46) as well as other sequence blocks suggesting the common origin of these genes. (SEQ ID NOs: 4-11). Murine Csp1 is the homolog of human DSCR1 and hamster Adapt78, while murine Csp2 is more closely related to human ZAK1-4. Csp homologs throughout the metazoan evolution were identified in a search of GenBank, including C. elegans, S. pombe, and S. cerevisiae.

1B. Interactions between calcineurin and calcipressins; Structure and characteristics of calcineurin subunits; Interaction analysis between calcipressins and calcineurin in the yeast two hybrid system. Left plate (-LW) shows permissive growth of all indicated strains harboring indicated baits (top line) including wildtype (WT) and mutant (DN) calcineurin catalytic subunits (CnA), calcineurin regulatory subunit (CnB), or empty vector (pBridge). The prey vectors (lower line) express murine Csp1 (Csp1) or lack an insert (pGAD). The right plate (-LWHM) shows strain growth dependent on interactions between calcineurin and Csp1.

FIG. 2 Csp1 and 2 Inhibit Calcineurin-Mediated NF-At Nuclear Import.

2A. Left panel, GFP-NF-AT4 is cytoplasmic in unstimulated BHK cells and translocates to the nucleus upon calcium ionophore treatment.

2A. Right panel, GFP-NF-AT4 coexpressed with Csp1 is cytoplasmic in the presence and absence of calcium ionophore.

2B. Right panel, GFP-NF-AT4 coexpressed with Csp2 is cytoplasmic despite calcium ionophore treatment.

2C. Csp 1 prevents calcineuring-induced NF-AT nuclear translocation. Constitutively active mutant of calcineurin, ΔCnA (HA-tagged)(red), GFP-NF-At4(green), and Mvc-tagged Csp1(Blue) were co-expressed in BHK cells. The proteins were visualized by immunofluorescence staining with Cy$_3$ (red) and Alexa (blue) conjugated secondary antibodies. Dynamin expression was used as a control in place of Csp1 (bottom panel).

FIG. 3 Calcipressin 1 Inhibits Calcineurin Phosphatase Activity In Vitro

3A. Schematic of in vitro calcineurin phosphatase assay using phosphorylated GsT-RII peptide. Free phosphate is quantitated by PhosphoImager.

3B. Csp1 and Csp2 Block Calcineurin-Dependent NF-AT Dephosphorylation. Myc-tagged NF-AT4 was expressed either alone or together with Csp1 and Csp2 in BHK cells. The transfected cells were either left untreated or treated with 1 μM calcium inonphore for 30 min, and the mobility of NF-AT4 was assessed by western blotting. The expression of Csp1 and 2 in the lysates was confirmed by western blot (bottom panel).

FIG. 4 Csp1 and 2 are potent inhibitors of calcineurin phosphatase activity.

4A. Csp 1 and 2-GST fusion proteins inhibit the dephosphorylation of the RII protein by purified calcineurin in vitro. GST-cyclophilin B(GST-CyB) was used as a control in the presence of 200 nM cyclosporin.

4B. Csp 1 and 2 efficiently block the hydrolysis of para-nitrophenylphosphate (PNPP) by purified calcineurin, whereas cyclophilin B in the presence of 200 nM cyclosporin A shows no inhibition of pNPP hydrolysis.

Figure 5:
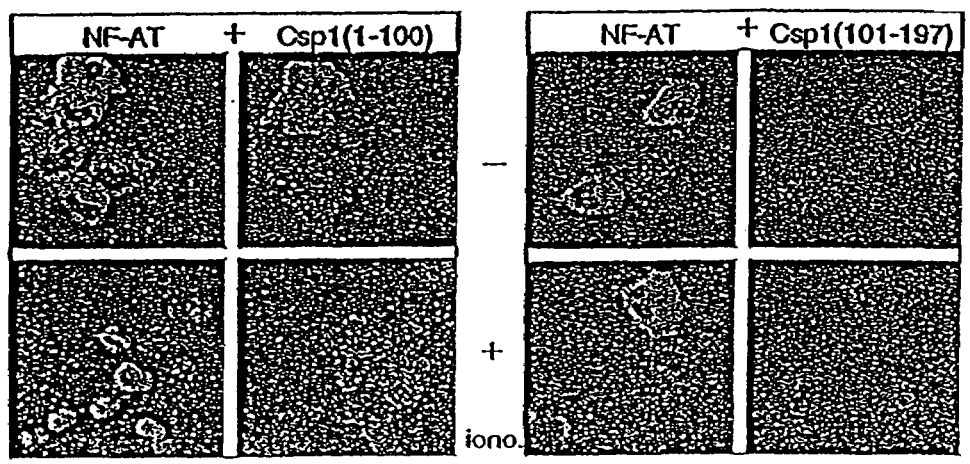

FIG. 5: Domains in Csp1 involved in calcineurin binding and inhibition.

5A. GST-fusions to indicated Csp1 deletion proteins were assayed for ability to bind 35S-labeled calcineurin A and B subunits produced by in vitro translation. Associated calcineurin subunits were detected and quantified by SDS-polyacrylamide gel electrophoresis and autoradiography. The same deletion mutants were co-expressed with GFP-NF-AT4 in BHK cells and assayed for their ability to block calcium ionophore-stimulated NF-AT4 nuclear import.

5B. Left panel, Csp1 lacking the C-terminal half (Csp1 1-100) fails to block calcium-activation NF-AT4 nuclear import.

Right panel, Csp1 lacking the N-terminus (Csp1 101-197) is sufficient to inhibit the nuclear import of NF-AT4 stimulated by calcium ionophore.

Figure 6:
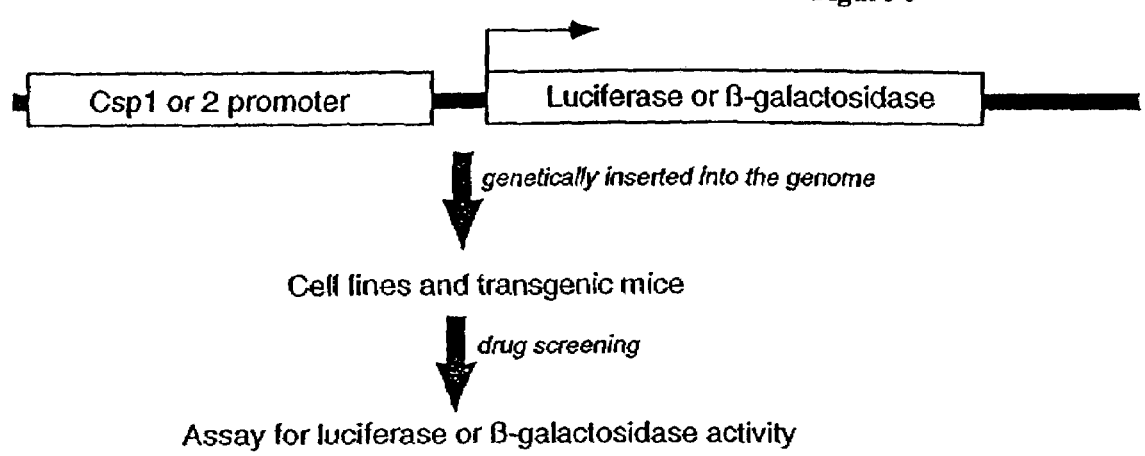

FIG. 6: Schematic of an assay to screen for drugs that modulate transcription from a Csp transcriptional nucleic acid.

Figure 7:
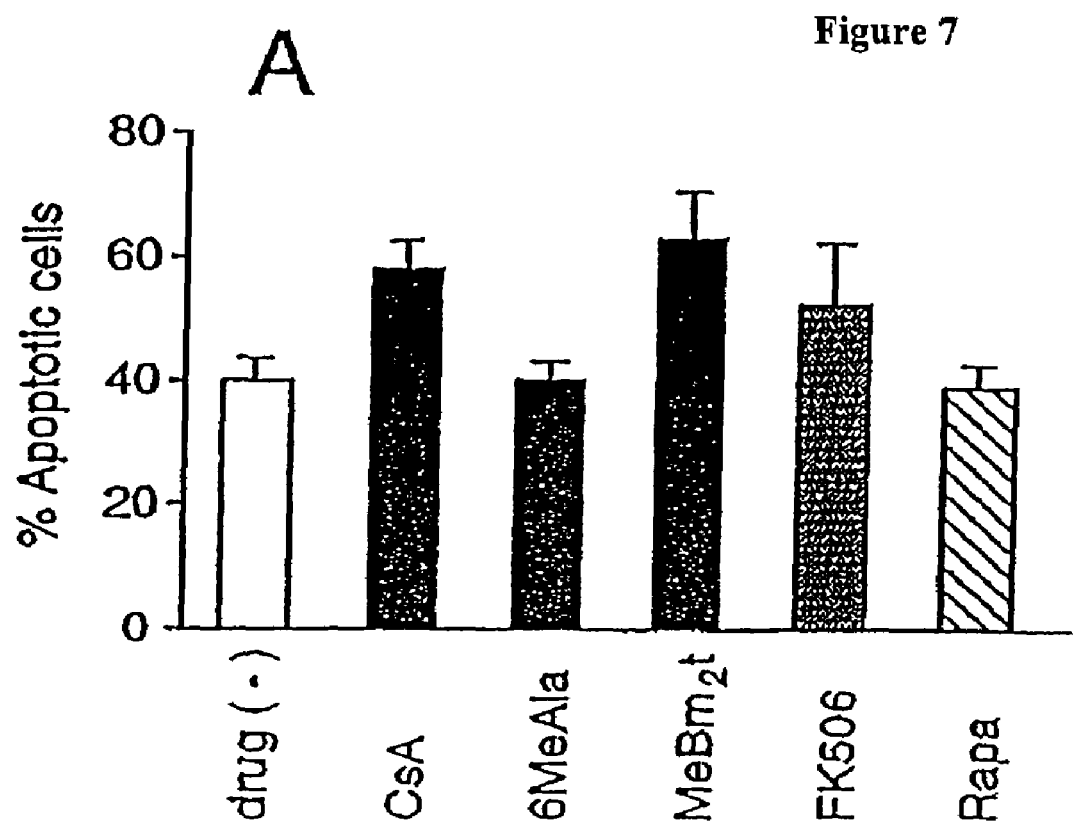

FIG. 7: Cells transfected with CnA/CnB (0.5 μg each) were serum deprived for four hours and stimulated with ionomycin (0.25 μM) for one hour in low serum media alone or containing CsA (800 nM), 6 MeAla-CsA (800 nM), and MeBm2t-CsA (800 nM), FK506 (100 nM).

Figure 8:
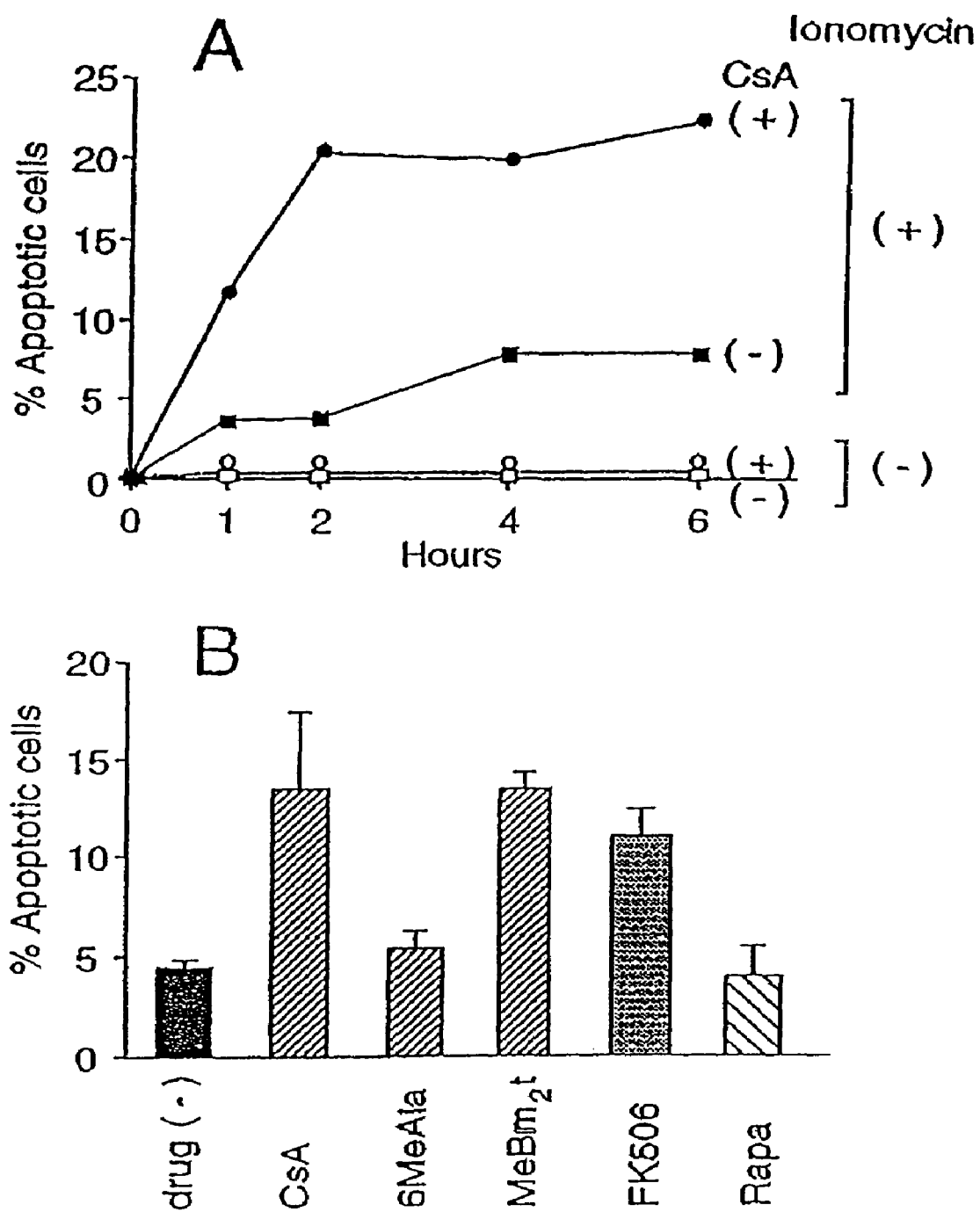

FIG. 8: Induction of Apoptosis in Non-Transfected BHK Cells by Immunosuppressants.

8A. Effect of immunosuppressants on non-transfected BHK cells stimulated by ionomycin. Normal BHK cells were preincubated with or without CsA (800 nM) in low serum medium (0.1% FCS) for four hours. They were then incubated in low serum media containing ionomycin (0.25 μM) alone (closed boxes), or with CsA (open circles), showed o toxicity over ten hours of serum deprivation. A total of 600 cells were scored for the apoptotic phenotype at each time point.

8B. Differential effect of immunosuppressants on induction of apoptosis on serum deprived BHK cells stimulated with ionomycin for one hour. Normal BHK cells were serum deprived for four hours in the presence of the indicated immunosuppressants. The cells were then exposed to ionomycin (0.25 μM) in low serum media together with the indicated immunosuppressants: CsA (800 nM), FK506 (100 nM), and Rapamycin (100 nM), respectively. The closed column shows cells stimulated by ionomycin in the absence of immunosuppressants. Vertical bars represent the standard deviation.

FIG. 9: Csp1 promoter sequence. (SEQ ID No: 1)
FIG. 10: Csp1 Coding sequence. (SEQ ID No: 2).
FIG. 11: Csp2 Coding sequence. (SEQ ID No: 3).
FIG. 12: Csp1 amino acid sequence. (SEQ ID No: 4).
FIG. 13: Csp2 amino acid sequence. (SEQ ID No: 5).
FIG. 14: Calcineurin-Dependent Nuclear Import and Dephosphorylation of NF-AT.

14A. GFP-NF-AT4, expressed in baby hamster kidney (BHK) cells, is localized cytoplasmically in resting cells but can be triggered by calcium ionophores to undergo nuclear import in a process lasting eight minutes. Upon washout of ionomycin or treatment with cyclosporin A, NF-At undergoes nuclear export in a process requiring 20 minutes.

14B. NF-AT dephosphorylation as a function of calcium signaling was monitored by western blots of lysates of cells treated with ionomycin for the indicated times. Upon ionomycin washout, NF-At rapidly returns to its phosphorylated, low mobility species.

FIG. 15. Csp Domains that Block Calcineurin Catalytic Activity.

15A. Alignment of Csp 1 RRPE motif with known calcineurin substrates (DARPP-32, phosphatase inhibitor-1, phosphorylase kinase, and RII subunit) and calcineurin auto-inhibitory motif (CnA-A1). The two conserved R residues are marked with (*). The phosphorylation site marked with a period (.) is conserved among calcineurin substrates. In CNA-AI, Csp1, and Csp2, the S/T residue is replaced by A, E, and G, respectively. (SEQ ID NOS: 15-21)

15B. Mutant Csp 1 lacking the RRPE motif fails to inhibit the hydrolysis of pNPPP by calcineurin in vitro whereas those lacking the LIS and ERM motifs are effective inhibitors of calcineurin towards the pNPP substrate.

FIG. 16. Induction of Csp 1 transcription by calcium and PMA.

16A. Calcium signaling induces Csp 1 expression in synergy with PKC pathways. Csp 1 Northern blot of Jurkat T cells were treated with either calcium ionophore (I), PMA (P) or both (I+P) for the indicated durations. GAPDH transcripts were used as sample loading control.

16B. Calcium-dependent Csp 1 induction requires calcineurin. Csp1 Northern blot of Jurkat T cells treated with calcium ionophore and PMA for the indicated durations in the presence and absence of cyclosporin A.

Figure 17:
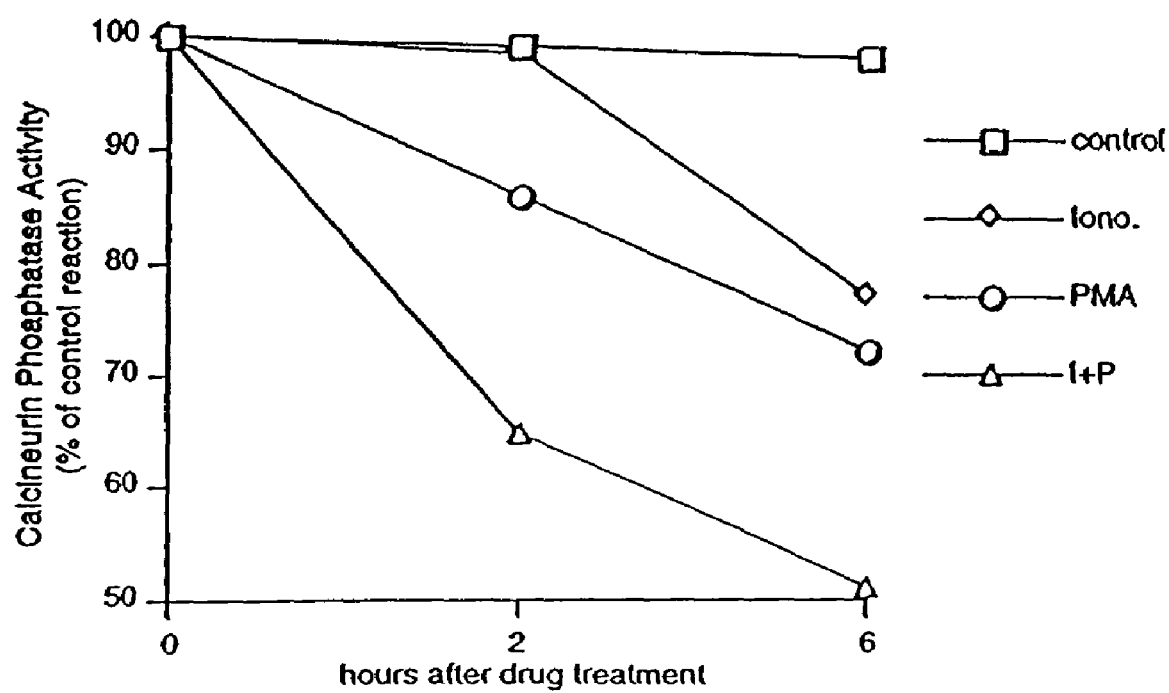

FIG. 17 Suppression of Calcineurin Activity during Prolonged Calcium Signaling. Analysis of total calcineurin activity in lysates of Jurkat cells stimulated with ionomycin, PMA, or both for the indicated durations. Activity was determined by dephosphorylation of a GsT-RII peptide previously phosphorylated by protein kinase A with 32P-ATP and expressed in relative units.

FIG. 18
Csp3 Coding Sequence
FIG. 19
Csp3 Coding Sequence Including the 5' and 3' UTR
FIG. 20
Csp3 Amino Acid Sequence
FIG. 21
Sequence Alignment of Csp3 with Csp1 and Csp2
FIG. 22

Shows that Csp3 inhibits Calcineurin mediated translocation of NFAT. Panel A demonstrates the cytoplasmic expression pattern of the transcription factor NFAT tagged with green fluorescent protein (GFP) in the absence of stimulus. Upon co-expression of calcineurin, NFAT shuttles into the nucleus as seen in panel B. Panel C demonstrates the cytoplasmic expression of NFAT in the presence of Csp3, suggesting inhibition of calcineurin activity by Csp3. Csp3 co-expression is demonstrated in Panel D by immunostaining with an anti-myc antibody to detect the myc-tagged Csp3 protein.

FIG. 23

Generation of anti-Csp2 and anti-Csp1 monoclonal antibodies 3F4A mAb was biotinylated and recognized cells transfected with both myc-tagged Csp2 (top panel) and Csp1 (bottom panel) as verified by immunostaining with a myc pAb.

FIGS. 24A and 24B
Genomic sequence of Csp1 (SEQ ID No: 25)
FIGS. 25A and 25B
Genomic sequence of Csp2 (SEQ ID No: 26)
FIGS. 26A and 26B
Genomic sequence of Csp3 (SEQ ID No: 27)
FIG. 27

Schematic representation of the Gene targeting vectors used to disrupt the Csp 1, -2, and -3 genes. The top portion of the schematic shows the organization of the Csp genes. The targeting vector used will replace exon 6 with the neomycin drug resistance genes. The exon contains the start of the inhibitory or C-terminal domain of all three genes which should effectively destroy the calcineurin inhibition activity. The genomic structure of all three genes is relatively similar with different size introns (15,116). Exons are denoted by the shaded boxes with numbers.

FIG. 28

Constructs used to generate tissue-specific expression of Csp1 in transgenic mice. The schematic shows the constructs injected into blastocysts to generate transgenic mice. Wild-type full length myc-tagged Csp 1 under the control of a myosin heavy chain (MHC) promoter will ensure cardiac specific expression. Similarly Csp1 with the sequence element, amino acids 188-191, "RRPE" deleted is also expressed under the MHC promoter. Myc-tagged wild type Csp1 and Csp1ΔΔRRPE are also expressed under the LCK promoter which will ensure T-cell specific expression.

SUMMARY OF THE INVENTION

The invention relates in part to the discovery of a family of endogenous inhibitors of calcineurin, called calcipressins herein, particularly Csp1, Csp2, and Csp3. The nucleic acid sequences encoding these calcipressins and the amino acid sequences of these polypeptides are disclosed herein as SEQ ID Nos: 2-5 and SEQ ID Nos:22-24. The genomic sequences of Csp1, Csp2, and Csp3 are designated SEQ ID Nos: 25-27

The present invention is also based in part on the discovery of nucleic acid sequences that can activate or regulate transcription of Calcipressin family of polypeptides, i.e, Csp1, Csp2, and Csp3. In preferred embodiments, the nucleic acids comprise a basic Csp promoter or an Csp regulatory element (e.g. transcription factor binding site). The nucleic acid sequence of the Csp1 promoter is represented in SEQ ID No: 1.

Accordingly, in one aspect, the invention features isolated Csp transcriptional nucleic acids and complements thereto. In one embodiment, the nucleic acid can hybridize to the transcriptional nucleic acids represented by SEQ ID No: 1 or to the complement of the regulatory nucleic acids represented by SEQ ID No: 1. In a preferred embodiment, the claimed nucleic acid can hybridize with at least a portion of the nucleic acid sequence provided as SEQ. ID. No: 1; or to at least a portion of the complement of the nucleic acid sequence designated as SEQ. ID. No.: 1.

The invention also provides probes and primers comprising substantially purified oligonucleotides, which hybridizes to at least 6, 10, 12, 15, 20, 25, 50, or 60 consecutive nucleotides of the sequence set forth as SEQ ID Nos: 1-3, SEQ ID Nos: 22-23, or SEQ ID Nos: 25-27 or to the complement thereof; or naturally occurring mutants thereof. In preferred embodiments, the probe/primer further includes a label group attached thereto, which is capable of being detected.

In one embodiment, the present invention makes available recombinant Csp polypeptides which are encoded by genes derived from vertebrate organisms, and which are capable of functioning as either an agonist of at least one biological activity of said Csp polypeptide or an antagonist of at least one biological activity of said Csp polypeptide. In one embodiment, the amino acid sequence of the subject Csp polypeptide is at least 80 percent identical to an amino acid sequence represented by SEQ ID. Nos. 4-5 or 24. In another embodiment, the amino acid sequence of the subject Csp polypeptide is at least 80 percent identical with an amino acid sequence selected from a group consisting of residues 123-130 of CSP1 and 153-160 of CSP2 (KQFLISPP (SEQ ID No: 12)); and residues 180-190 of CSP1 and 245-255 of CSP2

(PKPKINQTRRP (SEQ ID No: 13)) and residues 175-190 of Csp1 (ERMKRPKPKINQTRRP (SEQ ID No: 14)). In another embodiment, the amino acid sequence of the subject Csp polypeptide is at least 80 percent identical with an amino acid sequence selected from a group consisting of residues 101 to 197 of Csp 1, residue 150 to 197 of Csp, or residues 50 to 197 of Csp 1. In another embodiment, the polypeptide sequence is 90% identical with an amino acid sequence of SEQ ID Nos: 4-5, or SEQ ID No: 24, more preferably the polypeptide sequence is 95% identical and even more preferably the polypeptide sequence is 97-99% identical to the amino acid sequence of SEQ ID Nos: 4-5, or SEQ ID Nos: 24.

Nucleic acids which encode the Csp polypeptide and having at least about 90%, more preferably at least about 95%, and most preferably at least about 98-99% identity with a sequence of SEQ ID Nos: 2-3 or SEQ ID Nos: 22-23 are also within the scope of the invention.

Accordingly, one aspect of this invention pertains to isolated nucleic acids comprising nucleotide sequences encoding Csp polypeptides and fragments thereof having at least one biological activity of a Csp polypeptides, and/or equivalents of such nucleic acids. The term nucleic acid as used herein is intended to include such fragments and equivalents. The term equivalent is understanding to include nucleotide sequences encoding functionally equivalent Csp polypeptides or functionally equivalent peptides having an activity of a Csp polypeptides such as described herein.

The invention further describes vectors comprised of the disclosed nucleic acids i.e., Csp promoter sequences and nucleic acids encoding Csp polypeptides host cells transfected with said vectors whether prokaryotic or eukaryotic; and transgenic non-human animals which contain a heterologous form of a functional or non-functional Csp promoters as described herein. Such a transgenic animal can serve as an animal model for studying cellular and tissue disorders involving functional or non-functional Csp transcriptional nucleic acids or for use in drug screening or recombinant protein production.

This invention also provides expression vectors comprising a nucleotide sequence encoding the subject Csp polypeptides and operably linked to at least one heterologous regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of a Csp polypeptides. Accordingly, the term regulatory sequence includes promoters, enhancers and other expression control elements.

As will be apparent, the subject gene constructs can be used to cause expression of the subject Csp polypeptides in cells propagated in culture, e.g. to produce proteins or peptides, including fusion proteins or peptides, for purification.

In another aspect, the invention features pharmaceutical compositions comprised of molecules that modulate (agonize or antagonize) transcription from a Csp promoter, thereby activating, increasing, suppressing or decreasing the expression level of a gene under the control of the Csp transcriptional nucleic acids. In yet another embodiment, the invention includes pharmaceutical compositions comprised of molecules that modulate (agonize or antagonize) the biological activity of a Csp polypeptide, i.e., acts as immunosuppressants or immunostimulants. Particularly preferred molecules for use as pharmaceutical compositions are selected from the group consisting of: proteins, peptides, peptidomimetics, other small molecules (e.g. carbohydrates, lipids or small organic molecules) or nucleic acids (e.g. sense, antisense, ribozyme and triplex nucleic acid constructs).

In another aspect, the invention provides methods for treating a subject for a disease or condition, which is associated with (e.g., characterized, caused, or contributed to by) an aberrant Csp activity (e.g., insufficient or surplus functional Csp polypeptide or insufficient or surplus promoter activity), comprising administering to the subject an effective amount of a compound which is capable of modulating (agonizing or antagonizing) either the transcription from a Csp transcriptional nucleic acid, thereby activating, increasing, decreasing or suppressing the expression level of a gene under the control of the Csp transcriptional nucleic acid. For example, the compound can be an agonist of Csp transcriptional activity or an antagonist of Csp transcriptional activity. The compound can also be a compound that is capable of modulating an interaction between a basic promoter or a regulatory element and a transcription factor. Also within the scope of the invention are compounds used for modulating the activity of a transcription factor which itself modulates the activity of a Csp transcriptional nucleic acid. The invention also includes within its scope agonists and antagonists of the Csp polypeptides, which either mimic the biological activity of a Csp polypeptide or antagonize a Csp bioactivity.

Examples of diseases or conditions, which are associated with (e.g., characterized, caused, or contributed to by) an aberrant Csp activity, which affects calcium signaling, for example, broadly, these disorders include those conditions arising from one or more alterations in calcium regulating systems that result in a loss of cellular calcium homeostasis; accordingly, the Csp polypeptides may be used in treating various neurodegenerative disorders (for instance, Alzheimer's disease, Parkinsons, etc. in general, they act as neurotrophic or neuroprotective agents), autoimmune and/or inflammatory disorders (including systemic lupus erythematosus, Idiopathic Addison's disease, rheumatoid arthritis, lymphadenopathies, hemolytic anemias, purpura, spondylitis, multiple sclerosis, diabetes mellitus, psoriasis, Crohn's disease, and transplant rejection).

As will be apparent to the skilled artisan, antagonists of Csp polypeptides may be effective in ameliorating the pathogenic abnormalities of mental retardation and heart conditions associated with Downs Syndrome, antagonists will also be effective immunostimulants and may be effectively administered to immunocompromised hosts. Particularly preferred therapeutic molecules are selected from the group consisting of: proteins, peptides, peptidomimetics, other small molecules (e.g. carbohydrates, lipids or small organic molecules) or nucleic acids (e.g. sense, antisense, ribozyme and triplex nucleic acid constructs).

In yet another aspect, the invention provides assays for screening test compounds to identify molecules that modulate (agonize or antagonize) transcription from an Csp transcriptional nucleic acid, thereby activating, increasing, decreasing or suppressing the expression level of a gene under the control of the transcriptional nucleic acid. In one embodiment, the assay comprises: (i) combining a test compound with a functional reporter construct, wherein said reporter construct comprises a gene encoding a reporter molecule (e.g., luciferase) under the control of at least a basic Csp promoter and optionally also at least one regulatory element; and (ii) detecting the level of expression of the reporter gene, wherein a statistically significant change in the level of expression (relative to expression in the absence of the test compound) indicates that the test compound modulates (agonizes or antagonizes) transcription from an Csp promoter.

In another embodiment, the assay comprises of the steps of: (i) combining a Csp transcription factor with a test compound and a functional reporter construct comprising a gene encoding a reporter molecule (e.g. luciferase) under the control of the Csp basic promoter and at least one regulatory element, which is a binding site for the transcription factor; and (ii) detecting the level of expression of the reporter gene, wherein a statistically significant change in the level of expression (relative to expression in the absence of test compound) is indicative of a modulation of Csp promoter mediated gene expression.

A further aspect of the present invention provides a method for determining whether a subject has or is at risk for developing a disorder which is associated with (e.g. characterized, caused or contributed to by) an aberrant Csp activity. In a preferred embodiment, the disease or condition is caused by or contributed to by an inappropriate or aberrant (e.g. insufficient or surplus) calcipressin, calcineurin, and/or NF-AT concentrations. For example, very low level of calcipressins may be indicative of an increased risk for developing various autoimmune and/or inflammatory disorders. High levels of calcipressins may be associated with conditions associated with Down Syndrome.

In general, diagnostic methods of the invention can include detecting, in a tissue of the subject, the presence or absence of a genetic lesion characterized by at least one of: a deletion of one or more nucleotides from an Csp promoter or the nucleic acid encoding said Csp polypeptides; an addition of one or more nucleotides to an Csp promoter or the nucleic acid encoding said Csp polypeptides, or a substitution of one or more nucleotides in a Csp promoter or the nucleic acid encoding said Csp polypeptides. For example, detecting the genetic lesion can include (i) providing a probe/primer comprised of an oligonucleotide which hybridizes to an Csp promoter or the nucleic acid encoding said Csp polypeptides or naturally occurring mutants thereof; (ii) contacting the probe/primer with an appropriate nucleic acid containing sample; and (iii) detecting, by hybridization of the probe/primer to the nucleic acid, the presence or absence of the genetic lesion; e.g., wherein detecting the lesion comprises utilizing the probe/primer to determine the nucleotide sequence of the Csp promoter or the nucleic acid encoding said Csp polypeptides. For instance, the primer can be employed in a polymerase chain reaction (PCR) or in a ligation chain reaction (LCR).

Alternatively, the method can consist of determining the Csp mRNA or protein level in a subject and comparing that level to the mRNA or protein level determined for a normal subject, wherein a lower level of Csp mRNA or protein in the subject is indicative of a mutant Csp promoter or a mutant nucleic acid encoding said Csp polypeptides. The method can also include detecting chromosomal abnormalities, such as chromosomal rearrangements in the Csp gene.

Other features and advantages of the invention will be apparent from the following detailed description and claims.

DETAILED DESCRIPTION OF THE INVENTION

General

The present invention relates at least in part to the discovery of a family of endogenous calcineurin inhibitors, referred to herein as calcipressins. Included within the scope of this invention are Calcipressin 1 (Csp 1) and Calcipressin 2 (Csp 2). Calcineurin is a protein phosphatase implicated in a wide-range of calcium-dependent physiological processes including immune response, neuronal plasticity, muscle development, development of the heart, and apoptosis.

For instance, calcineurin plays a vital regulatory role in T-cell activation. Calcineurin activation leads to the rapid translocation of NF-AT family members from the cytoplasm to the nucleus. The NF-AT family of transcription factors are involved in the regulation of the early immune response genes. Beals et al., Genes and Dev. 11:824-834 (1997). Calcineurin mutants which are catalytically inactive are exclusively cytoplasmic and interfere with NF-AT translocation. In addition, immunosuppressive drugs such as CsA and FK506 inhibit calcineurin and block the nuclear localization of NF-ATs. The members of the calcipressins, Csp1 and Csp2 have also been shown as being potent inhibitors of calcineurin. Accordingly, in one aspect this invention provides endogenous immunosuppressive agents which do not present the problems faced when treating patients with CsA and/or FK506. For instance, high doses of CsA and FK506 are known to cause kidney damage.

Furthermore, CsA and FK506 act upon calcineurin by forming complexes with their intracellular receptors, cyclophilin and FKBP respectively. Therefore, the action of CsA and FK506 is dependent upon and limited by the cellular concentration of cyclophilin and FKBP. Accordingly, if the level of calcineurin in a cell exceeds the level of cyclophilin and FKBP these cells would be resistant to the action of CsA and FK506, even if these drugs were used at very high concentrations. Therefore, endogenous inhibitors disclosed herein and agonists which mimic their activity are potent immunosuppressive agents.

The sequences disclosed herein are summarized in the Table below:

TABLE 1

| Name of the Sequence | Sequence Identifier |
| --- | --- |
| Calcipressin 1 promoter | SEQ ID No: 1 |
| Calcipressin 1 (Nucleic acid sequence) | SEQ ID No: 2 |
| Calcipressin 2 (Nucleic acid Sequence) | SEQ ID No: 3 |
| Calcipressin 1 (Amino acid sequence) | SEQ ID No: 4 |
| Calcipressin 2 (Amino acid sequence) | SEQ ID No: 5 |
| Calcipressin 3 (Nucleic acid sequence) | SEQ ID Nos: 22-23 |
| Calcipressin 3 (Amino acid sequence) | SEQ ID No: 24 |
| Calcipressin 1 (Genomic sequence) | SEQ ID No: 25 |
| Calcipressin 2 (Genomic sequence) | SEQ ID No: 26 |
| Calcipressin 3 (Genomic sequence) | SEQ ID No: 27 |

DEFINITIONS

For convenience, the meaning of certain terms and agonist employed in the specification, examples, and appended claims are provided below.

The term "agonist", as used herein, is meant to refer to an agent that mimics or upregulates (e.g. potentiates or supplements) Csp bioactivity. A Csp agonist can be a wild-type Csp polypeptide or derivative thereof having at least one bioactivity of the wild-type Csp. A Csp agonist can also be a compound which increases at least one bioactivity of a Csp polypeptide. An agonist can also be a compound which increases the interaction of a Csp polypeptide with another molecule, e.g, a target peptide or nucleic acid.

"Antagonist" as used herein is meant to refer to an agent that downregulates (e.g. suppresses or inhibits) at least one Csp bioactivity. A Csp antagonist can be a compound which inhibits or decreases the interaction between a Csp polypeptide and another molecule, e.g., a target peptide, such as calcineurin. Accordingly, a preferred antagonist is a compound which increases translocation of NF-ATs to the nucleus and thereby acts as a immunostimulant.

The term "agonist of a Csp promoter", as used herein, is meant to refer to an agent (e.g. a transcription factor or enhancer molecule) that can directly or indirectly enhance, supplement or potentiate transcription from an Csp promoter. An agonist of the Csp promoter can also be any compound that upregulates expression of the Csp gene.

The term "antagonist of a Csp promoter", as used herein, is meant to refer to an agent (e.g., repressor) that directly or indirectly prevents or suppresses transcription from an Csp promoter. An antagonist can also be a compound that downregulates expression of the Csp gene or which reduces the amount of the Csp protein present.

"Cells", "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Complementary" sequences or "complements" as used herein refer to sequences which have sufficient complementarity to be able to hybridize under appropriate conditions to a specified nucleic acid, thereby forming a stable duplex.

The term "Csp activity" is intended to encompass any activity of an Csp polypeptide, such as those described in the previous paragraph, as well as activities which are mediated by Csp. Thus, Csp activity is intended to include binding activity, such as binding of a molecule, e.g., cacineurin to Csp. The term "aberrant Csp activity" or "abnormal Csp activity" is intended to encompass an activity of Csp which differs from the same Csp activity in a healthy subject. An aberrant Csp activity can result, e.g., from a mutation in the protein, which results, e.g., in lower or higher binding affinity of calcineurin to the mutated Csp. An aberrant Csp activity can also result from a lower or higher level of Csp polypeptide in cells, which can result, e.g., from a mutation in the Csp 5' flanking region of the Csp gene. Accordingly, an aberrant Csp activity can result from an abnormal Csp promoter activity.

The terms "abnormal Csp promoter activity" "aberrant Csp promoter activity", "abnormal Csp transcriptional activity" and "aberrant Csp transcriptional activity", which are used interchangeably herein, refer to the transcriptional activity of an Csp promoter which differs from the transcriptional activity of the same promoter in a healthy subject. An abnormal Csp activity can result from a higher or lower transcriptional activity than that in a healthy subject. An aberrant Csp promoter activity can result, e.g., from the presence of a genetic lesion in a promoter region, such as in a regulatory element located in the promoter. An "aberrant Csp promoter activity" is also intended to refer to the transcriptional activity of an Csp promoter which is functional (capable of inducing transcription of a gene to which it is operably linked) in tissues or cells in which the "natural" or wild-type Csp promoter is not functional or which is non functional in tissues or cells in which the "natural" or wild-type Csp promoter is non-functional. Thus, a tissue distribution of Csp in a subject which differs from the tissue distribution of Csp in a "normal" or "healthy" subject, can be the result of an abnormal transcriptional activity from the Csp promoter region. Such an abnormal transcriptional activity can result, e.g., from one or more mutations in a promoter region, such as in a regulatory element thereof. An abnormal transcriptional activity can also result from a mutation in a transcription factor involved in the control of Csp gene expression.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g., ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As used herein, the term "gene" or "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

As used herein, the term "transcriptional nucleic acid" refers to a nucleic acid that activates and/or regulates expression of a selected DNA sequence operably linked to the transcriptional nucleic acid, and which effects expression of the selected DNA sequence in cells. The term "5'flanking sequence" can include transcriptional nucleic acids, but is intended to refer more generally to any nucleic acid sequence located upstream of the transcription initiation site. Thus, a "5'flanking sequence" of an Csp gene is intended to include any nucleic acid sequence located upstream of the transcription initiation site whether or not it may have any transcriptional activity. The term "basic promoter" as used herein is intended to refer to the minimal transcriptional nucleic acid that is capable of initiating transcription of a selected DNA sequence to which it is operably linked. The term "basic promoter" is intended to represent a promoter element providing basal transcription. A basic promoter frequently consists of a TATA box or TATA-like box and is bound by an RNA polymerase and by numerous transcription factors, such as Tfs and TATA box Binding Proteins (TBPs)

A "regulatory element", also termed herein "regulatory sequence" or "regulatory element" is intended to include elements which are capable of modulating transcription from a basic promoter and include elements such as enhancers and silencers. The term "enhancer", also referred to herein as "enhancer element", is intended to include regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. Regulatory elements can also be present in genes other than in 5' flanking sequences. Thus, it is possible that Csp genes have regulatory elements located in introns, exons, coding regions, and 3' flanking sequences. Such regulatory elements are also intended to be encompassed by the present invention and can be identified by any of the assays that can be used to identify regulatory elements in 5' flanking regions of genes, such as those described herein.

The terms "basic promoter" and "regulatory element" further encompass "tissue specific" promoters and regulatory elements, i.e., promoters and regulatory elements which effect expression of the selected DNA sequence preferentially in specific cells (e.g., cells of a specific tissue). Gene expression occurs preferentially in a specific cell if expression in this cell type is significantly higher than expression in other cell types. The terms "promoter" and "regulatory element" also encompass so-called "leaky" promoters and "regulatory elements", which regulate expression of a selected DNA primarily in one tissue, but cause expression in other tissues as well. The terms "promoter" and "regulatory element" also encompass non-tissue specific promoters and regulatory elements, i.e., promoters and regulatory elements which are active in most cell types. Furthermore, a promoter or regulatory element can be a constitutive promoter or regulatory element, i.e., a promoter or regulatory element which constitutively regulates transcription, as opposed to a promoter or regulatory element which is inducible, i.e., a promoter or regulatory element which is active primarily in response to a stimulus. A stimulus can be, e.g., a molecule, such as a hormone, for example a thyroid hormone, hydrogen peroxide, a metal cation, for example calcium cations, a cytokine, phorbol esters, cyclic AMP (cAMP), or retinoic acid.

Regulatory elements are typically bound by transcription factors. The term "transcription factor" is intended to include proteins or modified forms thereof, which interact preferentially with specific nucleic acid sequences, i.e., regulatory elements, and which in appropriate conditions stimulate or repress transcription. Some transcription factors are active when they are in the form of a monomer. Alternatively, other transcription factors are active in the form of a dimer consisting of two identical proteins or different proteins (heterodimer). Modified forms of transcription factors are intended to refer to transcription factors having a post-translational modification, such as the attachment of a phosphate group. The activity of a transcription factor is frequently modulated by a post-translational modification. For example, certain transcription factors are active only if they are phosphorylated on specific residues. Alternatively, transcription factors can be active in the absence of phosphorylated residues and be inactivated by phosphorylation.

Additional transcription factors that may bind to and/or regulate the human Csp promoter can be identified, for example, from known transcription factors and the sequences to which they bind. One such database, the "Transcription Data Base", is available from the National Library of Medicine.

A nucleic acid can be transcribed from a promoter to which it is operably linked. The term "operably linked" is intended to mean that the promoter is associated with the nucleic acid in such a manner as to facilitate transcription of the nucleic acid from the promoter.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "interact" as used herein is meant to include detectable interactions between molecules, such as can be detected using, for example, a yeast two hybrid assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "lipid" shall refer to a fat or fat-like substance that is insoluble in polar solvents such as water. Including true fats (e.g. esters of fatty acids and glycerol); lipids (phospholipids, cerebrosides, waxes); sterols (cholesterol, ergosterol) and lipoproteins (e.g. HDL, LDL and VLDL).

The term "modulation" as used herein refers to both upregulation, (i.e., activation, enhancement or stimulation), for example by agonizing; and downregulation (i.e. inhibition or suppression), for example by antagonizing of a bioactivity (e.g. expression of a gene).

The "non-human animals" of the invention include mammals such as rodents, non-human primates, sheep, goats, horses, dogs, cows, chickens, or amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The term "chimeric animal" is used herein to refer to animals in which an exogenous sequence is found, or in which an exogenous sequence is expressed in some but not all cells of the animal. The term "tissue-specific chimeric animal" indicates that an exogenous sequence is present and/or expressed or disrupted in some tissues, but not others.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides.

The terms "protein", "polypeptide" and "peptide" are used interchangeably herein when referring to a gene product.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention.

As used herein, the term "specifically hybridizes" or "specifically detects" refers to the ability of a nucleic acid molecule of the invention to hybridize to at least approximately 6, 12, 20, 30, 40, 50, 60, 70, 80, 90, 100, 110, 120, 130 or 140 consecutive nucleotides of an Csp promoter or the nucleic acid encoding said Csp polypeptides or a sequence complementary thereto.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, or an antisense transcript, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). Alternatively, a transgene can also be present in an episome. A transgene can include one or more transcriptional regulatory sequences and any other nucleic acid, (e.g. intron), that may be necessary for optimal expression of a selected nucleic acid.

A "transgenic animal" refers to any animal, preferably a non-human animal, e.g. a mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of a protein, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Nucleic Acids of the Present Invention

As described below, one aspect of the invention pertains to isolated transcriptional nucleic acids selected from the group consisting of a nucleic acid having SEQ ID NO: 1, functional fragments thereof, Csp basic promoters, Csp regulatory elements, equivalents to any of these nucleic acids, and complements to any of these nucleic acids. The invention also pertains to nucleic acids capable of hybridizing to the complement of the nucleic acid sequence shown in SEQ ID NO: 1. Also within the scope of the invention are nucleic acids which are homologous, e.g., 80% homologous to any of the above-recited nucleic acids and in a preferred embodiment, the nucleic acid sequence is at least 85%, 90% or 98-99% identical to any of the above recited nucleic acid molecules. Accordingly, the invention provides nucleic acids which are capable of functioning as a promoter and nucleic acids which are capable of functioning as regulatory elements. A "functional" fragment of a transcriptional nucleic acid as used herein is a nucleic acid fragment capable of modulating transcription of a gene operably linked to the fragment. Thus, a "functional fragment" of a transcriptional nucleic acid is intended to include nucleic acids capable of functioning as a promoter or as a regulatory element in appropriate conditions. The term equivalent of a nucleic acid is understood to include nucleic acids which differ by one or more nucleotide substitutions, additions or deletions from the nucleic acid and which has a similar activity as the transcription nucleic acid of SEQ ID No: 1.

In another aspect, nucleic acids from vertebrate genes encoding Csp polypeptides are described herein. Particularly preferred vertebrate nucleic acids are mammalian nucleic acids. A particularly preferred nucleic acid of the invention is a mouse nucleic acid, such as a nucleic acid having SEQ ID Nos: 2-3, SEQ ID Nos: 22-23, or SEQ ID Nos: 25-27 or a portion thereof. Regardless of species, particularly preferred nucleic acids are at least 80%, 85% 90%, 95% or 99% similar or identical to the nucleic acids shown in any of SEQ ID Nos: 2-3, SEQ ID Nos: 22-23, or SEQ ID Nos: 25-27.

As discussed above, identity can be determined by comparing a position in each sequence which may be aligned for purposes of comparison. When a position in the compared sequence is occupied by the same base or amino acid, then the molecules are identical at that position. A degree of identity between sequences is a function of the number of matching or identical positions shared by the sequences. Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Accordingly, a preferred embodiment of the invention encompasses isolated nucleic acid molecules having a nucleotide sequence corresponding to at least a portion of the nucleic acid of SEQ ID NO: 1. In an even more preferred embodiment of the invention, the isolated nucleic acid comprises a nucleotide sequence corresponding to a functional portion or fragment of the nucleic acid of SEQ ID NO: 1, such that upon operably linking such a nucleic acid fragment to a second nucleic acid capable of being transcribed, the second nucleic acid can be transcribed. The functional portion of the nucleic acid, which can have the activity of a promoter or a regulatory element, can be a portion of the nucleic acid which provides tissue specific expression. A preferred portion of the nucleic acid, such as those represented in SEQ ID No: 1 provides tissue specific expression substantially similar to the tissue distribution of Csp. Accordingly, a preferred portion of a nucleic acid having SEQ ID NO: 1 is a portion which modulates transcription preferentially in the brain and heart. However, portions of a nucleic acid which modulate transcription in only some of these tissues, or tissues other than the brain or heart are also within the scope of the invention. In fact, it is likely that tissue specificity is determined by several regulatory elements in the Csp promoter. Accordingly, a portion of the promoter may modulate transcription only in certain tissues. Similarly, portions of the nucleic acid having SEQ ID NO: 1, which constitutively enhance or suppress transcription are also within the scope of the invention. Additional preferred portions of an Csp promoter include those which contain an inducible element.

In one aspect, the Csp promoters or regulatory elements disclosed herein are inducible in the presence of an external stimulus. This stimulus may be a hormone such as a thyroid hormone, a cation such as a calcium cation, hydrogen peroxide, cis (II) platinum, a heavy metal, phorbol esters, cAMP, or retinoic acid.

Other preferred nucleic acids of the invention are nucleic acids corresponding to one or more discrete regulatory elements, such as enhancers and silencers. Particularly preferred nucleic acids contained in nucleic acid having SEQ ID NO: 1. Accordingly, isolated nucleic acids of the invention also encompass those which do not contain a basic promoter. As set forth above, nucleic acids comprising one or more regulatory elements can provide tissue specific expression, including tissue specific expression other than that of the "natural" Csp gene, and/or can provide constitutive enhancement or suppression of transcription, or inducible enhancement or suppression of transcription.

Thus, in one embodiment of the invention, an isolated nucleic acid deriving from an Csp promoter comprises a nucleic acid sequence from about nucleic acid residue 1480 to about nucleic acid residue 1500 of SEQ ID NO: 1. Other preferred isolated nucleic acids comprise a nucleic acid sequence from about nucleic acid residue 1941 to about nucleic acid residue 1960, from about nucleic acid residue 1551 to about nucleic acid residue 1570, from about nucleic acid residue 1890 to about nucleic acid residue 1910, from about nucleic acid residue 400 to about nucleic acid residue 1595, of SEQ ID NO: 1.

Any nucleic acid fragment of the invention can be prepared according to methods well known in the art and described, e.g., in Sambrook, J. Fritsch, E. F., and Maniatis, T. (1989) *Molecular Cloning: A Laboratory Manual*, Cold Spring Harbor Laboratory Press, Cold Spring Harbor, N.Y. For example, discrete fragments of the promoter can be prepared and cloned using restriction enzymes. Alternatively, discrete fragments can be prepared using the Polymerase Chain Reaction (PCR) using primers having an appropriate sequence, such as a sequence in SEQ ID NO: 1. The activity of promoter fragments can then be tested, for example, in vitro in transfection assays or in vivo in transgenic animals as described herein.

Also within the scope of the invention are nucleic acids which are homologues or equivalents of the above-described nucleic acids.

In yet another embodiment of the invention, the isolated nucleic acid comprises a nucleic acid sequence of SEQ ID NO: 1 or portion thereof which has been modified, e.g., by adding, deleting, or substituting one or more nucleic acid residues. Such modifications can modulate the transcriptional activity of the Csp promoter or regulatory element. For example, a modification can increase or decrease the activity of a promoter or regulatory element. A modification can also affect the tissue specificity of a promoter or regulatory element. Thus, for example, an Csp promoter or regulatory element can be modified to stimulate transcription in only one of the tissues in which it is normally expressed. An Csp promoter or regulatory element can also be modified to be inducible by a desired drug, for example by creating in the sequence a site that is inducible by the specific drug.

Desired modifications of an Csp promoter or regulatory element can be performed according to methods well known in the art, such as by mutagenesis. The activity of the modified promoter or regulatory element can then be tested, e.g., by cloning the modified promoter upstream of a reporter gene, transfecting the construct and measuring the level of expression of the reporter construct. The activity of the modified promoter or regulatory element can also be analyzed in vivo in transgenic animals. It is also possible to create libraries of modified fragments which can be screened using a functional assay, in which, for example, only modified promoters or regulatory elements having the desired activity are selected. These assays can be based, e.g., on the use of reporter genes providing resistance to specific drugs, e.g., G418. Selection of cells having a reporter construct containing a promoter or regulatory element having the desired modification can be isolated by culture in the presence of the drug.

Another aspect of the invention provides a nucleic acid which hybridizes under stringent conditions to the nucleic acid shown in SEQ ID No: 1 or complement thereof. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a preferred embodiment, a nucleic acid of the present invention will bind to SEQ ID No. 1 under moderately stringent conditions, for example at about 2.0×SSC and about 40° C. In a particularly preferred embodiment, a nucleic acid of the present invention will bind to SEQ ID No: 1 or complement thereof under high stringency conditions.

In one embodiment, the invention provides nucleic acids which hybridize under low stringency conditions of 6×SSC at room temperature followed by a wash at 2×SSC at room temperature.

In another embodiment, the invention provides nucleic acids which hybridize under high stringency conditions of 2×SSC at 65° C. followed by a wash at 0.2×SSC at 65° C.

In yet another aspect of the invention provides a nucleic acid which hybridizes under stringent conditions to the nucleic acid shown in SEQ ID Nos: 2-3, 22-23, or 25-27 or complement thereof.

In one embodiment, the invention provides nucleic acids which hybridize under low stringency conditions of 6×SSC at room temperature followed by a wash at 2×SSC at room temperature.

In another embodiment, the invention provides nucleic acids which hybridize under high stringency conditions of 2×SSC at 65° C. followed by a wash at 0.2×SSC at 65° C.

Hybridization can be used to isolate nucleic acids corresponding to 5' flanking regions of Csp genes from various animal species. A comparison of these nucleic acids should be indicative of regions involved in the regulation of expression of the Csp gene, since these regions are expected to be conserved among various species.

Also within the scope of the invention are nucleic acids comprising an Csp promoter or regulatory element, e.g, having a nucleotide sequence of SEQ ID NO: 1, operably linked to a nucleic acid to be transcribed. The Csp promoter or regulatory element can be, e.g., any nucleic acid fragments having a sequence from SEQ ID No: 1, or modified form thereof. The Csp promoter can also be a combination of several fragments or regulatory elements having a sequence from SEQ ID NO: 1 or modified form thereof, as well as multimers of one or more of these fragments or regulatory elements or modified form thereof. The promoter can also contain regulatory elements derived from other genes.

In one embodiment, the nucleic acid to be transcribed encodes a protein or peptide. The protein can be any protein useful in gene therapy, including, but not limited to, cytokines, structural proteins, receptors, transcription factors. In a preferred embodiment, the protein to be expressed is Csp. In another embodiment, the nucleic acid is transcribed into a nucleic acid which is antisense to a desired nucleic acid sequence. Expression of antisense nucleic acids can be used, e.g., to reduce or inhibit translation of a mRNA into a specific protein. In a specific embodiment, the antisense molecule hybridizes to the Csp gene and reduces or inhibits expression of the Csp gene. Such methods are also useful in gene therapy methods.

In yet another embodiment, the nucleic acid to be transcribed from an Csp promoter, fragment or modified form thereof, is a reporter gene. Reporter genes include any gene encoding a protein, the amount of which can be determined. Preferred reporter genes include the luciferase gene, the beta-galactosidase gene (LacZ), the chloramphenicol acetyl transferase (CAT) gene, or any gene encoding a protein providing resistance to a specific drug.

A preferred nucleic acid containing a nucleic acid to be transcribed under the control of an Csp promoter or regulatory element comprises a nucleic acid having SEQ ID NO: 1 operably linked to the bacterial luciferase gene, e.g., the luciferase gene present in pGL3-basic. Another preferred nucleic acid of the invention comprises a nucleic acid having SEQ ID NO: 1 operably linked to the bacterial beta-galactosidase gene (LacZ). Yet another preferred nucleic acid comprises a nucleic acid having SEQ ID NO: 1 operably linked to a "Neo" gene providing resistance to the drug G418.

The nucleic acid to be transcribed can be operably linked to an Csp promoter, fragment or modified form thereof using methods well known in the art.

Vectors.

This invention also provides expression vectors comprised of the instant described nucleic acids operably linked to a nucleic acid to be transcribed, e.g., a gene. In one embodiment, the expression vector includes a recombinant gene encoding an Csp receptor. Such expression vectors can be used to transfect cells and thereby produce protein. Moreover, the gene constructs of the present invention can also be used as a part of a gene therapy protocol to deliver nucleic acids in vitro or in vivo. Thus, another aspect of the invention features expression vectors for in vivo or in vitro transfection and expression of genes in particular cell types (e.g. heart, brain).

A preferred approach for in vivo introduction of nucleic acid into a cell is by use of a viral vector containing nucleic acid, e.g. a cDNA, under the control of an Csp promoter or regulatory element. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) and promoter and/or regulatory elements have been replaced by nucleic acid comprising an Csp promoter or regulatory element and a nucleic acid encoding a protein of choice, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, including hepatic cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254: 1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079-9083; Julan et al. (1992) *J Gen Virol* 73:3251-3255; and Goud et al. (1983) *Virology* 163:251-254); or coupling cell surface receptor ligands to the viral env proteins (Neda et al. (1991) *J Biol Chem* 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Another viral gene delivery system useful in the present invention utilizes adenovirus-derived vectors. The genome of an adenovirus can be manipulated such that it encodes and expresses a gene product of interest under the control of an Csp promoter or regulatory element, but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109-127).

Yet another viral vector system useful for delivery of a gene under the control of an Csp promoter or regulatory element thereof is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In a representative embodiment, a gene under the control of an Csp promoter or regulatory element can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075). For example, lipofection of cells can be carried out using liposomes tagged with monoclonal antibodies against any cell surface antigen present on an hepatic cell, such as an asialoglycoprotein receptor.

In addition to viral transfer methods, such as those illustrated above, non-viral methods can also be employed to cause expression of a gene, which is under the control of a subject promoter in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of genes by the targeted cell. Exemplary targeting means of this type include liposomal derived systems, poly-lysine conjugates, and artificial viral envelopes.

Probes and Primers

Moreover, the Csp promoter nucleic acid sequences and Csp nucleic acid sequences encoding the Csp polypeptides provide for the generation of probes and primers which can be used, e.g., in diagnostic assays. For instance, the present invention also provides a probe/primer comprising a substantially purified oligonucleotide, which oligonucleotide comprises a region of nucleotide sequence that hybridizes under stringent conditions to at least approximately 6, 8, 10 or 12, preferably about 25, 30, 40, 50 or 75 consecutive nucleotides of SEQ ID Nos: 1-3, 22-23, or 25-27.

In preferred embodiments, the probe further comprises a label attached thereto, which is capable of being detected, e.g. the label group is selected from amongst radioisotopes, fluorescent compounds, enzymes, and enzyme co-factors.

As discussed in more detail below, such probes can also be used as a part of a diagnostic test kit, for example, to detect mutations in these sequences.

Antisense and Triplex Techniques

Another aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, to a nucleic acid, such as an RNA or an Csp transcriptional nucleic acid, so as to suppress translation of the RNA or initiation of gene transcription, respectively. Antisense molecules can be used, e.g., in gene therapy methods in which inhibition of production of a gene product is desired. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the Csp nucleic acid sequences, such as the Csp transcriptional nucleic acids. Alternatively, the antisense construct is an oligonucleotide probe which is generated ex vivo and which, when introduced into the cell suppresses the initiation of expression from an Csp promoter. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958-976; and Stein et al. (1988) *Cancer Res* 48:2659-2668.

Accordingly, in one aspect, antisense nucleotide sequences are useful in preventing or diminishing the expression of the Csp locus, as will be appreciated by those skilled in the art. For example, polynucleotide vectors containing all or a portion of the Csp locus or other sequences from the Csp region (particularly those flanking the Csp locus) may be placed under the control of a promoter in an antisense orientation and introduced into a cell. Expression of such an antisense construct within a cell will interfere with Csp transcription and/or translation and/or replication.

Thus, another aspect of the invention relates to the use of the isolated nucleic acid in "antisense" therapy. As used herein, "antisense" therapy refers to administration or in situ generation of oligonucleotide probes or their derivatives which specifically hybridize (e.g. binds) under cellular conditions, with the cellular mRNA and/or genomic DNA encoding a subject Csp polypeptide so as to inhibit expression of that protein, eg.e. by inhibiting transcription and/or translation.

Antisense approaches involve the design of oligonucleotides (either DNA or RNA) that are complementary, e.g., to portions of an RNA molecule or to portions of Csp nucleic acid (e.g. portions to which a transcriptional regulatory molecule binds). The RNA molecule can be, e.g., transcribed from a gene encoding a transcriptional regulatory molecule of a Csp promoter or regulatory element, such that antisense oligonucleotide binding prevents or suppresses the production of transcription factors, resulting in inhibition of transcription from the Csp promoter. Absolute complementarity, although preferred, is not required. A sequence "complementary" to a portion of a nucleic acid, as referred to herein, means a sequence having sufficient complementarity to be able to hybridize with the nucleic acid, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to inhibit the activation of gene expression. It is preferred that these studies utilize controls that distinguish between antisense gene inhibition and nonspecific biological effects of oligonucleotides. It is also preferred that these studies compare levels of the target protein with that of an internal control protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, *BioTechniques* 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an anomeric oligonucleotide. An anomeric oligonucleotide forms specific double-stranded hybrids with complementary RNA in which, contrary to the usual units, the strands run parallel to each other (Gautier et al., 1987, *Nucl. Acids Res.* 15:6625-6641). The oligonucleotide is a 2'-0-methylribonucleotide (Inoue et al., 1987, *Nucl. Acids Res.* 15:6131-6148), or a chimeric RNA-DNA analogue (Inoue et al., 1987, *FEBS Lett.* 215:327-330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448-7451), etc.

The antisense molecules should be delivered to cells containing an Csp promoter. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

A preferred approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology using methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpes virus vectors may be used), in which case administration may be accomplished by another route (e.g., systematically). Vectors which can be used are further described above in the section entitled "Vectors".

Targeted homologous recombination can also be used to "knock out" the ability of an Csp promoter to initiate gene transcription (e.g., see Smithies et al., 1985, Nature 317:230-234; Thomas & Capecchi, 1987, Cell 51:503-512; Thompson et al., 1989 Cell 5:313-321; each of which is incorporated by reference herein in its entirety). For example, a completely unrelated DNA sequence flanked by DNA homologous to the endogenous Csp promoter can be used, with or without a selectable marker and/or a negative selectable marker, to transfect cells that contain the Csp promoter in vivo. Insertion of the DNA construct, via targeted homologous recombination, results in inactivation of the Csp promoter. Such approaches are particularly suited in non-human animals where modifications to ES (embryonic stem) cells can be used to generate animal offspring with an inactive Csp promoter (e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, gene expression from an Csp promoter can be reduced or suppressed by targeting deoxyribonucleotide sequences complementary to the Csp promoter to form triple helical structures that prevent transcription of the gene in target cells in the body. (See generally, Helene, C. 1991, Anticancer Drug Des., 6(6):569-84; Helene, C., et al., 1992, Ann, N.Y. Acad. Sci., 660:27-36; and Maher, L. J., 1992, Bioassays 14(12):807-15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Antisense RNA and DNA and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2'O-methyl rather than phosphodiesterase linkages within the oligodeoxyribonucleotide backbone.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of routes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

Polypeptides of the Present Invention

The present invention makes available isolated Csp polypeptides which are isolated from, or otherwise substantially free of other cellular proteins. The term "substantially free of other cellular proteins" (also referred to herein as "contaminating proteins") or "substantially pure or purified preparations" are defined as encompassing preparations of Csp polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred Csp proteins of the invention have an amino acid sequence which is at least about 60%, 70%, 80%, 85%, 90%, or 95% identical or homologous to an amino acid sequence of SEQ ID NOs. 4-5 or 24. Even more preferred Csp proteins comprise an amino acid sequence which is at least about 97, 98, or 99% homologous or identical to an amino acid sequence of SEQ ID NOs. 4-5 or 24. Such proteins can be recombinant proteins, and can be, e.g., produced in vitro from nucleic acids comprising a nucleotide sequence set forth in SEQ ID NOs. 2-3, SEQ ID NOs 22-23, or homologs thereof. For example, recombinant polypeptides preferred by the present invention can be encoded by a nucleic acid, which is at least 85% homologous and more preferably 90% homologous and most preferably 95% homologous with a nucleotide sequence set forth in SEQ ID NOS. 2-3, or SEQ ID NOs 22-23. Polypeptides which are encoded by a nucleic acid that is at least about 98-99% homologous with the sequence of SEQ ID NOS: 2-3, or SEQ ID NOs 22-23 are also within the scope of the invention.

In a preferred embodiment, an Csp protein of the present invention is a mammalian Csp protein. In a particularly preferred embodiment an Csp protein is set forth as SEQ ID Nos: 4-5, or 24. In particularly preferred embodiment, an Csp protein has an Csp bioactivity. It will be understood that certain post-translational modifications, e.g., phosphorylation and the like, can increase the apparent molecular weight of the Csp protein relative to the unmodified polypeptide chain.

Csp polypeptides preferably are capable of functioning in one of either role of an agonist or antagonist of at least one biological activity of a wild-type ("authentic") Csp protein of the appended sequence listing. The term "evolutionarily related to", with respect to amino acid sequences of Csp proteins, refers to both polypeptides having amino acid sequences which have arisen naturally, and also to mutational variants of human Csp polypeptides which are derived, for example, by combinatorial mutagenesis.

Full length proteins or fragments corresponding to one or more particular motifs and/or domains or to arbitrary sizes, for example, at least 5, 10, 25, 50, 75 and 100, amino acids in length are within the scope of the present invention.

For example, isolated Csp polypeptides can be encoded by all or a portion of a nucleic acid sequence shown in any of SEQ ID NOS. 2-3, 22-23. Isolated peptidyl portions of Csp proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an Csp polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") Csp protein.

In general, polypeptides referred to herein as having an activity (e.g., are "bioactive") of an Csp protein are defined as polypeptides which include an amino acid sequence encoded by all or a portion of the nucleic acid sequences shown in one of SEQ ID NOS: 2-3, 22-23, and which mimic or antagonize all or a portion of the biological/biochemical activities of a naturally occurring Csp protein. According to the present invention, a polypeptide has biological activity if it is a specific agonist or antagonist of a naturally-occurring form of an Csp protein.

Assays for determining whether a compound, e.g., a protein, such as an Csp protein or variant thereof, has one or more of the above biological activities are well known in the art.

Other preferred proteins of the invention are those encoded by the nucleic acids set forth in the section pertaining to nucleic acids of the invention. In particular, the invention provides fusion proteins, e.g., Csp-immunoglobulin fusion proteins. Such fusion proteins can provide, e.g., enhanced stability and solubility of Csp proteins and may thus be useful in therapy. Fusion proteins can also be used to produce an immunogenic fragment of an Csp protein. For example, the VP6 capsid protein of rotavirus can be used as an immunologic carrier protein for portions of the Csp polypeptide, either in the monomeric form or in the form of a viral particle. The nucleic acid sequences corresponding to the portion of a subject Csp protein to which antibodies are to be raised can be incorporated into a fusion gene construct which includes coding sequences for a late vaccinia virus structural protein to produce a set of recombinant viruses expressing fusion proteins comprising Csp epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an Csp protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple antigen peptide system for peptide-based immunization can also be utilized to generate an immunogen, wherein a desired portion of an Csp polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of Csp proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the Csp polypeptides of the present invention. For example, Csp polypeptides can be generated as glutathione-S-transferase (GST-fusion) proteins. Such GST-fusion proteins can enable easy purification of the Csp polypeptide, as for example by the use of glutathione-derivatized matrices (see, for example, Current Protocols in Molecular Biology, eds. Ausubel et al. (N.Y.: John Wiley & Sons, 1991)).

The present invention further pertains to methods of producing the subject Csp polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant Csp polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant Csp polypeptide is a fusion protein containing a domain which facilitates its purification, such as GST fusion protein.

Moreover, it will be generally appreciated that, under certain circumstances, it may be advantageous to provide homologs of one of the subject Csp polypeptides which function in a limited capacity as one of either an Csp agonist (mimetic) or an Csp antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of Csp proteins.

Homologs of each of the subject Csp proteins can be generated by mutagenesis, such as by discrete point mutation(s), or by truncation. For instance, mutation can give rise to homologs which retain substantially the same, or merely a subset, of the biological activity of the Csp polypeptide from which it was derived. Alternatively, antagonistic forms of the protein can be generated which are able to inhibit the function of the naturally occurring form of the protein, such as by competitively binding to an Csp receptor.

The recombinant Csp polypeptides of the present invention also include homologs of the wildtype Csp proteins, such as versions of those protein which are resistant to proteolytic cleavage, as for example, due to mutations which alter ubiquitination or other enzymatic targeting associated with the protein.

Csp polypeptides may also be chemically modified to create Csp derivatives by forming covalent or aggregate conjugates with other chemical moieties, such as glycosyl groups, lipids, phosphate, acetyl groups and the like. Covalent derivatives of Csp proteins can be prepared by linking the chemical moieties to functional groups on amino acid sidechains of the protein or at the N-terminus or at the C-terminus of the polypeptide.

Modification of the structure of the subject Csp polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the Csp polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5)

amide=asparagine, glutamine; and (6) sulfur-containing=cysteine and methionine. (see, for example, Biochemistry, 2$^{nd}$ ed., Ed. by L. Stryer, WH Freeman and Co.: 1981). Whether a change in the amino acid sequence of a peptide results in a functional Csp homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject Csp proteins as well as truncation mutants, and is especially useful for identifying potential variant sequences (e.g., homologs). The purpose of screening such combinatorial libraries is to generate, for example, novel Csp homologs which can act as either agonists or antagonist, or alternatively, possess novel activities all together. Thus, combinatorially-derived homologs can be generated to have an increased potency relative to a naturally occurring form of the protein.

In one embodiment, the variegated library of Csp variants is generated by combinatorial mutagenesis at the nucleic acid level, and is encoded by a variegated gene library. For instance, a mixture of synthetic oligonucleotides can be enzymatically ligated into gene sequences such that the degenerate set of potential Csp sequences are expressible as individual polypeptides, or alternatively, as a set of larger fusion proteins (e.g., for phage display) containing the set of Csp sequences therein.

There are many ways by which such libraries of potential Csp homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential Csp sequences. The synthesis of degenerate oligonucleotides is well known in the art (see for example, Narang, S A (1983) Tetrahedron 39:3; Itakura et al. (1981) Recombinant DNA, Proc 3$^{rd}$ Cleveland Sympos. Macromolecules, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

Likewise, a library of coding sequence fragments can be provided for an Csp clone in order to generate a variegated population of Csp fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an Csp coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of Csp homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate Csp sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811-7815; Yourvan et al., 1992, Parallel Problem Solving from Nature, 2., In Maenner and Manderick, eds., Elsevir Publishing Co., Amsterdam, pp. 401-410; Delgrave et al., 1993, Protein Engineering 6(3): 327-331).

The invention also provides for reduction of the Csp proteins to generate mimetics, e.g., peptide or non-peptide agents, such as small molecules, which are able to disrupt interaction of an Csp polypeptide to Calcineurin. Thus, such mutagenic techniques as described above are also useful to map the determinants of the Csp proteins which participate in protein-protein interactions involved in, for example, binding of the subject Csp polypeptide to a target peptide. To illustrate, the critical residues of a subject Csp polypeptide which are involved in interaction with Calcineurin can be determined and used to generate Csp derived peptidomimetics or small molecules which competitively inhibit binding of the authentic Csp protein with that moiety. By employing, for example, scanning mutagenesis to map the amino acid residues of the subject Csp proteins which are involved in binding other proteins, peptidomimetic compounds can be generated which mimic those residues of the Csp protein which facilitate the interaction. Such mimetics may then be used to interfere with the normal function of an Csp protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295;

and Ewenson et al. in Peptides: Structure and Function (Proceedings of the 9<sup>th</sup> American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Communl26:419; and Dann et al. (1986) Biochem Biophys Res Commun 134:71).

Peptidomimetic Angonists of Calcipresins

In another aspect, the invention provides antagonists, or inhibitors, of a calcineurin activity, such as a calcineurin phosphatase catalytic activity or a calcineurin substrate recognition activity. The invention provides small peptide segments of a calcipressin protein which are essential to its calcineurin inhibitory activity. These small peptide segments of calcipressin contain the amino acid sequence RRP, which is found in the Csp proteins (see FIG. 15, panel A). A similar conserved sequence comprising an RR amino acid sequence is found in several known calcineurin substrates including DARPP-32, phosophatase inhibitor-1, phosphorylase kinase, and the RII subunit, as well as in the calcineurin autoinhibitory domain CnA-AI. Deletion of the RRP motif from Csp 1 inactivates the clacineurin-inhibitory activity of normal calcipressin, as measured by calcineurin's ability to hydrolyze small substrates such as pNPP (see FIG. 15, panel B). Accordingly, this polypeptide segment represents a pseudosubstrate site which is likely to bind to the catalytic domain of calcineurin and thereby block the calcineurin phosphatase activity. While not wishing to limit this inhibition to a specific mechanism, it is likely that inhibition of calcineurin by RRP motif polypeptides occurs by a competitive mechanism. Accordingly, the invention provides polypeptide and peptidomimetic inhibitors of calcineurin. As used herein, the terms calcineurin inhibitor and calcineuin antagonist are used interchangeably.

In certain embodiments, the calcineurin antagonists of the invention comprise the polypeptide sequence RR. In preferred embodiments, the calcineurin antagonists of the invention comprise a polypeptide sequence RRP; or, more preferrably, the sequence RRPZ (SEQ ID NO: 47), wherein Z is any amino acid residue other than a serine or a threonine; or, still most preferrably, RRPY (SEQ ID NO: 48), wherein Y is an alanine residue, a glycine residue or a glutamic acid residue. In still more preferred embodiments, the calcineurin antagonists comprise an RRPE (SEQ ID NO: 49) motif; or, most preferrably, a sequence motif conforming to the general structure PKPKIXQTRRPE (SEQ ID No. 28), wherein P is a proline residue, K is a lysine residue, I is an isoleucine residue, X is any amino acid residue, Q is a glutamine residue, T is a threonine residue, R is an arginine residue, and E is a glutamic acid residue. Examples of two preferred calcineurin antagonists are the peptides PKPKIIQTRRPE (SEQ ID No. 29) and PKPKINQTRRPG (SEQ ID No. 30).

In certain embodiments, the inhibitor has a molecular weight of less than 10,000 atomic mass units (amu), more preferably less than 7500 amu, 5000 amu, and even more preferably less than 3000 amu. For instance, the calcineurin inhibitor can be either a peptide or peptidomimetic, preferably corresponding in length to a 3-25 mer, e.g., and in certain preferred embodiments, containing a core sequence corresponding to an RRPE motif. In preferred embodiments, the calcineurin inhibitor conforms to the general structure:

n-b-n-b-n-n-p-p-R-R-P-a wherein "n" indicates a nonpolar residue such as alanine, valine, leucine, isoleucine, proline, phenylalanine, tryptophan, or methionine; "b" indicates a basic residue such as lysine, arginine, or histidine; "p" indicates an uncharged polar residue such as glycine, serine, threonine, cysteine, tyrosine, asparagine, or glutamine; "R" indicates an arginine residue; "P" indicates a proline residue, and "a" indicates an acidic residue such as aspartic acid or glutamic acid.

In another aspect of the invention, the invention provides certain other calcineurin inhibitors which block specific calcineurin activities. For example, the mutant Csp1 polypeptide ΔRRPE (see FIG. 15, panel A) blocks in vivo calcineurin activity towards NF-AT4, as judged by an NF-AT4 nuclear import assay (see FIG. 2) but does not block the phosphatase activity of calcineurin towards small molecule substrates such as pNPP (FIG. 15, panel B). Accordingly the Csp1 ΔRRPE polypeptide comprises one or more polypeptide segments which bind to a calcineurin NF-AT4 recognition domain. Significantly, this Csp1 ΔRRPE polypeptide corresponds to a segment which inhibits the specific recognition by calcineurin of substrates such as NF-AT4, without directly interfering with the phosphatase catalytic activity of calcineurin. Conventional deletion analysis of the Csp 1 ΔRRPE polypeptide provides a means of specifically locating the calcineurin substrate inhibitory segments. Indeed, the ability of calcipressin to inhibit the specific recognition of calcineurin with NF-AT4 has been localized to the carboxy-terminus of Csp-1 (amino acid residues 101 to 197) and calcipressin's interaction with calcineurin has been still further localized to Csp-1 residues 151 to 197 (see FIG. 5). The precise polypeptide segments of Csp-1 which are involved in these activities can be still further localized by conventional methods for generating deletion derivatives of proteins and by the calcipressin activity assays provided herein and elsewhere. Localization of these regions affords a means of inhibiting the interaction of calcineurin with particular calcineurin substrates, but not others, by means of competitive inhibitors of the calcineurin/specific substrate interaction. Such competitive inhibitors will not affect the general catalytic activity of calcineurin upon other substrates which do not utilize this particular calcineurin interface. Accordingly, this aspect of the invention provides substrate-specific inhibitors of calcineurin phosphatase activity as well as the broad-spectrum inhibitors of calcineurin phosphatase catalytic activity discussed above.

The following definitions and explanations are provided in support of the description of the exemplary RRPE motif and substrate-specific calcineurin of the invention.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., C1-C30 for straight chain, C3-C30 for branched chain), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxys, alkylthios, aminoalkyls, carbonyl-substituted alkyls, —CF3, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

The term "amino acid residue" is known in the art. In general the abbreviations used herein for designating the amino acids and the protective groups are based on recommendations of the IUPAC-IUB Commission on Biochemical Nomenclature (see Biochemistry (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers. D- and L-a-Amino acids are represented by the following Fischer projections and wedge-and-dash drawings. In the majority of cases, D- and L-amino acids have R- and S-absolute configurations, respectively.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman, M. and Chorev, M. Accounts of Chem. Res. 1979, 12, 423.

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention can be formed by utilizing an appropriate amino acid mimetic moiety to link the two adjacent portions of the sequences depicted above utilizing a reversed peptide (reversed amide) bond. In case (a) above, a central residue of a diketo compound may conveniently be utilized to link structures with two amide bonds to achieve a peptidomimetic structure. In case (b) above, a central residue of a diamino compound will likewise be useful to link structures with two amide bonds to form a peptidomimetic structure.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is preferably (D), and the configuration of the non-reversed portion is preferably (L). Opposite or mixed configurations are acceptable when appropriate to optimize a binding activity.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to bind to opioid receptors), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

As used herein, the term "transfection" means the introduction of a nucleic acid, e.g., an expression vector, into a recipient cell by nucleic acid-mediated gene transfer.

"Transcriptional regulatory sequence" is a generic term used throughout the specification to refer to DNA sequences, such as initiation signals, enhancers, and promoters, which induce or control transcription of protein coding sequences with which they are operably linked.

Operably linked is intended to mean that the nucleotide sequence is linked to a regulatory sequence in a manner which allows expression of the nucleotide sequence. Regulatory sequences are art-recognized and are selected to direct expression of the subject peptide. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990).

The term "gene construct" refers to a vector, plasmid, viral genome or the like which includes a coding sequence, can transfect cells, preferably mammalian cells, and can cause expression of e.g., the ubiquitin protein ligase-target polypeptide interaction domain hybrid of the cells transfected with the construct. The term "gene construct" does not include a wild-type papillomavirus genome, and preferably does not include expressible coding sequences for one or more of the polypeptides of the invention.

As used herein, the term "pharmaceutically acceptable" refers to a carrier medium which does not interfere with the effectiveness of the biological activity of the active ingredients and which is not excessively toxic to the hosts of the concentrations of which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

A variety of drug screening techniques can be readily adapted to the ubiquitin protein ligase/target polypeptide interaction in order to provide high throughput screening of peptide, peptidomimetic or other small molecule libraries. Such assays can be used to optimize a lead compound, or to assess the potential inhibitory effect of a test compound.

In one embodiment, simple competition assays can be used to assess the ability of a test compound to disrupt the interaction of a calcineurin with a calcipressin. In other embodiments, cell-based assays which detect a target polypeptide activity or a calcipressin e activity can be used to assess the biological activity of a test compound.

In certain embodiments of the present invention, such as for topical administration to the epidermis, the subject inhibitor pharmaceutical can be a peptide, e.g., having a naturally occurring peptide backbone and amino acid side chains, though it may be N-terminally and/or C-terminally protected.

In preferred embodiments, the peptidyl component of the subject compounds includes, in addition to the RRPE sequence, as described herein, no more than about 25 amino acid residues of a protein in which a RRPE motif naturally exists, more preferably no more than 10-15, and even more preferably 6 or less. With the exception of certain chimeric RRPE compositions described herein, such as fusion proteins, a preferred composition (especially for ectopic application) includes a peptide comprising a RRPE core motif and having a molecular weight in the range of about 1500 to 7500 daltons, more preferably from about 2000 to 5000 daltons, and even more preferably in the range of about 2000 to 2750 daltons. The peptide, in addition to the RRPE core motif, may include other amino acid residues, such as a transcytosis peptide, and may be derivatized at one or more backbone or sidechain points with, e.g. peptides, nucleic acids, carbohydrates, etc. In certain embodiments, the peptide is derivatized with one or more functional groups that enhance cellular uptake and/or alter the half-life of the RRPE core motif.

This invention further contemplates a method of generating sets of combinatorial libraries of the subject RRPE peptides which is especially useful for identifying potential variant sequences (e.g. homologs) that are functional in inhibiting RRPE mediated interactions with target polypeptides.

Combinatorially-derived homologs can be generated which have, e.g., greater affinity, a enhanced potency relative to native peptide sequences, or intracellular half-lives different than the corresponding wild-type polypeptide. For example, the altered peptide can be rendered either more stable or less stable to proteolytic degradation or other cellular process which result in destruction of, or otherwise inactivation of, the peptide. Such homologs can be utilized to alter the envelope of therapeutic application by modulating the half-life of the peptide. For instance, a short half-life can give rise to more transient biological effects and can allow tighter control of peptide levels within the cell.

In a representative embodiment of this method, the amino acid sequences for a population of RRPE motifs are aligned, preferably to promote the highest homology possible. Amino acids which appear at each position of the aligned sequences are selected to create a degenerate set of combinatorial sequences. To illustrate, multiple RRPE containing proteins are aligned and, based on these alignments, combinatorial libraries can be generated representing RRPE peptides which have an amino acid sequence that includes a RRPEcore sequence represented by the formula:

$$G\text{-}H\text{-}X^{(3\text{-}6)}\text{-}h\text{-}X\text{-}X\text{-}h\text{-}X\text{-}r\text{-}X\text{-}t^{(2\text{-}3)}\text{-}p\text{-}X\text{-}h\text{-}h\text{-}X\text{-}X\text{-}X\text{-}X\text{-}D\text{-}X\text{-}X\text{-}X\text{-}X\text{-}h\text{-}W\text{-}D$$

Peptides larger than the 15-mer core are, of course, also contemplated. Further expansion of the combinatorial library can be made, for example, by including amino acids which would represent conservative mutations at one or more of the degenerate positions. Inclusion of such conservative mutations can give rise to a library of potential RRPEpeptide sequences represented by the above formula, but wherein Xaa(1) can be an amino acid residue having a polar sidechain, such as arg, asn, asp, cys, glu, gln, his, lys, ser, thr or tyr, as set out by the core structures above. Alternatively, amino acid replacement at degenerate positions can be based on steric criteria, e.g. isosteric replacement, without regard for polarity or charge of amino acid sidechains. Similarly, completely random mutagenesis of one or more of the variant positions (Xaa) can be carried out, e.g., each of Xaa(1)-(11) can be any of the 20 amino acids (or other analogs thereof).

In one embodiment the RRPE peptide library can be derived by combinatorial chemistry, such as by techniques which are available in the art for generating combinatorial libraries of small organic/peptide libraries. See, for example, Blondelle et al. (1995) Trends Anal. Chem. 14:83; the Affymax U.S. Pat. Nos. 5,359,115 and 5,362,899; the Ellman U.S. Pat. No. 5,288,514; the Still et al. PCT publication WO 94/08051; Chen et al. (1994) JACS116:2661; Kerr et al. (1993) JACS115:252; PCT publications WO92/10092, WO93/09668 and WO91/07087; and the Lerner et al. PCT publication WO93/20242).

In a preferred embodiment, the combinatorial peptide library is produced by way of a degenerate library of genes encoding a library of polypeptides which each include at least a portion of potential RRPEsequences. For instance, a mixture of synthetic oligonucleotides can be enzymatically ligated into gene sequences such that the degenerate set of potential RRPEnucleotide sequences are expressible as individual polypeptides, or alternatively, as a set of larger fusion proteins (e.g. for phage display) containing the set of RRPEpeptide sequences therein.

There are many ways by which the gene library of potential RRPEhomologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential RRPEsequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp. 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

A wide range of techniques are known in the art for screening gene products of combinatorial libraries made by point mutations. Such techniques will be generally adaptable for rapid screening of the gene libraries generated by the combinatorial mutagenesis of RRPE sequences. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Such illustrative assays are amenable to high throughput analysis as necessary to screen large numbers of degenerate sequences created by combinatorial mutagenesis techniques.

In an illustrative embodiment of a screening assay, the RRPE gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007-16010; Griffths et al. (1993) EMBO J. 12:725-734; Clackson et al. (1991) Nature 352:624-628; and Barbas et al. (1992) PNAS 89:4457-4461).

For example, the recombinant phage antibody system (RPAS, Pharmacia Catalog number 27-9400-01) can be easily modified for use in expressing and screening RRPE motif combinatorial libraries of the present invention. For instance, the pCANTAB 5 phagemid of the RPAS kit contains the gene which encodes the phage gill coat protein. The RRPE combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate RRPE gene insert. The resulting recombinant phage contain phagemid DNA encoding a specific candidate RRPE peptide, and display one or more copies of the corresponding fusion coat protein. The phage-displayed candidate proteins which are capable of, for example, binding a calcineurin protein, are selected or enriched by panning. For instance, the phage library can be panned on glutathione immobilized calcineurin-GST fusion proteins, and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for RRPE proteins which can then be screened for further calcineurin inhibitory activities. Subsequent selection, e.g. of a reduced set of variants from the library, may then be based upon more meaningful criteria rather than simple calcineurin-binding ability. For instance, intracellular half-life or selectivity can become selection criteria in secondary screens.

Combined with certain formulations, such peptides can be effective intracellular agents for, e.g., inhibiting PV infection of epithelial cells. However, in order to increase the efficacy of such peptides, the RRPE peptide can be provided a fusion peptide along with a second peptide which promotes "transcytosis", e.g., uptake of the peptide by epithelial cells. To illustrate, the RRPE peptide of the present invention can be provided as part of a fusion polypeptide with all or a fragment of the N-terminal domain of the HIV protein Tat, e.g., residues 1-72 of Tat or a smaller fragment thereof which can promote transcytosis. In other embodiments, the RRPEpeptide can be provided a fusion polypeptide with all or a portion of the antenopedia III protein.

To further illustrate, the RRPE peptide (or peptidomimetic) can be provided as a chimeric peptide which includes a heterologous peptide sequence ("internalizing peptide") which drives the translocation of an extracellular form of a RRPE peptide sequence across a cell membrane in order to facilitate intracellular localization of the RRPE peptide. In this regard, the therapeutic RRPE sequence is one which is active intracellularly. The internalizing peptide, by itself, is capable of crossing a cellular membrane by, e.g., transcytosis, at a relatively high rate. The internalizing peptide is conjugated, e.g., as a fusion protein, to the RRPE peptide. The resulting chimeric peptide is transported into cells at a higher rate relative to the activator polypeptide alone to thereby provide an means for enhancing its introduction into cells to which it is applied, e.g., to enhance topical applications of the RRPE peptide.

In one embodiment, the internalizing peptide is derived from the *Drosophila* antennapedia protein, or homologs thereof. The 60 amino acid long homeodomain of the homeo-protein antennapedia has been demonstrated to translocate through biological membranes and can facilitate the translocation of heterologous polypeptides to which it is couples. See for example Derossi et al. (1994) J Biol Chem 269: 10444-10450; and Perez et al. (1992) J Cell Sci 102:717-722.

Recently, it has been demonstrated that fragments as small as 16 amino acids long of this protein are sufficient to drive internalization. See Derossi et al. (1996) J Biol Chem 271: 18188-18193.

The present invention contemplates a RRPE peptide or peptidomimetic sequence as described herein, and at least a portion of the Antennapedia protein (or homolog thereof) sufficient to increase the transmembrane transport of the chimeric protein, relative to the RRPE peptide or peptidomimetic, by a statistically significant amount.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol. 63:1-8).

Another exemplary transcellular polypeptide can be generated to include a sufficient portion of mastoparan (T. Higashijima et al., (1990) J. Biol. Chem. 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefor serve as an internalizing peptide for the subject transcellular peptides and peptidomimetics. Preferred growth factor-derived internalizing peptides include EGF (epidermal growth factor)-derived peptides, such as CMHIESLDSYTC (SEQ ID No. 31) and CMYIEALDKYAC (SEQ ID No. 32); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of RRPE peptides and peptidomimetics, taken up by an endocytic mechanism, from endosomal compartments to the cytoplasm.

A particularly preferred pH-dependent membrane-binding internalizing peptide in this regard is aa1-aa2-aa3-EAALA (EALA)4-EALEALAA-amide (SEQ ID No. 33), which represents a modification of the peptide sequence of Subbarao et al. (Biochemistry 26:2964, 1987). Within this peptide sequence, the first amino acid residue (aa1) is preferably a unique residue, such as cysteine or lysine, that facilitates chemical conjugation of the internalizing peptide to a targeting protein conjugate. Amino acid residues 2-3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2-3 are neutral amino acids, the internalizing peptide will insert into neutral membranes.

Yet other preferred internalizing peptides include peptides of apo-lipoprotein A–1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the RRPE peptide or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyltransferase, such as GNAAAARR (SEQ ID No. 34) (Eubanks et al., in: Peptides. Chemistry and Biology, Garland Marshall (ed.), ESCOM, Leiden, 1988, pp. 566-69) In this construct, an internalizing peptide would be attached to the C-terminus of the accessory peptide, since the N-terminal glycine is critical for the accessory moiety's activity. This hybrid peptide, upon attachment to a RRPE peptide or peptidomimetic at its C-terminus, is N-myristylated and further anchored to the target cell membrane, e.g., it serves to increase the local concentration of the peptide at the cell membrane.

To further illustrate use of an accessory peptide, a phosphorylatable accessory peptide is first covalently attached to the C-terminus of an internalizing peptide and then incorporated into a fusion protein with a RRPE peptide or peptidomimetic. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) Ann. Rev. Biochem. 56:63-87). Accessory peptides that contain the sequence x-NLT-x thus will enhance target cell retention of corresponding polypeptide.

In another embodiment of this aspect of the invention, an accessory peptide can be used to enhance interaction of the RRPE peptide or peptidomimetic with the target cell. Exemplary accessory peptides in this regard include peptides derived from cell adhesion proteins containing the sequence "RGD", or peptides derived from laminin containing the sequence CDPGYIGSRC. Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type I, lambda receptor of *E. Coli*, fibrinogen and Sindbis coat protein (E. Ruoslahti, Ann. Rev. Biochem. 57:375-413, 1988). Cell surface receptors that recognize RGD sequences have been grouped into a superfamily of related proteins designated "integrins". Binding of "RGD peptides" to cell surface integrins will promote cell-surface retention, and ultimately translocation, of the polypeptide.

As described above, the internalizing and accessory peptides can each, independently, be added to RRPE peptide or peptidomimetic by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In an exemplary embodiment, a RRPE peptide or peptidomimetic is engineered to include an integrin-binding RGD peptide/SV40 nuclear localization signal (see, for example Hart S L et al., 1994; J. Biol. Chem., 269:12468-12474), such as encoded by the nucleotide sequence provided in the Nde1-EcoR1 fragment:

catatgggtggctgccgtggcgatatgt-tcggttgcggtgctcctccaaaaaagaagagaaaggtagctggattc (SEQ ID No. 35), which encodes the RGD/SV40 nucleotide sequence: MGGCRGDMFGCGAPPKKKRKVAGF (SEQ ID No. 36). In another embodiment, the protein can be engineered with the HIV-1 tat(1-72) polypeptide, e.g., as provided by the Nde1-EcoR1 fragment: catatggagccagtagatcctagacta-gagcctggaagcatccaggaagtcagcctaaaactgcttgtaccaattgctattgt aaaaagtgttgctttcattgc-caagtttgtttcataacaaaagcccttg-gcatctcctatggcaggaagaagcggagacagcgacgaagacct cctcaag-gcagtcagactcatcaagtttctctaagtaagcaaggattc (SEQ ID No. 37), which encodes the HIV-1 tat(1-72) peptide sequence: MEPVDPRLEPWKHPGSQPKTACTNCYCK-KCCFHCQVCFITKALGISYGRKKRRQRRRPP QGSQTHQVSLSKQ (SEQ ID No. 38). In still another embodiment, the fusion protein includes the HSV-1 VP22 polypeptide (Elliott G., O'Hare P (1997) Cell, 88:223-233) provided by the NdeI-EcoR1 fragment:

cat atg acc tct cgc cgc tcc gtg aag tcg ggt ccg cgg gag gtt ccg cgc gat gag tac gag gat ctg tac tac acc ccg tct tca ggt atg gcg agt ccc gat agt ccg cct gac acc tcc cgc cgt ggc gcc cta cag aca cgc tcg cgc cag agg ggc gag gtc cgt ttc gtc cag tac gac gag tcg gat tat gcc ctc tac ggg ggc tcg tca tcc gaa gac gac gaa cac ccg gag gtc ccc cgg acg cgg cgt ccc gtt tcc ggg gcg gtt ttg tcc ggc ccg ggg cct gcg cgg gcg cct ccg cca ccc gct ggg tcc gga ggg gcc gga cgc aca ccc acc acc gcc ccc cgg gcc ccc cga acc cag cgg gtg gcg act aag gcc ccc gcg gcc ccg gcg gcg gag acc acc cgc ggc agg aaa tcg gcc cag cca gaa tcc gcc gca ctc cca gac gcc ccc gcg tcg acg gcg cca acc cga tcc aag aca ccc gcg cag ggg ctg gcc aga aag ctg cac ttt agc acc gcc ccc cca aac ccc gac gcg cca tgg acc ccc cgg gtg gcc ggc tit aac aag cgc gtc ttc tgc gcc gcg gtc ggg cgc ctg gcg gcc atg cat gcc cgg atg gcg gcg gtc cag ctc tgg gac atg tcg cgt ccg cgc aca gac gaa gac ctc aac gaa ctc ctt ggc atc acc acc atc cgc gtg acg gtc tgc gag ggc aaa aac ctg ctt cag cgc gcc aac gag ttg gtg aat cca gac gtg gtg cag gac gtc gac gcg gcc acg gcg act cga ggg cgt tct gcg gcg tcg cgc ccc acc gag cga cct cga gcc cca gcc cgc tcc gct tct cgc ccc aga cgg ccc gtc gag gaa ttc (SEQ ID No. 39)

which encodes the HSV-1 VP22 peptide having the sequence:

MTSRRSVKSGPREVPRDEYEDLYYTPSS-GMASPDSPPDTSRRGALQTRSRQRGEVRFVQ YDES-DYALYGGSSSEDDEHPEVPRTRRPVS-GAVLSGPGPARAPPPPAGSGGAGRTPTTAP RAPRTGRVATKAPAAPAAETTRGRK-SAQPESAALPDAPASTAPTRSKTPAQGLARKLHF STAPPNPDAPWTPRVAGFNKRVF-CAAVGRLAAMHARMAAVQLWDMSRPRTDEDLNE LLGITTIRVTVCEGKNLLQRANELVNPD-VVQDVDAATATRGRSAASRPTERPRAPARSA SRPRRPVE (SEQ ID No. 40)

In still another embodiment, the fusion protein includes the C-terminal domain of the VP22 protein from, e.g., the nucleotide sequence (Nde1-EcoR1 fragment):

cat atg gac gtc gac gcg gcc acg gcg act cga ggg cgt tct gcg gcg tcg cgc ccc acc gag cga cct cga gcc cca gcc cgc tcc gct tct cgc ccc aga cgg ccc gtc gag gaa ttc (SEQ ID No. 41)

which encodes the VP22 (C-terminal domain) peptide sequence: MDVDAATATRGRSA-ASRPTERPRAPAR-SASRPRRPVE (SEQ ID No. 42)

In certain instances, it may also be desirable to include a nuclear localization signal as part of the RRPE peptide.

In the generation of fusion polypeptides including the subject RRPE peptides, it may be necessary to include unstructured linkers in order to ensure proper folding of the various peptide domains, and prevent steric or other interference of the heterologous domains with the PV inhibitory activity of the RRPE peptide. Many synthetic and natural linkers are known in the art and can be adapted for use in the present invention, including the (Gly3Ser)4 linker.

In other embodiments, the subject RRPE therapeutics are peptidomimetics of the RRPE peptide. Peptidomimetics are compounds based on, or derived from, peptides and proteins. The RRPE peptidomimetics of the present invention typically can be obtained by structural modification of a known RRPE peptide sequence using unnatural amino acids, conformational restraints, isosteric replacement, and the like. The subject peptidomimetics constitute the continum of structural space between peptides and non-peptide synthetic structures; RRPE peptidomimetics may be useful, therefore, in delineating pharmacophores and in helping to translate peptides into nonpeptide compounds with the activity of the parent RRPE peptides. Moreover, as is apparent from the present disclosure, mimetopes of the subject RRPE peptides can be provided. Such peptidomimetics can have such attributes as being non-hydrolyzable (e.g., increased stability against proteases or other physiological conditions which degrade the corresponding peptide), increased specificity and/or potency for inhibition of PV replication, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), b-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124: 141), and methyleneamino-modified (Roark et al. in Peptides: Chemistry and Biology, G. R. Marshall ed., ESCOM Publisher: Leiden, Netherlands, 1988, p134). Also, see generally, Session III: Analytic and synthetic methods, in in Peptides: Chemistry and Biology, G. R. Marshall ed., ESCOM Publisher: Leiden, Netherlands, 1988) In addition to a variety of sidechain replacements which can be carried out to generate the subject RRPE peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Additionally, peptidomimietics based on more substantial modifications of the backbone of the RRPE peptide can be used. Peptidomimetics which fall in this category include (i) retro-inverso analogs, and (ii) N-alkyl glycine analogs (so-called peptoids).

Furthermore, the methods of combinatorial chemistry are being brought to bear, e.g., by G. L. Verdine at Harvard University, on the development of new peptidomimetics. For example, one embodiment of a so-called "peptide morphing" strategy focuses on the random generation of a library of peptide analogs that comprise a wide range of peptide bond substitutes.

Such retro-inverso analogs can be made according to the methods known in the art, such as that described by the Sisto et al. U.S. Pat. No. 4,522,752. For example, the illustrated retro-inverso analog can be generated as follows. The geminal diamine corresponding to the N-terminal tryptophan is synthesized by treating a protected tryptophan analog with ammonia under HOBT-DCC coupling conditions to yield the N-Boc amide, and then effecting a Hofmann-type rearrangement with I,I-bis-(trifluoroacetoxy)iodobenzene (TIB), as described in Radhakrishna et al. (1979) J. Org. Chem. 44:1746. The product amine salt is then coupled to a side-chain protected (e.g., as the benzyl ester) N-Fmoc D-lys residue under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid, as described in U.S. Pat. No. 5,061,811 to Pinori et al., to yield the retro-inverso tripeptide analog WKH. The pseudotripeptide is then coupled with an L-methionine analog under standard conditions to give the protected tetrapeptide analog. The protecting groups are removed to release the product, and the steps repeated to enlogate the tetrapeptide to the full length peptidomimetic. It will be understood that a mixed peptide, e.g. including some normal peptide linkages, will be generated. As a general guide, sites which are most susceptible to proteolysis are typically altered, with less susceptible amide linkages being optional for mimetic switching. The final product, or intermediates thereof, can be purified by HPLC.

Retro-enantio analogs such as this can be synthesized commercially available D-amino acids (or analogs thereof) and standard solid- or solution-phase peptide-synthesis techniques. For example, in a preferred solid-phase synthesis method, a suitably amino-protected (t-butyloxycarbonyl, Boc) D-trp residue (or analog thereof) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid (D-lys) is introduced by coupling with diisopropylcarbodiimide. The resin is again washed, and the cycle repeated for each of the remaining amino acids in turn (D-his, D-met, etc). When synthesis of the protected retro-enantio peptide is complete, the protecting groups are removed and the peptide cleaved from the solid support by treatment with hydrofluoric acid/anisole/dimethyl sulfide/thioanisole. The final product is purified by HPLC to yield the pure retro-enantio analog.

The trans olefin analog of a RRPE peptide can be synthesized according to the method of Y. K. Shue et al. (1987) Tetrahedron Letters 28:3225. Referring to the illustrated example, Boc-amino L-Ile is converted to the corresponding a-amino aldehyde, which is treated with a vinylcuprate to yield a diastereomeric mixture of alcohols, which are carried on together. The allylic alcohol is acetylated with acetic anhydride in pyridine, and the olefin is cleaved with osmium tetroxide/sodium periodate to yield the aldehyde, which is condensed with the Wittig reagent derived from a protected tyrosine precursor, to yield the allylic acetate. The allylic acetate is selectively hydrolyzed with sodium carbonate in methanol, and the allylic alcohol is treated with triphenylphosphine and carbon tetrabromide to yield the allylic bromide. This compound is reduced with zinc in acetic acid to give the transposed trans olefin as a mixture of diastereomers at the newly-formed center. The diastereomers are separated and the pseudodipeptide is obtained by selective transfer hydrogenolysis to unveil the free carboxylic acid.

The pseudodipeptide is then coupled at the C-terminus, according to the above example, with a suitably protected tyrosine residue, and at the N-terminus with a protected alanine residue, by standard techniques, to yield the protected tetrapeptide isostere A-I-Y-Y. The terapeptide is then further condensed with the olefinic tripeptide analog derived by similar means for Lys-Ala-Arg, and so forth to build up the full RRPE peptide. The protecting groups are then removed with strong acid to yield the desired peptide analog, which can be further purified by HPLC.

Other pseudodipeptides can be made by the method set forth above merely by substitution of the appropriate starting Boc amino acid and Wittig reagent. Variations in the procedure may be necessary according to the nature of the reagents used, but any such variations will be purely routine and will be obvious to one of skill in the art.

It is further possible couple the pseudodipeptides synthesized by the above method to other pseudodipeptides, to make peptide analogs with several olefinic functionalities in place of amide functionalities. For example, pseudodipeptides corresponding to Met-Arg or Tyr-Lys, etc. could be made and then coupled together by standard techniques to yield an analog of the RRPE peptide which has alternating olefinic bonds between residues.

The synthesis of such phosphonate derivatives can be adapted from known synthesis schemes. See, for example, Loots et al. in Peptides: Chemistry and Biology, (Escom Science Publishers, Leiden, 1988, p. 118); Petrillo et al. in Peptides: Structure and Function (Proceedings of the 9th American Peptide Symposium, Pierce Chemical Co. Rockland, Ill., 1985).

Many other peptidomimetic structures are known in the art and can be readily adapted for use in the subject RRPE peptidomimetics. To illustrate, the RRPE peptidomimetic may incorporate the 1-azabicyclo[4.3.0]nonane surrogate (see Kim et al. (1997) J. Org. Chem. 62:2847), or an N-acyl piperazic acid (see Xi et al. (1998) J. Am. Chem. Soc. 120: 80), or a 2-substituted piperazine moiety as a constrained amino acid analogue (see Williams et al. (1996) J. Med. Chem. 39:1345-1348). In still other embodiments, certain amino acid residues can be replaced with aryl and bi-aryl moieties, e.g., monocyclic or bicyclic aromatic or heteroaromatic nucleus, or a biaromatic, aromatic-heteroaromatic, or biheteroaromatic nucleus. The subject RRPE peptidomimetics can be optimized by, e.g., combinatorial synthesis techniques combined with such high throughput screening as described herein.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of inhibiting calcineurin-RRPE interaction. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

According to another aspect of this invention, RRPE peptides and peptidomimetics may be administered directly to PV infected cells. Direct delivery of such RRPE therapeutics may be facilitated by formulation of the peptidyl compound in any pharmaceutically acceptable dosage form, e.g., for delivery orally, intratumorally, peritumorally, interlesionally, intravenously, intramuscularly, subcutaneously, periolesionally, or (preferably) topical routes, to exert local therapeutic effects.

Topical administration of the therapeutic is advantageous since it allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the affected cells. Successful intracellular delivery of agents not naturally taken up by cells has been achieved by exploiting the natural process of intracellular membrane fusion, or by direct access of the cell's natural transport mechanisms which include endocytosis and pinocytosis (Duzgunes (1985) Subcellular Biochemistry 11:195-286). Such processes are also useful in the direct delivery and uptake of the subject RRPE peptides and peptidomimetic by papillomavirus-infected cells.

In one embodiment, the membrane barrier can be overcome by associating the RRPE protein in complexes with lipid formulations closely resembling the lipid composition of natural cell membranes. In particular, the subject RRPE peptidomimetics are encapsulated in liposomes to form pharmaceutical preparations suitable for administration to living cells and, in particular, suitable for topical administration to human skin. The Yarosh U.S. Pat. No. 5,190,762 demonstrates that proteins can be delivered across the outer skin layer and into living cells, without receptor binding, by liposome encapsulation.

These lipids are able to fuse with the cell membranes on contact, and in the process, the associated RRPE peptidomimetic is delivered intracellularly. Lipid complexes can not only facilitate intracellular transfers by fusing with cell membranes but also by overcoming charge repulsions between the cell membrane and the molecule to be inserted. The lipids of the formulations comprise an amphipathic lipid, such as the phospholipids of cell membranes, and form hollow lipid vesicles, or liposomes, in aqueous systems. This property can be used to entrap the RRPE peptidomimetic within the liposomes.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Liposomes have been described in the art as in vivo delivery vehicles. The structure of various types of lipid aggregates varies, depending on composition and method of forming the aggregate. Such aggregates include liposomes, unilamellar vesicles, multilameller vesicles, micelles and the like, having particle sizes in the nanometer to micrometer range. Methods of making lipid aggregates are by now well-known in the art. For example, the liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

In one embodiment, pH sensitive liposomes are a preferred type of liposome for use with the present invention. One pathway for the entry of liposomes into cellular cytoplasm is by endocytosis into lysozymes of low pH. Accordingly, liposomes which are stable at neutral pH but release their contents at acidic pH can be used to deliver enzymes into the lysozymes of the cytoplasm, whereupon the contents are released.

Liposomes can be made sensitive to the low pH of the lysozymes by the lipid composition. In particular, pH sensitive liposomes can be prepared by using phospholipids which form lipid bilayers when charged but fail to stack in an ordered fashion when neutralized. An example of such a phospholipid is phosphatidylethanolamine, which is negatively charged above pH 9. The net charge of a phospholipid can be maintained at a pH which would otherwise neutralize the head groups by including charged molecules in the lipid bilayer which themselves can become neutralized. Examples of these charged molecules are oleic acid and cholesteryl hemisuccinate, which are negatively charged at neutral pH but become neutralized at pH 5. The effect of combining these together in a lipid bilayer is that at pH 9 all molecules are charged; at pH 7 the net negative charge of the oleic acid and cholesteryl hemisuccinate maintains the stability of the phosphatidylethanolamine, and at pH 5 all components are protonated and the lipid membrane is destabilized. Additional neutral molecules, such as phosphatidylcholine, can be added to the liposomes as long as they do not interfere with stabilization of the pH sensitive phospholipid by the charged molecules.

In another embodiment, the RRPE peptidomimetic is formulated with a positively charged synthetic (cationic) lipid N-[1-(2,3-dioleyloxy)propyl]-N,N,N-trimethylammonium chloride (DOTMA), in the form of liposomes, or small vesicles, which can fuse with the negatively charged lipids of the cell membranes of mammalian cells, resulting in uptake of the contents of the liposome (see, for example, Felgner et al. (1987) PNAS 84:7413-7417; and U.S. Pat. No. 4,897,355 to Eppstein, D. et al.). Another cationic lipid which can be used to generate RRPE peptidomimetic containing liposomes is the DOTMA analogue, 1,2-bis(oleoyloxy)-3-(trimethylammonio)propane (DOTAP) in combination with a phospholipid to form delivery vesicles.

Lipofectin™ (Bethesda Research Laboratories, Gaithersburg, Md.) and/or LipofectAMINE™, commercially available reagents, can be used to deliver the RRPE peptidomimetic directly into cells. Positively charged complexes prepared in this way spontaneously attach to negatively charged cell surfaces, fuse with the plasma membrane, and can efficiently deliver functional RRPE peptidomimetic into, for example, keratinocytes. Sells et al. (1995) Biotechniques 19:72-76 describe a procedure for delivery of purified proteins into a variety of cells using such ploycationic lipid preparations.

A significant body of information is emerging regarding the use of other cationic lipids for the delivery of macromolecules into cells. Other suitable lipid vesicles for direct delivery of the RRPE peptidomimetic include vesicles containing a quaternary ammonium surfactant (Ballas et al. (1988) Biochim. Biophys Acta 939:8-18); lipophilic derivatives of spermine (Behr et al. (1989) PNAS 86:6982-6986).

The lipid formulations of the subject RRPE peptidomimetic can be used in pharmaceutical formulations to deliver the RRPE peptidomimetic by various routes and to various sites in the animal body to achieve the desired therapeutic effect. Local or systemic delivery of the therapeutic agent can be achieved by administration comprising application or insertion of the formulation into body cavities, inhalation or insufflation of an aerosol, or by parenteral introduction, comprising intramuscular, intravenous, intradermal, peritoneal, subcutaneous and topical administration.

Topical formulations are those advantageously applied to the skin or mucosa. Target mucosa can be that of the vaginal, cervical, vulvar, penal or anorectal mucosa, or target mucosa can be that of the gastrointestinal tract, comprising the mouth, larynx, esophagous and stomach. Lipids present in topical formulations can act to facilitate introduction of therapeutic RRPE peptidomimetic into the target tissue, such as the stratum or corneum of the skin, by perturbing the barrier properties of the protective membrane, or by introducing perturbing agents or penetration enhancers such as DMSO, Azone™ or by promoting the activity of these penetration enhancers.

Other pharmaceutical formulations comprising the cationic lipids of the invention are topical preparations containing an anesthetic or cytostatic agent, immunomodulators, bioactive peptides or oligonucleotides, sunscreens or cosmetics. Preparations for topical use are conveniently prepared with hydrophilic and hydrophobic bases in the form of creams, lotions, ointments or gels; alternatively, the preparation may be in the form of a liquid that is sprayed on the skin. The effect of the cationic lipids is to facilitate the penetration of the active antiviral agent through the stratum corneum of the dermis.

The composition and form of pharmaceutical preparations comprising the liposome, in combination with the RRPE peptidomimetic, can vary according to the intended route of administration.

Also, by suitable modifications of the liposome membranes, the liposomes can be made to bind to specific subpopulations of cells.

In still another embodiment, the therapeutic RRPE peptidomimetic can be delivered by way of an artificial viral envelope (AVE). The art as described a number of viral envelopes which exploit molecular recognition of cell surface receptors by viral surface proteins as a means for selective intracellular delivery of macromolecules, including proteins. According to the method of Schreier, et. al., U.S. Pat. No. 5,252,348, a virtually unlimited number of artificial viral envelopes can be prepared and applied using recombinant or isolated surface determinants. For example, the AVEs be generated as viral mimetics of a number of human viruses including arboviruses; flaviviridae; bunyaviridae; hepatitis viruses; Epstein-Barr viruses; herpes viruses; paramyxoviruses; respiratory syncytical virus; retroviruses including human T-lymphotrophic virus type I and II (HTLV-I/II) and human immunodeficiency virus type 1 and 2 (HIV-1/2); rhinoviruses;

orthopoxviruses; and human papilloma viruses (particularly those engineered not to express E6 and/or E7).

In another embodiment, direct delivery of a therapeutic RRPE peptidomimetic may be facilitated by chemical modification of the polypeptide itself. One such modification involves increasing the lipophilicity of the RRPE peptidomimetic in order to increase binding to the cell surface, in turn, stimulating non-specific endocytosis of the protein. Lipophilicity may be increased by adding a lipophilic moiety (e.g., one or more fatty acid molecules) to the RRPE peptidomimetic. A wide variety of fatty acids may be employed. For example, the protein may be palmitoylated. Alternatively, a lipopeptide may be produced by fusion or cross-linking, to permit the RRPE peptidomimetic to resemble the natural lipopeptide from *E. coli*, tripalmitoyl-S-glycerylcysteil-seryl-serine, at its amino terminus. This lipopeptide has been shown to increase the uptake of fused peptides (P. Hoffmann et al., (1988) Immunobiol. 177:158-70). Lipophilicity may also be increased by esterification of the protein at tyrosine residues or other amino acid residues. And uptake of the RRPE peptidomimetic may be increased by addition of a basic polymer such as polyarginine or polylysine (Shen et al. (1978) PNAS 75:1872-76).

Direct delivery of RRPE peptidomimetics according to this invention may also be effected by the use of transport moieties, such as protein carriers known to cross cell membranes. For example, a RRPE peptide may be fused to a carrier protein, preferably by a genetic fusion which may be expressed in a system such as *E. coli*, barulovirus or yeast. According to one embodiment of this invention, the amino terminus of the RRPE peptide may be fused to the carboxy terminus of a transport moiety using standard techniques.

Nucleotide sequences encoding such carrier-RRPE peptide fusion proteins, operatively linked to regulatory sequences, may be constructed and introduced into appropriate expression systems using conventional recombinant DNA procedures. The resulting fusion protein may then be purified and tested for its capacity to (1) enter intact eukaryotic cells and (2) inhibit viral DNA replication once inside the intact eukaryotic cells.

Useful carrier proteins include, for example, bacterial hemolysins or "blending agents", such as alamethicin or sulfhydryl activated lysins. Other carrier moieties which may be used include cell entry components of bacterial toxins, such as *Pseudomonas* exotoxin, tetanus toxin, ricin toxin, and diphtheria toxin. Also useful is melittin, from bee venom. Other useful carrier proteins include proteins which are viral receptors, cell receptors or cell ligands for specific receptors that are internalized, i.e., those which cross mammalian cell membranes via specific interaction with cell surface receptors, recognized and taken into the cell by cell surface receptors. Such cell ligands include, for example, epidermal growth factor, fibroblast growth factor, transferrin and platelet-derived growth factor. Alternatively, the ligand may be a non-peptide, such as mannose-6-phosphate, which permits internalization by the mannose-6-phosphate receptor. The transport moiety may also be selected from bacterial immunogens, parasitic immunogens, viral immunogens, immunoglobulins or fragments thereof that bind to target molecules, cytokines, growth factors, colony stimulating factors and hormones. A transport moiety may also be derived from the tat protein of HIV-1.

As an alternative or addition to the above-described chemical modifications and protein carriers, which may be employed alone or in combination, other agents which allow penetration of the keratinized cell layer may be employed to facilitate delivery of the RRPE peptidomimetics of this invention to papillomavirus-infected cells. In topical applications, for example, the RRPE peptidomimetic may be administered in combination with dimethylsulfoxide, an agent which promotes penetration of cell membranes by substances mixed with it. Useful keratinolytic agents include, for example, salicylic acid, urea, and alpha-hydroxyacids. For such applications, the RRPE peptidomimetic and any other agent may be administered topically, in cream or gel form.

According to an alternate embodiment of this invention, the therapeutic RRPE peptidomimetic may be administered serially or in combination with other therapeutics used in the treatment of papillomavirus infections or diseases caused by them. Such therapeutics include interferons, such as IFN-g, IFN-a and IFN-b derived from natural sources or produced by recombinant techniques, other cell mediators formed by leukocytes or produced by recombinant techniques such as for example, interleukin-1, interleukin-2, tumor necrosis factor, macrophage colony stimulating factor, macrophage migration inhibitory factor, macrophage activation factor, lymphotoxin and fibroblast growth factor. Alternatively, the RRPE peptidomimetic may be administered serially or in combination with conventional therapeutic agents or regimens such as, for example, salicylic acid, podophyllotoxin, retinoic acid, surgery, laser therapy and cryotherapy. Such combination therapies may advantageously utilize less than conventional dosages of those agents, or involve less radical regimens, thus avoiding any potential toxicity or risks associated with those therapies.

It will also be understood by those skilled in the art that any of the above enumerated delivery methods may be augmented, where topical application is being carried out, by the use of ultrasound or iontophoretic delivery devises which facilitate transdermal delivery of proteins. See, for example, Banga et al. (1993) Pharm Res 10:697-702; and Mitragotri et al. (1995) Science 269:850-853.

In another aspect, the present invention relates to gene therapy constructs containing a nucleic acid encoding, for example in an exemplary method, a RRPE peptide of the present invention, operably linked to at least one transcriptional regulatory sequence. The gene constructs of the present invention are formulated to be used as a part of a gene therapy protocol to deliver the subject therapeutic protein to an animal to be treated.

Any of the methods known to the art for the insertion of DNA fragments into a vector may be used to construct expression vectors consisting of appropriate transcriptional/translational control signals and the desired RRPE peptide-encoding nucleotide sequence. See, for example, Maniatis T., Fritsch E. F., and Sambrook J. (1989): Molecular Cloning (A Laboratory Manual), Cold Spring Harbor Laboratory, Cold Spring Harbor, N.Y.; and Ausubel F. M., Brent R., Kingston R. E., Moore, D. D., Seidman J. G., Smith J. A., and Struhl K. (1992): Current Protocols in Molecular Biology, John Wiley & Sons, New York. These methods may include in vitro DNA recombinant and synthetic techniques and in vivo genetic recombination. Expression of a nucleic acid sequence encoding a RRPE peptide may be regulated by a second nucleic acid sequence so that the peptide is expressed in a host infected or transfected with the recombinant DNA molecule. For example, expression of a RRPE peptide may be controlled by any promoter/enhancer element known in the art. The promoter activation may be tissue specific or inducible by a metabolic product or administered substance.

Promoters/enhancers which may be used to control the expression of the RRPE peptide in vivo include, but are not limited to, the native RRPE promoter, the cytomegalovirus (CMV) promoter/enhancer (Karasuyama et al., 1989, J. Exp.

Med., 169:13), the human b-actin promoter (Gunning et al. (1987) PNAS 84:4831-4835), the glucocorticoid-inducible promoter present in the mouse mammary tumor virus long terminal repeat (MMTV LTR) (Klessig et al. (1984) Mol. Cell. Biol. 4:1354-1362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bemoist et al. (1981) Nature 290:304-310; Templeton et al. (1984) Mol. Cell. Biol., 4:817; and Sprague et al. (1983) J. Virol., 45:773), the promoter contained in the 3' long terminal repeat of Rous sarcoma virus (RSV) (Yamamoto et al., 1980, Cell, 22:787-797), the herpes simplex virus (HSV) thymidine kinase promoter/enhancer (Wagner et al. (1981) PNAS 82:3567-71), and the herpes simplex virus LAT promoter (Wolfe et al. (1992) Nature Genetics, 1:379-384), and Keratin gene promoters, such as Keratin 14.

Expression constructs of the subject RRPE peptides may be administered in any biologically effective carrier, e.g. any formulation or composition capable of effectively delivering the recombinant gene to cells in vivo. Approaches include insertion of the RRPE peptide coding sequence in viral vectors including recombinant retroviruses, adenovirus, adeno-associated virus, and herpes simplex virus-1, or recombinant eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO4 precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid into a cell is by use of a viral vector containing nucleic acid encoding the particular RRPE peptide desired. Infection of cells with a viral vector has the advantage that a large proportion of the targeted cells can receive the nucleic acid. Additionally, molecules encoded within the viral vector, e.g., the recombinant RRPE peptide, are expressed efficiently in cells which have taken up viral vector nucleic acid.

In addition to viral transfer methods, such as those illustrated above, non-viral methods can also be employed to cause expression of a RRPE peptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the RRPE peptide-encoding gene by the targeted cell. Exemplary gene delivery systems of this type include liposomal derived systems, poly-lysine conjugates, and artificial viral envelopes.

In clinical settings, the gene delivery systems for the therapeutic RRPE peptide coding sequence can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or "gene gun" techniques. In preferred embodiments, the gene therapy construct of the present invention is applied topically to an infected or transformed cells of the skin or mucusal tissue. A RRPE peptide gene construct can, in one embodiment, be delivered in a gene therapy construct by electroporation using techniques described, for example, by Dev et al. ((1994) Cancer Treat Rev 20:105-115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Antibodies of this Invention

Another aspect of the invention pertains to an antibody specifically reactive with a mammalian Csp (Csp1 or Csp2) polypeptide, e.g., a wild-type or mutated Csp polypeptide. For example, by using immunogens derived from an Csp polypeptide, e.g., based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian Csp polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of an Csp polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of an Csp polypeptide of a mammal, e.g., antigenic determinants of a protein set forth in SEQ ID Nos: 4-5 or 24, closely related homologs (e.g., at least 90% homologous, and more preferably at least 94% homologous).

Following immunization of an animal with an antigenic preparation of an Csp polypeptide, anti-Csp antisera can be obtained and, if desired, polyclonal anti-Csp antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a mammalian Csp polypeptide of the present invention and monoclonal antibodies isolated from a culture comprising such hybridoma cells. In one embodiment anti-human Csp antibodies specifically react with the protein encoded by a nucleic acid having SEQ ID Nos: 2-3 or 22-23.

The term antibody as used herein is intended to include fragments thereof which are also specifically reactive with one of the subject mammalian Csp polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for an Csp polypeptide conferred by at least one CDR region of the antibody. In preferred embodiments, the antibodies, the antibody further comprises a label attached thereto and able to be detected, (e.g., the label can be a radioisotope, fluorescent compound, enzyme or enzyme cofactor).

Anti-Csp antibodies can be used, e.g., to monitor Csp polypeptide levels in an individual for determining, e.g., whether a subject has a disease or condition associated with an aberrant Csp polypeptide level, or allowing determination of the efficacy of a given treatment regimen for an individual afflicted with such a disorder. The level of Csp polypeptides may be measured from cells in bodily fluid, such as in blood samples.

Another application of anti-Csp antibodies of the present invention is in the immunological screening of cDNA libraries constructed in expression vectors such as gt11, gt18-23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of an Csp polypeptide, e.g., other orthologs of a particular Csp polypeptide or other paralogs from the same species, can then be detected with antibodies, as, for example, reacting nitrocellulose filters lifted from infected plates with anti-Csp antibodies. Positive phage detected by this assay can then be isolated from the infected plate. Thus, the presence of Csp homologs can be detected and cloned from other animals, as can alternate isoforms (including splice variants) from humans.

Antibodies specifically binding to an Csp conversion product are also within the scope of the invention. In an illustrative embodiment, the invention provides antibodies which specifically bind to kinetensin (1-8) and not to kinetensin (1-9).

Characterizing the Calcipressin (Csp 1 and Csp 2) Genotype

Nucleic acid probes can be used to determine the calcipressin, i.e., Csp 1 and Csp 2 phenotype of cell and tissue samples, e.g., as a part of a diagnostic test kit for identifying cells or tissue which misexpress calcipressin, i.e., Csp 1 and Csp 2, such as by measuring a level of a calcipressin, i.e., Csp 1 and Csp 2 encoding nucleic acid in a sample of cells from a patient; e.g. detecting calcipressin, i.e., Csp 1 and Csp 2 mRNA levels or determining whether a genomic calcipressin, i.e., Csp 1 and Csp 2 gene has been mutated or deleted.

To illustrate, nucleotide probes can be generated from the subject calcipressin, i.e., Csp 1 and Csp 2 genes which facilitate histological screening of intact tissue and tissue samples for the presence (or absence) of calcipressin, i.e., Csp 1 and Csp 2-encoding transcripts. Probes directed to calcipressin, i.e., Csp 1 and Csp 2 messages, or to genomic calcipressin, can be used for both predictive and therapeutic evaluation of allelic mutations which might be manifest in, for example, neurodegenerative disorders, inflammatory and/or autoimmune disorders or various pathologies associated with Downs Syndrome. Used in conjunction with immunoassays as described below, the oligonucleotide probes can help facilitate the determination of the molecular basis for developing disorders which may involve some abnormality associated with expression (or lack thereof) of a calcipressin, i.e., Csp 1 and Csp 2 protein. For instance, variation in polypeptide synthesis, post-translational modification, or half-life can be differentiated from a mutation in a coding sequence.

Accordingly, the present method provides a method for determining if a subject is at risk for a disorder characterized by disorders of the nervous system or the immune system. In preferred embodiments, method can be generally characterized as comprising detecting, in a sample of cells from the subject, the presence or absence of a genetic lesion characterized by at least one of (i) an alteration affecting the integrity of a gene encoding an calcipressin, i.e., Csp 1 and Csp 2 protein, (ii) the mis-expression of the calcipressin, i.e., Csp 1 and Csp 2 gene, or (iii) aberrant modification of the calcipressin, i.e., Csp 1 and Csp 2 gene product. To illustrate, such genetic lesions can be detected by ascertaining the existence of at least one of (i) a deletion of one or more nucleotides from a calcipressin, i.e., Csp 1 and Csp 2 gene, (ii) an addition of one or more nucleotides to a calcipressin, i.e., Csp 1 and Csp 2 gene, (iii) a substitution of one or more nucleotides of a calcipressin, i.e., Csp 1 and Csp 2 gene, (iv) a gross chromosomal rearrangement of a calcipressin, i.e., Csp 1 and Csp 2 gene, (v) a gross alteration in the level of a messenger RNA transcript of a calcipressin, i.e., Csp 1 and Csp 2 gene, (vii) aberrant modification of a calcipressin, i.e., Csp 1 and Csp 2 gene, such as of the methylation pattern of the genomic DNA, (vii) the presence of a non-wild type splicing pattern of a messenger RNA transcript of a calcipressin, i.e., Csp 1 and Csp 2 gene, (viii) a non-wild type level of a calcipressin, i.e., Csp 1 and Csp 2 protein, (ix) allelic loss of the calcipressin, i.e., Csp 1 and Csp 2 gene, and (x) inappropriate post-translational modification of a calcipressin, i.e., Csp 1 and Csp 2-protein. As set out below, the present invention provides a large number of assay techniques for detecting lesions in a calcipressin, i.e., Csp 1 and Csp 2 gene, and importantly, provides the ability to discern between different molecular causes underlying calcipressin, i.e., Csp 1 and Csp 2-dependent disorders of the nervous and/or immune system.

In preferred embodiments, the methods of the invention can be characterized as comprising detecting, in a sample of cells from the subject, the presence or absence of a genetic lesion characterized by the mis-expression of a gene whose expression is initiated by an Csp promoter. To illustrate, such genetic lesions can be detected by ascertaining the existence of at least one of (i) a deletion of one or more nucleotides from an Csp promoter, (ii) an addition of one or more nucleotides to an Csp promoter, or (iii) a substitution of one or more nucleotides in an Csp promoter. The genetic lesion can also be a chromosomal rearrangement, such as chromosomal dislocation. As set out below, the present invention provides a large number of assay techniques for detecting lesions in an Csp promoter or regulatory element thereof.

In one embodiment of the invention, a genetic lesion is identified by a method comprising sequencing a 5'flanking region of an Csp gene. Sequencing primers can be designed which hybridize to a portion of an Csp 5' flanking region. Primers can also be designed to hybridize to a portion of an Csp gene that is transcribed, since this will allow sequencing of the most proximal portion of the promoter. In one embodiment, sequencing primers are located about 250, or about 300 nucleotides apart for sequencing a stretch of about 250 or 300 nucleotides. Examples of primers that can be used include:

downstream sequencing primer:

5' AGGAGGTGGATCTGC 3' (SEQ ID No. 43, corresponding to nucleotides 5-19 of the mouse Csp1 cDNA sequence shown in SEQ ID NO: 2)

In an exemplary embodiment, there is provided a nucleic acid composition comprising a (purified) oligonucleotide probe or primer including a region of nucleotide sequence which is capable of hybridizing to a sense or antisense sequence of an Csp promoter, such as represented in SEQ ID No: 1 or naturally occurring mutants thereof. The nucleic acid of a cell is rendered accessible for hybridization, the probe is exposed to nucleic acid of the sample, and the hybridization of the probe to the sample nucleic acid is detected. It is anticipated that use of an amplification step (e.g. PCR and/or LCR) may be a desirable first step in conjunction with any of the techniques used for detecting mutations described herein.

In an exemplary embodiment, there is provided a nucleic acid composition comprising a (purified) oligonucleotide probe including a region of nucleotide sequence which is capable of hybridizing to a sense or antisense sequence of a calcipressin, i.e., Csp gene, such as represented by SEQ ID Nos: 2-3, 22-23, or naturally occurring mutants thereof, or 5' or 3' flanking sequences or intronic sequences naturally associated with the subject calcipressin, i.e., Csp 1, Csp2, or and Csp 3 gene or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1944) PNAS 91:360-364), the later of which can be particularly useful for detecting point mutations in the calcipressin, i.e., Csp 1, Csp2, and Csp 3 gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a calcipressin gene under conditions such that hybridization and amplification of the calcipressin, i.e., Csp 1, Csp2, and Csp 3 gene (if present) occurs, and (iv) detecting the presence or absence of an amplification product, or detecting the size of the amplification product and comparing the length to a control sample.

In a preferred embodiment of the subject assay, mutations in a calcipressin, i.e., Csp 1, Csp2, and Csp 2 gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the calcipressin gene and detect mutations by comparing the sequence of the sample calcipressin, i.e., Csp 1, Csp2, and Csp 3 with the corresponding wild-type (control) sequence. Exemplary sequencing reactions include those based on techniques developed by Maxim and Gilbert (*Proc. Natl. Acad Sci USA* (1977) 74:560) or Sanger (Sanger et al (1977) *Proc. Nat. Acad. Sci.* 74:5463). It is also contemplated that any of a variety of automated sequencing procedures may be utilized when performing the subject assays (*Biotechniques* (1995) 19:448), including by sequencing by mass spectrometry (see, for example PCT publication WO 94/16101; Cohen et al. (1996) *Adv Chromatogr* 36:127-162; and Griffin et al. (1993) *Appl Biochem Biotechnol* 38:147-159). It will be evident to one skilled in the art that, for certain embodiments, the occurrence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type calcipressin, i.e., Csp 1, Csp2, and Csp 3 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl. Acad Sci USA* 85:4397; Saleeba et al (1992) Methods Enzymod. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in calcipressin cDNAs obtained from samples of cells. For example, the mutY enzyme of *E. coli* cleaves A at G/A mismatches and the thymidine DNA glycoslase from HeLa cells cleaves T at G/T mismatches (Hsu et al. (1994) *Carcinogenesis* 15:1657-1662). According to an exemplary embodiment, a probe based on a calcipressin sequence, e.g., a wild-type calcipressin, i.e., Csp 1, Csp2, and Csp 3 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in calcipressin genes. For example, single strand conformation polymorphism (SSCP) may be used to detect differences in electrophoretic mobility between mutant and wild type nucleic acids (Orita et al. (1989) *Proc Natl. Acad. Sci. USA* 86:2766, see also Cotton (1993) *Mutat Res* 285:125-144; and Hayashi (1992) *Genet Anal Tech Appl* 9:73-79). Single-stranded DNA fragments of sample and control calcipressin nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al (1989) Proc. Natl. Acad. Sci. USA 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437-2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

In yet another exemplary embodiment, aberrant methylation patterns of a calcipressin gene can be detected by digesting genomic DNA from a patient sample with one or more restriction endonucleases that are sensitive to methylation and for which recognition sites exist in the calcipressin gene (including in the flanking and intronic sequences). See, for example, Buiting et al. (1994) Human Mol Genet. 3:893-895. Digested DNA is separated by gel electrophoresis, and hybridized with probes derived from, for example, genomic or cDNA sequences. The methylation status of the calcipressin, i.e., Csp 1, Csp2 and Csp 3 gene can be determined by comparison of the restriction pattern generated from the sample DNA with that for a standard of known methylation.

In still another embodiment, the level of a calcipressin protein can be detected by immunoassay. For instance, the cells of a biopsy sample can be lysed, and the level of a calcipressin, i.e., Csp 1, Csp2, and Csp 3 protein present in the cell can be quantitated by standard immunoassay techniques.

In yet another aspect of the invention, the subject calcipressin polypeptides can be used to generate a "two hybrid" assay or an "interaction trap" assay (see, for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; Iwabuchi et al. (1993) Oncogene 8:1693-1696; and Brent WO94/10300), for detecting point mutations in the calcipressin coding sequence which produce proteins that no longer bind calcineurin.

Briefly, the interaction trap relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a calcipressin polypeptide. The second hybrid protein encodes a transcriptional activation domain fused in frame to calcineurin. If the calcipressin, i.e., Csp 1, Csp2, and Csp 3 and calcineurin hybrid proteins are able to interact, e.g., form a calcipressin, i.e., Csp 1, Csp2 and Csp 3-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the calcipressin, calcineurin.

In yet other embodiments, the subject assay can be designed to detect aberrant post-translational modification of the Csp protein, such as aberrant phosphorylation, prenylation, lipid modification, ubiquitination, and/or degradation. The assay can also be used to assess cellular localization of calcipressin.

According to the diagnostic and prognostic method of the present invention, alterations of the wild-type calcipressin, i.e., Csp locus which result in loss-of-function of Csp 1, Csp2, and Csp 3 are detected. In addition, the method can be performed by detecting the wild-type Csp locus and confirming the lack of a predisposition to neurodegenerative disorders, autoimmune and/or inflammatory disorders at the Csp locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, e.g., in the tumor tissue, and are not inherited in the germline. The finding of Csp mutations can thus provide both diagnostic and prognostic information. A Csp allele which is not deleted (e.g., found on the sister chromosome to a chromosome carrying a Csp deletion) can be screened for other mutations, such as insertions, small deletions, and point mutations. It is believed that many mutations found in tissues from subjects having neurodegenerative, inflammatory and/or autoimmune disorders will be those leading to loss-of-function or decreased expression of Csp gene product. Point mutational events may occur in regulatory regions, such as in the promoter of the gene, leading to loss or diminution of expression of the mRNA. Point mutations may also abolish proper RNA processing, leading to loss of expression of Csp gene product, or to a decrease in mRNA stability or translation efficiency.

As set forth above, useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis LCR, and PCR-SSCP.

Predisposition to neurodegenerative, inflammatory and/or autoimmune disorders can be ascertained by testing any tissue of a human for mutations of Csp gene. For example, a person who has inherited a germline Csp mutation may be prone to developing these disorders. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the Csp 1, Csp2 and Csp 3 gene. Alteration of a wild-type Csp allele, whether, for example, by point mutation or deletion, can be detected by any of the means discussed herein.

Continuing from the discussion above, there are several methods that can be used to detect DNA sequence variation. Direct DNA sequencing, either manual sequencing or automated fluorescent sequencing can detect sequence variation. For a gene as large as Csp, manual sequencing is not necessarily labor-intensive, and under optimal conditions, mutations in the coding sequence of a gene will rarely be missed. Another approach is the single-stranded conformation polymorphism assay (SSCA). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE), heteroduplex analysis (HA), and chemical mismatch cleavage (CMC). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. Once a mutation is known, an allele specific detection approach such as allele specific oligonucleotide (ASO) hybridization can be utilized to rapidly screen large numbers of other samples for that same mutation.

In order to detect the alteration of the wild-type Csp 1 gene in a tissue, it is helpful to isolate the tissue free from surrounding normal tissues.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of cases having neurodegenerative, inflammatory, and/or autoimmune disorders. Southern blots displaying hybridizing fragments (differing in length from control DNA when probed with sequences near or including the Csp locus) indicate a possible mutation. If restriction enzymes which produce very large restriction fragments are used, then pulsed field gel electrophoresis (PFGE) is employed.

Detection of point mutations may be accomplished by molecular cloning of the Csp allele(s) and sequencing the allele(s) using techniques well known in the art. The DNA sequence of the amplified sequences can then be determined.

There are many well known methods for a more complete, yet still indirect, test for confirming the presence of a susceptibility allele, including: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. For allele-specific PCR, primers are used which hybridize at their 3' ends to a particular calcipressin, i.e., Csp 1, Csp2, and Csp 3 mutation. If the particular calcipressin mutation is not present, an amplification product is not observed. Amplification Refractory Mutation System (ARMS) can also be used, as disclosed in European Patent Application Publication No. 0332435. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment.

Such a method is particularly useful for screening relatives of an affected individual for the presence of Csp mutations found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type Csp gene coding sequence. The riboprobe and either mRNA or DNA isolated from the subject tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the Csp mRNA or gene but can be a segment of either. If the riboprobe comprises only a segment of the Csp mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA which might contain a mutation can be amplified using PCR (see below) before hybridization. Changes in DNA of the Csp gene can also be detected using Southern hybridization, especially if the changes are gross rearrangements, such as deletions and insertions.

DNA sequences of the Csp gene which have been amplified by use of PCR may also be screened using allele-specific probes. These probes are nucleic acid oligomers, each of which contains a region of the Csp 2 gene sequence harboring a known mutation. For example, one oligomer may be about 30 nucleotides in length, corresponding to a portion of the Csp gene sequence. By use of a battery of such allele-specific probes, PCR amplification products can be screened to identify the presence of a previously identified mutation in the Csp gene. Hybridization of allele-specific probes with amplified Csp sequences can be performed, for example, on a nylon filter. Hybridization to a particular probe under stringent hybridization conditions indicates the presence of the same mutation in the subject tissue as in the allele-specific probe.

The most definitive test for mutations in a candidate locus is to directly compare genomic Csp sequences from patients having autoimmune and/or inflammatory disorders with those from a control population. Alternatively, one could sequence messenger RNA after amplification, e.g., by PCR, thereby eliminating the necessity of determining the exon structure of the candidate gene.

Mutations from patients having neurodegenerative, autoimmune and/or inflammatory disorders falling outside the coding region of Csp can be detected by examining the non-coding regions, such as introns and regulatory sequences near or within the Csp genes. An early indication that mutations in noncoding regions are important may come from Northern blot experiments that reveal messenger RNA molecules of abnormal size or abundance in these patients as compared to control individuals.

Alteration of Csp mRNA expression can be detected by any techniques known in the art. These include Northern blot analysis, PCR amplification and RNase protection. Diminished mRNA expression indicates an alteration of the wild-type Csp gene. Alteration of wild-type Csp genes can also be detected by screening for alteration of wild-type Csp protein. For example, monoclonal antibodies immunoreactive with Csp can be used to screen a tissue. Lack of cognate antigen would indicate a Csp mutation. Antibodies specific for products of mutant alleles could also be used to detect mutant Csp gene product. Such immunological assays can be done in any convenient formats known in the art. These include Western blots, immunohistochemical assays and ELISA assays. Any means for detecting an altered Csp protein can be used to detect alteration of wild-type Csp genes. Functional assays, such as protein binding determinations, can be used. In addition, assays can be used which detect Csp 1, Csp2, and Csp 3 biochemical function. Finding a mutant Csp gene product indicates alteration of a wild-type calcipressin gene.

Generally, the primers can be made using oligonucleotide synthesizing machines which are commercially available.

Methods of Use: Nucleic Acid Diagnosis and Diagnostic Kits

In order to detect the presence of a Csp allele predisposing an individual to neurodegenerative, inflammatory and/or autoimmune diseases, a biological sample such as a blood sample or biopsy, is prepared and analyzed for the presence or absence of susceptibility alleles of Csp. In order to detect increases susceptibility to these disorders, and abnormal pathologies associated with Down Syndrome, a biological sample from a subject is prepared and analyzed for the presence or absence of mutant alleles of Csp. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method can involve amplification of the relevant Csp sequences. In certain embodiments of the invention, the screening method involves a non-PCR based strategy for amplification, such as strand-displacement amplification (SDA) and the like. Such screening methods may include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 21. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., supra and Sambrook et al., supra. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety.

As noted above, non-PCR based screening assays are also contemplated in this invention. An exemplary non-PCR based procedure includes hybridization of a nucleic acid probe (or an analog such as a methyl phosphonate backbone replacing the normal phosphodiester) to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$-$10^6$ increase in sensitivity.

Two-step label amplification methodologies are known in the art. These assays work on the principle that a small ligand (such as digoxigenin, biotin, or the like) is attached to a nucleic acid probe capable of specifically binding Csp. Exemplary probes can be developed on the basis of the sequence set forth in SEQ ID NOs: 1-3, 22-23, and 25-27. Allele-specific probes are also contemplated within the scope of this example, and exemplary allele specific probes include probes encompassing the predisposing mutations resulting in loss of calcineurin binding specificity.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. In a second example, the small ligand is recognized by a second ligand-enzyme conjugate that is capable of specifically complexing to the first ligand. A well known embodiment of this example is the biotin-avidin type of interactions.

It is also contemplated within the scope of this invention that the nucleic acid probe assays of this invention can employ a cocktail of nucleic acid probes capable of detecting Csp sequences. Thus, in one example to detect the presence of Csp in a cell sample, more than one probe complementary to Csp is employed and in particular the number of different probes is alternatively 2, 3, or 5 different nucleic acid probe sequences. In another example, to detect the presence of mutations in the Csp gene sequence in a patient, more than one probe complementary to Csp is employed where the cocktail includes probes capable of binding to the allele-specific mutations identified in populations of patients with alterations in Csp. In this embodiment, any number of probes can be used, and will preferably include probes corresponding to the major gene mutations identified as predisposing an individual to, e.g., autoimmune and/or inflammatory disorder. Some candidate probes contemplated within the scope of the invention include probes that include the allele-specific mutations which result in loss of calcineurin binding activity.

Drug Screening Assays and Transgenic Animals Cell Based and Cell-Free Assays

The invention provides method for treating a subject having a disorder or condition associated with aberrant Csp activity, such as Csp expression. In one embodiment of the invention, the treatment of the subject consists of administering to the subject a compound which modulates Csp expression. The following section describes various methods that can be used for isolating such compounds.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements.

In one embodiment of the invention, a compound, e.g., a small molecule, can be identified, by performing assays in which a Csp promoter binding partner is incubated with a nucleic acid comprising an Csp promoter or regulatory element thereof and the effect of a test compound on the specific binding of the Csp promoter binding partner to the nucleic acid is determined. The Csp promoter binding partner can be, for example, a nuclear extract prepared from a cell expressing Csp. Alternatively, the Csp promoter binding partner can be an isolated, purified or cloned transcription factor. Modulation of binding to the nucleic acid can be determined, e.g., in an EMSA assay, such as those described above. Thus, a test compound can be incubated together with a DNA, which is preferably labeled, comprising a Csp promoter or regulatory element thereof, and the Csp promoter binding partner. The reaction mixture is then subjected to an electrophoresis and the amount of "retarded" protein-DNA complex is compared to the amount of retarded complex from a binding reaction in which the test compound has not been added. A lower level of complex observed in the reaction that contains the test compound compared to the level of complex observed in the reaction that does not contain the test compound indicates that the test compound inhibits or reduces binding of one or more Csp promoter binding partners to the Csp promoter or regulatory element thereof.

This type of reaction can be performed in high throughput type of assays. For example, it is possible to attach the Csp promoter binding partner to 96 well plates, add labeled nucleic acid and a test compound. After the binding reaction, and washing of the plates to remove non specific binding, it is then possible to "read" the amount of label present in each well.

Several in vivo methods can also be used to identify compounds that modulate a Csp activity. In one embodiment, the invention provides a method comprising incubating a cell expressing Csp with a test compound and measuring the Csp mRNA or protein level. Csp mRNA levels can be determined by Northern blot hybridization. Csp mRNA levels can also be determined by methods involving PCR. Other sensitive methods for measuring mRNA, which can be used in high throughput assays, e.g., a method using a DELFIA endpoint detection and quantification method, are described, e.g., in Webb and Hurskainen (1996) *Journal of Biomolecular Screening* 1:119. Csp protein levels can be determined by immunoprecipitations or immunohistochemistry using an antibody that specifically recognizes Csp.

The invention further provides for another in vivo assay for identifying compounds which modulate Csp activity. For example, a reporter construct can be constructed in which a reporter gene is under the control of an Csp nucleic acid comprising a promoter or at least one regulatory element thereof. In one embodiment the Csp nucleic acid comprises the nucleic acid shown as SEQ ID NO: 1. In yet another embodiment, the Csp nucleic acid comprises at least about 6 consecutive nucleotides from SEQ ID NO: 1 or a homolog thereof. In other preferred embodiments of the invention, the Csp nucleic acid comprises at least about 10, at least about 15, at least about 20, or at least about 25 consecutive nucleotides from SEQ ID NO: 1 or homolog thereof.

The reporter gene can be any gene encoding a protein which can readily be detected. The reporter gene is preferably a gene encoding luciferase. According to the method of the invention, cells are transfected with the reporter construct comprising an Csp promoter or at least one regulatory element thereof. Transfection can be transient or stable. It is also possible to transfect a cell with more than one reporter construct. The transfected cells can then be incubated in the presence or absence of a test compound for an appropriate amount of time and the level of expression of the reporter gene can be determined. Compounds which produce a statistically significant change in expression of the reporter gene (either suppression indicating that the test compound is an antagonist of Csp initiated gene expression or potentiation indicating that the test compound is an agonist of Csp initiated gene expression) can be identified.

Similar assays can also be performed using a cell or nuclear extract instead of cells. Thus, in one embodiment, the invention provides a method for identifying a compound which modulates Csp activity, comprising incubating a reporter construct comprising a Csp promoter or at least one regulatory element thereof with a nuclear or cellular extract, or isolated nuclei, in the presence or absence of a test compound. Expression of the test compound is then measured, e.g., by including a labeled nucleotide in the reaction and measuring the amount of label incorporated in the product transcribed from the reporter construct. Other methods can also be used to determine the amount of reporter gene expression in this system, such as the measure of the amount of protein encoded by the reporter gene.

It is preferable to use cells expressing Csp for use in the transfection assays described above. Further, the transgenic animals discussed herein may be used to generate cell lines, containing one or more cell types involved, for example, in inflammatory disorders, that can be used as cell culture models for this disorder. The generation of continuous cell lines is preferred. For examples of techniques which may be used to derive a continuous cell line from the transgenic animals, see Small et al., (1985) *Mol. Cell. Biol.* 5:642-648.

Monitoring the influence of compounds on cells may be applied not only in basic drug screening, but also in clinical trials. In such clinical trials, the expression of a panel of genes may be used as a "read out" of a particular drug's therapeutic effect.

Animal-Based Systems

In yet another embodiment of the invention, compounds that modulate Csp activity in vivo can be identified in non-human animals. In one embodiment of the invention, a non-human animal, e.g., a mouse, is treated with a compound, such as a compound identified in one of the assays described above. After an appropriate amount of time, the level of Csp activity is determined and compared to its activity in a mouse which has not received the test compound. Csp activity in the mouse can be determined by various methods, e.g., by determining mRNA levels, by Northern blot hybridization, or by in situ hybridization. Alternatively, Csp activity can be determined by measuring Csp protein levels, e.g., by immunohistochemistry.

To identify a compound which modulates a Csp promoter or regulatory element thereof, where the Csp promoter or regulatory element is from the human species, the invention provides a method using transgenic non-human mammals. The transgenic animals comprise cells (of that animal) which contain a transgene of the present invention and which preferably (though optionally) express an exogenous Csp promoter in one or more cells in the animal. The transgene preferably contains a Csp promoter or at least one regulatory element thereof and is preferably of human origin. A preferred nucleic acid is a nucleic acid having SEQ ID NO: 1, a fragment thereof or homolog thereof, as well as complements thereto. A Csp promoter transgene can be wildtype or mutant. The promoter or at least one regulatory element is preferably operably linked to a reporter gene. In a preferred embodiment, the reporter gene encodes a protein which can readily be detected, e.g, by a colorimetric assay. A preferred reporter gene is the bacterial beta-galactosidase gene encoded by the lacZ gene.

In preferred embodiments, the expression of the transgene is restricted to specific subsets of cells, tissues or developmental stages utilizing, for example, cis-acting sequences that control expression in the desired pattern. In the present invention, such mosaic expression of a Csp promoter can be essential for many forms of lineage analysis and can additionally provide a means to assess the effects of, for example, the absence of a functional Csp promoter which might grossly alter development in small patches of tissue within an otherwise normal embryo. Temporal patterns of expression can be provided by, for example, conditional recombination systems or prokaryotic transcriptional regulatory sequences.

Genetic techniques which allow for the expression of transgenes, which can be regulated via site-specific genetic manipulation in vivo are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or suppression of expression by one of the subject Csp promoters. For example, excision of a target sequence which interferes with the expression of a recombinant gene, such as one which encodes an antagonistic homolog or an antisense transcript, can be designed to activate expression of that gene. This interference with expression of the protein can result from a variety of mechanisms, such as spatial separation of the gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232-6236; Orban et al. (1992) PNAS 89:6861-6865) or the FLP recombinase system of *Saccharomyces cerevisiae* (O'Gorman et al. (1991) *Science* 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509-1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of a recombinant protein can be regulated via control of recombinase expression.

Use of the cre/loxP recombinase system to regulate expression of a recombinant protein requires the construction of a transgenic animal containing transgenes encoding both the Cre recombinase and the subject protein. Animals containing both the Cre recombinase and a recombinant gene can be provided through the construction of "double" transgenic animals. A convenient method for providing such animals is to mate two transgenic animals each containing a transgene, e.g., a gene and recombinase gene.

One advantage derived from initially constructing transgenic animals containing a transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic transgene is silent will allow the study of progeny from that founder in which disruption of mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVβ lines are often used (Jackson Laboratory, Bar Harbor, Me.). Preferred strains are those with $H-2^b$, $H-2^d$ or H-2q haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) *PNAS* 82:4438-4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method is to incubate the embryos in vitro for about 1-7 days, depending on the species, and then reimplant them into the surrogate host.

For the purposes of this invention, a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a protein (either agonistic, antagonistic or a reporter protein), antisense transcript, or a mutant protein. Further, in such embodiments the sequence is linked to an Csp promoter or regulatory elementmoter fragment, or modified form thereof.

Transgenic animals of the invention can be used to identify functional promoter elements of an Csp promoter. In one embodiment, transgenic animals are prepared which contain a reporter gene under the control of different Csp promoter fragments or modifications thereof. The level of expression of the reporter construct is then measured in various tissues. These transgenic mice can be used to identify regions of the promoter involved in tissue specific expression of Csp, by, e.g., determining the level of expression of the reporter gene in various tissues. These transgenic mice can also be used to identify regions of the Csp promoter which have inducible elements.

Transgenic animals of the invention can also be used to identify compounds which modulate transcription from an Csp promoter. Accordingly, an animal transgenic for a reporter construct under the control of an Csp promoter, fragment thereof, or modified form thereof is treated with compounds, e.g., small molecules, and the level of expression of the transgene is determined in different tissues. Such assays are further described in the Examples. These in vivo assays are particularly useful to confirm the effect of a compound which has been shown in in vitro assays to affect transcription from an Csp promoter.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260-1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) *PNAS* 82:6148-6152). Transfection is easily and efficiently obtained by culturing the blastomeres on a monolayer of virus-producing cells (Van der Putten, supra; Stewart et al. (1987) *EMBO J.* 6:383-388). Alternatively, infection can be performed at a later stage. Virus or virus-producing cells can be injected into the blastocoele (Jahner et al. (1982) *Nature* 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from preimplantation embryos cultured in vitro and fused with embryos (Evans et al. (1981) *Nature* 292:154-156; Bradley et al. (1984) *Nature* 309:255-258; Gossler et al. (1986) *PNAS* 83: 9065-9069; and Robertson et al. (1986) *Nature* 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468-1474.

In one embodiment, gene targeting, which is a method of using homologous recombination to modify an animal's genome, can be used to introduce changes into cultured embryonic stem cells. By targeting a gene of interest in ES cells, these changes can be introduced into the germlines of animals to generate chimeras. The gene targeting procedure is accomplished by introducing into tissue culture cells a DNA targeting construct that includes a segment homologous to a target locus, and which also includes an intended sequence modification to the genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a gene function through the use of a targeting transgene construct designed to undergo homologous recombination with one or more genomic sequences. The targeting construct can be arranged so that, upon recombination with an element of a gene, a positive selection marker is inserted into (or replaces) coding sequences of the targeted gene. The inserted sequence functionally disrupts the gene, while also providing a positive selection trait. Exemplary targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Morphol.* 87:27-45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357-7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357-371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., b-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the coding sequence, transcriptional regulatory sequence, etc. Typically, less than about 1-5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10-30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2-3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice. Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the gene knocked out in various tissues of the offspring by probing the Western blot with an antibody against the particular protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

In one aspect, peptides which have Csp1 activity can be supplied to cells which carry mutant or missing Csp1 alleles. The sequence of a mouse Csp1 and Csp 2 protein is disclosed in SEQ ID NOs: 4-5, and 24. Protein can be produced by expression of the cDNA sequence in bacteria, for example, using known expression vectors. Alternatively, the Csp polypeptides can be extracted from Csp-producing mammalian cells. In addition, the techniques of synthetic chemistry can be employed to synthesize Csp protein. Any of such techniques can provide the preparation of the present invention which comprises the Csp 1 and 2 protein. The preparation is substantially free of other human proteins. This is most readily accomplished by synthesis in a microorganism or in vitro.

Active Csp molecules can be introduced into cells by microinjection or by use of liposomes, for example. Alternatively, some active molecules may be taken up by cells, actively or by diffusion. However, in addition to choice of formulations to enhance uptake of the polypeptide, the Csp polypeptide can be a fusion protein including a second peptide sequence that promotes transcytosis, e.g. amino acid residues 1-72 of the HIV tat protein.

Extracellular application of the Csp gene product may be sufficient to ameliorate neurodenerative and/or inflammatory disorders. Other molecules with Csp activity (for example, peptides, drugs or organic compounds) may also be used to effect such a reversal. Modified polypeptides having substantially similar function are also used for peptide therapy.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. In one approach, one first determines the three-dimensional structure of a protein of interest (e.g., Csp polypeptide) or, for example, of the Csp protein alone or complexed with calcineurin, by x-ray crystallography or NMR, by computer modeling or most typically, by a combination of approaches. In other embodiments, useful information regarding the structure of a polypeptide may be gained by modeling based on the structure of homologous proteins, e.g., by homology modeling. The structure of the protein and velocities of each atom are calculated at a simulation temperature (To) at which the docking simulation to a potential inhibitor is to be determined.

Computer programs for performing energy minimization routines are commonly used to generate molecular models. For example, both the CHARMM (Brooks et al. (1983) *J Comput Chem* 4:187-217) and AMBER (Weiner et al (1981) *J. Comput. Chem.* 106: 765) algorithms handle all of the molecular system setup, force field calculation, and analysis (see also, Eisenfield et al. (1991) *Am J Physiol* 261:C376-386; Lybrand (1991) *J Pharm Belg* 46:49-54; Froimowitz (1990) *Biotechniques* 8:640-644; Burbam et al. (1990) *Proteins* 7:99-111; Pedersen (1985) *Environ Health Perspect* 61:185-190; and Kini et al. (1991) *J Biomol Struct Dyn* 9:475-488).

The availability of biomacromolecule structure of Csp1 or Csp 2 can prompt the development of a variety of direct computational methods for molecular design, in which the steric and electronic properties of substrate binding sites are use to guide the design of potential inhibitors (Cohen et al. (1990) *J. Med. Cam.* 33: 883-894; Kuntz et al. (1982) *J. Mol. Biol.* 161: 269-288; DesJarlais (1988) *J. Med. Cam.* 31: 722-729; Bartlett et al. (1989) (*Spec. Publ., Roy. Soc. Chem.*) 78: 182-196; Goodford et al. (1985) *J. Med. Cam.* 28: 849-857; DesJarlais et al. *J. Med. Cam.* 29: 2149-2153). Directed methods generally fall into two categories: (1) design by analogy in which 3-D structures of known molecules (such as from a crystallographic database) are docked to the protein structure and scored for goodness-of-fit; and (2) de novo design, in which the ligand model is constructed piece-wise in the enzyme. The latter approach, in particular, can facilitate the development of novel molecules, uniquely designed to bind to the calciunerin.

Thus, one may design drugs which act as inhibitors, agonists, antagonists, etc. of Csp polypeptide activity.

Methods of Treating Diseases

As discussed above, calcium signaling is involved in numerous cellular pathways and is implicated in immune response, neuronal disorders, cell death etc. Broadly, calcipressins play a role in disorders arising from one or more alterations in calcium regulating systems that result in a loss of cellular calcium homeostasis; accordingly, the Csp polypeptides may be used in treating various neurodegenerative disorders (for instance, Alzheimer's disease, Parkinsons, cerebral ischemia, stroke etc.; in general, they act as neurotrophic and/or neuroprotective agents), autoimmune and/or inflammatory disorders (including systemic lupus erythematosus, Idiopathic Addison's disease, rheumatoid arthritis, lymphadenopathies, hemolytic anemias, purpura, spondylitis, multiple sclerosis, diabetes mellitus, psoriasis, Crohn's disease, and transplant rejection).

As will be apparent to the skilled artisan, antagonists of Csp polypeptides may be effective in ameliorating the pathogenic abnormalities of mental retardation and heart conditions associated with Downs Syndrome, antagonists will also be effective immunostimulants and may be effectively administered to immunocompromised hosts. There are a number of diseases or conditions that can be caused by or contributed to by aberrant Csp activity in a subject. For example, aberrant Csp promoter activity can result in neurodegeneartive, inflammatory and/or autoimmune disorders in a subject. For example, individuals who have too low a level of Csp 1 or Csp 2 polypeptide are at an increased risk for developing inflammatory and/or autoimmune disorders. Individuals who have too high a level of Csp 1 or Csp 2 polypeptide are at an increased risk for developing or disorders associated with Down Syndrome. Based on the ability of Csp polypeptide to regulate the immune response, regulating the availability of cellular Csp polypeptide provides useful immunosuppressive or immunostimulant therapies. For instance, molecules described herein, which modulate (e.g. agonize or antagonize) Csp promoter activity can be administered to regulate the availability of cellular Csp polypeptides in a subject and thereby provide prophylactic and therapeutic benefit against various disorders of the immune system.

In one aspect, calcipressins, Csp1 and Csp2, act as neuroprotective agents. It is known in the art that calcineurin is highly localized in the central nervous system, especially in those neurons vulnerable to ischemic and traumatic insults. For these reasons, calcineurin and in turn calcineurin inhibitors Csp1 and Csp2, may play an important role in neuron-specific functions. For example, calcineurin is involved in many neuronal functions such as neurotransmitter release, regulation of receptor functions, signal transduction systems, neurite outgrowth, gene expression and neuronal cell death.

In particular, it is known in the art, that calcineurin dephosphorylates protein kinase C-mediated phosphorylation of nitric oxide synthase. Endogenous inhibitors such as Csp 1 and Csp 2, would prevent the calcineurin-mediated dephosphorylation of nitric oxide synthase and thereby regulate the catalytic activity of nitric oxide synthase. Therefore, enhanced phosphorylation of nitric oxide synthase would diminish its catalytic activity and de-phosphorylation would enhance its catalytic activity. Accordingly, Csp 1 and Csp 2 by preventing dephosphorylation of nitric oxide synthase would be effective in protecting against glutamate induced neurotoxicity.

There are many similarities in traumatic and ischemic pathogenesis of the brain in which the release of excessive glutamate is followed by an intracellular Ca2+ increase. Although, the intracellular cascade which leads to neuronal cell death after the release of excess Ca2+ is unclear, calcineurin is thought to be a key toxic enzyme, and inhibitors such as Csp1 and Csp2 acts as substrates for calcineurin and protect against neuronal cell death. Accordingly, Csp1 and Csp2, may exert a neuroprotective effect in various neurodegenerative disorders, for example these compounds may have a protective action in cerebral ischemia, stroke etc.

In yet another aspect, it is thought that these polypeptides would have a role in ameliorating the pathologies associated with Down Syndrome.

In another aspect, calcipressins may have a role in modulating the stress response in mammals. For instance, calcipressins may be strongly induced by multiple chemical stress, for example in response to thyroid hormone, a cation such as a calcium cation, hydrogen peroxide, a heavy metal, phorbol esters, cis (II) platinum, cAMP, or retinoic acid. These inductions may occur under protective or adaptive response conditions suggesting a role as a important physiologic mediator of organ and cellular shock response in mammals.

According to the methods of the invention, a subject having a disease associated with an aberrant Csp activity is treated by administration to the subject of an effective amount of a compound which modulates Csp activity. In one aspect, the compound modulates Csp promoter activity. The compound can also be an antagonist of Csp promoter activity. Thus, a patient having low Csp activity can be treated with an agent which increases Csp promoter activity, i.e., an Csp promoter agonist. Alternatively, a patient having abnormally high Csp promoter activity can be treated with a compound which decreases Csp promoter activity, i.e., an Csp promoter antagonist.

The compound can be a compound which modulates the interaction of at least one transcription factor with an Csp promoter or regulatory element thereof.

The compound can also be a compound which modulates the activity of a transcription factor binding to an Csp promoter or regulatory element thereof. In fact, it is known that the activity of transcription factors can be modulated by post translational modification, e.g., phosphorylation. Accordingly, in one embodiment of the invention, a subject having a condition associated with an aberrant Csp activity is treated by administration of a compound which modulates the activity of a transcription factor binding specifically to an Csp promoter or regulatory element thereof.

The compound is preferably selected from the group consisting of nucleic acids, peptides and small molecules. For example, the compound can be an antisense nucleic acid that binds specifically to a region of an Csp promoter or regulatory element thereof thereby inhibiting or decreasing promoter activity. The compound can also be an antisense nucleic acid that specifically interacts with a gene encoding a transcription factor modulating Csp promoter activity, such that interaction of the antisense nucleic acid with the gene encoding the Csp transcription factor will decrease production of this transcription factor, resulting in either an increase or a decrease of Csp promoter activity depending on whether the transcription factor enhances or reduces Csp promoter activity.

EXEMPLIFICATION

The invention now being generally described, it will be more readily understood by reference to the following examples which are included merely for purposes of illustration of certain aspects and embodiments of the present invention, and are not intended to limit the invention.

Examples

Identification of Calcipressins as Calcineurin Binding Proteins

Potential targets of calcineurin, which is involved in neuronal calcium signaling, were identified using two hybrid screens of a murine hippocampal cDNA library as the prey and using calcineurin as a bait. Amongst positive clones were several encoding murine homologs of DSCR1 (Csp1), a gene located in the minimal Down Syndrome locus at chromosome 21q22, and those encoding a related gene, Zaki-4 (Csp2). Analysis in various yeast strains revealed that both Csp1 and Csp 2 specifically bind to the catalytic subunit of calcineurin (CnA), particularly one rendered constitutively activated by deletion of the C-terminal autoinhibitory domain (CnA). Calcineurin activity per se is not required for binding Csp1 and Csp2, as both interact with the catalytically-deficient CnA-$D^{130}N$ mutant. FIG. 1B. discloses 60 percent amino acid identity between Csp1 and CSP2.

Methods

To construct a library of murine hippocampal cDNAs in a two hybrid "prey" vector, 350 ug of total RNA was isolated from hippocampal tissue dissected from 15 4-6 week-old mice using RNAZole extraction. 3 ug of mRNA was isolated from the total RNA using oligo-dT affinity chromatography (Fast-Tract, InVitroGen) and cDNA produced using the primer-adaptor method with reverse transcriptase (Super-script™ Plasmid System, Gibco). cDNAs were size-selected by column chromatography and the 2 Kb fraction was cloned into the pGAD424 vector (Clontech) and used to transformed DH10B E. coli cells to ampicillin resistance using electroporation (ElectroMax, Gibco). A library of $3 \times 10^6$ independent clones was produced in this manner.

The calcineurin bait vector was constructed by cloning the human calcineurin A subunit (ΔCnAD130N; Zhu and McKeon, 1999) into pBRIDGE (Clontech) to create a fusion protein with the Gal4 DNA binding domain. The calcineurin regulatory B subunit (CnB) was cloned into the same pBridge vector under a separate, constitutive promoter. To test for interactions between calcineurin and proteins expressed in the hippocampus, the yeast strain CG1945, in which HIS3 expression is controlled by the Gal1 upstream activating sequence (UAS), was transfected with both the pBRIDGE vector as well as vector DNA from the murine hippocampal cDNA library. Cells were selected for growth on SD media lacking leucine, tryptophan, methionine, and histidine (-LWMH) containing 25 mM 3-aminotriazole, an inhibitor of alternative histidine biosynthetic pathways (REF). After five days of growth at 30 degrees, His+ colonies were screened by filter assays for b-galactosidase activity, a secondary assay for true positives based on an independent Gal1-regulated gene in the CG1945 strain, b-galactosidase (Clontech). pGAD424 vector DNA from positive colonies was isolated by transforming E. coli for kanamycin resistance with phenol extracted cell lysates. cDNA inserts from plasmid DNA isolated from bacterial cells were selectively amplified using common flanking oligonucleotides in PCR reactions, and products subjected to automated DNA sequencing at the HHMI microchemistry facility at the Harvard Medical School.

Secondary screens testing independent promoters and assays were performed to rid the candidate pool of false positives and cDNAs from thirty clones analyzed by direct sequencing. Eighty percent of these clones proved to be dynamin or amphiphysin, proteins involved in endocytosis of synaptic vesicle components and known calcineurin binding proteins (Bauerfeind et al., 1997, J. Biol. Chem. 272, 30984-30992). We obtained one clone encoding the murine homolog of DSCR1/Adapt78, and one clone homologous to ZAKI-4. DSCR1 is one of an estimated 30 genes on the minimal fragment of chromosome 21 responsible for Down syndrome (Fuentes et al., 1995, Hum. Mol. Genet. 4, 1935-1944.), and the homologous gene was cloned from hamster cells as an oxidative responsive factor (Crawford et al., 1997 Arch. Biochem. Biophys. 342, 6-12.). ZAKI-4 was originally cloned in a screen for genes responding to thyroid hormone (Miyazaki et al, 1996 J. Biol. Chem. 271, 14567-14571.). A search of genomic data bases revealed homologs of DSCR1/Adapt78/ZAKI-4 throughout metazoan evolution, including C. elegans, S. pombe, and S. cerevisiae (FIG. 1B). Given the 60 percent amino acid identity between DSCR1 and Zaki-4, coupled with their common binding to and, as shown below, inhibition of calcineurin, a more functional designation of these genes as calcipressin (Csp) 1 and 2, respectively, is used for simplicity.

Figure 1A:
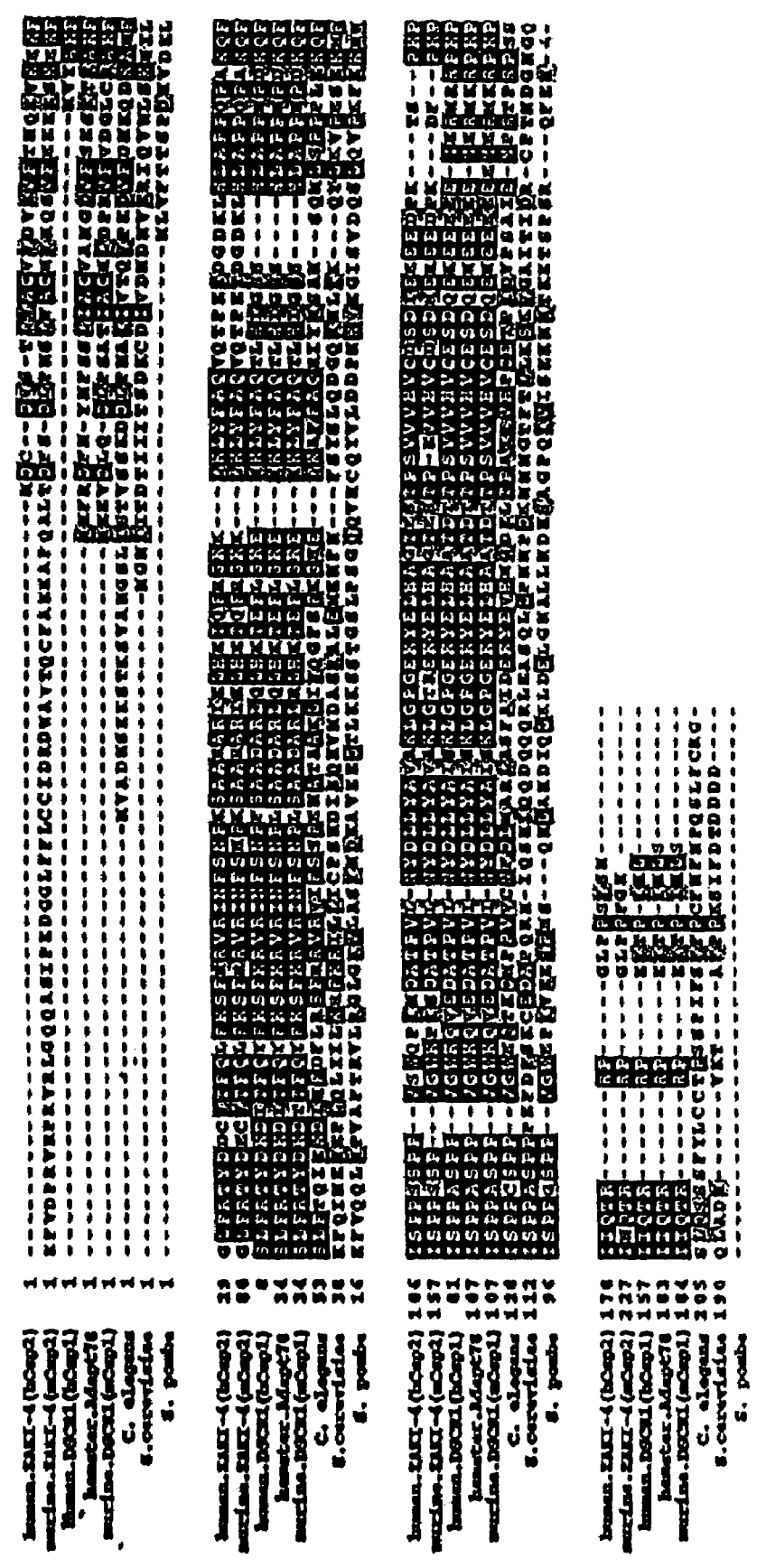
Figure 1B:
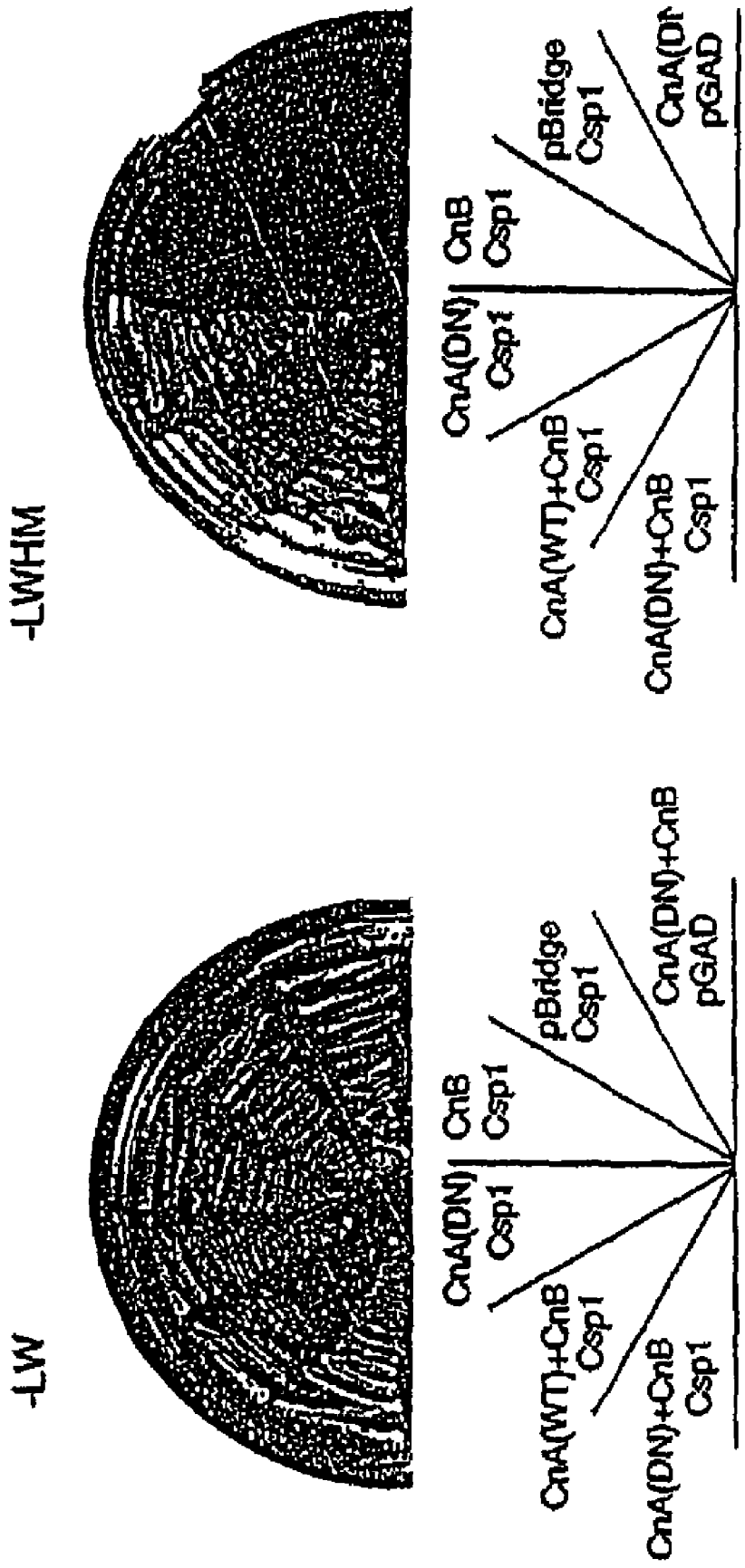

Analyses in various two-hybrid yeast strains revealed that both Csp1 and Csp2 require the catalytic subunit of calcineurin (CnA), in this case one rendered constituitively active by deletion of the C-terminal autoinhibitory domain (ΔCnA) (FIG. 1). Calcineurin activity per se, however, is not required for binding murine Csp 1 and 2, as both interact with the catalytically deficient ΔCnA-D130N mutant (FIG. 1A).

A third calcipressin family member was identified in the EST database and its cDNA cloned from activated murine T cells using a reserve transcriptase (RT)-PCR strategy. This Clone was designated as calcipressin 3 (Csp3) and sequence analysis revealed high sequence homology to Csp1,-2 (FIG. 21). We demonstrate that csp3, similar to csp1 and -2, inhibits the calcineurin mediated translocation of NFAT from the cytoplasm to the nucleus implicating its function as a calcineurin inhibitor. FIG. 22 shows immunofluorescent images of NFAT localized cytoplasmic in unstimulated BHK cells and upon co-expression with constitutively actived calcineurin, its translocation and exclusively nuclear pattern of expression (FIG. 22A, 22B). However, when NFAT is co-expressed with constituvely activated calcineurin and csp3, it remains exclusively cytoplasmic and is prevented from shuttling into the nucleus (FIG. 22C, 22D).

Inhibition of Calcineurin function by Calcipressins

To assess the significance of the interactions between calcipressins and calcineurin, we tested whether Csp1 and 2 could affect endogenous calcineurin activity in vivo. To do this, we assayed the effect of Csp1 and Csp2 on the nuclear import of NF-AT in mammalian cells, a process requiring calcineurin and blocked by cyclosporin A and FK506 (Shibasaki et al., 1996).

Baby hamster kidney (BHK) cells were transfected with mammalian expression vectors encoding murine Csp1 or Csp2 together with one expressing NF-AT4. While neither Csp1 nor Csp2 perturbed the cytoplasmic distribution of NF-AT4 in resting cells, both showed profound suppression of the calcineurin-dependent nuclear import of NF-AT4 in cells stimulated by calcium ionophores (FIG. 2a). Significantly, NF-AT4 in cells co-expressing Csp1 or Csp2 was hyperphosphorylated despite calcium ionophore treatment, a further indication that calcineurin activity is suppressed by these binding proteins (FIG. 2b). To establish a direct link between calcipressins and the inhibition of calcineurin, we assayed the effects of Csp1 and 2 expression on NF-AT4 nuclear import driven by the constitutively active ΔCnA mutant rather than by calcium signaling. Both Csp1 and 2 proved to be strong inhibitors of ΔCnA-induced NF-AT nuclear import, whereas the expression of another calcineurin binding protein, dynamin, failed to block NF-AT nuclear import (FIG. 2B).

Given the strong inhibitory activities of Csp1 and Csp2 on NF-AT4, we asked whether the calcipressins could block the catalytic activity of calcineurin in vitro. Using the protein kinase A (PKA)-phosphorylated RII peptide as a substrate for calcineurin, both Csp1 and Csp2 proved to be potent calcineurin inhibitors with 50 percent inhibition concentrations ($IC_{50}$) of 2 nM and 5 nM for Csp1 and Csp2, respectively (FIG. 4).

These data, coupled with those from the functional cellular assays, indicate that both Csp1 and Csp2 effectively suppress dephosphorylation of protein substrates by calcineurin. Thus the calcipressins share properties with the immunosuppressants cyclosporin A and FK506, which, as complexes with their respective intracellular receptors or "immunophillins", sterically hinder access of substrates such as the RII peptide or NF-AT to the active site of calcineurin (Milan et al., 1994 Cell 79, 437-447.; Kissinger et al., 1995 Nature 3 78, 641-644.; Griffith et al., 1995 Cell 82, 507-522.). However, small phosphatase substrates, such as para-nitrophenyl phosphate (pNPP), are actually hydrolysed more efficiently by calcineurin bound to the immunosuppressant-immunophilin complexes (Liu et al., 1991 Cell 66, 807-815.). To determine whether the calcipressins; inhibit calcineurin in a manner similar to the immunosuppressants, we assayed pNPP hydrolysis by calcineurin-calcipressin complexes. Significantly, both Csp1 and Csp2 blocked the hydrolysis of pNPP by calcineurin, indicating that these proteins, unlike the drug-immunophillin complexes, may be interacting with the active site of calcineurin (FIG. 4).

To determine the domains (of the calcipressins required for binding and inhibiting calcineurin, we tested Csp1 deletion mutants for their interaction with calcineurin in vitro and their ability to inhibit NF-AT nuclear import in vivo. S-methionine-labelled calcineurin subunits ΔCnA and CnB were produced by in vitro translation and assayed for interaction with Csp1 deletion mutants purified from E. coli as GST fusion proteins. While the N-terminal half of Csp1 demonstrated no obvious interaction with calcineurin in vitro, at least two regions of the Cterminal half of these proteins appeared sufficient to bind calcineurin (FIG. 5).

We then asked which of these Csp1 mutants could interfere with calcium-induced NF-AT4 nuclear import in mammalian cells (Shibasaki et al., 1996). As might be expected, none of the Csp1 mutants that failed to bind calcineurin in vitro in inhibited calcineurin-dependent NF-AT4 nuclear import in BHK cells (FIG. 5). Interestingly, truncation mutants containing either of the calcineurin-binding domains of the C-terminal half of Csp1 were effective inhibitors of NF-AT4 nuclear import, suggesting that these mutants interfered with substrate recognition, phosphatase activity, or both. One sequence element (ERMRRP, SEQ ID No. 44) in the distal portion of the C-terminal half of Csp1 appeared similar to the consensus autoinhibitory domain of mammalian calcineurin A (ERMPPRRD, SEQ ID No. 45; Hashimoto et al., 1990). Csp2 lacks the ERM sequence, but shares considerable homology with Csp1 in an adjacent sequence block that is highly conserved in the Csps and contains basic residues (PKPKIIQTRRPE, SEQ ID No. Separate mutations affecting the ERM, RRPE (SEQ ID NO: 49), or other conserved sequence elements such as LIS108, did not prevent Csp1's inhibition of calcineurin-dependent translocation of NF-AT to the nucleus, nor Csp1 binding to calcineurin in vitro. However, when these Csp1 mutants were assessed for their ability to block hydrolysis of pNPP by calcineurin, the one lacking the RRPE (SEQ ID NO: 49) sequence proved remarkably defective in this assay (FIG. 20). Together, these data suggest that the calcipressins inhibit calcineurin by duel mechanisms involving competition for substrate binding as well as suppression of catalytic activity via the RRPE (SEQ ID NO: 49) "pseudosubstrate" domain.

Methods

To determine whether murine Csp1 and Csp2 can inhibit calcineurin in vivo, the calcineurin-dependent NF-AT4 nuclear import assay (Shibasaki et al., 1996) was employed. This assay monitors the subcellular location of GFP-tagged NF-AT4, a transcription factor that resides in the cytoplasm of unstimulated BHK cells. Following stimulation of BHK cells with ionomycin, a calcium ionophore, GFP-NF-AT4 translocates to the nucleus with a t1/2 of five minutes. This translocation event is accompanied by a dephosphorylation of NF- AT4 in a process dependent on calcineurin. Both cyclosporin A and FK506 block the nuclear import of GFP-NF-AT4, further evidence that this translocation process requires calcineurin activity.

Baby hamster kidney cells were grown on sterile glass coverslips in DMEM media with 10% fetal calf serum and transfected using calcium phosphate methods (Heald et al., 1993). The mammalian vector encoding the HA epitope tagged murine Csp1 was constructed using polymerase chain reaction (PCR) techniques to transfer the murine Csp1 coding sequence from the yeast two hybrid vector to pcDNA3 containing the lamin 5' untranslated sequence and the HA eiptope tag. NF-AT4 expression was based on the vector pcDNA3-GFP-NF-AT4 (Shibasaki et al., 1996). Transfected cells were grown for 18 hours prior to drug treatments. Cells were fixed 30 minutes after ionomycin (0.5 uM) treatment or washout using 3% formaldehyde in PBS for 10 minutes at room temperature. HA-tagged murine Csp1 protein in cells was detected using an anti-HA-epitope polyclonal antibody and a secondary, Cy3-labeled anti-rabbit IgG antibody. GFP and Cy3 signals were observed in a Zeiss epifluorescence photomicroscope and recorded by a CCD camera.

Phosphorylated RII-Peptide Assay:

The RII peptide of the cAMP-regulatory subunit of PKA was produced as a fusion protein with GsT and labeled with $^{32}$P-phosphate using protein kinase A followed by glutathione-Sepharose affinity purification (Milan et al., 1994). The radiolabeled RII GsT fusion protein was incubated with 1.5u of purified bovine brain calcineurin (ProMega) and 200 nM calmodulin (Sigma) in the presence of 0-20 nM GsT-Csp1 or GsT-Csp2 for 15 minutes. The reaction was stopped by the addition of an equal volume of 2xSDS sample buffer. After fractionation by SDS-polyacrylamide gel electrophoresis, free phosphate was measured by PhosphorImager analysis.

Para-nitrophenyl phosphate hydrolysis assay (Sagoo et al., 1996): Phosphatase assays using pNPP as a substrate were performed in 50 ul buffer C (100 mM Tris-HCl, pH 7.5, 100 mM NaCl, 0.5 mM DTT, 100 ug/ml bovine serum albumen, and 0.4 mM CaCl2) containing 60 mM pNPP, 50 nM purified bovine brain calcineurin, 200 nM calmodulin (Sigma), and 0-100 nM GsT-mDSCR1 or GsT-mZaki-4. Reactions were performed for 30 min at 30 degrees, and stopped by the addition of 950 uL of 1M NaOH. The reaction product was measured by absorbance at 405 nm in a Beckman Du 64 spectophotometer.

Sequence Requirements for Inhibition

To test murine Csp1 and Csp2 interactions with calcineurin in vitro, glutathione S-transferase (GsT) Csp1 and Csp2 fusion proteins were purified from E. coli transformed with the respective pGEX4T-3-m Csp1 and—Csp2 vectors, and calcineurin was produced from pcDNAmCsp1 and pcDNA3mCsp2 vectors in a coupled transcription-translation system using $^{35}$S-methionine to label the calcineurin A and B subunits. Purified GsT-Csp1 and -Csp2 fusion proteins were mixed with calcineurin in vitro translation lysates in buffer A (50 mM Tris-HCl, pH7.5, 140 mM NaCl, 1 mM CaCl$_2$, and 0.4% Triton X-100), incubated for 60 minutes at 4 degrees, and absorbed with glutathione-agarose beads. The agarose beads were washed three times with buffer A, resuspended in 2xSDS sample buffer, and fractionated on SDS-polyacrylamide gels. Dried gels were analyzed by the phosphoImager to detect and quantify GsT-Csp1 or -Csp2-associated calcineurin subunits. Deletion mutations of murine Csp1 and Csp2 were produced using standard PCR methods.

Induction of Calcipressin Transcription by Calcium Signaling

Interestingly, both Csp 1 homologs and Csp2 have been isolated in screens for genes transcribed in response to oxidative stress or in response to thyroid hormone stimulation (REF$_s$). In the former case, Adapt78 hamster Csp1 was shown to be rapidly induced by hydrogen peroxide, in a manner dependent on ionophore (I), PMA (P) or both (I+P) for the indicated duration.

To examine the transcriptional responses of these genes, we first monitored Csp1 and Csp2 transcripts in several human cell lines stimulated with the calcium ionophore, ionomycin. Interestingly, Csp1 transcripts accumulated to high levels by five hours of ionomycin treatment, whereas Csp2 showed no similar rise in transcript levels during the first 12 hours of observation. We also found that the activation of the Csp1 transcripts was reversed within several hours of removing the calcium ionophore, suggesting the Csp1 gene is responding to changes in the intracellular calcium concentration.

Unlike that shown for Adapt78 in CHO cells, Csp1 transcripts are not significantly elevated in human Jurkat T cells by the presence of ionomycin through eight hours of stimulation (FIG. 16). A weak yet detectable stimulation of Csp1 transcription was noted following phorbol 12-myristate 13-acetate (PMA) treatment. Significantly, treatment with both calcium ionophore and PMA resulted in a strong induction of Csp1 message in Jurkat cells through eight hours. Given the synergistic activities of calcium ionophores and PMA on Csp1 upregulation, and the ability of Csp1 to inhibit calcineurin, we asked if this induction was dependent on calcineurin activity. Cyclosporin A at levels sufficient to block activation of NF-AT nuclear import suppressed the accumulation of Csp 1 transcripts to that seen by PMA alone (FIG. 16).

Considering that Csp1 is both a potent inhibitor of calcineurin and induced by calcium signaling, we asked if the Csp1 transactivation process is controlled by calcineurin activation. To do this, we treated cells with ionomycin to trigger calcium signaling, but as well with cyclosporin A to block calcineurin activity. Significantly, cyclosporin A abolished the induction of Csp1 transcripts in cells by ionomycin, supporting the notion that the Csp1 transactivation process is dependent on calcineurin activation rather than other calcium activated factors. As further evidence for the sufficiency of calcineurin activation of the Csp1 gene, we assayed Csp 1 transcript levels in cells transfected with the calcium-independent, constitutively activated form of calcineurin, ΔCnA. Expression of ΔCnA, even in the absence of calcium ionophore, resulted in a strong induction of the Csp1 transcript in these cells.

Inhibition of Calcineurin Activity During Extended Periods of Calcium Signaling Rationale:

The induction of Csp1 transcripts in response to prolonged calcium (together with PMA) signaling raises the possibility that the Csps constitute part of a negative feedback mechanism directed against calcineurin. A first step in investigating this hypothesis would be to examine calcineurin activity throughout extended periods of calcium signaling in the Jurkat T cell line.

In this experiment the activities of the other major phosphatases in the cell, namely PP1 and PP2A was removed. Both of these phosphatases are substantially inhibited by the presence of 500 μM okadaic acid, a natural product phosphatase inhibitor that does not block calcineurin. We examined Jurkat cell lysates from cells treated continuously with ionomycin and PMA for periods up to 10 hours, assaying for the dephosphorylation of the RII-peptide-GST fusion protein (Milan et al., 1994). Significantly, the calcineurin activity assayed in Jurkat cells receiving combined stimulation by both calcium ionphores and PMA declined markedly three hours after addition of drugs, whereas calcineurin activity measured in lysates of untreated cells, or those from cells receiving calcium ionophore or PMA alone, remained high (FIG. 17).

These data are consistent with the notion that calcineurin is down-regulated during prolonged calcium signaling, and yet present no information on any mechanism for this inhibition. As presented in the Research Design and Methods, significantly more directed experiments will be possible with the production of monoclonal antibodies to Csp1 and Csp2 to determine whether they in fact participate in a negative feedback process to limit calcineurin activity.

Structure/Function Analysis Using Csp Mutants

It will be obvious to one of ordinary skill in the art that Csp-calcineurin interactions may also be analyzed by constructing site-directed mutants and analyzing them in cellular and enzymatic assays. The above experiments show that the C-terminal halves of Csp1 and Csp2 are sufficient to bind to and inhibit the activity of calcineurin, in addition the above experiments also show that certain mutations within the C-terminus of Csp1 yields remarkable effects. This domain, at the extreme C-terminus of Csp1, contains the sequence RRPE. A Csp1 mutant lacking the RRPE sequence still binds calcineurin and still blocks calcineurin activity in vivo towards NF-AT4, as judged by the NF-AT4 nuclear import assay. However, the Csp1(ΔRRPE) mutant fails to inhibit calcineurin's ability to hydrolyze small substrates such as pNPP (FIG. 15), indicating that this domain is responsible for affecting the catalytic site on calcineurin. The significance of the RRPE domain, in addition to the observation that mutations within this sequence inhibits the ability of Csp1 to block the catalytic activity of calcineurin, is that this region shares homology with phosphorylation sites on known substrates of calcineurin, as well as with the autoinhibitory domain of calcineurin, which is thought to represent a pseudosubstrate site (Hashimoto et al., 1990). The skilled artisan can appreciate that a series of point mutations in this domain can be constructed and the mutants expressed in vitro, and tested using in vitro enzyme assays of calcineurin (Swanson et al., 1992; Milan et al., 1994).

The Csp2 domain corresponding to that of the putative Csp1 contains the sequence RRPG rather than RRPE, suggesting that this domain is less effective in inhibiting the calcineurin's catalytic activity due to the loss of the glutamate residue. Csp2 can also be used in calcineurin assays wherein pNPP is a substrate, and Csp2 mutant in which the RRPG sequence has been altered to RRPE may also be generated. Eight other domains are highly conserved in the C-terminal halves of Csp1 and Csp2, and eand can be the subject of similar mutational analysis and functional assays for their effect on calcineurin binding, calcineurin-induced NF-AT nuclear import, and in vitro phosphatase assays.

Co-Crystals of Calcineurin and Csp1 and Csp2

Calcineurin consists of two subunits (Klee et al., 1998), CnA (60 kDa) and CnB (18 kDa), neither of which is soluble when expressed individually in E. coli. The structure of calcineurin was studied by taking advantage of the high level of calcineurin in the central nervous system to directly isolate it from bovine brain (Griffith et al., 1995). It has also been found that both unstable calcineurin subunits were expressed as a polycistronic message in E. coli, the encoded proteins would efficiently assemble into a soluble complex suitable for crystallization (Kissinger et al., 1995). The co-expression approach used in the art is especially interesting with regards to Csp1 and Csp2, as neither full length molecule is significantly soluble upon expression in E. coli, regardless of the temperature of expression (15, 22, or 30° C.), with a typical yield of 3% total protein in the soluble fraction. It is likely that the insolublility of Csp expression in E. coli is due to the absence of binding proteins such as calcineurin, thereby leaving hydrophobic stretches of amino acids uncomplemented (FIG. 1). As with the calcineurin subunits, it is possible that Csp 1 and Csp2 interact with calcineurin in a manner that will form a properly folded, soluble complex. Since the E. coli calcineurin A and B expression vector is controlled by the lac repressor and is maintained by its ampicillin resistance gene, a compatible vector may be constructed with kanamycin selection for expression of Csp1 and Csp2 under the control of the lac repressor. The E. coli host containing the calcineurin expression vector will be transformed with these Csp vectors and selected for kanamycin resistance.

Alternatively the given protein or complex may be obtained in sufficient quantities and quality and crystallization protocols may be attempted. To mitigate risks accompanying efforts to coexpress full-length Csp1 or Csp2 and the calcineurin subunits, the solubility of Csp deletion mutants in E. coli may be studied. The above experiments show that the C-terminal half of Csp1 (amino acids 101-197) contains all of the calcineurin inhibitory activity of the full length molecule (FIG. 5). Our solubility assays have revealed that approximately 70 percent of this truncated molecule, containing only the C-terminal half of Csp1, is soluble in E. coli. This result suggests two alternative methods for producing calcineurin-Csp complexes, including coexpression of the C-terminal halves of Csp1 or Csp2 with the calcineurin subunits in E. coli or an in vitro assembly between the C-terminal halves of Csp1 and Csp2 and calcineurin, all of which can be produced separately in bacteria. The skilled artisan will appreciate that other protein expression systems, such as baculovirus, may also be used.

Expression Dynamics of Csp1 and Csp2

Expression data for Csp1, i.e., tissue northern blots, showed Csp transcripts in the brain, heart, and muscle. Similar expression data can be readily obtained by the skilled artisan for Csp2 also. For example, Csp expression data may be obtained from developing embryos, adult organs, and cells in culture using reagents such as monoclonal antibodies and RNA probes.

In addition, homologs may be identified using low stringency hybridization and intron bridging techniques on genomic DNA (Yang et al., 1998) to determine whether additional members of the Csp family are present in the mammalian genome.

Monoclonal, Antibodies Against Csp1 and Csp2

Mice may be immunized to bacterially derived GST-Csp1 and Csp2, already available in the lab, using standard protocols (Harlow and Lane, 1998). Briefly, an emulsion of complete Freund's adjuvant containing 50 ug of antigen is injected subcutaneously at several sites at day 0, followed by intraperitoneal injections of 50 ug antigen in incomplete Freund's adjuvant at intervals of 21 days. Retro-orbital bleeds are obtained approximately 10 days after a given injection, and serum antibody titers determined using immunofluorescence on Csp1- or Csp2-transfected BHK cells (Yang et al., 1998). Fusions between spleen cells of mice with a positive titer and a non-secreting myeloma cell line defective in hypoxanthine-guanine phosphoribosyl-transferase (HGPT) are performed six days after the final boost. The fusion is performed using a 4:1 ratio of spleen cells to myeloma cells in 50% polyethylene glycol, and cells are then distributed in 96 well plates under methotrexate selection in the presence of nucleotide precursors hypoxanthine and thymidine used in salvage pathways. While more rapid methods exist for screening hybridoma supernatants, such as antigen-coated plates, we have been most successful screening pools of four supernatants using mammalian cells transfected with cDNAs encoding the specific antigen. This method has worked well for monoclonals against the nuclear lamins, Bub1, Mad3, and p63 (McKeon et al., 1986; Taylor et al., 1997, Yang et al., 1998). The alternative, plate screening, has often yielded antibodies of low affinity or ones that failed to work in multiple applications, such as immunofluorescence, paraffin sections, or immunoprecipitation. Positive hybridomas secreting anti-Csp antibodies will be subcloned, expanded to yield sufficient quantities of antibody, and frozen in multiple vials.

Figure 23:
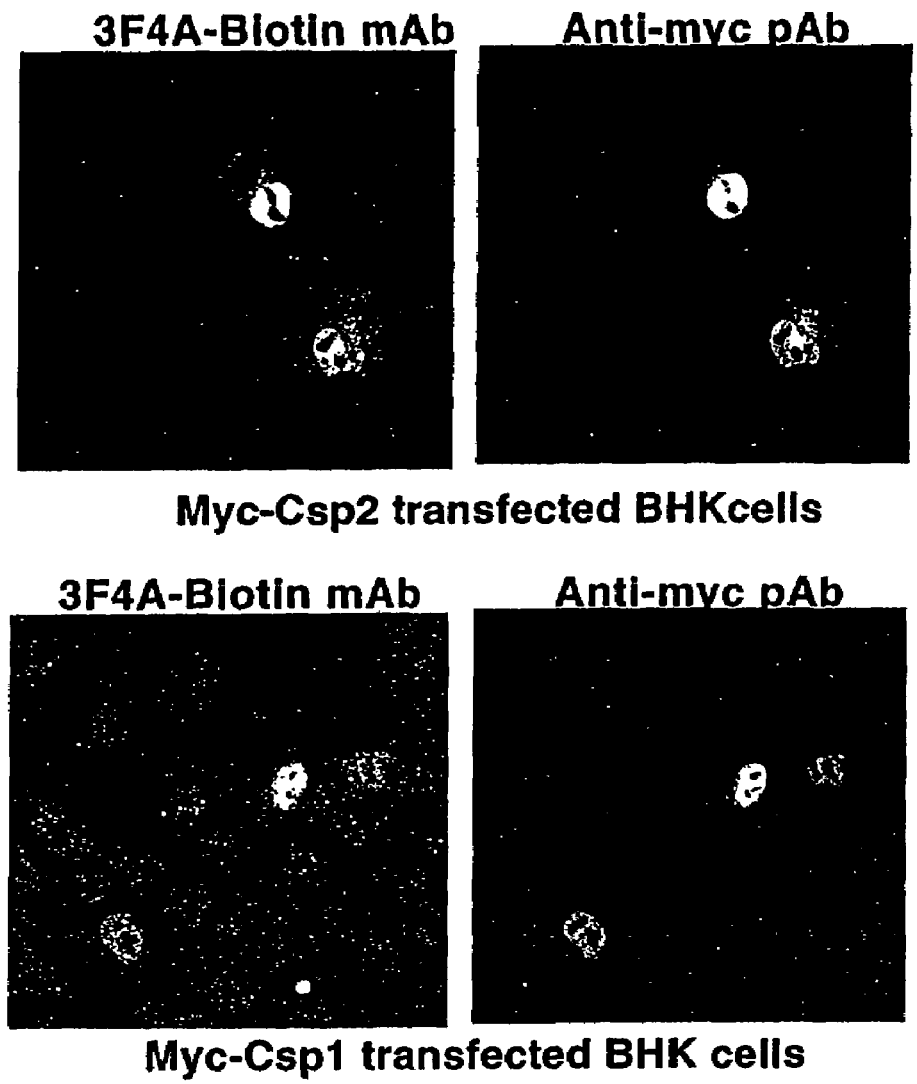

Mouse monoclonal antibodies have been generated primarily against csp2 and include hybridoma clones and designated 9A11, 25D6, 11E1, 16G5 and 3F4A. However, 3F4A recognizes both csp1 and csp2 as shown in FIG. 3 by immunoflourescence. BHK cells were transfected with myc-tagged csp1 or csp2 cDNA containing a nuclear localization signal at the amino terminus to allow nuclear expression of csp 1 and csp2 and thus quick visualization of antibody reactivity. 3F4A was biotinylated and shown to recognize csp2 (FIG. 23, top row) as verified by co-staining with myc pAb. Biotinylated-3F4A also recognizes csp1, although much more weakly than csp2 as seen in FIG. 23, bottom row.

Csp1 and Csp2 Expression and Induction

Upon ensuring the monospecificity and the species cross-reactivity of the antibodies using Western blots of transfected cells and tissues known to express Csp transcripts, paraffin or frozen sections of staged mouse embryos and adult tissues may be stained. Endogenous mouse immunoglobulin and circulating B cells will be masked using the HistoMouse kit (ZyMed). These monoclonal antibodies will allow examination of the inducibility and stability of Csp expression in cell lines under various conditions as well as in studies examining the Csps interaction with calcineurin, as described below. In addition, in situ hybridizations with Cy3-labelled RNA probes specific to each transcript (Yang et al., 1999a) may also be performed. Together, the patterns obtained by these antibody and RNA probes would provide further Csp1 and Csp2 expression data. It will enable determination of what organ or tissues express Csp isotypes, and whether Csp1 and Csp2 occupy unique or overlapping sites of expression. The second is whether the transcript patterns directly reflect protein expression patterns, as discrepancies could reflect post-transcriptional regulation such as protein degradation. The patterns themselves will provide insight into specific cell and tissue types where the Csps regulate calcineurin. In addition, this information will facilitate analysis of the Csp knockout phenotype in mice. For example, the phenotypic defects would appear in tissues showing high expression of the genes, and not in regions with little or no expression.

In addition to the general patterns of Csp1 and Csp2 expression, this will also help in the development of tools for probing the conditional expression of these genes. Given that calcium signaling and oxidative stress induce the transcription of Csp1 homologs (FIG. 10, Crawford et al., 1997), it is important to examine these conditions in more detail and at the levels of both the transcripts and the proteins.

Conditional Interactions Between Csps and Calcineurin Using Monoclonal Antibodies The use of monoclonal antibodies to Csp1 and Csp2 will allow for the determination of the consequences of the inducible expression of these genes. In particular, western blots may be used to determine how Csp protein expression correlates with the induction of Csp transcripts upon treatment of cell lines with calcium ionophores, oxidative stress, and other challenges. In addition, these antibodies may be used for assessing Csp-calcineurin interactions by immunoprecipitation from lysates of cells treated with calcium ionophores and other drugs for various times. Calcineurin may be co-precipitated using the Csp monoclonal antibodies. To detect calcineurin in Csp immunoprecipitate samples, these samples may be separated by SDS-PAGE, transferred to nitrocellulose and probed with calcineurin antibodies. Further, if Csp1, Csp2, and Csp3 constitute a feedback mechanism to inhibit calcineurin during prolonged calcium signaling, it may be possible that these proteins would be unstable in the absence of elevated levels of intracellular calcium. In this manner, Csp1, Csp2, and Csp3 would be degraded when they are no longer needed to inhibit calcineurin. Csp1, Csp2, and Csp3 protein levels may be monitored in Jurkat cells previously treated by prolonged calcium ionophore and PMA exposure while new protein synthesis will be blocked using cycloheximide. The rate of Csp degradation as calcium levels return to basal levels will be compared with identical populations of cells continuously exposed to calcium ionophore by comparing Csp protein levels in these two different treatment groups. Should prove to be unstable at basal intracellular calcium levels then this instability may be characterized by using deletion mutants to identify domains of Csp responsible for their instability.

Cloning of Additional Csp Family Members

The two-hybrid screens in yeast for calcineurin-interacting proteins yielded Csp1 and Csp2 but no other family members. However, only one clone of each was detected, suggesting that the screen was not saturated. Additional family members may be obtained by rescreening the library in yeast and analyzing a larger numbers of positive clones. Currently approximately 150 more clones are being analyzed. The library is limited, however, in that it is made from RNA of the hippocampus and therefore we would miss Csp homologs with tissue distributions outside of the hippocampus. Therefore, separate cDNA library made from RNA derived from E18 murine whole embryos which should be relatively unbiased in tissues, may be examined, although, such a library may not contain cDNAs for certain developmentally regulated genes. This library may be probed using standard hybridization techniques (Maniatis et al., 1989) with randomly primed Csp1 and Csp2 sequences. All positive colonies so obtained, regardless of their hybridization signal intensity, may be transferred to 96 well arrays, replica plated onto nitrocellulose filter-covered agar plates, and grown to saturation. Filters derived from these replicas will be probed separately with Csp1 and Csp2 sequences, and clones yielding weak but positive signals on each will be selected for direct sequencing.

Failure to obtain novel Csp homologs by the methods described herein raises the possibility that none exist or that our conditions of the two-hybrid or hybridization screens were insufficient in terms of complexity or stringency for detecting more distantly related gene products. An alternative is to use the intron bridging technique developed for cloning p53 homologs (Yang et al., 1998). Briefly, it was known that the p53 and p73 genes shared the same intron-exon structure, and yet the size and sequences of the introns showed no similarity. Human genomic DNA was used as a template for PCR primers designed against highly conserved sequences in adjacent exons. The PCR reactions yielded products corresponding in size to introns of p53 and p73, as well as a novel band which, upon sequencing, proved to be a novel member of the family. The benefit of this latter technique is that, since it relies on genomic DNA as a template, it has no bias due to expression levels or tissue specificity of cDNA libraries.

Targeted Disruption of Csp1, Csp2, and Csp3 Genes in Mice

To examine the consequences of Csp deficiencies, mice bearing targeted disruptions of these genes may be generated. Csp1, Csp2, and Csp3 genomic clones have been isolated from a mouse genomic library in order to construct targeting vectors necessary to make Csp1, -2, and -3 knock out mice. Generating mice with targeted deletions in the Csp genes will allow determination of the functions of Csp, in the context of the whole organism. Csp1−/−, Csp2−/−, and Csp3−/− mice may be interbred to assess any functional redundancies of the two genes and examine the phenotypic severity when two endogenous inhibitors of calcineurin are absent. Analysis of Csp function may be done by histological examination of the anatomical structures that normally contain Csp in order to determine whether the absence of these genes affects structural development of these organs.

In Fact, gene targeting vectors were constructed to generate calcipressin knock-out mice. The genomic structure of Csp1,-2, and -3 are very similar so the strategy for all three mice is the same. Since the carboxy terminal half of the calcipressins has been determined to be critical for calcineuring inhibition, we will delete exons 6 which contains the start of the c-terminus. FIG. 27 demonstrates the scheme we will use to generate the targeting vectors.

Transgenic mice are in the progress using tissue specific promoters to overexpress full length csp1 and csp1 RRPE which is the sequence element previously shown to act at the "pseudo-substrate" domain. The myosin heavy chain (MHC) promoter is being used for cardiac specific expression and the Lck promoter will ensure expression of the transgenes in resting and activate T cells.

Cloning of murine Csp1 and Csp2 Genomic Clones and Construction of Targeting Vectors As discussed above, the C-terminal halves of Csp1 and -2 are the domains that are necessary for interaction with calcineurin. Therefore, genomic clones containing these C-terminal coding regions may be isolated. Estivill and colleagues have characterized the genomic structure of human Csp1 (Fuentes et al., 1997) and based on the sequence homology between the coding regions of the mouse and human genes, PCR primers can be designed that would span intron-exon boundaries of the C-terminal coding regions that interact with calcineurin. Using mouse genomic DNA as a template, these primer pairs may be tested for their ability to generate specific sized products that are larger than the size predicted if the primer pair simply amplified coding regions of Csp1 and Csp2. A phage library containing 17-21 Kb fragments of murine genomic DNA is then divided into pools of 80,000 clones which can be screened by PCR using the intron-spanning primers. Phage stocks corresponding to positive pools may be plated and screened by plaque hybridization using the PCR products containing primarily intronic sequences. Phage inserts of approximately 18 Kb in size have been subcloned into pZero (Clontech) and may be analyzed by restriction digestion, PCR, and partial sequencing. The gene structure of Csp1 and Csp2 in the region of the highly conserved exons 5, 6, and 7 will be determined from genomic clones as described above. Based on the human Csp1 genomic structure, it is thought that exons 5, 6, and 7 in the murine Csp1 and 2 genes to be the exons containing the coding regions involved in calcineurin binding and inhibition. Therefore, these three exons may be deleted and replaced with a neomycin resistance cassette as well as a thymidine kinase gene at the 5' end of the vector to provide a selection against random insertional events using FIAU (Mansour et al., 1988).

The identity of both genomic clones isolated by PCR primers that span intron 5 (which was used as a probe) and intron 6 has been verified and compared to the PCR product size with those generated when using genomic DNA as a template. Thus we are certain of the identity of the clones corresponding to Csp1 and Csp2. These clones are being and this will be used to determine the gene structure of Csp1 and Csp2. Subsequent gene disruption with the Neo cassette will be confirmed using restriction digestion and PCR analysis.

Generation of Csp1−/−, Csp2−/−, and Double-Knockout Mice

We will electroporate the targeting vector into mouse embryonic stem (ES) cells and G418 and FIAU-resistant clones will be selected, expanded, and screened by southern blot hybridization with two probes flanking the regions designed to undergo homologous recombination. The ES cell line that incorporates the targeting vector will be microinjected into blastocysts from C57BL/6 and Balb/c mice, giving rise to chimeric mice with the potential of germline transmission of the Csp1 and -2 mutations. These chimeric founders will be bred to wildtype C57BL/6 or Balb/c mice and the F1 progeny genotyped by southern blotting to identify Csp1+/− and Csp2+/− mice. We will mate the heterozygote mice to generate homozygotes and then we will interbreed the Csp1−/− and Csp2−/− to generate double knock-outs.

The severity in phenotype of gene disruption often leads to analysis of embryonic and neonatal lethality. It is conceivable that homozygotes for either or both of these genes may die at a very early embryonic stage (<E8). In which case, viable cells lacking these genes for functional studies may be obtained by rendering the ES cells bearing a single disruption of Csp1 or Csp2 homozygous for deletion by using elevated G418 and thereby selecting in culture for clones that have undergone mitotic gene conversion events (Ranger et al., 1998). Chimeric mice can be generated with these ES clones by reconstitution into Rag2−/− blastocysts, which normally produce mice lacking T and B cells. Any lymphoid cells in the Rag2−/− mice are therefore the product of the injected ES cells and therefore would be Csp1−/− and Csp2−/−. These cells may then be functionally analyzed.

Characterization of the Phenotypes of the Csp1 and -2 Knock-Out Mice

Standard histological analyses on Csp1−/− and Csp2−/− embryos, new born mice, and adult tissues may be performed. Tissues are fixed, dehydrated and embedded in paraffin, sectioned and stained with standard histological stains such as hematoxylin and eosin, one of the most commonly used techniques in histology and routine pathology. The basic dye hematoxylin stains acidic structures a purplish blue while the acid dye eosin stains basic structures red or pink.

Calcineurin has been implicated in calcium-dependent cell death in the central nervous system and in lymphocytes, but its precise role in these events is unclear (Morioka et al., 1999). If calcineurin activity does contribute to developmentally programmed cell death or conditional events in adult tissues, the Csp knockout phenotypes should reflect the consequences of an elevation in calcineurin activity which may include increased cell death. To assess cell death patterns in these mice, we will use TUNEL assays on paraffin sections of embryonic and adult tissues. This assay is technically straightforward and takes advantage of the increase of free, 3'-hydroxyl ends of DNA of cells undergoing DNA fragmentation to add tagged nucleotides using terminal transferase (Heatwole, 1999). Similarly, analysis of rates of proliferation in timed embryos and adult tissues can be done by fluorescence techniques. Briefly, mice are injected intraperitoneally with 50-100 ug/g body weight 5-bromo-2'-deoxyuridine (BrdU) prior to sacrifice, when embryos or tissues are removed, fixed and embedded, and sectioned. Sections are dewaxed in Xylene, rehydrated, and probed with an anti-BrdU antibody (Becton Dickinson) and a Cy3-labelled secondary antibody, and examined using a fluorescence microscope. These data on cell death and proliferation in whole embryos and adult tissues will be considered together with those of cellular assays of T cell activation, which should also reveal alterations in cell death or proliferation as a consequence of Csp deficiencies.

Based upon the knowledge of calcineurin-dependent pathways and Csp expression patterns the neuronal structures, cardiac and skeletal muscle, as well as the spleen and lymph nodes may be examined. If the knock-out mice die during embryogenesis, determining the cause of this lethality may reveal important sites of calcipressin-calcineurin activity during development. Also, Csp heterozygotes may be studied for any effect of gene dosage or haploinsufficiency.

Functional Analysis of Csp1 and Csp2 in the Immune System

Calcium signaling and calcineurin activity in particular influence many aspects of lymphoid development, differentiation, and function (Guse, 1998; Crabtree, 1999), suggesting the possibility that these pathways would be influenced by the absence of Csp function in the knockout mouse models. Indeed, the immunosuppressant cyclosporin A has been shown to disrupt the processes of both positive and negative selection in the thymus (Hollander et al., 1994; Huby et al., 1995) and therefore the development of mature thymocytes from their CD4+CD8+ precursors. If cyclosporin A affects normal T cell differentiation, the possibility exists that the Csps normally impart control of calcineurin during these processes and therefore their absence might affect T and B cell development and differentiation. It will be important to know, both from expression studies and functional assays using cells derived from mice with particular Csp genotypes, whether Csp1 and Csp2 function differentially in various processes of lymphocyte development and differentiation. Cyclosporin A prevents the activation-dependent proliferation of T cells that forms the basis of clonal expansion in the immune response. Mature T cells from Csp knockout mice and control animals may be tested to determine if this response is altered by the loss of Csp function. Given the apparent function of Csp1 and Csp2 as calcineurin inhibitors, it is likely that Csp-knockout mice could experience a hyperproliferation response. T helper cells differentiate into two major subsets of cells known as Th1 and Th2 cells. Th1 cells are associated with cell-mediated immunity functions and generally secrete IL-2 and interferon gamma (IFN-γ), while Th2 cells are involved in humoral and tolerance responses and secrete IL-4 and IL-10 (O'Gara et al., 1997). As these differentiation programs play a critical role in the immune response and involve cytokines known to be target genes of NF-ATs, we will examine these processes in cells derived from wild-type and Csp mutant mice to determine if the Csp proteins participate in these differentiation steps.

Differentiation Analysis of T and B Cells in Csp1 and Csp2 Knock-Out Mice

The expression of thymocyte markers will be examined to determine the differentiation status of these cells in the Csp knock-out mice (Ceredig et al., 1988). Immature CD4−CD8− cells can be classified into four distinct precursor populations by the differential expression of the CD25 and CD44 antigens, following the general sequence CD25−CD44, CD25CD44+, CD25+CD44+, and CD25−CD44− (Godfrey and Zlotnik, 1993). Single cell suspensions of thymocytes will be isolated from the thymus, stained with the appropriate cell surface marker antibodies, and analyzed for the expression of differentiation markers by flow cytometry (FACS). This analysis will determine whether specific populations are either over- or under-represented in the thymus of these animals. A "normal" distribution is 80% CD4+CD8+, 5% CD4−CD8−, 10% CD4+CD8−, and 3-5% CD4−CD8+. Chronic cyclosporin A treatment appears to block the appearance of TCR-positive cells which have high levels of CD3 and are either CD4+ or CD8+, with a particular depletion of CD4+ CD8− cells (Gao et al., 1988). To test whether autoreactive cells avoid negative selection in the thymus, we will assay Csp knockout and control mice for their repertoire of Vβ chains of the TCR expressed in particular NIHC backgrounds (Kappler et al., 1987). Cells bearing particular Vβ chains should be deleted in response to endogenous superantigens unless there is some disruption in negative selection (Kappler et al., 1987). Vβ-positive cells will be quantified using FACS analysis with a monoclonal antibody that recognizes particular Vβ determinants. The presence of normally deleted Vβ cells would be one indication that the Csps are involved in the negative selection process.

These experiments will show whether T cell development is altered in the Csp knockout strains, although the RAG24-complementation studies would be needed to determine if this effect is cell or lymphocyte autonomous. If the maturation profile and the ratio of CD4+/CD8+ thymocytes in the Csp knock-out mice is unchanged, we will conclude that the Csps are not necessary for developmental programs in the thymus. We will then examine the possibility that the Csps function in the process of maturation of CD4+ CD8+ cells to CD4+ CD8− and CD4-CD8+ lymphocytes. If these thymic populations are affected, we will have to investigate whether the loss of Csp function is interfering with a differentiation step by directly affecting T cell populations or rather through effects on the thymus medullary epithelium, which atrophies, for instance, during long-term cyclosporin A treatment (Gao et al., 1988). All questions regarding the cell-autonomous nature of immune cell defects would be addressed in the RAG2−/− background.

Measurement of Invoked Proliferation of Csp-Deficient T and B Cells

Spleen and lymph node cells will be isolated from mice and placed into 96 well plates. T cells will be activated by anti-CD-3 antibodies with or without anti-CD28, PMA plus A23617, or Con A in the presence or absence of IL-2. Cells will be pulsed with [3H]-thymidine and harvested at 48 or 72 hours. The incorporation of thymidine will be measured by a beta counter.

TCR transgenic mice, in which all T cells express a TCR recognizing against a defined antigen may be used (Berg et al., 1989; McKnight et al., 1994). This allows for simultaneously testing T cell responses to antigen at many stages of development (Singer and Abbas, 1994). The Csp knockout mice will be crossed with mice harboring the 2B4-TCRα/B, which recognizes a peptide within pigeon cytochrome C in a class II MHC-restricted manner (Berg et al., 1989). Injections of the pigeon cytochrome C peptide over three days result in a rapid depletion of CD4+TCR+ cells by day seven, as well as a similar loss of mature T cells from lymph nodes and the spleen (Singer and Abbas, 1994). The 2B4-TCR/Csp−/− mice may be tested under similar conditions for the loss of thymic and peripheral T cells using the pigeon cytochrome C peptide. Additionally, naive lymph node T cells will be tested in vitro for their ability to proliferate in response to the cytochrome C peptide, using the incorporation of [³H]-thymidine as a marker for DNA synthesis. These studies will determine whether the loss of Csp genes affect T cell development and whether the Csps play a differential role in the deletion of peripheral versus thymic T cells. To examine B cell proliferation, spleen cells will be isolated and depleted of Thy 1.2+ T cells using anti-Thy1.2 antibodies. B cells will be isolated using Lympholite M and plated into 96 well plates. They will be activated with anti-CD40, anti-IgM, LPS or PMA +Ca2+ ionophore in the presence or absence of IL-4 and [1H]-thymidine uptake will be measured after 48 and 72 hours. To assess immunocompetence of these animals, the 2B4-TCRICsp−/− mice will be immunized with ovalbumin with adjuvant and the antibody response then tested by ELISA analysis of serum-derived antibodies.

If there is a defect in the proliferation of T cells, this will be tested to determine whether it is rescued by the addition of exogenous IL-2. Defective IL-2 production by these cells will be apparent by the measurements of IL-2 in the supernatant of primary cultures of T cells harvested from the lymph nodes of the Csp−/− mice. If impaired proliferation is not rescued by IL-2, then the expression of transcription factors known to be involved in lymphocyte proliferation such as Stat5α, Stat5B, and IRF-4 (Gilmour et al., 1995) may be measured. A more likely possibility is that, in the absence of the Csp calcineurin inhibitors, T cell proliferation is enhanced or prolonged, yielding significantly elevated levels of [³H] thymidine incorporation. Similarly, if a proliferation defect in B cells is rescued by exogenous IL-4, it will suggest that the levels of IL-4 secreted by B cells are impaired.

Differentiation of T Helper Cells into Th1 and Th2 Subsets

Naive peripheral helper T cells undergo a well characterized decision of cell fate to become Th1 or Th2 cells, each marked by different effector functions and cytokine production. Cytokines play an important role in this cell fate polarization, with EL-12 driving Th1 outcomes and IL-4 resulting in Th2 cells(Paul and Seder, 1994; Yoshida et al., 1998). While it is unclear these cytokines impart instructive or selective information to helper T cells (Reiner and Seder, 1999), is known that this is a post-activation event that is tied to proliferation. Whether calcineurin suppression, mediated possibly by Csp1 and Csp2, is a necessary event for this post-activation proliferation state to permit the evolution of these effector subsets is unknown. We will compare the ability of helper T cells from wildtype and Csp1 and Csp2 knockout mice to differentiate into Th1 and Th2 cells using established protocols.

Lymph node and spleen T cells will be isolated and stimulated in 96 well dishes by plate-bound anti-CD3 antibodies in the presence of either IL-12, to promote Th1 differentiation, or IL-4 to promote Th2 differentiation (Paul and Seder, 1994; Yoshida et al., 1998). After four days, the culture media is changed with fresh media, and three days later the cells are harvested and restimulated with plate-bound anti-CD3 antibodies in the absence of added cytokines for 24 hours. To examine Th responses, the supernatants will be analyzed by ELISA for the presence of INF-γ and TNF-α, whereas Th2 cytokine production will be assayed by determining levels of IL-4 and IL-6.

The pathways by which cytokines drive CD4+ helper T cells to different pathways are only now being dissected, but obviously involve multistep processes involving an array of signal transduction steps and gene regulation events. Csp1 is known to be activated within 60 min. of combined calcium ionophore/PMA treatment of Jurkat cells, and therefore may play a role in calcineurin inhibition necessary for these cells to begin the differentiation program. Alternatively, the Csp genes might be functioning to suppress calcineurin activity while permitting other calcium-dependent steps in the differention program not involving calcineurin. Should the cytokine profiles of the induced cells suggest a failure of one or both of the differentiation programs, we will need to examine whether the defect is one of proliferation, or whether the cells continue to proliferate but merely fail to express the cytokines typical of a given subclass of Th cells.

Csp1 and Csp2 Promoter/Enhance Regions for Drug and Gene Discovery:

Calcium signaling is though to play a fundamental role in triggering cell death of neurons in stroke and neurodegenerative diseases, cardiomyocytes in cardiomyopathies, and of B and T cells during lymphocyte development. While the nature of the calcium-induced event leading to cell death is unclear, calcineurin, a calcium-activated phosphatase, is a candidate transducing enzyme in this process (Shibasaki et al., 1995, Morioka, 1999; Wang et al., 1999). Given the evidence that Csp1 and Csp2 are inhibitors of calcineurin, and that their expression is inducible by calcium and oxidative stress, it is likely that they function to protect various cells against prolonged calcium and calcineurin signaling accompanying various pathological states. Therefore a drug that would induce Csp1 or Csp2 gene expression might offer a means of selectively inhibiting calcineurin independent of calcium signaling or other toxic stimuli. Small molecules that might promote Csp1 and Csp2 expression could be screened using the following assays based on promoter/enhancer reporter assays in mammalian cells and transgenic animals.

Identification of the Human Csp1 Enhancer/Promoter:

An unannotated block of 100 Kbp DNA sequence from human chromosome 21q22.1 was deposited in GenBank (Unfinished genomic sequence HTG division AP000054.1 *Homo sapiens* chromosome 21 clone 245P17-f4A4f__4 map 21q22.1) by the international human genome consortium. This region encompasses the entire Csp1 coding sequence (Fuentes et al., 1997), and, in addition, contains approximately 60,000 bp upstream of the Csp1 start of translation. We have examined this region and have found that this region, especially that within 3000 bp of the start of the Csp1 coding sequence, contains many recognition sites of transcription factors known to mediate calcium signaling in lymphocytes, muscles, and neurons. For instance, regulatory transcription factors bind the promoter/enhancer region 5' from the start of transcription and activate gene expression from the promoter. The DNA binding sequence of these regulatory factors can be found in NCBI transcription factor databases. Scanning the putative Csp1 promoter/enhancer sequence in the database revealed that it contained binding sites for NF-AT, NF-κB, MyoD, p53 and an olfactory neuron-specific factor. Among this short list, at least NF-AT and NF-κB are known to be activated by calcium signaling. These regulatory factors can thus mediate calcium-dependent and tissue-specific expression of Csp1.

Construction of Csp1 Enhancer/Promoter-Reporter Gene

Three separate constructions of the Csp1 promoter/enhancer were produced containing 1, 2, and 3 Kb of the sequence 5' of that corresponding to the start condon of the Csp1(DSCR1) protein, using PCR primers described below. These PCR products were cloned into the XXX vector (Invitrogen) in front of the either the luciferase or beta-galactosidase gene such that the respective proteins would be produced when the Csp1 gene was activated by signaling/transcription factor cascades in mammalian cells. The resultant recombinant plasmid can be used to monitor the effect of various drug compounds on the promoter/enhancer activity of Csp1 gene. For high through-put drug screening, these reporter plasmids could be introduced into mammalian cells by transfection or by virally mediated transduction using retroviruses or DNA viruses such as adenoviruses. Alternatively, cells or tissues derived from transgenic mice harboring integrated copies of the Csp1 reporter construct can be used to monitor conditions or compounds that regulate Csp1 expression. The production of reporter enzymes are quantitated with chemilluminescent substrates of these enzymes. To further evaluate the therapeutic use of drug compounds, the Csp1-reporter transgenic mice can be used to monitor in vivo pharmacology of such compounds. After administration of drugs, tissue sections from these mice are embedded in color-generating substrate solutions to detect luciferase or beta-galacosidase expression to monitor the effect of drug compounds on the expression of Csp1 genes. The transgenic mice may also allow one to assess the side-effects or toxicity of drug compounds prior to clinical trials on human subjects.

Csp2 Promoter/Enhance Reporter Constructs

Similar reporter constructs will be developed from the Csp2 promoter/enhancer fused to luciferase and beta-galactosidase. We will use the murine Csp2 cDNA to isolate the genomic phage clone spanning the promoter/enchancer region of this gene. We will subclone the regions 5' to that encoding the amino terminus of the Csp2 protein and make constructions with one, two, and three Kbp of this 5' region to luciferase or beta-galactosidase expression cassettes. As with the Csp1 reporter constructs, these will be introduced into cells as well as to produce transgenic mice to establish systems for the analysis of conditions and compounds that regulate this gene.

Assays for Identifying Csp Promoter Fragments and Regulatory Elements Capable of Regulating Transcription of a Gene to which it is Operably Linked This example describes assays for identifying regions in the 5' flanking portion of the Csp gene which are capable of regulating expression of a gene to which such a portion is operably linked.

In one assay, various fragments of the Csp nucleic acid shown in SEQ ID NO: 1, are cloned upstream of the luciferase gene in the multiple cloning site of the pGL3-b vector (Promega). The nucleic acid fragments can be fragments having the 3' end of the promoter region and extending to various positions upstream of the transcription initiation site. The nucleic acid fragments can also be chosen based on the potential transcription factor binding sites. Accordingly, nucleic acid fragments containing one or more of these potential binding sites are prepared, e.g., by polymerase chain reaction (PCR), and cloned in pGL3-b vector. Positive controls for this assay may be prepared by using promoters of CMV, liver-specific ApoA1 etc, which are inserted in the pGL3-b vector.

The vectors are then transiently transfected in cells expressing Csp, such as HeLa, fibroblasts cells etc. For the transfection, cells are plated onto poly-D-lysine coated 6-well dishes and allowed to attach overnight. The cells are transfected with the prepared reporter constructs using lipofectamine following the manufacturer's instructions (Gibco). Forty-eight hours following the transfection, the cells are assayed for luciferase activity. The luciferase assay was performed by washing the transfected cells with phosphate buffered saline (PBS) and lysed with 500 µl of lysis buffer (50 mM Tris, 150 mM NaCl, 0.02% NaAzide, 1% NP-40, 100 µg/ml AEBSF, and 5 µg/ml Leupeptin). 50 µl of this lysate was added to 100 µl of a luciferase substrate (Promega) and read in a micro-plate reader within 5 minutes of adding the lysate. Data are expressed as units of relative luciferase activity. Reporter constructs producing high levels of luciferase in transfected cells are those which contain an Csp promoter fragment capable of stimulating transcription.

In another example, regulatory elements of the 5' flanking region of the Csp gene are identified. Fragments of the Csp nucleic acid shown in SEQ ID NO: 1 can then be inserted upstream of a basic promoter in a reporter construct containing the luciferase gene, such as the pGLZ promoter vector from Promega. This will permit the identification of Csp promoter fragments which act as enhancers or silencers of a basic promoter. In this assay, the same or different promoter fragments as those described above are cloned in the reporter vector containing a basic promoter. Csp positive cells are transiently transfected with the reporter constructs and the level of expression of luciferase is measured as described above. Accordingly, reporter constructs containing Csp promoter fragments resulting in higher expression of the luciferase gene compared to the reporter construct containing only the basic promoter contain an Csp enhancer element. Reporter constructs containing Csp promoter fragments resulting in lower expression of the luciferase gene compared to the reporter construct containing only the basic promoter contain a Csp silencer element.

In yet another example, a method is used that allows the screening of a high number of promoter fragments for transcription modulating activity. In this method, the Csp promoter shown in SEQ ID No: 1 is subjected to digestion with an exonuclease, e.g., BalI, and aliquots of the digestion are removed at various time points to generate promoter fragments of various sizes. These mixtures of promoter fragments are then cloned upstream of a reporter gene encoding a selection marker, e.g, a protein providing resistance to a drug. HeLa or other Csp positive cells are stably transfected with mixtures of reporter constructs and cultured in medium containing the drug to which the selection marker provides resistance. Thus, clones of stably transfected cells containing an Csp promoter fragment which is capable of stimulating transcription of the reporter gene can be isolated. The identity of the promoter fragment is determined by PCR amplification and sequencing.

The assay described in the previous paragraph can also be used to identify enhancer elements present in the promoter. In this particular assay, the reporter construct in which the Csp promoter fragments are inserted contains a basic promoter providing low level expression of the reporter gene. Reporter constructs containing an enhancer element will allow high level expression of the selection marker.

A similar assay can be used to identify silencer elements present in the Csp promoter. In this particular assay, the reporter construct contains a basic promoter resulting in relatively high transcription of the reporter gene. Furthermore, in this assay, the reporter gene encodes a protein which stimulates cell death. Such genes are known in the art. Thus, only cells containing a reporter construct containing a silencer will survive.

Tissue Culture Based Reporter Assay for Identifying Compounds which Modulate Csp Promoter Activity In this assay, pGL3-b containing the Csp promoter shown in SEQ ID No: 1 or a fragment thereof, which has transcriptional activity, and located upstream of the luciferase gene is stably transfected into Csp positive cells. These stably transfected cells are then distributed in 96 well plates, incubated overnight, and test compounds are added to individual wells. Following incubation for an appropriate amount of time, the cells are washed and lysed as described above. The amount of luciferase present in each well is determined using the luciferase assay described above and reading of the optical density with a 96 well plate reader. This technique allows rapid and simultaneous testing of numerous compounds and dosages of these compounds.

In Vivo Assay for Identifying Compounds that Modulate Csp Promoter Activity

Once a compound modulating the Csp promoter activity has been identified, e.g., by using the tissue culture based reporter assay described above, the effect of the compound can be tested in vivo as follows.

The test compound is administered to a non-human mammal, such as a mouse, and the level of expression of Csp is measured and compared to its level of expression in an animal to which the compound was not administered. The compound can be administered locally or systemically and various dosages can be tested. At various times after administration of the compound to the animal, the animal is sacrificed and the level of expression of the Csp gene is measured in tissues known to express Csp, e.g., heart and brain and in other tissues. The determination of the level of expression of Csp in tissues not known to express Csp to a great extent will indicate whether a test compound is capable of stimulating the expression of the Csp gene in tissues which do not normally express the protein.

The level of expression of Csp in the tissues can be measured by Northern blot analysis, using a probe hybridizing specifically to the mouse Csp mRNA. mRNA is isolated from the tissues, as described, e.g., in Sambrook, J. Fritsch, E. F., and Maniatis, T. (1989) *Molecular Cloning: A Laboratory Manual*, Cold Spring Harbor Laboratory Press, Cold Spring Harbor, N.Y. To determine the level of expression of Csp in individual cells, one can use in situ hybridization on tissue sections.

Alternatively, the level of expression of Csp can be determined by measuring the level of Csp protein, such as by immunohistochemistry using an antibody binding specifically to Csp.

Comparison of the level of expression of Csp will indicate whether the test compound modulates transcription from the Csp promoter in vivo. Thus, a higher level of Csp mRNA and/or protein in the mice to which the test compound was administered as compared to mice to which the compound was not administered indicates that the test compound stimulates the Csp promoter in vivo. A lower level of Csp mRNA and/or protein in the mice to which the test compound was administered as compared to mice to which the compound was not administered indicates that the test compound inhibits transcription from the Csp promoter in vivo.

In another example, the effect of the test compound on the human Csp promoter is measured in vivo. Accordingly, a mouse transgenic for a reporter gene which is operably linked to and positioned downstream of the human Csp promoter is prepared, according to techniques known in the art and described above. The reporter gene is, for example, a gene encoding beta-galactosidase (LacZ). The transgenic mouse is then treated with the test compound or with nothing, as described above, sacrificed, and the level of expression of the reporter gene is measured in various tissues using, e.g., a calorimetric assay. For example, the level of expression of the beta-galactosidase gene can be determined by performing a beta-galactosidase assay, according to methods known in the art. Comparison of the level of expression of the reporter gene will indicate whether the test compound modulates transcription from the human Csp promoter in vivo.

The reporter gene can also be a gene encoding any marker protein which can be recognized, for example, by an antibody or through specific binding to another molecule.

Assays for Isolating Compounds which Inhibit Binding of a Transcription Factor to the Csp Promoter Factors binding to the Csp promoter can be factors which upon binding stimulate transcription, i.e., activators, or which repress transcription, i.e., inhibitors. Accordingly, inhibition of binding of such transcription factors to the Csp promoter will result in inhibition or stimulation of transcription from the promoter. Compounds which inhibit binding of transcription factors to the Csp promoter can be identified as follows.

The transcription factor is produced recombinantly, such as in *E. coli* and purified. This protein is then incubated in vitro together with labeled Csp promoter, as described above in the EMSA assays, in the presence or absence of the test compound. Following incubation, the mixtures are submitted to EMSA and autoradiography. Reduced amount of retarded complex in binding reactions containing a test compound indicates that the test compound interferes with binding of the factor to the Csp promoter.

In another assay, the recombinant transcription factor is attached to 96 well plates and the DNA binding reactions are carried in the individual wells in the presence or absence of a test compound. After the binding reaction, the wells are washed to removed unbound DNA and the amount of labeled DNA attached to the wells is determined by measuring the amount of label in each well. This assay is a rapid and efficient method for testing numerous compounds.

Calcium Signaling and Cell Death

Calcium signaling plays an important and yet mechanistically vague role in a wide range of cell death, including neuronal cell death in stroke and lymphocyte cell death during positive and negative selection. To test the possibility that calcineurin, a calcium-activated phosphatase, participates in cell death, we asked if cells overexpressing calcineurin would show an enhanced sensitivity to calcium ionophore-induced cell death (Shibasaki and McKeon, 1995). We co-transfected calcineurin A and B subunits into baby hamster kidney (BHK) cells and treated them with calcium ionophore approximately 16 hours later. Whereas cells in 10% fetal calf serum (FCS) showed negligible levels of cell death upon calcium ionophore treatment, cells transferred to 0.25% FCS underwent rapid apoptosis upon calcium ionophore treatment. Similar results were obtained in non-transfected cells, suggesting that endogenous levels of calcineurin can promote cell death under defined conditions. These experiments provided support for the possibility that calcineurin is a candidate mediator of calcium induced cell death.

Mentioned but not shown in the Shibasaki and McKeon (1995) paper was the paradoxical result that cyclosporin A and FK506 do not block this calcineurin-mediated cell death as expected, but in fact enhance the level of cell death observed (FIG. 6). For instance, 40% of BHK cells transfected with CnA and CnB die within 30 min of ionomycin treatment in low serum, whereas this number rises to nearly 60% in the presence of cyclosporin A (FIG. 6). Interestingly, non-immunosuppressive cyclosporin A analogs, such as 6MeAla-CsA, show no enhancement of the calcineurin-induced apoptosis, while CsA analogs that induce immunosuppression at lower concentrations (super-CsA) such as MeBm2t-CsA, augment the apoptotic effect of calcineurin to a greater extent than CsA. Similarly, FK506, but not an analog that lacks interaction with calcineurin, such as rapamycin, also promote apoptosis in this system. A similar trend was seen in BHK cells treated with ionomycin in low serum but not transfected with calcineurin, suggesting that these drugs can affect calcium-induced apoptosis by affecting endogenous calcineurin (FIG. 7).

One interpretation of these data is that calcineurin mediates calcium-induced apoptosis in a manner not blocked, and in fact favored by, the docking of the two major calcineurin inhibitors, CsA and FK506. It is known that both drugs bind to intracellular receptors (immunophilins cyclophilins and FKBPs, respectively) and dock as complexes onto the calcineurin A/B dimer such that large substrates, including the RII peptide or NF-AT, are shielded from the phosphatase active site. However, the docking of immunosuppressant-immunophilin complexes actually promote the interaction of small substrates with the active site of calcineurin. For instance, para-nitrophenylphosphate (PNPP) is hydrolyzed 10-fold faster by calcineurin bound to cyclosporin A and cyclophilin, suggesting that this drug-protein complex constrains the active site of calcineurin such that it favors the hydrolysis of p-NPP.

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for identifying a compound that modulates the activity or level of a calcipressin (Csp) protein, comprising contacting a cell comprising a Csp protein with a test compound and determining the level or activity of the Csp protein in the cell, wherein a higher or lower level or activity of the Csp protein in the cell contacted with the test compound relative to a cell that was not contacted with the test compound indicates that the test compound is a compound that modulates the activity or level of the Csp protein, wherein said activity of the Csp protein is the binding activity of the Csp protein to calcineurin or the inhibitory activity of the Csp protein toward calcineurin, and wherein the Csp protein comprises an amino acid sequence that has at least 95% or about 95% sequence identity to amino acids 50-197 of SEQ ID NO: 4.

2. The method of claim 1, wherein the method comprises determining the level of the Csp protein, wherein a higher or lower level of the Csp protein in the cell contacted with the test compound relative to a cell that was not contacted with the test compound indicates that the test compound is a compound that modulates the level of the Csp protein.

3. The method of claim 2, wherein determining the level of the Csp protein comprises using an antibody binding specifically to the Csp protein.

4. The method of claim 1, wherein the Csp protein comprises an amino acid sequence that has at least 99% or about 99% sequence identity to amino acids 50-197 of SEQ ID NO: 4.

5. The method of claim 4, wherein the Csp protein comprises an amino acid sequence that is identical to amino acids 50-197 of SEQ ID NO: 4.

6. A method for identifying a compound that modulates the activity or level of a calcipressin (Csp) protein, comprising contacting a cell comprising a Csp protein with a test compound and determining the level or activity of the Csp protein in the cell, wherein a higher or lower level or activity of the Csp protein in the cell contacted with the test compound relative to a cell that was not contacted with the test compound indicates that the test compound is a compound that modulates the activity or level of the Csp protein, wherein said activity of the Csp protein is the binding activity of the Csp protein to calcineurin or the inhibitory activity of the Csp protein toward calcineurin, and wherein the Csp protein comprises an amino acid sequence that has at least 95% or about 95% sequence identity to SEQ ID NO: 4.

7. The method of claim 6, wherein the Csp protein comprises an amino acid sequence that has at least 99% or about 99% sequence identity to SEQ ID NO: 4.

8. The method of claim 7, wherein the Csp protein comprises an amino acid sequence that is identical to SEQ ID NO: 4.

9. A method for identifying a compound that modulates the activity or level of a calcipressin (Csp) protein, comprising contacting a cell comprising a Csp protein with a test compound and determining the level or activity of the Csp protein in the cell, wherein a higher or lower level or activity of the Csp protein in the cell contacted with the test compound relative to a cell that was not contacted with the test compound indicates that the test compound is a compound that modulates the activity or level of the Csp protein, wherein said activity of the Csp protein is the binding activity of the Csp protein to calcineurin or the inhibitory activity of the Csp protein toward calcineurin, and wherein the Csp protein comprises an amino acid sequence that has at least 95% or about 95% sequence identity to SEQ ID NO: 5.

10. The method of claim 9, wherein the method comprises determining the level of the Csp protein, wherein a higher or lower level of the Csp protein in the cell contacted with the test compound relative to a cell that was not contacted with the test compound indicates that the test compound is a compound that modulates the level of the Csp protein.

11. The method of claim 10, wherein determining the level of the Csp protein comprises using an antibody binding specifically to the Csp protein.

12. The method of claim 9, wherein the Csp protein comprises an amino acid sequence that has at least 99% or about 99% sequence identity to SEQ ID NO: 5.

13. The method of claim 12, wherein the Csp protein comprises an amino acid sequence that is identical to SEQ ID NO: 5.

\* \* \* \* \*